(12) United States Patent
D'Angelo et al.

(10) Patent No.: US 8,710,014 B2
(45) Date of Patent: Apr. 29, 2014

(54) COMPOSITIONS AND METHODS FOR INHIBITION OF MMP13:MMP-SUBSTRATE INTERACTIONS

(75) Inventors: Marina D'Angelo, Philadelphia, PA (US); Abdulhafez Selim, Long Beach, NJ (US)

(73) Assignee: ProteaPex Therapeutics LLC, Philadelphia, PA (US)

( * ) Notice: Subject to any disclaimer, the term of this patent is extended or adjusted under 35 U.S.C. 154(b) by 0 days.

(21) Appl. No.: 13/269,518

(22) Filed: Oct. 7, 2011

(65) Prior Publication Data
US 2012/0088722 A1 Apr. 12, 2012

Related U.S. Application Data

(60) Provisional application No. 61/391,446, filed on Oct. 8, 2010.

(51) Int. Cl.
| | | |
|---|---|---|
| *A61K 38/48* | (2006.01) | |
| *A61K 38/55* | (2006.01) | |
| *C07K 14/81* | (2006.01) | |
| *A61K 38/00* | (2006.01) | |
| *A61K 38/18* | (2006.01) | |
| *C07K 14/495* | (2006.01) | |
| *A61P 19/02* | (2006.01) | |
| *A61P 19/00* | (2006.01) | |
| *C07K 2/00* | (2006.01) | |
| *C07K 4/00* | (2006.01) | |
| *C07K 5/00* | (2006.01) | |
| *C07K 7/00* | (2006.01) | |
| *C07K 14/00* | (2006.01) | |
| *C07K 16/00* | (2006.01) | |
| *C07K 17/00* | (2006.01) | |
| *A61K 38/04* | (2006.01) | |

(52) U.S. Cl.
USPC ........... 514/20.1; 514/1.1; 514/8.9; 514/16.8; 514/17.1; 530/300; 530/326; 530/327; 530/328

(58) Field of Classification Search
None
See application file for complete search history.

(56) References Cited

U.S. PATENT DOCUMENTS

| | | | |
|---|---|---|---|
| 2005/0004111 A1 | 1/2005 | Klingler et al. | |
| 2006/0286085 A1* | 12/2006 | Silbiger et al. | 424/94.6 |

FOREIGN PATENT DOCUMENTS

| | | |
|---|---|---|
| EP | 0 935 963 | 8/1999 |
| EP | 2 186 894 | 5/2010 |
| WO | WO 2006/072563 | 7/2006 |
| WO | WO 2009/111083 | 9/2009 |

OTHER PUBLICATIONS

Kevorkian L, et al. Arthritis and Rheumatism 50(1):131-141, Jan. 2004.*
Ramnath N, et al. Current Oncology Reports 6(2):96-102, 2004.*
Mitchell PG, et al. J. Clin. Investig. 97(3):761-768, Feb. 1996. Found online at http://www.jci.org/articles/view/118475.*
Park M-J, et al. Cancer Res. 62:6318-6322, 2002. Found online at http://cancerres.aacrjournals.org/content/62/21/6318.*
Janusz, M. J., Hookfin, E. B., Heitmeyer, S. A. et al. (2001) Osteoarthritis Cartilage 9, 751-760.
Guingamp, C., Gegout-Pottie, P., Philippe, L., Terlain, B., Netter, P., and Gillet, P. (1997) Arthritis Rheum. 40, 1670-1679.
Mankin Scale (Pritzker, K. P., Gay, S., Jimenez, S. A., Ostergaard, K., Pelletier, J. P., Revell, P. A., Salter, D., and van den Berg, W. B. (2006) Osteoarthritis Cartilage 14, 13-29.
Messent, E. A., Ward, R. J., Tonkin, C. J., and Buckland-Wright, C. (2005) Osteoarthritis Cartilage 13, 463-470.
Hruska, R. E., Kennedy, S., and Silbergeld, E. K. (1979) Life Sci. 25, 171-179.
Kubinyi Structure-based design of enzyme inhibitors and receptor ligands, Curr. Op. in Drug Disc. and Development, 1998 vol. 1 No. 1; incorporated in its entirety by express reference).
Fajardo et al,, Matrix metalloproteinases that associate with and cleave bone morphogenetic protein-2 in vitro are elevated in hypertrophic fracture nonunion tissue. J Orthop Trauma. Sep. 2010;24(9):557-63.
Eisenberg et al. J. Mol. Bio. 179:125-142, 1984.
Anwer et. al. Int. J Pep. Protein Res. 36:392-399, 1990.
Rivera-Baeza et al. Neuropeptides 30:327-333, 1996.
Nachman et al., Regul. Pept. 57:359-370 1995.
Henrick et al., Tetrahedron Lett. 37:5289-5292, 1996.
Moriuchi et al., J. Am. Chem. Soc. 123:68-75, 2001.
Barisic et al., Chem. Commun. 17:2004-2005, 2004.
Greenwald et al., Crit Rev Therap Drug Carrier Syst. 2000; 17:101-161.
Kopecek et al., J Controlled Release, 74:147-158, 2001.
Harris et al., Clin Pharmacokinet. 2001; 40(7):539-51.
Zalipsky et al., Bioconjug Chem. 1997.; 8:111-118.
Nathan et al., Macromolecules. 1992; 25:4476-4484.
Stewart and Young, Solid Phase Peptide Synthesis, 2d. ed., Pierce Chemical Co., (1984).
Tam et al., J. Am. Chem. Soc., 105:6442, 1983.
Merrifield, Science, 232:341-347, 1986.

(Continued)

*Primary Examiner* — Robert Landsman
(74) *Attorney, Agent, or Firm* — Kenneth E. Levitt; Dorsey & Whitney LLP

(57) ABSTRACT

The present invention provides compounds for disrupting the binding of a matrix metalloprotease (MMP) protein to a substrate protein at an interaction site other than the protease catalytic site. In particular the inventive compounds inhibit the MMP's ability to cleave a substrate protein. In some cases the compound may prevent activation of transforming growth factor beta (TGFβ). The compounds are preferably polypeptide fragments of the hemopexin-like domain of the MMP, but may be mimetics thereof or peptides or mimetics of the portion of the MMP substrate protein to which the MMP interacts.

13 Claims, 48 Drawing Sheets

(56) References Cited

OTHER PUBLICATIONS

Barany and Merrifield, The Peptides, Gross and Meienhofer, eds, Academic Press, New York, 1-284, 1979.
Fields, (1997) Solid-Phase Peptide Synthesis. Academic Press, San Diego.
Remington's Pharmaceutical Sciences 16th edition, Osol, A. Ed., 1980.
D'Angelo, et al., J. Cell. Biochem. 77:678-693, 2000.
Pacifici et al., Exp. Cell Res. 192:266-270, 1991.
D'Angelo et al., J. Bone Miner. Res. 16:2339-2347, 2001.
D'Angelo et al., J. Bone Miner. Res. 12:1368-1377, 1997; and D'Angelo et al., 2001.
Dallas et al., J. Cell Biol. 131:539-549, 1995.
Selim et al., J Bone Miner. Res. 20:S131, 2005.
Mattioli et al., J. Bone Miner. Res. 19:S216, 2004.
Taipale, J; Miyazono, K; Heldin, C-H and J. Keski-Oja (1994) JCB 124, 171-181.
Averna et al. "Abstract 647.2: Collagenase 3 (MMP13) modulates activation of Transforming Growth Factor b (TGFb) by hypertrophic growth plate chondrocytes" The FASEB Journal, vol. 23 Apr. 1, 2009.
Dragann et al. "Abstract 774.6; Activation of Transforming Growth Factor beta (TGFbeta) by interaction of Matrix Metalloproteinase 13 (MMP-13) with the large latent complex", The FASEB Journal, vol. 22, Mar. 1, 2008.

\* cited by examiner

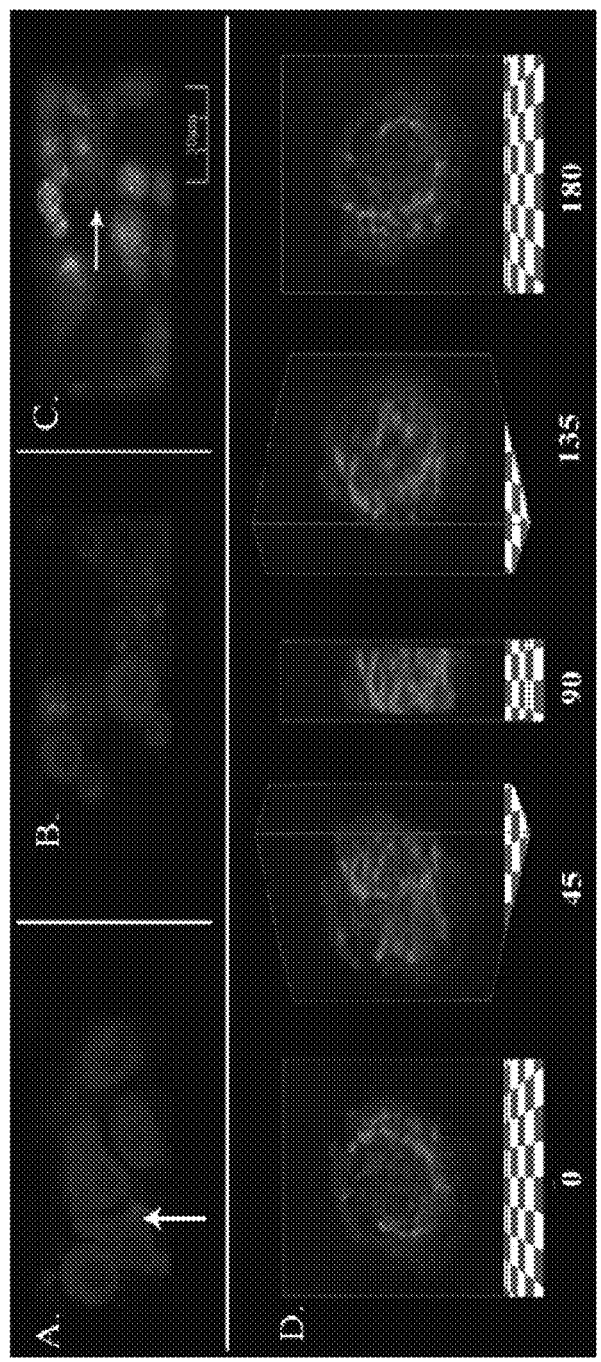
FIG. 6A-D

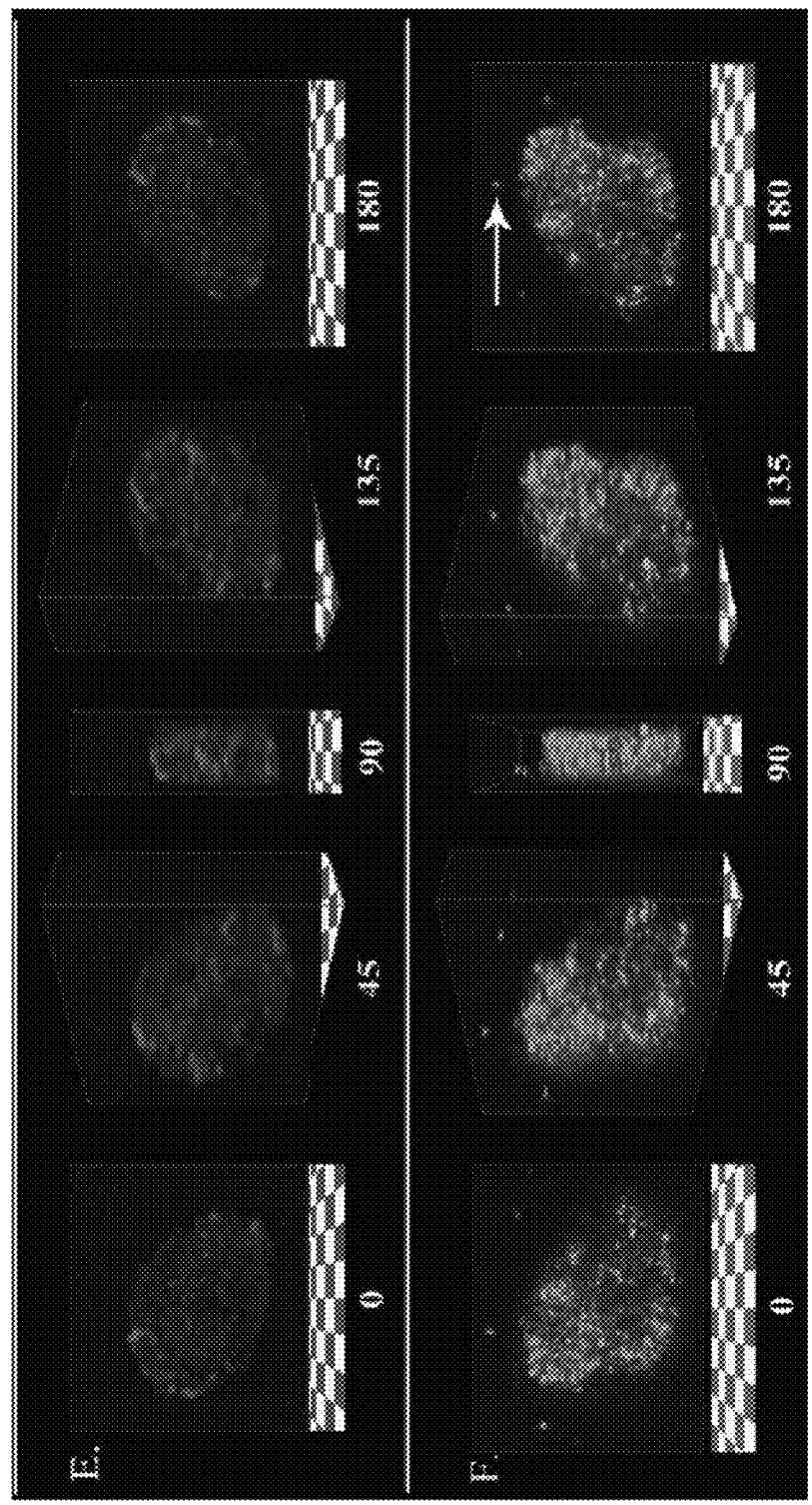
FIG. 6E-F

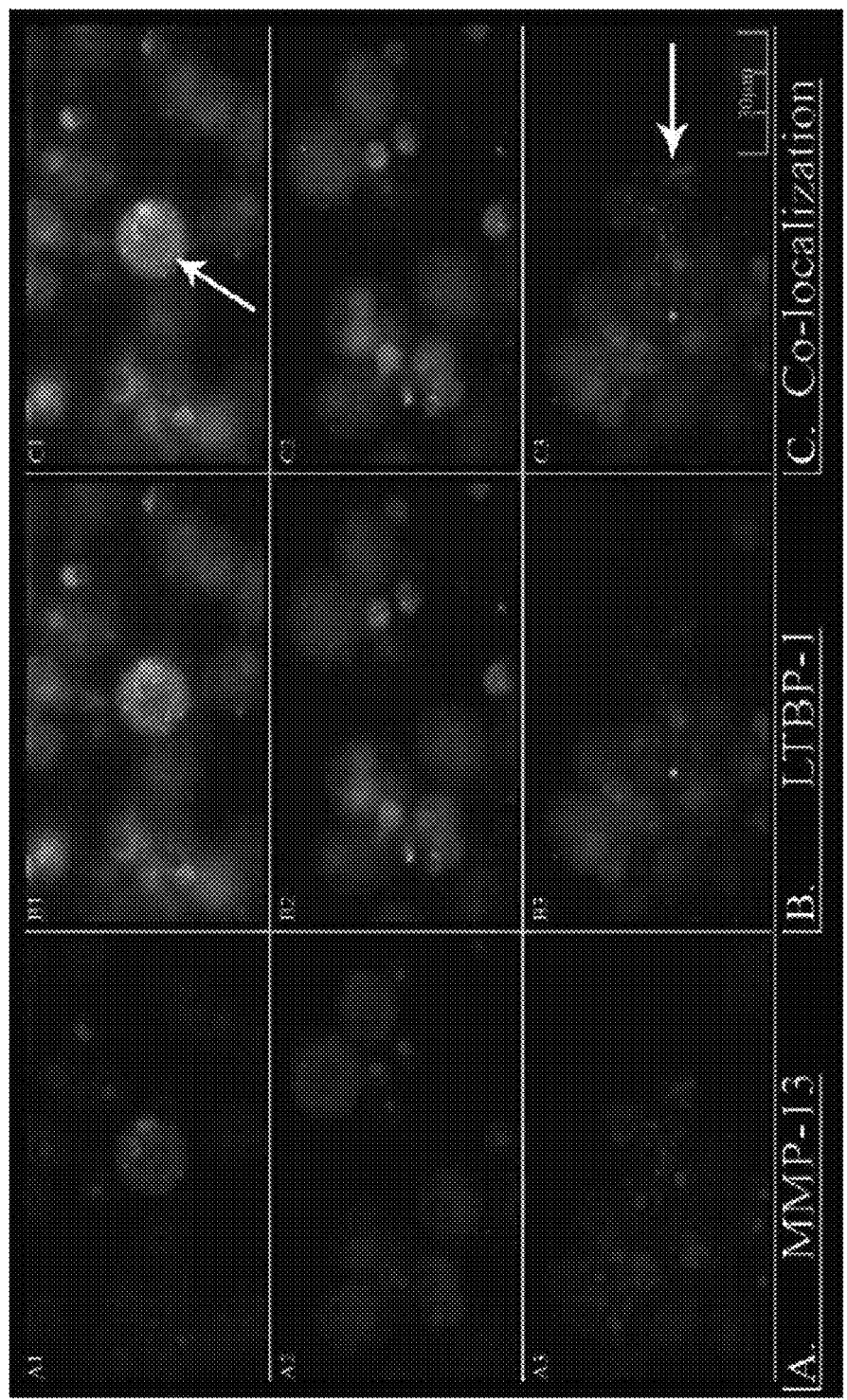
FIG. 7A-C

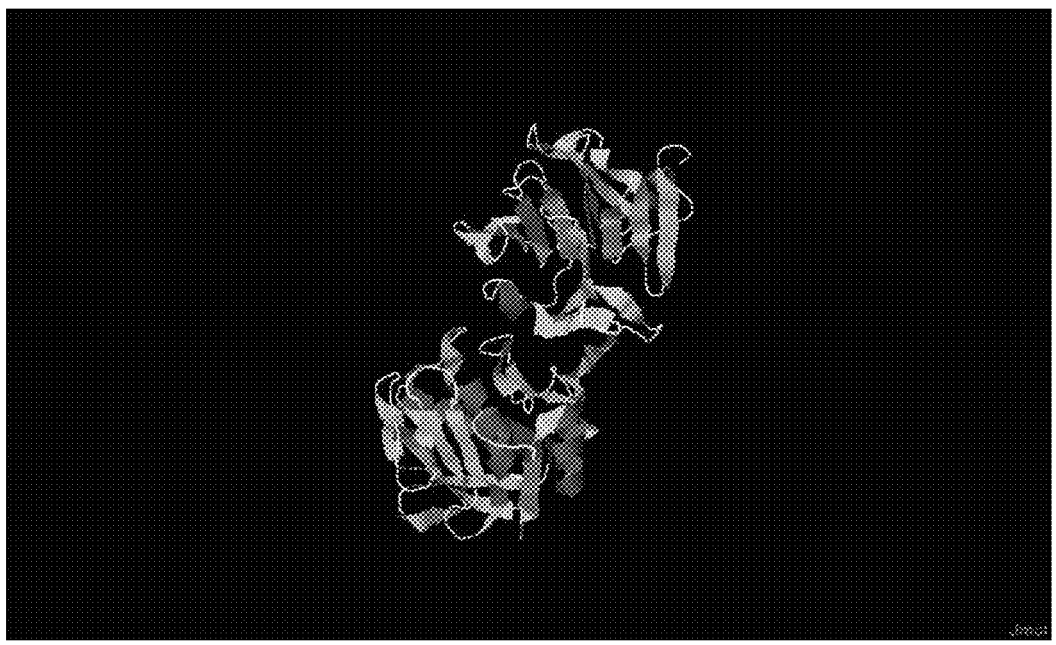
FIG. 13: Dog MMP13

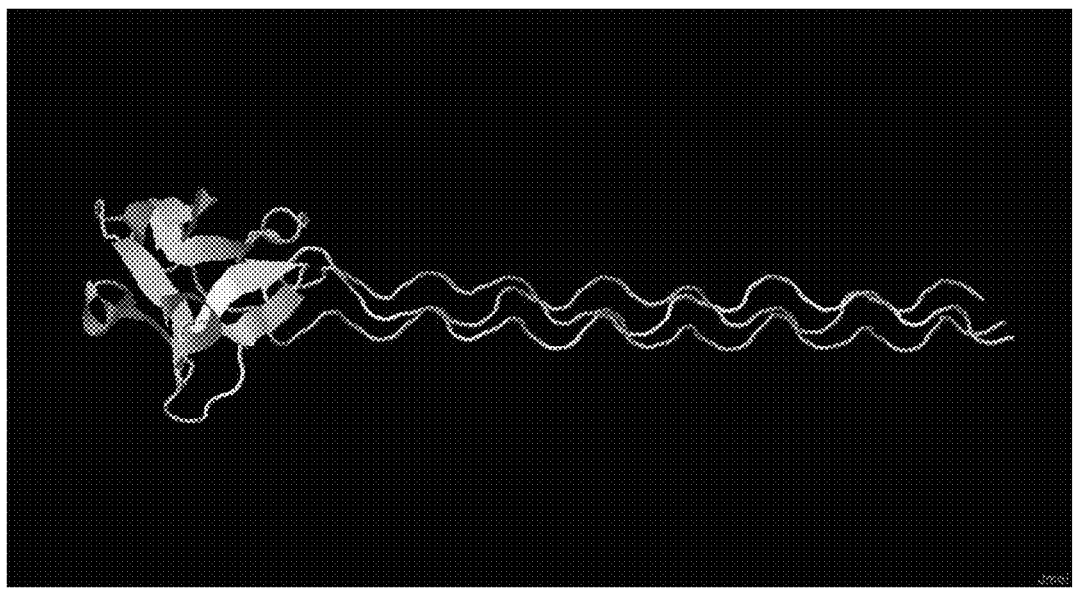
FIG. 14: Collagen

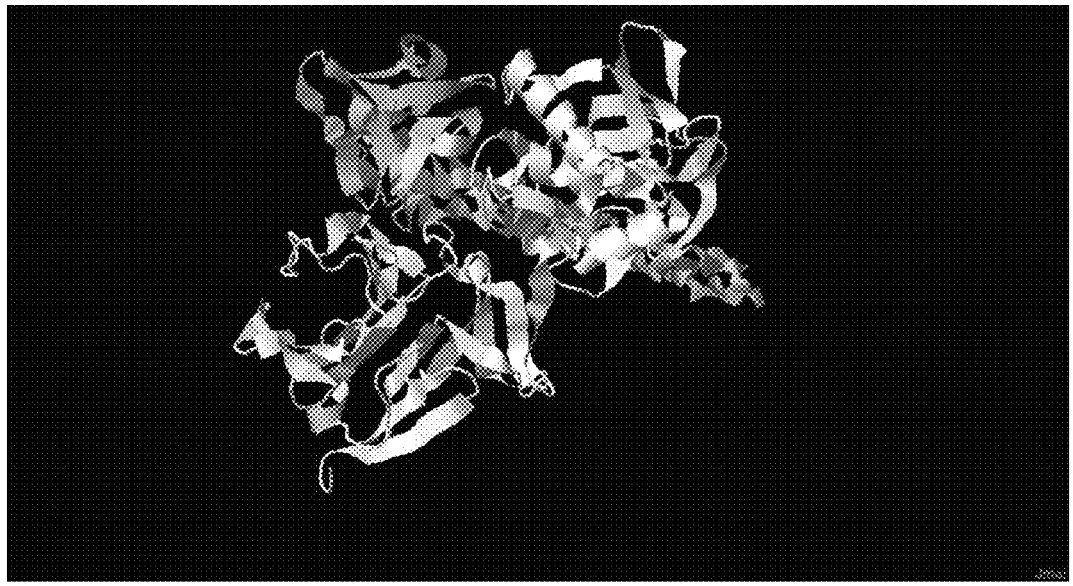
FIG. 15: MMP13-Collagen complex
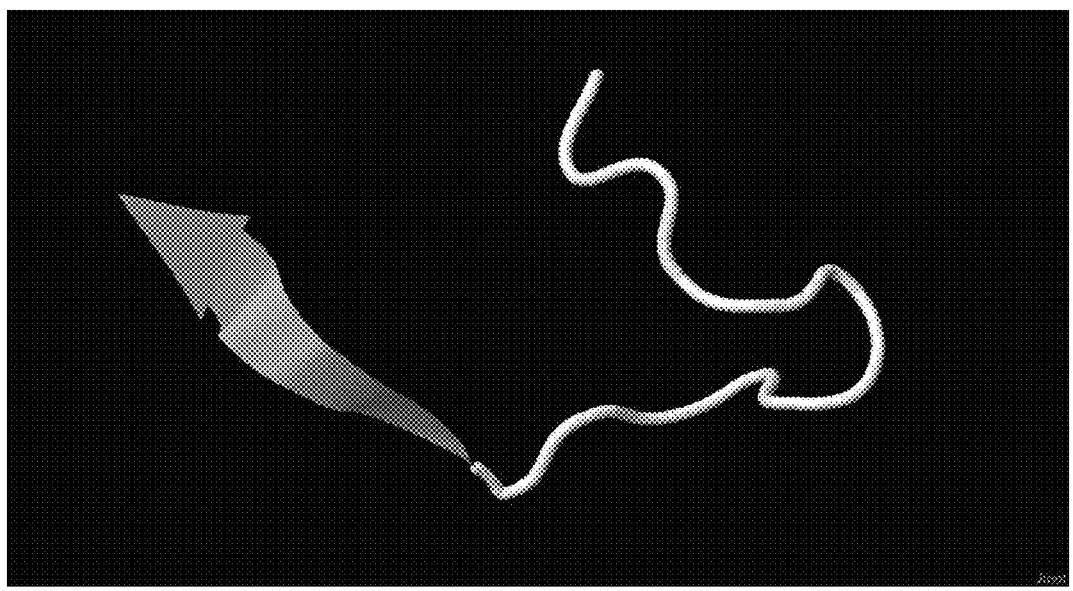
FIG. 16: MMP13 -derived peptide

FIG. 17: MMP 13-Collagen-Peptide complex

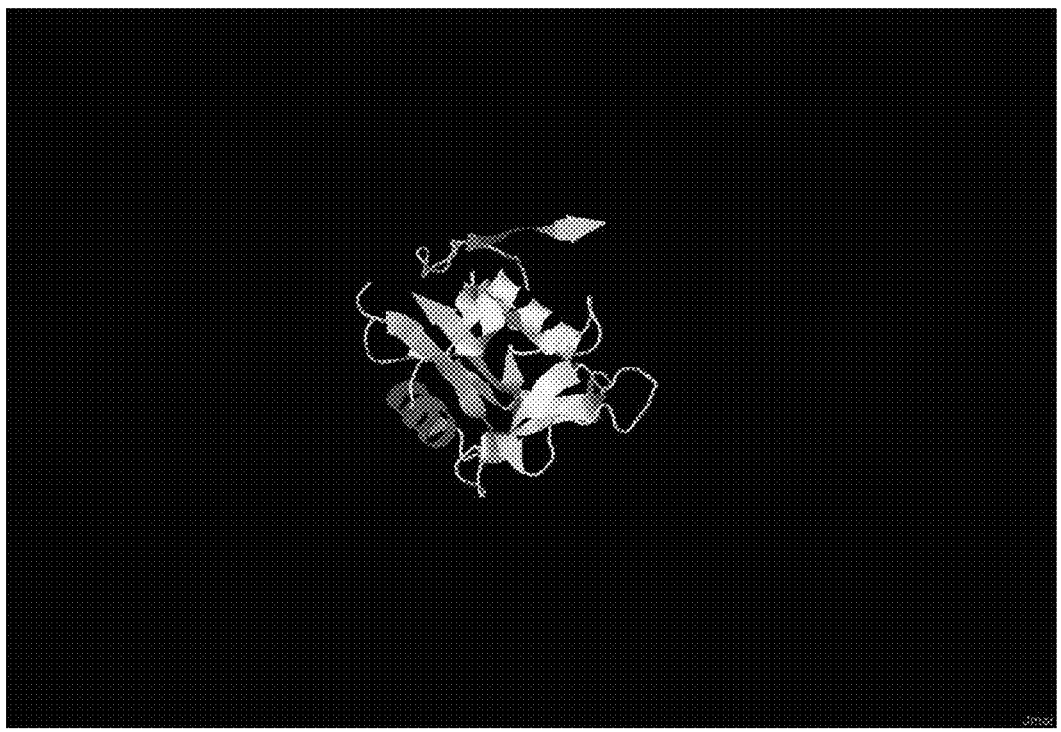
FIG. 18: Peptide-aggrecan complex.

FIG. 19: Peptide-Fibronectin III complex

MMP13-Derived Peptide Sequences

SEQ ID NO:35 (aa 17-26 of SEQ ID NO: 1)
LRGETMIFKD

SEQ ID NO:36 (aa 93-111 of SEQ ID NO: 1)
ELGLPKEVKKISAAVHFED

SEQ ID NO:37 (aa 101-150 of SEQ ID NO: 1)
KKISAAVHFEDTGKTLLFSGNQVWRYDDTNHIMDKDYPRLIEE DFPGIGD

SEQ ID NO:38 (aa 109-147 of SEQ ID NO: 1)
FEDTGKTLLFSGNQVWRYDDTNHIMDKDYPRLIEEDFPG

SEQ ID NO:39 (aa 125-147 of SEQ ID NO: 1)
RYDDTNHIMDKDYPRLIEEDFPG

SEQ ID NO:40 (aa 151-192 of SEQ ID NO:1)
KVDAVYEKNGYIYFFNGPIQFEYSIWSNRIVRVMPANSILWC

SEQ ID NO:41 (aa 160-180 of SEQ ID NO: 1)
GYIYFFNGPIQFEYSIWSNRI

SEQ ID NO:42 (aa 51-100 of SEQ ID NO: 1)
LPNRIDAAYEHPSHDLIFIFRGRKFWALNGYDILEGYPKKISELG LPKEV

SEQ ID NO:43 (aa 60-83 of SEQ ID NO: 1),
EHPSHDLIFIFRGRKFWALNGYDI

SEQ ID NO:44 (aa 1-50 of SEQ ID NO: 1),
TPDKCDPSLSLDAITSLRGETMIFKDRFFWRLHPQQVDAELFLT KSFWPE

SEQ ID NO:45 (aa 16-50 of SEQ ID NO: 1),
SLRGETMIFKDRFFWRLHPQQVDAELFLTKSFWPE

SEQ ID NO:46 (aa 168-186 of SEQ ID NO: 1)
PIQFEYSIWSNRIVRMPA

SEQ ID NO:47 (aa 109-129 of SEQ ID NO: 1)
FEDTGKTLLFSGNQVWRYDDT

MMP14-Derived Peptide Sequences

SEQ ID NO:48 (aa 323-366 of SEQ ID NO: 2)
FDTVAMLRGEMFVFKERWFWRVRNNQVMDGY PMPIGQFWRGLPA

SEQ ID NO:49 (aa 368-412 of SEQ ID NO: 2)
INTAYERKDGKFVFFKGDKHWVFDEASLEPGYPKHIKELGRGL PT

SEQ ID NO:50 (aa 415-461 of SEQ ID NO: 2)
IDAALFWMPNGKTYFFRGNKYYRFNEELRAVDSEYPKNIKVW EGIPE

SEQ ID NO:51 (aa 463-508 of SEQ ID NO: 2)
PRGSFMGSDEVFTYFYKGNKYWKFNNQKLKVEPGYPKSALRD WMGC

FIG. 20A

MMP16-Derived Peptide Sequences

SEQ ID NO:52 (aa 347-390 of SEQ ID NO: 3)
FNTLAILRREMFVFKDQWFWRVRNNRVMDGYPMQITYFWRG LPP

SEQ ID NO:53 (aa 392-436 of SEQ ID NO: 3)
IDAVYENSDGNFVFFKGNKYWVFKDTTLQPGYPHDLITLGSGI PP

SEQ ID NO:54 (aa 439-485 of SEQ ID NO: 3)
IDSAIWWEDVGKTYFFKGDRYWRYSEEMKTMDPGYPKPITV WKGIPE

SEQ ID NO:55 (aa 487-532 of SEQ ID NO: 3)
PQGAFVHKENGFTYFYKGKEYWKFNNQILKVEPGYPRSILKD FMGC

MMP2 -Derived Peptide Sequences

SEQ ID NO:56 (aa 475-518 of SEQ ID NO: 4)
FDGIAQIRGEIFFFKDRFIWRTVTPRDKPMGPLLVATFWPELP

SEQ ID NO:57(aa 520-563 of SEQ ID NO: 4)
 IDAVYEAPQEEKAVFFAGNEYWIYSASTLERGYPKPLTSLGLPP

SEQ ID NO:58 (aa 568-615 of SEQ ID NO: 4)
VDAAFNWSKNKKTYIFAGDKFWRYNEVKKKMDPGFPKLIA DAWNAIPD

SEQ ID NO:59 (aa 617-660 of SEQ ID NO: 4)
LDAVVDLQGGGHSYFFKGAYYLKLENQSLKSVKFGSIKSDWL GC

MMP9 -Derived Peptide Sequences

SEQ ID NO:60 (aa 521-565 of SEQ ID NO: 5)
FDAIAEIGNQLYLFKDGKYWRFSEGRGSRPQGPFLIADKWPAL PR

SEQ ID NO:61 (aa 567-608 of SEQ ID NO: 5)
LDSVFEERLSKKLFFFSGRQVWVYTGASVLGPRRLDKLGLGA

SEQ ID NO:62 (aa 613-659 of SEQ ID NO: 5)
VTGALRSGRGKMLLFSGRRLWRFDVKAQMVDPRSASEVDRM FPGVPL

SEQ ID NO:63 (aa 661-704 of SEQ ID NO: 5)
THDVFQYREKAYFCQDRFYWRVSSRSELNQVDQVGYVTYD ILQC

MMP19 -Derived Peptide Sequences

SEQ ID NO:64 (aa 293-335 of SEQ ID NO: 6)
LDAMMLGPRGKTYAFKGDYVWTVSDSGPGPLFRVSALWEGLP G

SEQ ID NO:65 (aa 337-378 of SEQ ID NO: 6)
LDAAVYSPRTQWIHFFKGDKVWRYINFKMSPGFPKKLNRVEP

SEQ ID NO:66 (aa 380-427 of SEQ ID NO: 6)
LDAALYWPLNQKVFLFKGSGYWQWDELARTDFSSYPKPIKG LFTGVPN

SEQ ID NO:67 (aa 429-472 of SEQ ID NO: 6)
PSAAMSWQDGRVYFFKGKVYWRLNQQLRVEKGYPRNISHN WMHC

FIG. 20B

MMP17 -Derived Peptide Sequences

SEQ ID NO:68 (aa 336-380 of SEQ ID NO: 7)
FDAVAQIRGEAFFFKGKYFWRLTRDRHLVSLQPAQMHRFWRG LPL

SEQ ID NO:69 (aa 385-428 of SEQ ID NO: 7)
VDAVYERTSDHKIVFFKGDRYWVFKDNNVEEGYPRPVSDFSLP P

SEQ ID NO:70 (aa 431-477 of SEQ ID NO: 7)
IDAAFSWAHNDRTYFFKDQLYWRYDDHTRHMDPGYPAQSPL WRGVPS

SEQ ID NO:71 (aa 479-523 of SEQ ID NO: 7)
IDAAFSWAHNDRTYFFKDQLYWRYDDHTRHMDPGYPAQSPL WRGVPS

MMP15 -Derived Peptide Sequences

SEQ ID NO:72 (aa 374-417 of SEQ ID NO: 8)
FDTVAMLRGEMFVFKGRWFWRVRHNRVLDNYPMPIGHFWR GLPG

SEQ ID NO:73 (aa 419-463 of SEQ ID NO 8)
ISAAYERQDGRFVFFKGDRYWLFREANLEPGYPQPLTSYGLGI PY

SEQ ID NO:74 (aa 466-512 of SEQ ID NO: 8)
IDTAIWWEPTGHTFFFQEDRYWRFNEETQRGDPGYPKPISVW QGIPA

SEQ ID NO:75 aa 514-559 of SEQ ID NO: 8)
PKGAFLSNDAAYTYFYKGTKYWKFDNERLRMEPGYPKSILRD FMGC (

MMP20 SEQ ID NO: 9

SEQ ID NO:76 (aa 302-345 of SEQ ID NO: 9)
FDAVTMLGKELLLFKDRIFWRRQVHLRTGIRPSTITSSFPQLMS

SEQ ID NO:77 (aa 347-389 of SEQ ID NO: 9)
VDAAYEVAERGTAYFFKGPHYWITRGFQMQGPPRTIYDFGFPR

SEQ ID NO:78 (aa 394-441 of SEQ ID NO: 9)
IDAAVYLREPQKTLFFVGDEYYSYDERKRKMEKDYPKNTEE EFSGVNG

SEQ ID NO:79 (aa 443-483 of SEQ ID NO: 9)
IDAAVELNGYIYFFSGPKTYKYDTEKEDVVSVVKSSSWIGC

MMP1 -Derived Peptide Sequences

SEQ ID NO:80 (aa 284-326 of SEQ ID NO: 10)
FDAITTIRGEVMFFKDRFYMRTNPFYPEVELNFISVFWPQLPN

SEQ ID NO:81 (aa 328-372 of SEQ ID NO: 10)
LEAAYEFADRDEVRFFKGNKYWAVQGQNVLHGYPK

SEQ ID NO:82 (aa 377-424 of SEQ ID NO: 10)
IDAALSEENTGKTYFFVANKYWRYDEYKRSMDPGYP KMIAHD FPGIGH

SEQ ID NO:83 (aa 426-466 of SEQ ID NO: 10)
VDAVFMKDGFFYFFHGTRQYKFDPKTKRILTLQKANSWFNC

FIG. 20C

MMP24 -Derived Peptide Sequences

SEQ ID NO:84 (aa 357-400 of SEQ ID NO: 11)
RQPRPPRPPLGDRPSTPGTKPNICDGNFNTVALFRGEMFVFKDR

SEQ ID NO:85 (aa 402-446 of SEQ LD NO: 11)
FWRLRNNRVQEGYPMQIEQFWKGLPARIDAAYERAD GRFVFFKGD

SEQ ID NO:86 (aa 449-495 of SEQ ID NO: 11)
WVFKEVTVEPGYPHSLGELGSCLPREGIDTALRWEPVGKTYFFKGER

SEQ ID NO:87 (aa 497-542 of SEQ ID NO: 11)
WRYSEERRATDPGYPKPITVWKGIPQAPQGAFISKEGY YTYFYKGR

MMP25 -Derived Peptide Sequences

SEQ ID NO:88 (aa 321-365 of SEQ ID NO: 12)
FDAIANIRGETFFFKGPWFWRLQPSGQLVSPRPARLHRFWEGLP

SEQ ID NO:89 (aa 370-412 of SEQ ID NO: 12)
VQAAYARHRDGRILLFSGPQFWVFQDRQLEGGARPLTELGLPP

SEQ ID NO:90 (aa 416-462 of SEQ ID NO: 12)
VDAVFSWPQNGKTYLVRGRQYWRYDEAAARPDPGYP RDLSLWEGAPP and SEQ ID NO:91 aa 464-508 of SEQ ID NO: 12)
PDDVTVSNAGDTYFFKGAHYWRFPKNSIKTEPDAPQPM GPNWLDC (

MMP3 SEQ ID NO: 13

SEQ ID NO:92 (aa 296-338 of SEQ ID NO: 13)
FDAVSTLRGEILIFKDRHFWRKSLRKLEPELHLISSFWPSLPS

SEQ ID NO:93 (aa 340-383 of SEQ ID NO: 13)
VDAAYEVTSKDLVFIFKGNQFWAIRGNEVRAGYPRGIH TLGFPP.

SEQ ID NO:94(aa 388-435 of SEQ ID NO: 13)
IDAAISDKEKNKTYFFVEDKYWRFDEKRNSMEPGFPKQ IAEDFPGIDS

SEQ ID NO:95 (aa 437-477 of SEQ ID NO: 13)
PSGVDAAYEVTSKDLVFIFKGNQFWAIRGNEVRAGYPRGIH

MMP21 -Derived Peptide Sequences

SEQ ID NO:96 (aa 333-391 of SEQ ID NO: 14)
FDTAFDWIRKERNQYGEVMVRFSTYFFRNSWYWLYE NRNNRTRYGDPIQILTGWPGIPT

SEQ ID NO:97(aa 394-449 of SEQ ID NO: 14)
IDAFVHIWTWKRDERYFFQGNQYWRYDSDKDQALTE DEQGKSYP KLISEGFPGIPS

SEQ ID NO:98 (aa 451-499 of SEQ ID NO: 14)
LDTAFYDRRQKLIYFFKESLVFAFDVNRNRVLNSYPKR ITEVTPAVIPQ

SEQ ID NO:99 (aa 506-549 of SEQ ID NO: 14)
IDSAYYSYAYNSIFFFKGNAYWKVVNDKDKQQNSWLP ANGLFPK

FIG. 20D

MMP28 -Derived Peptide Sequences

SEQ ID NO:100 (aa 328-371 of SEQ ID NO: 15)
FDAITVDRQQQLYIFKGSHFWEVAADGNVSEPRPLQERW VGLPP

SEQ ID NO:101 (aa 373-416 of SEQ ID NO: 15)
IEAAAVSLNDGDFYFFKGGRCWRFRGPKPVWGLPQLC RAGGLPR

SEQ ID NO:102 (aa 418-464 of SEQ ID NO: 15); and
PDAALFFPPLRRLILFKGARYYVLARGGLQVEPYYPRS LQDWGGIPE SEQ ID NO:103 (aa 466-510 of SEQ ID NO: 15)
VSGALPRPDGSIIFFRDDRYWRLDQAKLQATTSGRWAT ELPWMGC

MMP8 -Derived Peptide Sequences

SEQ ID NO:104 (aa 285-327 of SEQ ID NO: 16)
FDAITTLRGEILFFKDRYWRRHPQLQRVEMNFISLFWPSLPT

SEQ ID NO:105 (aa 329-372 of SEQ ID NO: 16)
IQAAYEDFDRDLIFLFKGNQYWALSGYDILQGYPKDISNYGFPS

SEQ ID NO:106 (aa 377-422 of SEQ ID NO: 16); and
IDAAVFYRSKTYFFVNDQFWRYDNQRQFMEPGYPKSI SGAFPGIES SEQ ID NO:107 (aa 424-464 of SEQ ID NO: 16).
VDAVFQQEHFFHVFSGPRYYAFDLIAQRVTRVARGNKWLNC

MMP12 -Derived Peptide Sequences

SEQ ID NO:108 (aa 288-330 of SEQ ID NO: 17)
FDAVTTVGNKIFFFKDRFFWLKVSERPKTSVNLISSLWPTLPS

SEQ ID NO:109 (aa 332-375 of SEQ ID NO: 17)
IEAAYEIEARNQVFLFKDDKYWLISNLRPEPNYPKSIHSFGFPN

SEQ ID NO:110 (aa 380-427 of SEQ ID NO: 17)
IDAAVFNPRFYRTYFFVDNQYWRYDERRQMMDPGYPKLITKN FQGIGP

SEQ ID NO:111 (aa 429-470 of SEQ ID NO: 17)
IDAVFYSKNKYYYFFQGSNQFEYDFLLQRITKTLKSNSWFGC

MMP27 -Derived Peptide Sequences

SEQ ID NO:112 (aa 285-327 of SEQ ID NO: 18)
FDAITTFRREVMFFKGRHLWRIYYDITDVEFELIASFWPSLPA

SEQ ID NO:113 (aa 329-371 of SEQ ID NO: 18)
LQAAYENPRDKILVFKDENFWMIRGYAVLPDYPKSIHTLGFPG

SEQ ID NO:114 (aa 376-423 of SEQ ID NO: 18)
IDAAVCDKTTRKTYFFVGIWCWRFDEMTQTMDKGFPQRVVKH FPGISI ; and SEQ ID NO:115 (aa 425-465 of SEQ ID NO: 18)
VDAAFQYKGFFFFSRGSKQFEYDIKTKNITRIMRTNTWFQC .

FIG. 20E

MMP11-Derived Peptide Sequences

SEQ ID NO:116 (aa 298-341 of SEQ ID NO: 19)
FDAVSTIRGELFFFKAGFVWRLRGGQLQPGYPALASR HWQGLPS

SEQ ID NO:117 (aa 343-384 of SEQ ID NO: 19)
VDAAFEDAQGHIWFFQGAQYWVYDGEKPVLGPAPLTELGLVR

SEQ ID NO:118 (aa 387-434 of SEQ ID NO: 19)
VHAALVWGPEKNKIYFFRGRDYWRFHPSTRRVDSPVPRRATD WRGVPS

SEQ ID NO:119 (aa 436-480 of SEQ ID NO: 19)
IDAAFQDADGYAYFLRGRLYWKFDPVKVKALEGFPRLVGPDF FGC .

MMP10-Derived Peptide Sequences

SEQ ID NO:120 (aa 295-337 of SEQ ID NO: 20)
FDAISTLRGEYLFFKDRYFWRRSHWNPEPEFHLISAFWPSLPS

SEQ ID NO:121 (aa 339-382 of SEQ ID NO: 20)
LDAAYEVNSRDTVFIFKGNEFWAIRGNEVQAGYPRGIHTLGFPP

SEQ ID NO:122 (aa 387-434 of SEQ ID NO: 20); and
IDAAVSDKEKKKTYFFAADKYWRFDENSQSMEQGFPR LIADDFPG VEP SEQ ID NO:123 (aa 436-476 of SEQ ID NO: 20).
VDAVLQAFGFFYFFSGSSQFEFDPNARMVTHILKSNSWLHC

FIG. 20F

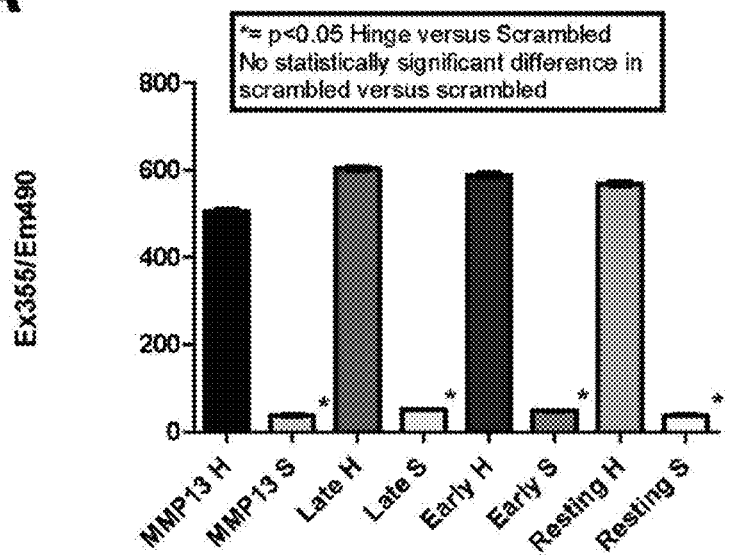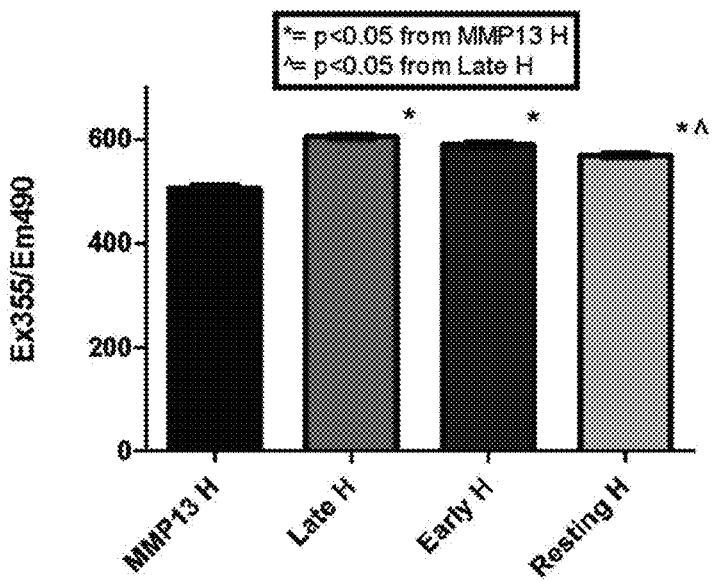
FIG. 22

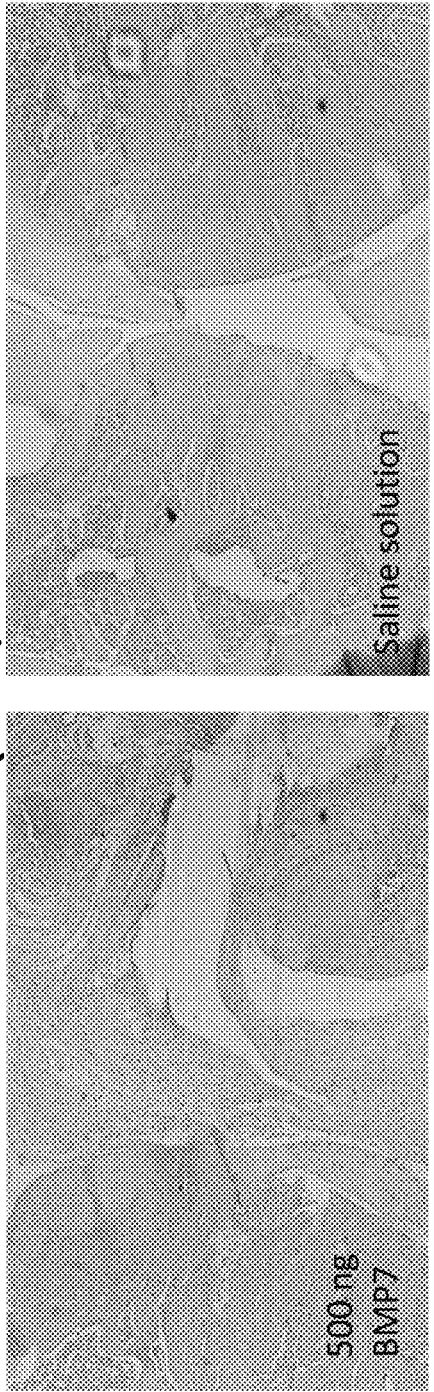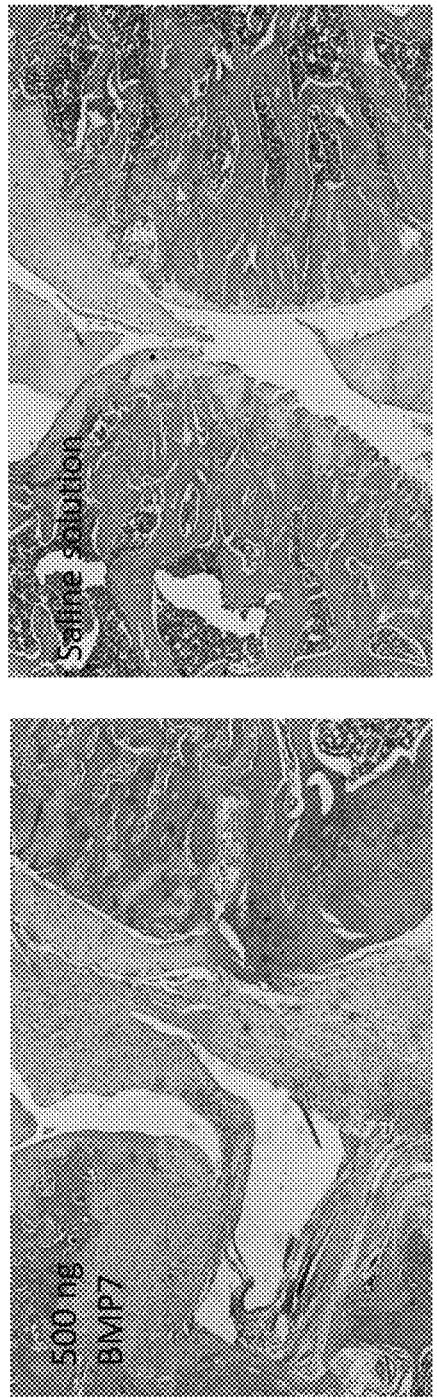
FIG. 33
Saline and BMP7 Mid Joints (40x)

OA control Peptide Tx

| | | Total Volume | *Bone Volume | *BV/TV |
|---|---|---|---|---|
| Patellar Cartilage d21 | Saline (OA) | 6.0544 | 0.3204 | 0.0529 |
| | Peptide | 7.7109 | 0.1912 | 0.0248 |
| Total Joint Cartilage d21 | | Total Volume | Bone Volume | BV/TV |
| | Saline (OA) | 24.5334 | 1.3883 | 0.0566 |
| | Peptide | 24.367 | 0.6164 | 0.0253 |

*A lower value for Bone Volume and a lower value for BV/TV ratio indicates cartilage that is not mineralized (Healthy cartilage).

| AA | MMP16 | MMP2 | MMP9 | MMP19 | MMP17 | MMP15 | MMP1 | MMP28 | MMP20 | MMP25 | MMP24 | MMP21 | MMP10 | MMP12 | MMP8 | MMP27 | MMP11 | MMP14 | MMP8 | Rate of Occurrence |
|---|---|---|---|---|---|---|---|---|---|---|---|---|---|---|---|---|---|---|---|---|
| E | | | | | | | | | | | | | | | | | | | | 27% |
| L | | | | | | | | | | | | | | | | | | | | 44% |
| G | | | | | | | | | | | | | | | | | | | | 100% |
| L | | | | | | | | | | | | | | | | | | | | 22% |
| P | | | | | | | | | | | | | | | | | | | | 94% |
| K | | | | | | | | | | | | | | | | | | | | 5% |
| E | | | | | | | | | | | | | | | | | | | | 11% |
| V | | | | | | | | | | | | | | | | | | | | 50% |
| K | | | | | | | | | | | | | | | | | | | | 16% |
| K | | | | | | | | | | | | | | | | | | | | 22% |
| I | | | | | | | | | | | | | | | | | | | | 27% |
| S | | | | | | | | | | | | | | | | | | | | 11% |
| A | | | | | | | | | | | | | | | | | | | | 38% |
| A | | | | | | | | | | | | | | | | | | | | 55% |
| V | | | | | | | | | | | | | | | | | | | | 27% |
| H | | | | | | | | | | | | | | | | | | | | 22% |
| F | | | | | | | | | | | | | | | | | | | | 44% |
| E | | | | | | | | | | | | | | | | | | | | 16% |
| D | | | | | | | | | | | | | | | | | | | | 38% |

FIG. 41

A: MMP7/BMP2 complex (BMP2, elongated protein at right; MMP7, globular protein at left).

B: MMP12/BMP2 complex (BMP2, elongated protein at right; MMP7, globular protein at left).

COMPOSITIONS AND METHODS FOR INHIBITION OF MMP13:MMP-SUBSTRATE INTERACTIONS

CROSS REFERENCE TO RELATED APPLICATIONS

This application claims benefit of priority pursuant to 35 U.S.C. §119(e) of U.S. provisional patent application No. 61/391,446, filed Oct. 8, 2010, which is hereby incorporated herein by reference in its entirety.

SEQUENCE LISTING

A sequence listing submitted in computer readable format is hereby incorporated by reference. The computer readable file is named P224717sequencelist_ST25.txt, was created on Mar. 25, 2013, and contains 260 kilobytes.

FIELD OF THE INVENTION

The present invention is directed to peptides, peptide-like mimetic compounds, and methods of using same in inhibiting proteolytic interactions between the hemopexin domain of matrix metalloprotease (MMP) and substrate proteins. In some embodiments, the present invention may be used to inhibit activation of Transforming Growth Factor β.

BACKGROUND OF THE INVENTION

Osteoarthritis (OA) is a disease affecting joints following (a) cartilage injury; (b) exposure to excessive load-bearing, or repetitive use; or (c) general aging. OA affects 10% of the world's 60 years and older population. It is characterized by joint pain and dysfunction, degradation of joint cartilages, decreased proteoglycan content in articular cartilage, production of osteophytes (calcified tissue in the margins of the articular cartilage) and fibrosis of the synovial lining of the joint. The unchecked actions of MMPs and elevated activation of transforming growth factor beta (TGFβ) have been implicated as a primary cause for osteoarthritic cartilage degradation.

TGFβ biological activity is modulated by protease-mediated activation to disassemble latency complexes. TGFβ is secreted as a small latent complex that is covalently associated with latent TGFβ binding protein 1 (LTBP1) to form the TGFβ large latent complex. LTBP1 anchors the TGFβ large latent complex (TGFβ LLC) to the extracellular matrix (ECM). This complex must be released from the extracellular matrix in order for TGFβ to become activated for signaling. TGFβ is secreted as a small latent complex in non-covalent association with its N-terminal latency associated peptide, β-LAP. β-LAP and LTBP1 have been implicated in proper processing, secretion, and guidance of the TGFβ LLC to the ECM for storage. Analysis of TGFβ distribution in bone indicates that the bulk of TGFβ is stored in the ECM as a 100 kD TGFJ3 small latent complex (TGFJ3 SLC) and a 270 kD TGFβ LLC. TGFβ is only capable of binding the signaling receptor complex in its mature, 25 kD, homodimeric form. Therefore, activation must occur through a tightly controlled series of proteolytic steps. Plasmin, elastase, chymase, thrombospondin, MMP9, MMP3 and MMP13 have all been implicated in activation of TGFβ resulting in release of the mature receptor-binding homodimer. In addition, an alternatively spliced short form of LTBP1 can form the large latent complex with TGFβ. It has been demonstrated that this form of the TGFβ LLC including the short LTBP1 can be more readily removed from the extracellular matrix.

MMP inhibitors, such as batimastat, marimastat, CGS-27023A, and prinomastat, have been used to treat OA. However, those attempts have resulted in severe side-effects known as MMP-induced musculoskeletal syndrome which includes joint stiffness, inflammation, and symptoms manifested as pain in the hands, arms, and shoulders. Therefore, there remains a need for compounds and methods for inhibiting activation of TGFβ, and treating OA as well as other TGFβ-associated indications without the adverse effect of MMP-induced musculoskeletal syndrome.

SUMMARY OF THE INVENTION

The presently disclosed novel compounds and methods described herein aid in inhibiting the binding of MMPs to target substrate proteins. In some cases the inventive compounds may aid in preventing cleavage of MMP substrate proteins. Substrate proteins include Latent TGFβ Binding Protein 1 (LTBP1), collagen, aggrecan, perlecan and fibronectin. Exemplary MMPs include MMP1, MMP2, MMP3, MMP7, MMP8, MMP9, MMP11, MMP12, MMP13, MMP14, MMP15, MMP16, MMP17, MMP19, MMP20, MMP21, MMP23B, MMP24, MMP25, MMP27, MMP28, MMP29.

In one embodiment, the compounds and methods may comprise peptide sequences derived from the hemopexin domain of an MMP protein. In some embodiments the compounds and methods are used to inhibit cleavage, by MMP, of Latent TGFβ Binding Protein 1 (LTBP1), preventing the release of activated transforming growth factor beta (TGFβ) from the LTBP1 complex. In one particular embodiment the presently described compounds and methods aid in inhibiting the binding of the hemopexin domain of MMP13 to LTBP1.

The disclosed invention provides compounds and methods of using same having matrix metalloprotease (MMP) inhibitory activity without affecting the enzyme's catalytic domain. In some embodiments, the presently disclosed compounds and methods inhibit binding of the MMP protein to a substrate protein by disrupting binding at non-catalytic sites. In various embodiments, the compounds prevent the binding of MMP proteins and substrate proteins by binding to the substrate protein at or near the MMP biding site. In some embodiments the MMP binding site may be a calcium-binding, EGF-like domain.

The present inventors have discovered that certain MMPs function by interacting with substrate proteins at the MMP hemopexin-like domain. In some MMP proteins, the hemopexin-like domain and the catalytic domain may be located at different, physically separated portions of the enzyme. The MMPs include MMP13, MMP14, MMP16, MMP2, MMP9, MMP19, MMP17, MMP15, MMP20, MMP1, MMP24, MMP25, MMP3, NIMP 21, MMP28, MMP8, MMP12, MMP27, MMP11, and MMP10.

In an embodiment, the present invention provides compounds having matrix metalloprotease 13 (MMP13) inhibitory activity. In particular the compounds inhibit MMP13's ability to cleave LTBP1, thereby, inhibiting the activation of TGFβ. Because the disclosed compounds inhibit TGFβ activation, they are useful in combating conditions to which TGFβ activation contributes. Diseases and conditions involving dis-regulation of TGFβ include cartilage degeneration and osteoarthritis (OA). Accordingly, the present invention also provides pharmaceutical compositions and methods for treating such conditions.

In another embodiment, the present invention relates to compounds having MMP13 inhibitory activity and TGFβ activation dysregulation activity. In one particular embodiment, the compound is a peptide fragment of the hemopexin-like (1PEX) domain of the MMP13 protein. In some embodiments, the compound includes peptide-like or non-peptide compounds. In various embodiments, the compound may be a mimetic compound designed to mimic the size, shape, charge, and binding characteristics of the all or a portion of a hemopexin domain or binding surface of a hemopexin domain.

One particular polypeptide sequence of a 1PEX domain of MMP13 is depicted in SEQ ID NO: 1. Fragments of the 1PEX domain active for inhibiting TGFβ activation can be identified as shown in Example 2 below. Bioinformatics is used to identify candidate fragments that can interact with latent TGFβ binding protein (LTBP 1). Those candidate fragments are then tested for their ability to inhibit TGFβ activation. Preferably, the fragment contains at least 6 amino acids, more preferably 6 to 50 amino acids, most preferably about 19 amino acids. The preferred fragments of SEQ ID NO: 1, suitable for inhibiting MMP13-LTBP 1 interaction, and subsequent TGFβ activation comprise; amino acids 17-26; amino acids 93-111; amino acids 101-150; amino acids 109-147; amino acids 125-147; amino acids 151-192; amino acids 160-180; amino acids 51-100; amino acids 60-83; amino acids 1-50; amino acids 16-50; amino acids 168-186; and amino acids 109-129.

In various embodiments the inventive compound may disrupt a protein:protein interaction that is between a MMP and a substrate protein, wherein the interaction is not mediated by the hemopexin domain of MMP and/or the calcium-binding, EGF-like domain of a substrate protein. Thus, in one embodiment the inventive compound may be derived from an MMP protein but have no homology to a hemopexin domain.

In various embodiments, the inventive peptide may be non-identical to the peptides fragments of the MMP protein. In some embodiments, the inventive compound may be greater than about 95% identical or similar to a peptide disclosed herein, or greater than about 90%, about 85%, about 80%, about 75%, about 70%, about 65%, about 60%, about 55%, about 50%, about 45% about 40%, about 30%, or about 20% identical or similar to a peptide sequence disclosed herein. For example, where one inventive compound comprises amino acids 93-101 of SEQ ID NO: 1, other inventive compounds may be 95% identical to that peptide. In some embodiments the non-identical amino acids may be natural amino acids, non-natural amino acids, may be a modified version of the identical amino acid, conservative amino acid substitution, non-conservative amino acid substitution, or a small molecule with a property very similar to that of the non-substituted, non-modified, amino acid. Non-natural and derivatized amino acids are readily available from common suppliers of chemical reagents, for example, Sigma-Aldrich. In some embodiments, the native amino acid may be substituted with a small molecule that lacks a peptide backbone.

In yet another embodiment, the present invention relates to methods for inhibiting the activation of TGFβ, by contacting LTBP1 with the inventive compound to prevent cleavage of LTBP1 by a MMP. Preferably, the MMP-LTBP1 interaction disrupted by the inventive compounds is between LTBP1 and MMP14, MMP13, MMP9, MMP3 or MMP2.

In a further embodiment, the present invention relates to methods for inhibiting the activation of TGFβ by contacting the MMP with an amount of a compound according to the present invention effective to inhibit the activation of TGFβ. In some embodiments the inventive compound may comprise peptide sequences similar to a region of a substrate protein, for example, LTBP1. In further embodiments, the region of the substrate protein may be a calcium-binding, EGF-like domain.

In a further embodiment, the invention also relates to methods for treating a mammal suffering from osteoarthritis or cartilage degeneration by administering to the mammal an amount of a compound according to the invention sufficient to alleviate the effects of osteoarthritis or cartilage degeneration. In some embodiments the inventive compound may be administered locally or systemically. In various local administration embodiments, the administration may be by injection, patch, cream, lotion, etc. In some embodiments where systemic administration is appropriate, for example osteoarthritis, administration of the inventive compound may be oral or nasal, for example, a nasal spray.

In further embodiments, the present invention relates to compounds for inhibiting the interaction of MMP13, MMP14, MMP16, MMP2, MMP9, MMP19, MMP17, MMP15, MMP20, MMP1, MMP24, MMP25, MMP3, MMP21, MMP28, MMP8, MMP12, MMP27, MMP11, and MMP10 and their substrates, without affecting the catalytic domain. The amino acid sequence for the substrate interacting, hemopexin-like domain of MMP13 is depicted in SEQ ID NO: 1; MMP14 is depicted in SEQ ID NO: 2; MMP16 is depicted in SEQ ID NO: 3; MMP2 is depicted in SEQ ID NO: 4; MMP9 is depicted in SEQ ID NO: 5; MMP19 is depicted in SEQ ID NO: 6; MMP17 is depicted in SEQ ID NO: 7; MMP15 is depicted in SEQ ID NO: 8; MMP20 is depicted in SEQ ID NO: 9; MMP1 is depicted in SEQ ID NO: 10; MMP24 is depicted in SEQ ID NO: 11; MMP25 is depicted in SEQ ID NO: 12; MMP3 is depicted in SEQ ID NO: 13; MMP21 is depicted in SEQ ID NO: 14; MMP28 is depicted in SEQ ID NO: 15; MMP8 is depicted in SEQ ID NO: 16; MMP12 is depicted in SEQ ID NO: 17; MMP27 is depicted in SEQ ID NO: 18; MMP11 is depicted in SEQ ID NO: 19; and MMP10 is depicted in SEQ ID NO: 20.

BRIEF DESCRIPTION OF THE DRAWINGS

FIG. 6A-6F shows TGFβ2, MMP-13, and LTBP-1 localize to both the extracellular matrix and cytoplasm. Two-dimensional analysis of late hypertrophic chondrocytes labeled with polyclonal antibodies: (A) TGF-132; (B) MMP-13; and (C) LTBP-1. Three-dimensional analysis depicted every 45° of rotation: (D) TGFβ2; (E) MMP-13; and (F) LTBP-1. Nuclei are counterstained with Hoechst dye (blue). Arrows in panels C and F indicate extracellular matrix staining.

FIG. 7A-7D shows co-localization of MMP-13 and LTBP-1 produced by late hypertrophic chondrocytes. Hypertrophic chondrocytes were double-labeled with MMP-13 (red) and LTBP-1 (green) and nuclei counter-stained (blue) as described in Materials and Methods. Co-localization of the proteins appears as a yellow to orange color. (A1-A3) MMP-13 polyclonal antibody, (B1-B3) LTBP-1 polyclonal antibody, and (C1-C3) co-localized image of the same field. Co-localization within ECM (arrow, panel C3) and cytoplasm (arrow, panel C1) is observed. (D) Three-dimensional analysis of co-localized MMP-13 and LTBP-1 demonstrating staining within the extracellular matrix and cytoplasm.

FIG. 13: Three dimension model of dog mmp13.
FIG. 14: Collagen triple helix.
FIG. 15: dog MMP13-collagen complex.
FIG. 16: MMP13-derived modifying compound (MC1).
FIG. 17: MMP13-collagen-MC1 complex.
FIG. 18: MC1-aggrecan complex.
FIG. 19: MC2-Fibronectin III complex.
FIG. 20; List of various embodiments of the present inventive compounds for interfering with interactions of various MMPs and their substrates

A.) MMP13 enzymatic activity on the REHARGS peptide.
    B.) MMP13 enzymatic activity on the REHARGS peptide versus a scrambled control sequence, AREHGSR FIG. 22A-22B are bar graphs. FIG. 22A is a bar graph showing enzymatic activity of various cartilage extracts, and 22B is a bar graph comparing MMP13 to various extracts. CHAPS buffer extracts of avian sterna cartilage were assayed with the fluorescence labeled REHARGS substrate (H) versus a scrambled control sequence (S) as described in the legend for FIG. 5. Extracts of late hypertrophic, early hypertrophic and resting cartilage were assayed.

A.) MMP13 catalytic domain and the three cartilages were assayed with Hinge and Scrambled peptide. ANOVA with Tukey's test were performed with Prism GraphPad software.
    B.) ANOVA with Tukey's test were performed to compare Hinge peptide activity in the different conditions.

Figure 23:
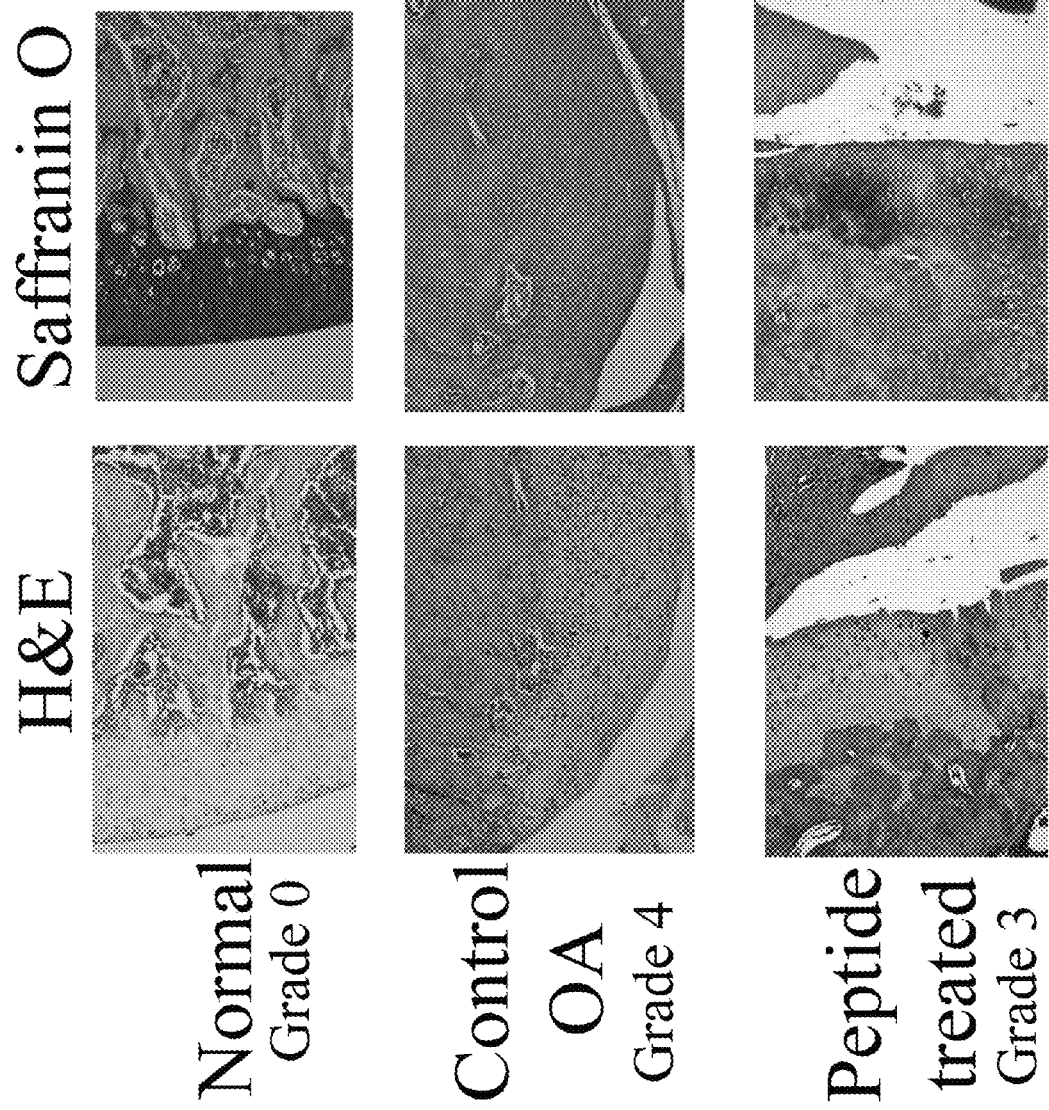

FIG. 23 shows histopathology slides of chronic treatment of an MIA-induced OA. rat model MIA (3 mg in 50 ul) will be injected into the capsule of the stifle through the infrapatellar ligament of the right knee (Janusz, M. J., Hookfin, E. B., Heitmeyer, S. A. et al. (2001) Osteoarthritis Cartilage 9, 751-760; Guingamp, C., Gegout-Pottie, P., Philippe, L., Terlain, B., Netter, P., and Gillet, P. (1997) Arthritis Rheum. 40, 1670-1679) The contralateral knee, injected with saline, will serve as control for the experiment. Disease parameters are clearly measurable within three to four weeks following injection. Animals were injected bi-weekly (weeks 4-12) with various doses of MMP13-19 peptide. Saline and BMP-7 (50 uM) included as negative and positive controls, respectively. Animals were sacrificed, joints dissected, fixed in formalin, decalcified, embedded in paraffin and sectioned. Samples were stained with H&E or saffranin O. Grading of OA pathology followed the Mankin Scale (Pritzker, K. P., Gay, S., Jimenez, S. A., Ostergaard, K., Pelletier, J. P., Revell, P. A., Salter, D., and van den Berg, W. B. (2006) Osteoarthritis Cartilage 14, 13-29).

Figure 24:
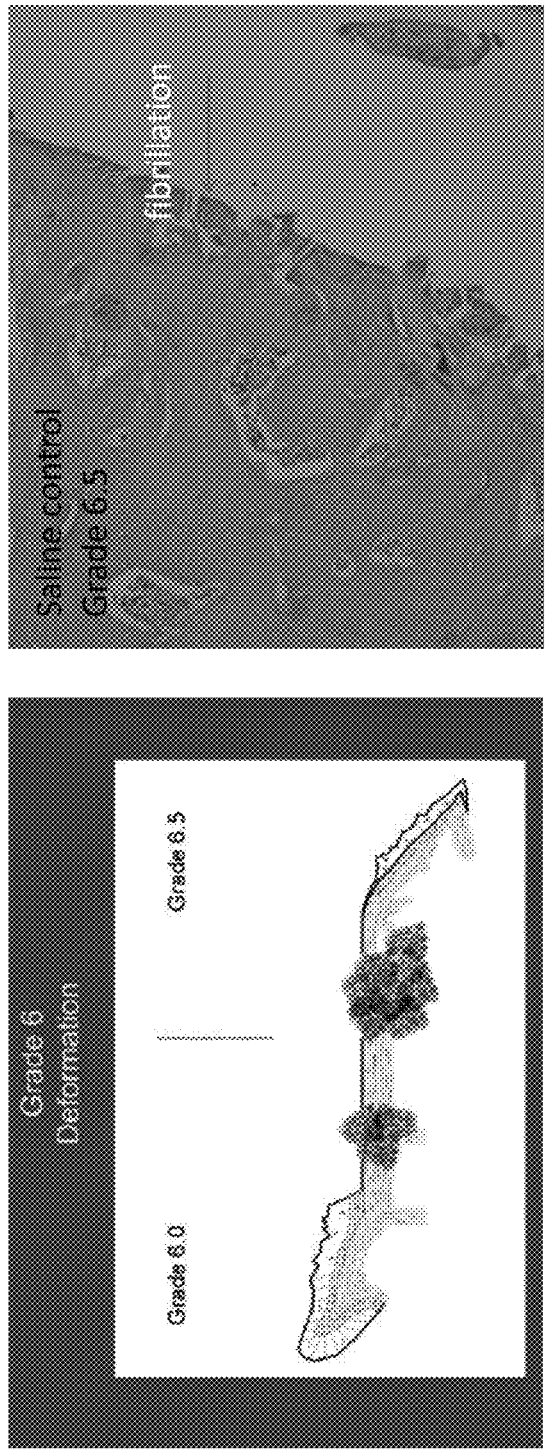

FIG. 24 shows safranin-O stained histopathology and grading of acute treatment of a positive control in an MIA-induced model of OA. OA was induced as described in FIG. 23. Animals were injected weekly (weeks 1-4) with various doses of MMP13-19 peptide. Saline and BMP-7 (50 uM) included as negative and positive controls, respectively. Animals were sacrificed, joints dissected, fixed in formalin, decalcified, embedded in paraffin and sectioned. Samples were stained with H&E or saffranin O. Grading of OA pathology followed the Mankin Scale (Pritzker, K. P., Gay, S., Jimenez, S. A., Ostergaard, K., Pelletier, J. P., Revell, P. A., Salter, D., and van den Berg, W. B. (2006) Osteoarthritis Cartilage 14, 13-29).

Figure 25:
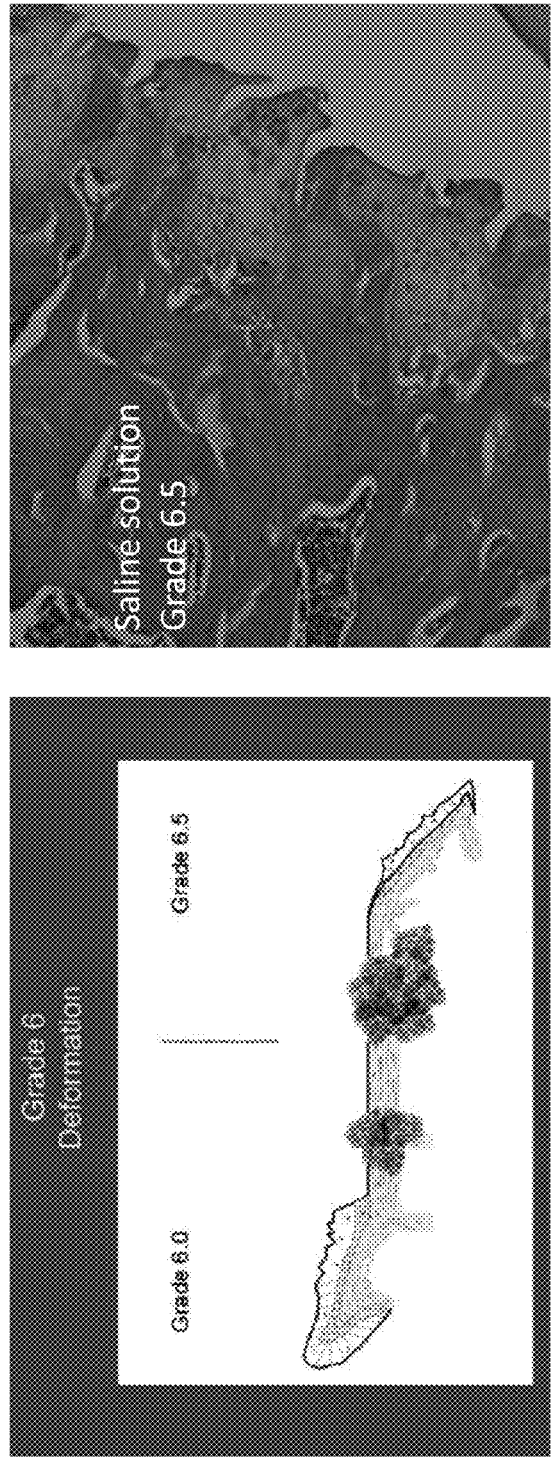

FIG. 25 shows hematoxaylin and eosin stained histopathology and grading of acute treatment positive control in osteoarthritis model.

Figure 26:
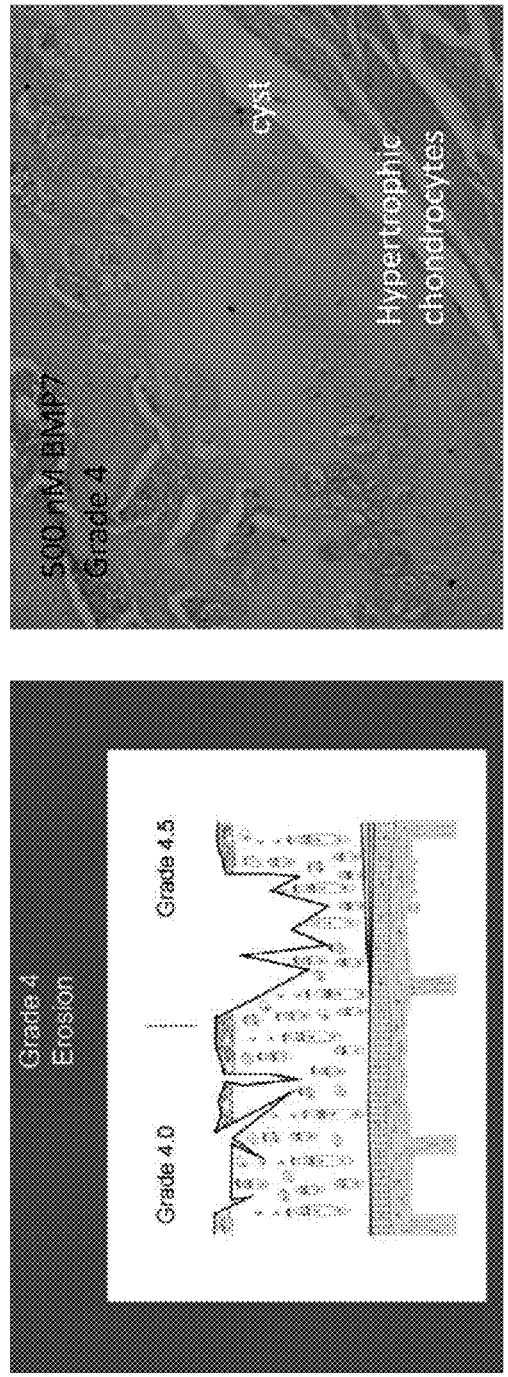

FIG. 26 shows safranin-O stained histopathology and grading of positive treatment control (50 uM BMP7) in osteoarthritis model.

Figure 27:
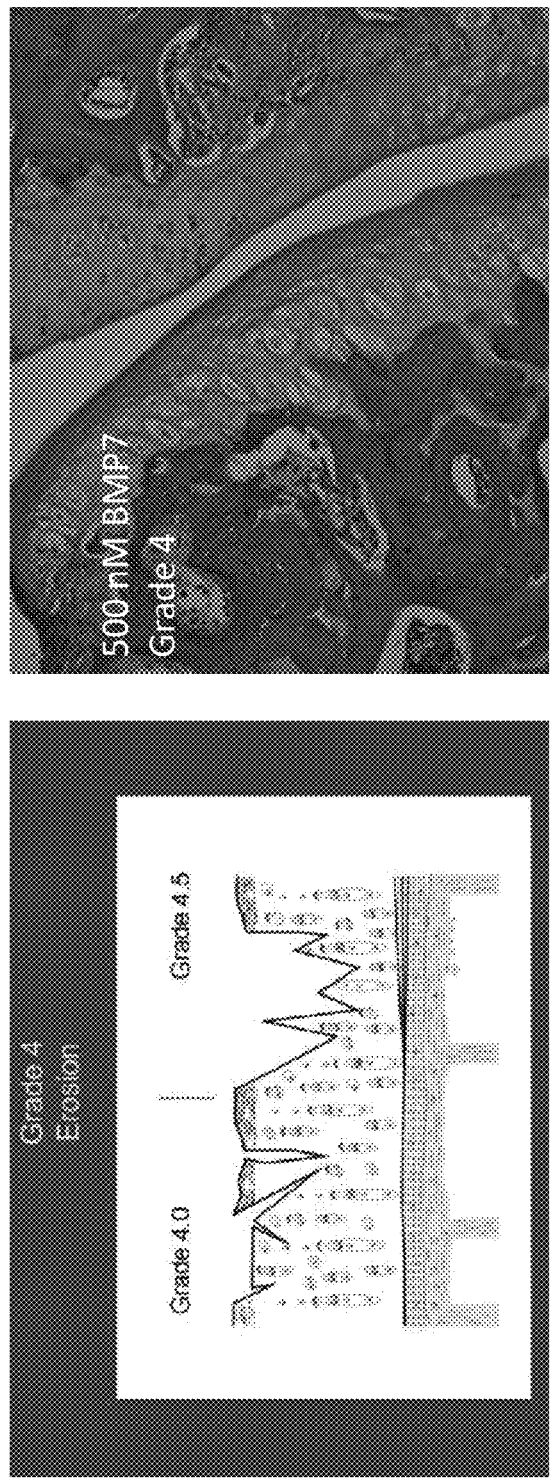

FIG. 27 shows hematoxaylin and eosin stained histopathology and grading of positive treatment control (50 uM BMP7) in osteoarthritis model.

Figure 28:
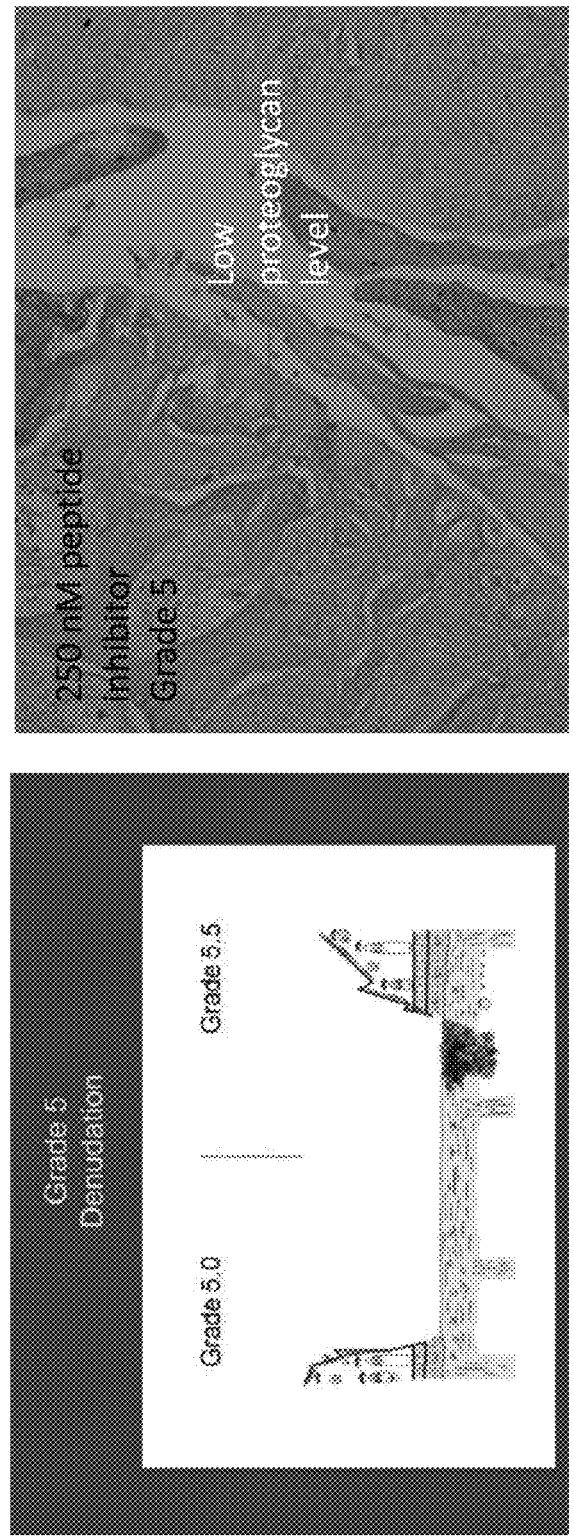

FIG. 28 shows safranin-O stained histopathology and grading of low dose treatment (250 nM MMP13-19 peptide) in osteoarthritis model.

Figure 29:
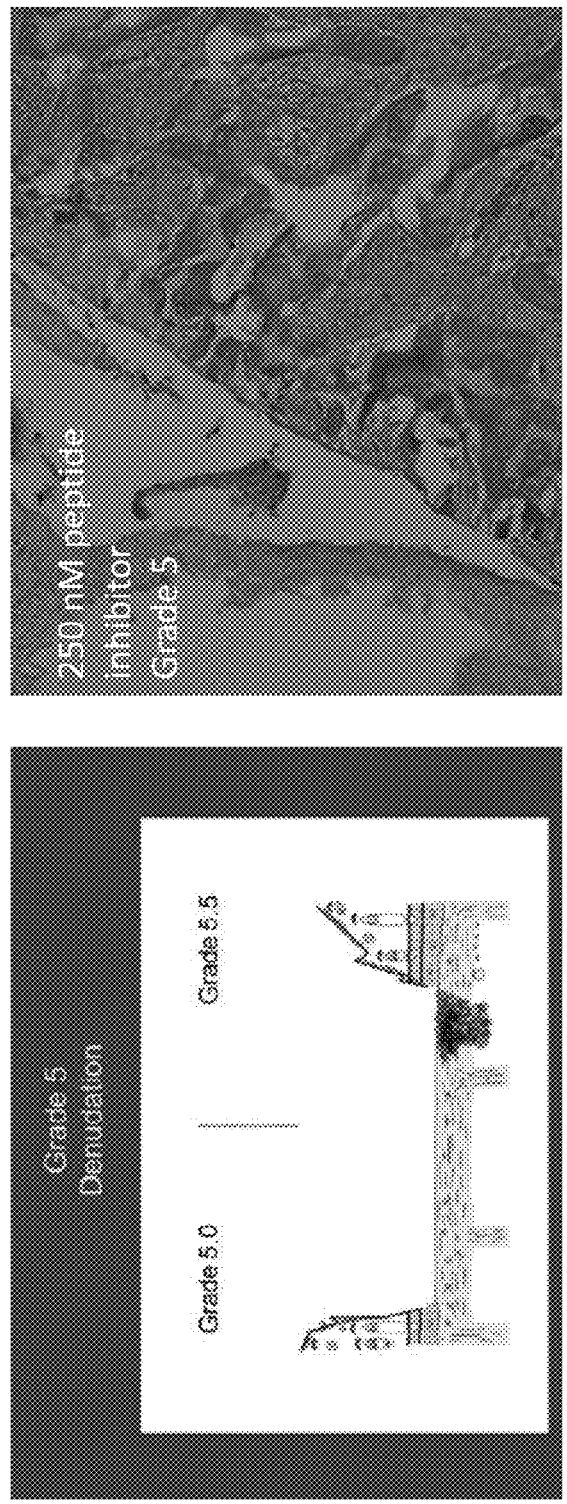

FIG. 29 shows hematoxaylin and eosin stained histopathology and grading of low dose treatment (250 nM MMP13-19 peptide) in osteoarthritis model.

Figure 30:
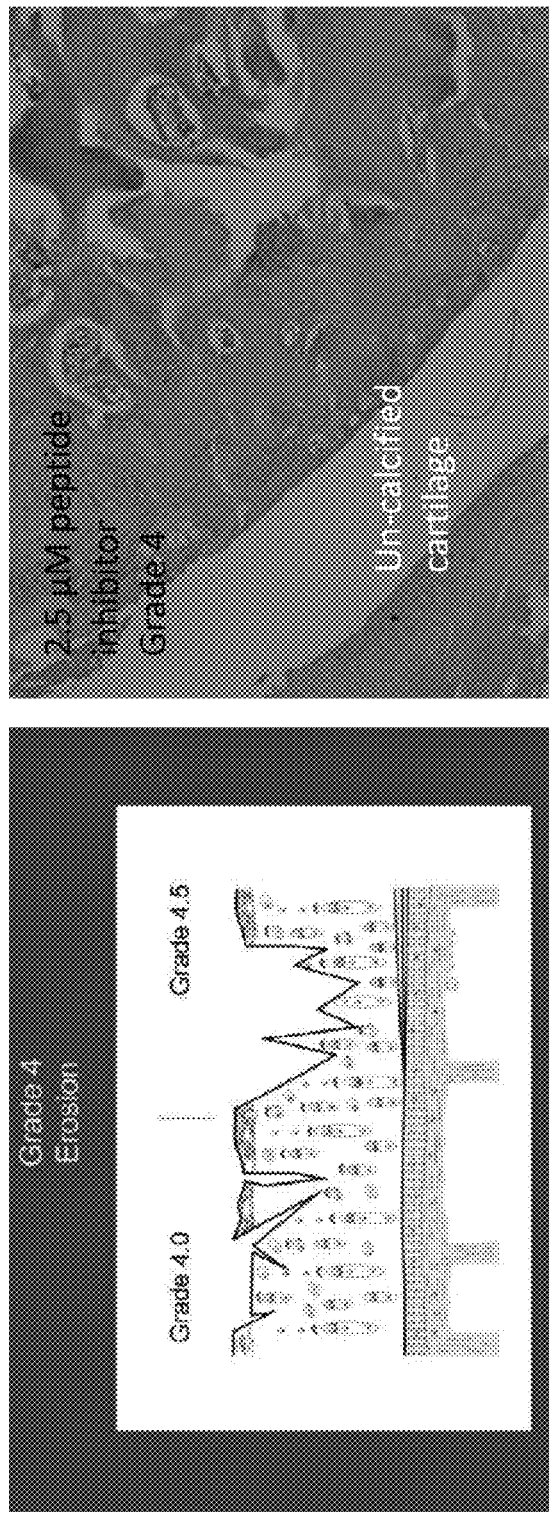

FIG. 30 shows safranin-O stained histopathology and grading of high dose treatment (2.5 uM MMP13-19 peptide) in osteoarthritis model.

Figure 31:
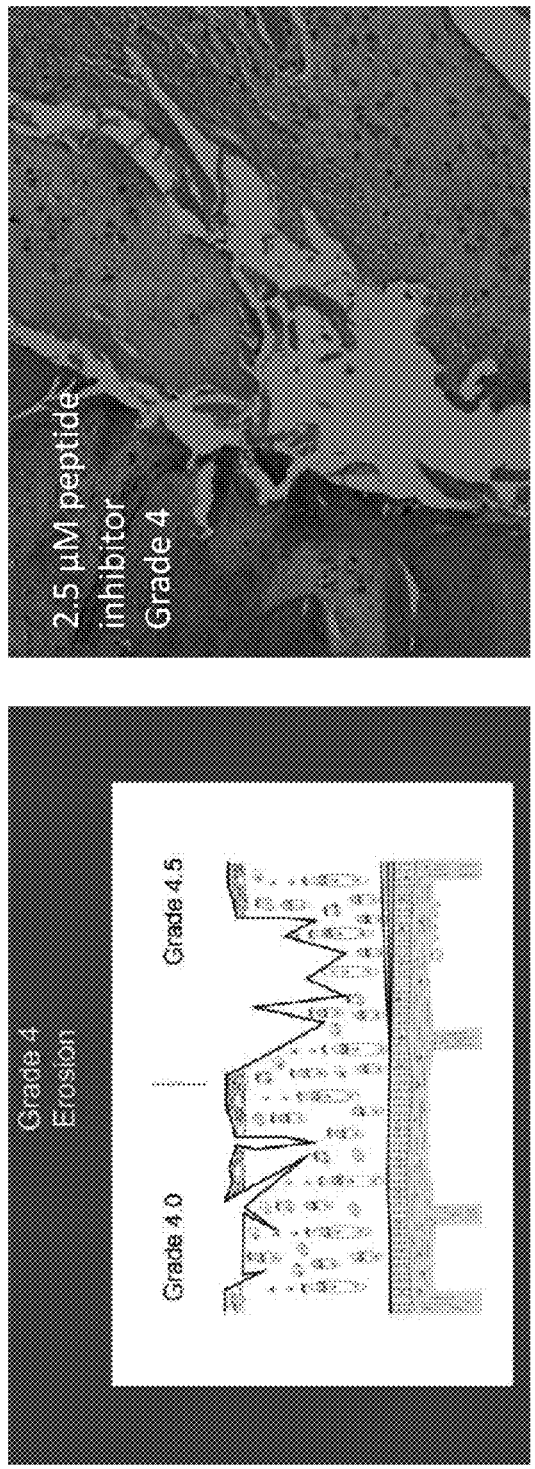

FIG. 31 shows hematoxaylin and eosin stained histopathology and grading of high dose treatment (2.5 uM MMP13-19 peptide) in osteoarthritis model.

Figure 32:
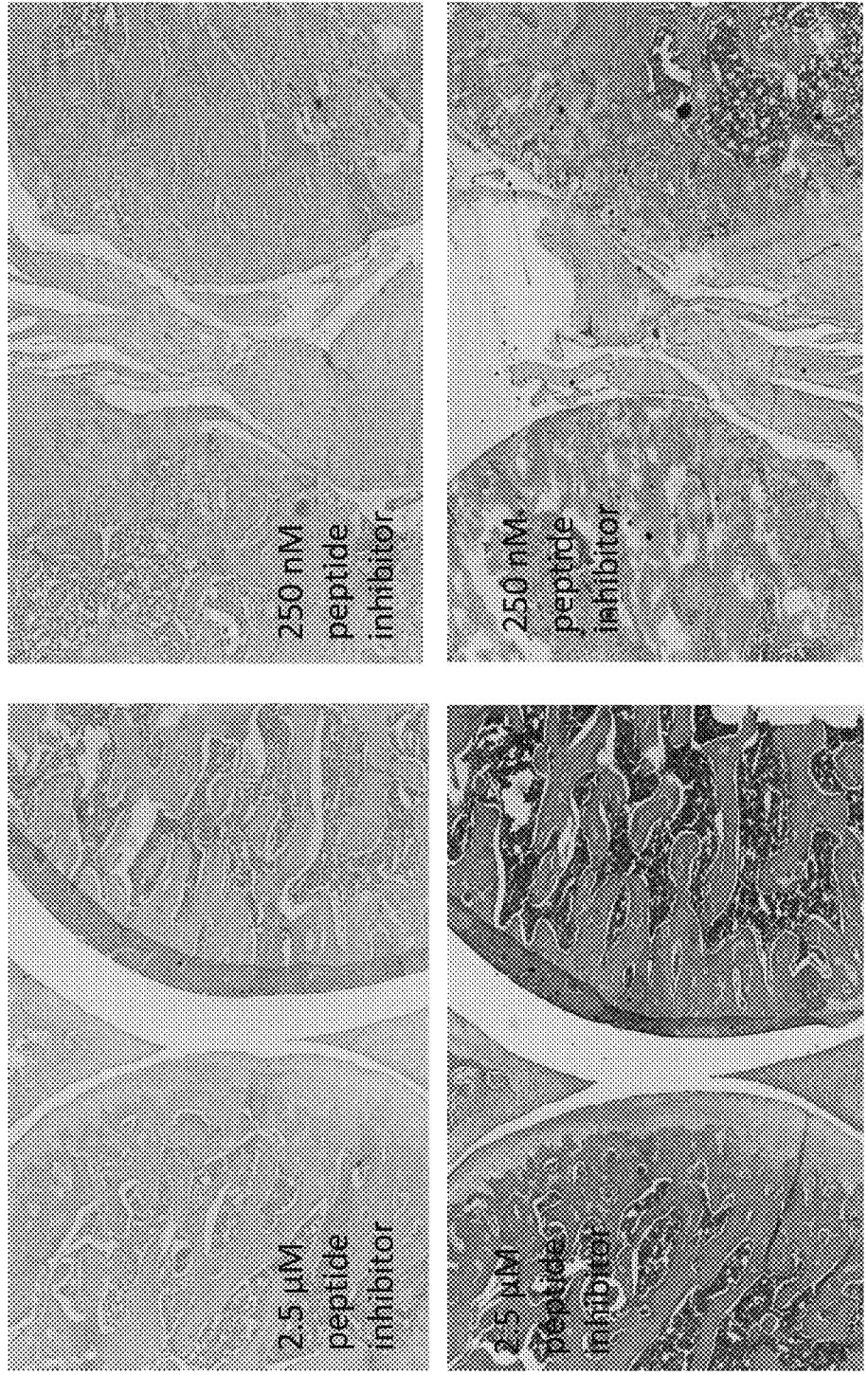

FIG. 32 shows safranin-O, and hematoxaylin and eosin stained mid joint histopathology of low dose peptide inhibitor treatment in osteoarthritis model.

FIG. 33 shows safranin-O, and hematoxaylin and eosin stained mid joint histopathology of saline and BMP7 treatment in osteoarthritis model.

Figure 34:
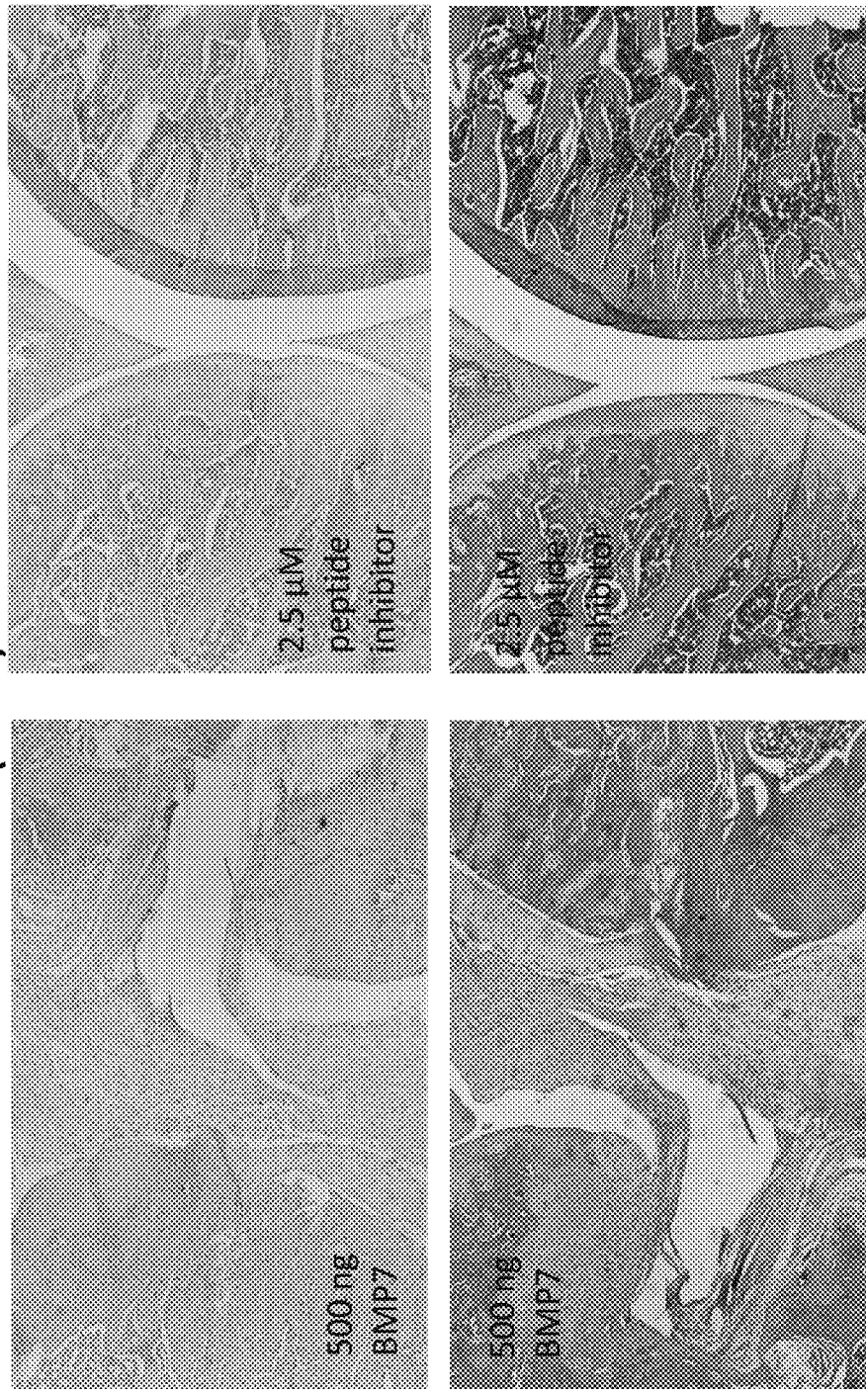

FIG. 34 shows safranin-O, and hematoxaylin and eosin stained mid joint histopathology comparing BMP7 treatment and high dose peptide inhibitor treatment in osteoarthritis model.

Figure 35:
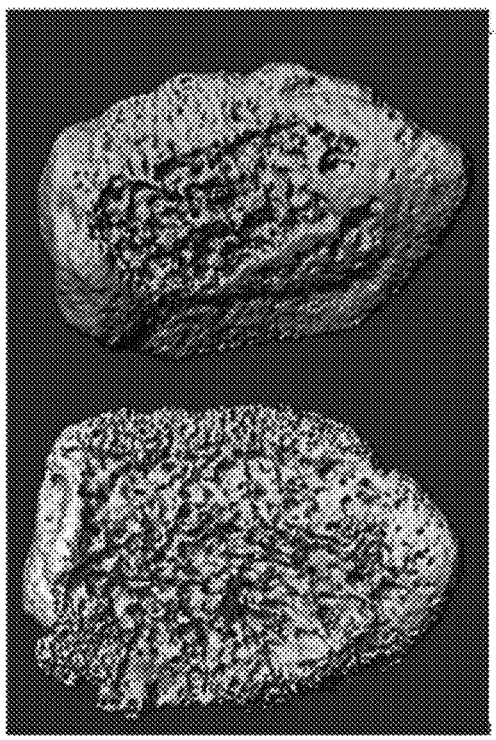

FIG. 35 shows micro computer tomography (micro CT) and table of total and bone volume in patellar and total joint 21 days post OA inducement with and without peptide treatment. Isolated joints were analyzed by Micro CT to measure cortical bone, trabecular bone and cartilage of the patella, femur and tibia, the production of chondrophytes and tissue mineralization in response to treatment. Total mineralization in the patella, femur and tibial cartilages, as well as subchondral bone, were calculated with Scanco µCT software. Micro-CT was conducted with a Scanco uCT 35 (Scanco Medical, Bassersdorf, Switzerland) system. Scans of 15 µm voxel size, 55 KVp, 0.36 degrees rotation step (180 degrees angular range) and a 600 ms exposure per view produced from joints immersed in phosphate buffered saline.

Figure 36:
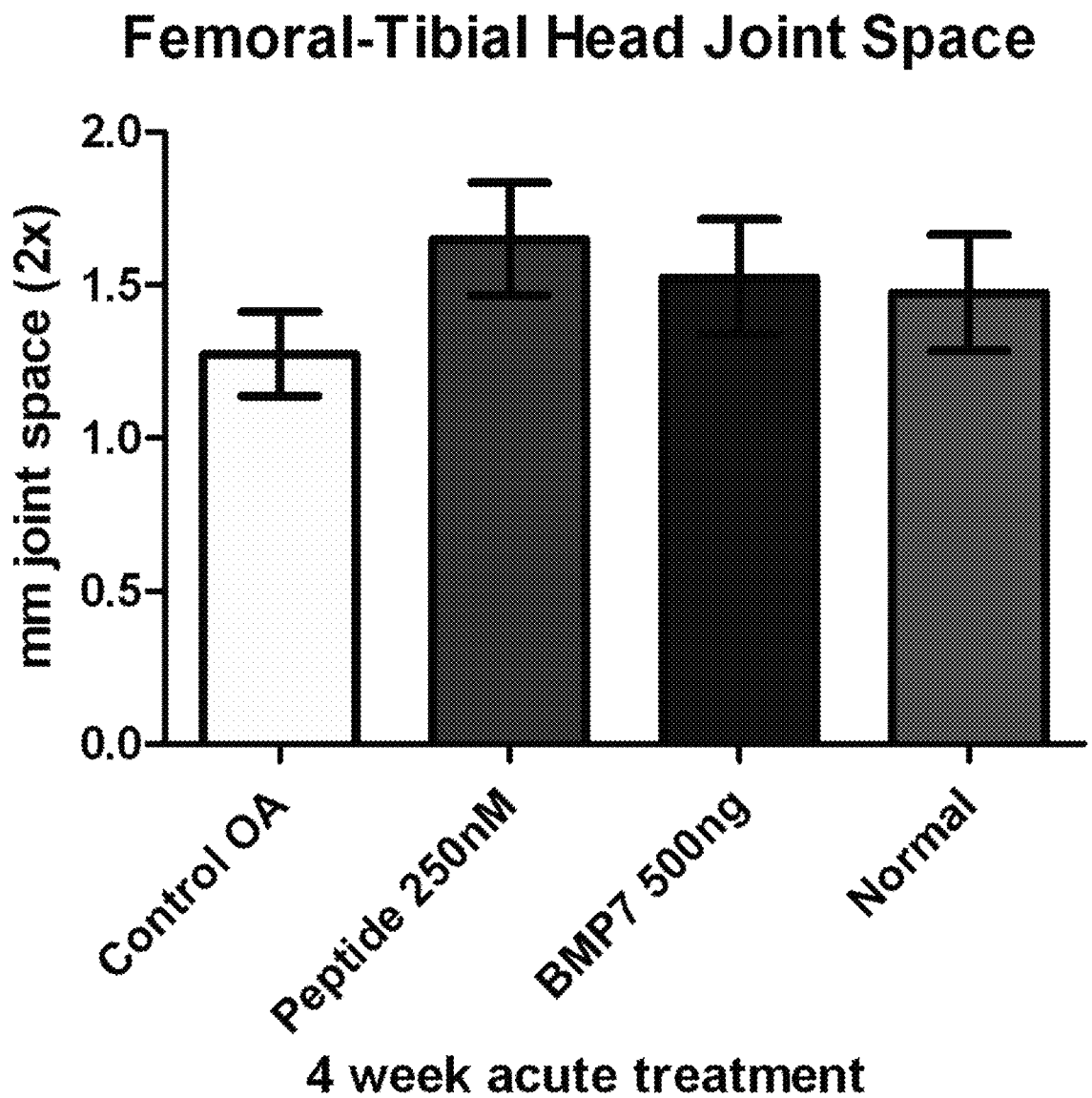

FIG. 36 is a bar graph showing femoral-tibial head joint space for 4 week acute treatment Osteoarthritis control, normal, and peptide treated animals. The joint were X-rayed to measure joint space changes as an indicator of the progression of OA (Messent, E. A., Ward, R. J., Tonkin, C. J., and Buckland-Wright, C. (2005) *Osteoarthritis Cartilage* 13, 463-470).

Figure 37:
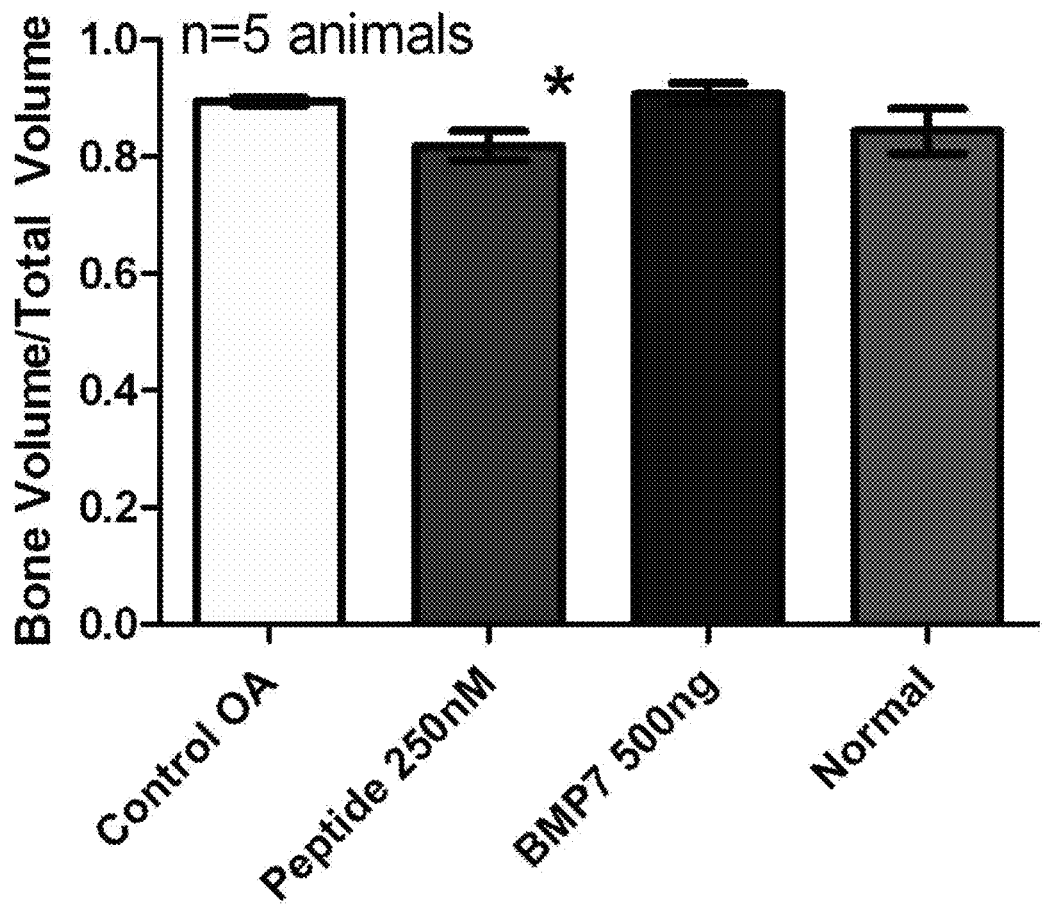

FIG. 37 is a bar graph showing micro CT calculated ratio of bone volume to total volume for 4 week acute Osteoarthritis control, normal, and peptide treated animals.

Figure 38:
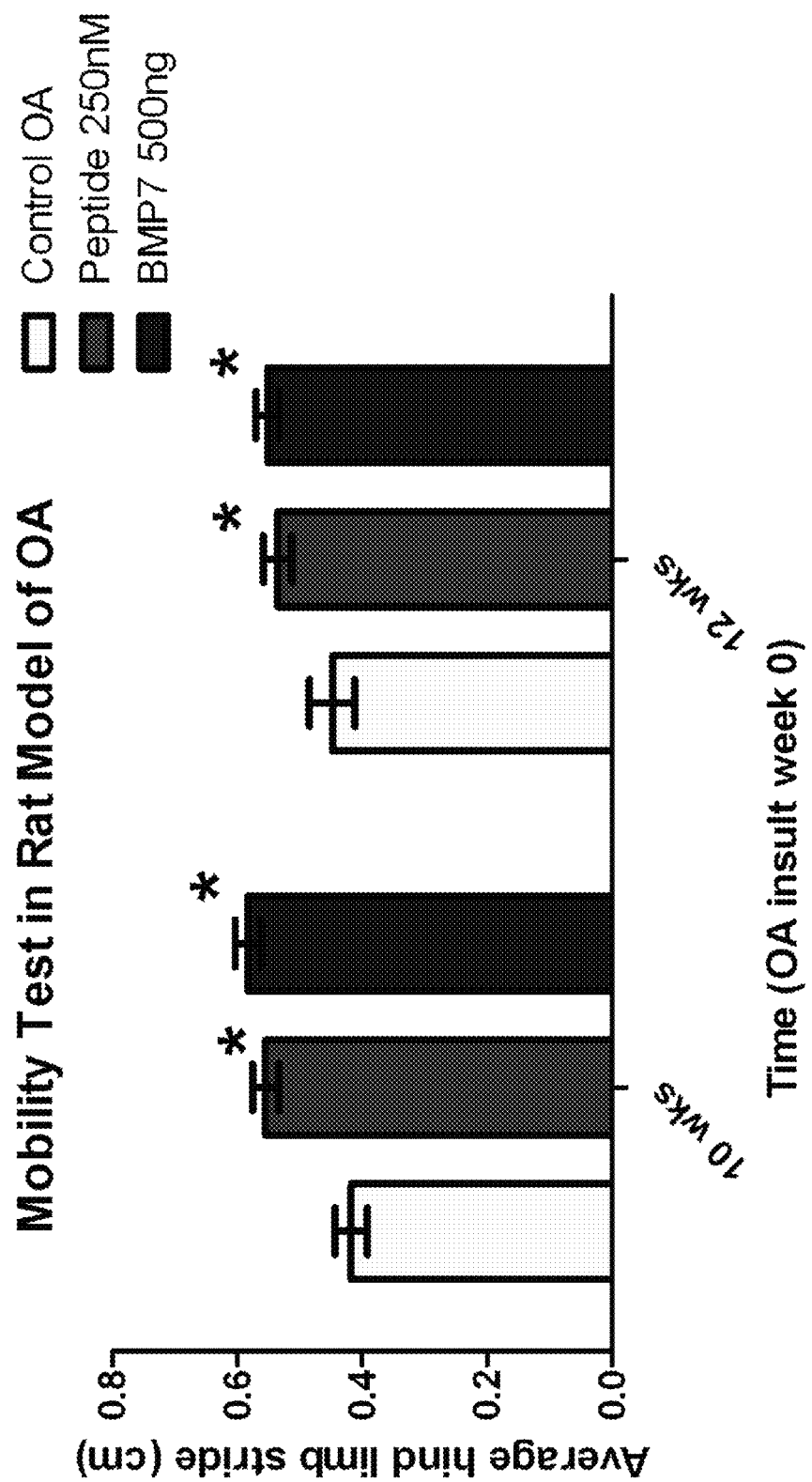

FIG. 38 is a bar graph showing average stride for 10 week and 12 week Osteoarthritis control, normal, and peptide treated animals. A stride test was administered weekly during the course of treatment to determine functional mobility in the animals. Briefly, rat's hind paws were inked, the animals timed while they walked a short path and the distance between hind leg strides measured (Hruska, R. E., Kennedy, S., and Silbergeld, E. K. (1979) *Life Sci.* 25, 171-179)

Figure 39:
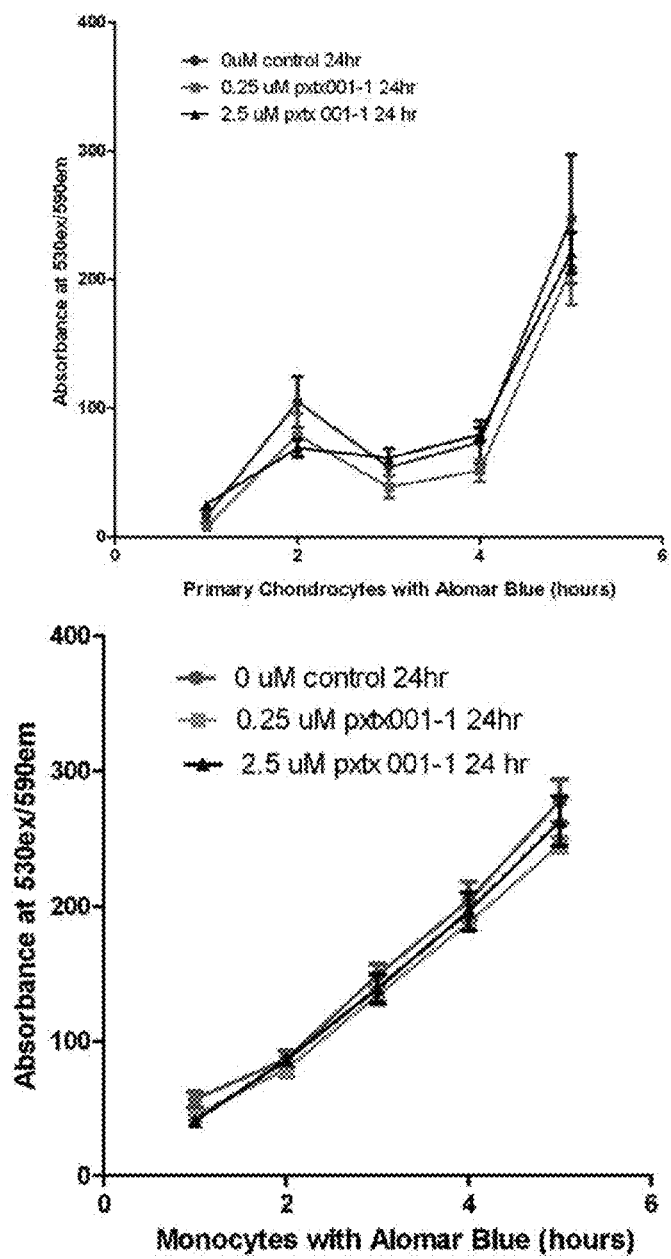

FIG. 39 shows details cytotoxicity data for treatment in vitro with MMP13-19 peptide. Primary chondrocytes from early and late hypertrophic stage were cultured from Day 17 avian upper sternum. Late hypertrophic chondrocytes were isolated from the core region of the avian sterna. Following 3-4 hours collagenase and trypsin digestion, cells were centrifuged and filtered through 0.45 um Nitex filter. Isolated cells were resuspended in 1.2% alginate and forced into beaded structures with 102 mM CaCl2 and rinsed in 0.15M NaCl for a final density of $5\times10^6$ cells/ml. Alginate bead cultures were covered in 2 mls complete serum free DMEM high glucose media including 1 mM cysteine, 1 mM sodium pyruvate, 2 mM L-glutamine, 50 µg/ml penicillin/streptomycin. L-ascorbic acid was added to the culture at 30 ug/ml on day 2 and 50 ug/ml on day 5. Cytotoxicity was assessed by Alomar Blue Assay (Invitrogen) on primary chondrocytes and a monocyte cell line incubated for 24 hours with PxTx001-1. Absorbance was recorded at 570 nm for every hour up to 24 hrs to monitor both proliferation and metabolic activity.

Figure 40:
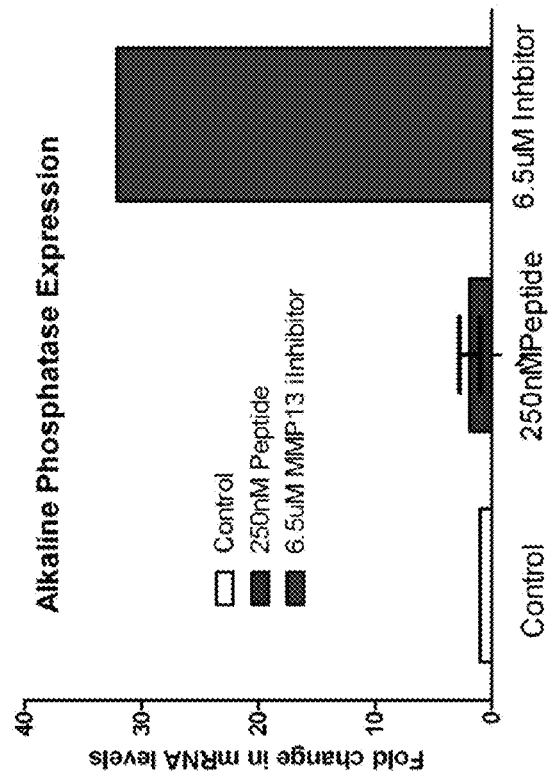

FIG. 40 is a bar graph showing mRNA expression in chondrocytes treated with MMP13-19 or a commercially available MMP inhibitor. Time course treatment was performed at 6, 12 or 24 hours with 10 nM, 100 nM, 250 nM PxTx001-1 or 6.5 uM commercially available MMP13 specific inhibitor (Calbiochem). Following a quick dissolution in 0.5M EDTA to release cells from alginate cultures, total RNA was isolated through Trizol method and reverse-transcribed via SuperScript First-Strand Synthesis System (Invitrogen). cDNA samples were subjected to QuantiTech SyBrGreen (Qiagen) real time PCR. Samples were loaded into a 96 well plate in triplicate as 1 ul or 2 ul cDNA for each condition and primers respectively. Expression of markers of chondrocyte maturation (collagen type X, MMP13 and alkaline phosphatase) was compared to an internal standard of 18srRNA using ABI Prism 7000 sequence detection system (Applied Biosystems). Fold difference compared to untreated cultures was graphed using Prism Graph Pad and statistical analysis of one-way ANOVA and standard error of the mean were calculated with associated software.

FIG. 41 is a matrix showing conservation of amino acids in the MMP13-19 inhibitory peptide throughout the MMP family of proteins.

Figure 42:
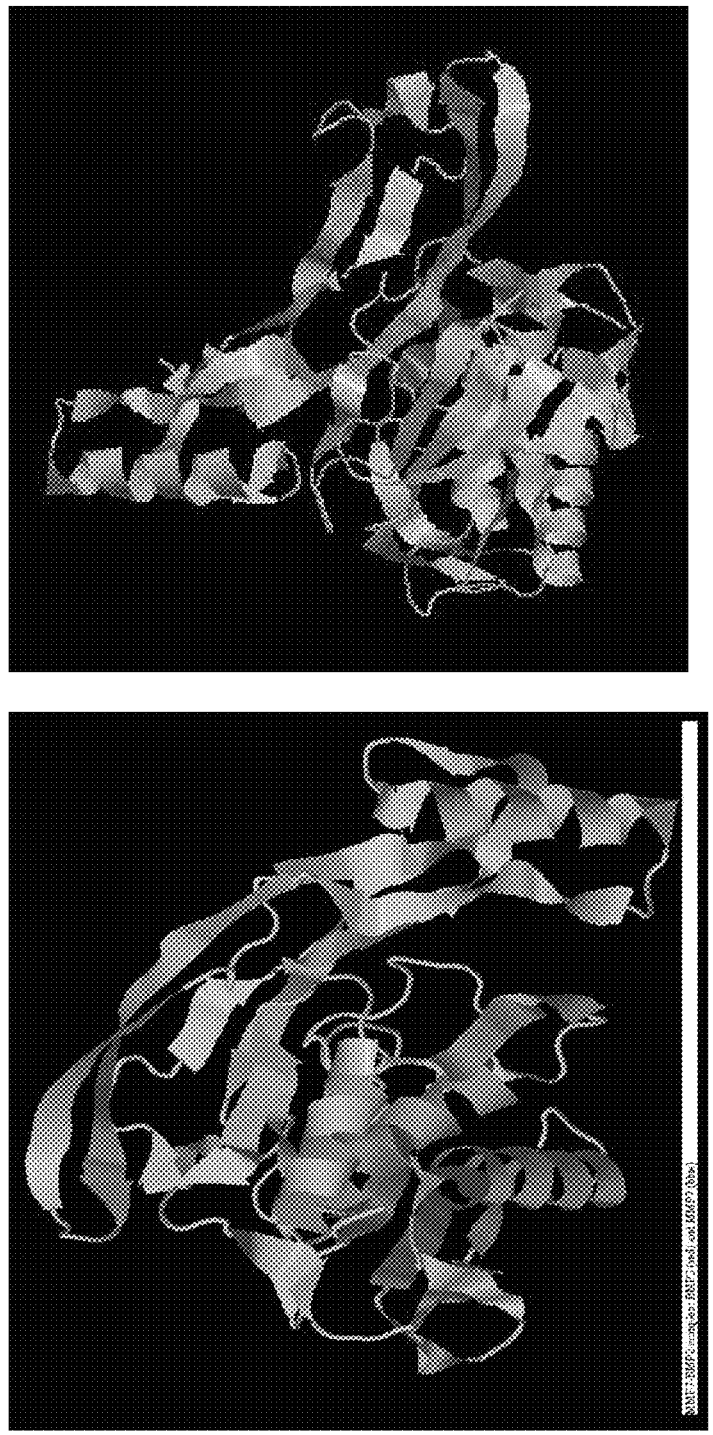

FIG. 42A-42B shows binding of BMP2 with MMP7 (42A) or MMP12 (42B).

DETAILED DESCRIPTION OF THE PREFERRED EMBODIMENT

Described herein are compounds for inhibiting matrix metalloprotease (MMP)-substrate protein-protein interactions. The present inventive compounds are designed using high definition modeling of the MMP-substrate binding interface. In some embodiments, inhibition does not affect protease activity. In various embodiments, the inventive compounds are fragments of the hemopexin-like domain of a MMP or fragments of an MMP binding protein. In some embodiments, the inventive compound may be a an engineered peptide, peptide derivative, or other molecule comprising a chemical and three-dimensional structure designed to bind either MMP or the MMP-substrate at the binding interface.

In various embodiments, the inventive peptide, peptide derivative, or other peptide-like molecule may be identical to a peptide fragment of a MMP protein. In various other embodiments the inventive compound may be non-identical to a peptide fragment of MMP. In various embodiments the inventive compound may include non-natural amino acids, derivatized natural amino acids, conservative substitution, non-conservative substitutions, or combinations thereof. In various embodiments the inventive compound may be greater than about 95%, about 90%, about 85%, about 80%, about 75%, about 70%, about 65%, about 60%, about 55%, about 50%, about 45%, about 40%, about 30%, or about 20% identical or similar to a peptide sequence disclosed herein. One of skill in the art of peptide synthesis may use various programs and algorithms to determine homology among proteins and peptides. In various embodiments, homology may be determined by a weighted system that counts non-conservative substitutions at a specific position differently than conservative substitutions (based on charge, hydrophobicity, size, etc). On such weighting algorithm may be found at homology database server www.clustal.org/clustal2/, among others.

One of skill in the art of peptide synthesis may choose to incorporate non-natural amino acids, derivatized amino acids, or small molecules to aid in preventing or reducing degradation of the inventive compound. Design of ligands and small molecules, such as is described by Kubinyi, is well known in the art (Structure-based design of enzyme inhibitors and receptor ligands, Curr. Op. in Drug Disc. and Development, 1998 Vol 1 No 1; incorporated in its entirety by express reference).

In some embodiments, the compound may be referred to as a mimetic. A mimetic is a protein-like chain designed to mimic the pharmacological activity and the structure of a peptide. Mimetics typically arise from modification of an existing peptide in order to alter the molecule's properties. For example, they may arise from modifications (such as using unnatural amino acids, conformational restraints, etc.) to change the molecule's stability or biological activity. Preferably, mimetic, as used herein, means a molecule that is designed to resemble the hemopexin-like fragment and to function as a MMP inhibitor. Because the hemopexin like domain is spaced apart from the catalytic domain on the MMP, the compound inhibits the MMP by interfering with the interaction of the hemopexin-like domain with the substrate. That way, the catalytic domain is not affected.

MMPs include MMP13, MMP14, MMP16, MMP2, MMP9, MMP19, MMP17, MMP15, MMP20, MMP1, MMP24, MMP25, MMP3, MMP21, MMP28, MMP8, MMP12, MMP27, MMP11, and MMP10.

In some embodiments, the inventive compound is a fragment of the hemopexin-like domain of the MMP or mimetics thereof. The polypeptide sequence of hemopexin-like domains for MMP13, MMP14, MMP16, MMP2, MMP9, MMP19, MMP17, MMP15, MMP20, MMP1, MMP24, MMP25, MMP3, MMP21, MMP28, MMP8, MMP12, MMP27, MMP11, and MMP10 are depicted in SEQ. ID NOS: 1-20, respectively. The fragments appropriate for the present invention can be determined using the methods of the Examples below. Bioinformatics is used to select candidate fragments in the hemopexin-like domain of the MMP that can potentially interact with its substrate (e.g., LTBP-1). Those candidate fragments are then tested for their ability to inhibit activation of the substrate by the MMP. Preferably, the fragment contains at least 6 amino acids, more preferably 6 to 50 amino acids, and most preferably 19 amino acids.

The present invention provides compounds and methods for disrupting interactions between matrix metalloprotease (MMP) and a variety of substrate target proteins that interact with MMP through a MMP hemopexin domain. Substrate target proteins include LTBP1, aggrecan, fibronectins, and collagens.

Compounds of the present invention for inhibiting various MMPs are presented in FIG. 20.

The compounds of the present invention can also encompass other fragments of the MMP which can be determined by first generating a three dimension (3D) structure(s) for the molecules of interest (the MMP and its substrate), preferably by computer Modeling. The modeling can be done using software well-known and available in the art, such as the PPI-Pred database from Leads University in the United Kingdom. From the 3D structure, the interacting portions of the hemopexin-like domain of the MMP and the substrate are determined. Branching or non-branching peptides may block the interaction between the MMP and its substrate protein. Inventive compounds, including peptides and peptide mimetics, may be designed from analysis of the sequences of the two proteins at the protein-protein interlace. The protein-protein interface may describe the surfaces of the MMP and substrate protein that may interact non-covalently.

Designed compounds and peptides may be tested for their ability to inhibit the MMP-substrate interaction. In some embodiments, the inventive compound may compete with an MMP or its substrate protein for binding.

In some embodiments, the best performing peptides are selected based on in-vitro evaluation-of their ability to inhibit the interaction of interest. For example, if inhibition of TGFβ release is desired, the peptide performance is based on its ability to inhibit TGFβ release in tissue culture system as described in the Examples below. In some embodiments, the "best performing peptide" may be based on its binding affinity for its target, which may be MMP or a substrate protein. In some embodiments the "best performing peptide" may be the compound which has the greatest resistance to degradation.

In the case of MMP9, for example, a peptide may be chosen for its ability to prevent homodimerization. In that case, the peptides are evaluated by examining tissue cultures treated with the peptides by, e.g., western blot for MMP9. In-vitro evaluation techniques are apparent to one skilled in the art depending on the desired MMP and substrate interaction.

In various embodiments of the inventive compound, the compound may disrupt an MMP's ability to bind a substrate protein other than LTBP1. For example, the inventive compound may prevent the biding of MMP13 to collagen type II. In some embodiments, the inventive compounds may be useful in combating conditions such as Matrix degeneration. Accordingly, the present invention also provides pharmaceutical compositions and methods for treating such conditions.

In many embodiments, the inventive compound may be similar to a human MMP protein or a human MMP substrate protein. In other embodiments, the inventive compound may be based upon a non-human MMP protein or MMP substrate protein. In some embodiments, for example, the inventive compound may be homologous to a dog protein, for example dog MMP13. The inventive compound may also be homologous to a dog MMP substrate protein.

In various embodiments the inventive compound may disrupt a protein:protein interaction that is between a MMP and a substrate protein, wherein the interaction is not mediated by the hemopexin domain of MMP and/or the calcium-binding, EGF-like domain of a substrate protein. Thus, in one embodiment the inventive compound may be derived from an MMP protein but have no homology to a hemopexin domain. For example, interactions between MMP7 and BPM2 or MMP12 and BMP2 (FIG. 42), which may be involved in fracture healing and/or fracture nonunion, In some embodiments, In some embodiments, interface data based upon MMP7 or 12 interacting with BMP2 indicates low energy needed for the interaction (average–10.7 kcal/mol), and a large surface area (Average 967.5 kcal/mol). This data indicates strong binding due to hydrogen bonds and disulfide bonds formations, and may help to explain previously published data (Fajardo et al., Matrix metalloproteinases that associate with and cleave bone morphogenetic protein-2 in vitro are elevated in hypertrophic fracture nonunion tissue. J Orthop Trauma. 2010 September; 24(9):557-63; incorporated herein by reference in its entirety). MMP7 and MMP12 are modeled to interface with different regions of BMP2. These data suggest that at least these two MMPs are not competing and potentially have synergistic effect on BMP2. The negative effect of MMPs on BMP2 function might be through degradation (enzymatic activity or through interfering with dimerization of the BMP protein).

MMP may interact with a variety of substrate proteins. For example, MMPs may interact with For example, For example, MMPs may interact with For example, the substrate protein may be selected from among the group consisting of MCP-1, MCP-2, MCP-3, MCP-4, Stromal cell-derived factor (SDF), Pro-1L-1β, Pro-IL-8, IL-1-β, IGF-BP, IGF-BP-2, IGF-BP-3, Perlecan, Pro-TNF-α, Pro-MMP-1, Pro-MMP-2, Pro-MMP-2, Pro-MMP-3, Pro-MMP-7, Pro-MMP-8, Pro-MMP-9, Pro-MMP-10, Pro-MMP-13, α1-proteinase inhibitor, α1-antichymotrypsin, α2-macroglobulin, L-selection, Pro-TGF-β1, Pro-IL-1β, IGFBP-3, IGFBP-5, FGFR-1, Big endothelin-1, Pregnancy zone protein, Substance P, Decorin, Galectin-3, CTAP-III/NAP-2, GROα, PF-4, Cell-surface IL-2Rα, Plasminogen, Pro-a-definsin, Cell surface bound Fas-L, E-cadherin; β4 integrin, Pro-a-definsin, Cell-surface CD44, Cell-surface BOUND tissue transglutaminase (tTG), 1-selecting, Pro-HB-EGF, e-Cadherin. In many embodiments the MMP substrate protein may, or may not, have a hemopexin domain. In various embodiments, the MMP may interact with a substrate protein by binding the substrate with its hemopexin domain. In other embodiments the interaction between MMP and the substrate protein may be through a domain other than the MMP hemopexin domain.

In some embodiments, the inventive compound may comprise modifications that may be present on the parent MMP or MMP substrate, which the compound is based upon. For example, the MMP or MMP-substrate may include glycosylation and phosphorylation within the region corresponding to the inventive compound. Thus, bioinformatic tools may be used to predict these biochemical modification, and the inventive compounds may be modified to match parent protein features. These modifications may be accomplished by derivativization of the amino acid, or by treating the inventive compound with the appropriate modifying enzyme, for example a kinase in the case of phosphorylation.

In many embodiments, the inventive compound may be modified to increase the thermodynamic stability of the inventive compound. In embodiments where greater thermodynamic stability is desired, one of skill in the art may choose among many available modifications. For example, one of skill in the art may engineer di-sulfide bonds within the inventive compound to increase stability. In other embodiments, the hydrophobic core of the inventive compound may be engineered to be more stable, or secondary or tertiary interactions may be engineered or modified to increase thermodynamic stability.

In various embodiments, the inventive compound may be modified to aid in preventing, reducing, or inhibiting degradation of the inventive compound. For example, degradative stability may be enhanced by terminal modifications, such as acetylation and/or amidation. Other modifications which may prevent, reduce, or inhibit degradation of the inventive compounds may include PEG-ylation and/or use of modified amino acids.

In various embodiments, the inventive compound may be linked to other heterologous peptides or proteins to enhance resistance to degradation or enhance targetting of the inventive compound to a particular tissue or matrix. For example, in some embodiments the inventive compound may be linked to a protein which may have affinity for a protein or molecule present at or near the site where the inventive compound is needed. For example, the inventive compound may be linked to a protein which binds to hyaluronic acid, which may be present within the matrix or tissue where the compound is needed. In some embodiments the linkage may be covalent or non-covalent.

In some embodiments, the inventive compounds may be linked to peptides or proteins that may, in turn, bid specifically to a carrier in a pharmaceutical composition. For example, inventive compounds may include cellulose binding domains, which may be designed to interact with a methylcellulose carrier. Binding to a carrier molecule may aid in prolonging the half-life of an inventive compound.

In an embodiment, the present invention may provide inventive compounds having multiple interfacing domains. In many cases protein-protein interaction involves multiple domains. For efficient modifications, branching molecules might be needed. Bioinformatic tools will be used to determine appropriate spacing and orientations to achieve the best design.

In an embodiment, the present invention provides compounds that have hybrid structure of peptide and small molecules. In these compounds, the peptide portion of the compound will provide specificity while the small molecule will provide function modification roles.

In another embodiment, the present invention provides methods for treating a dog suffering from osteoarthritis or cartilage degeneration by administering to the dog a compound of the invention in an amount sufficient to alleviate the effects of osteoarthritis or cartilage degeneration (100-10,000 microgram). Preferably, the compound is administered directly to the cartilage of the dog, for example, by injection.

Figure 8:
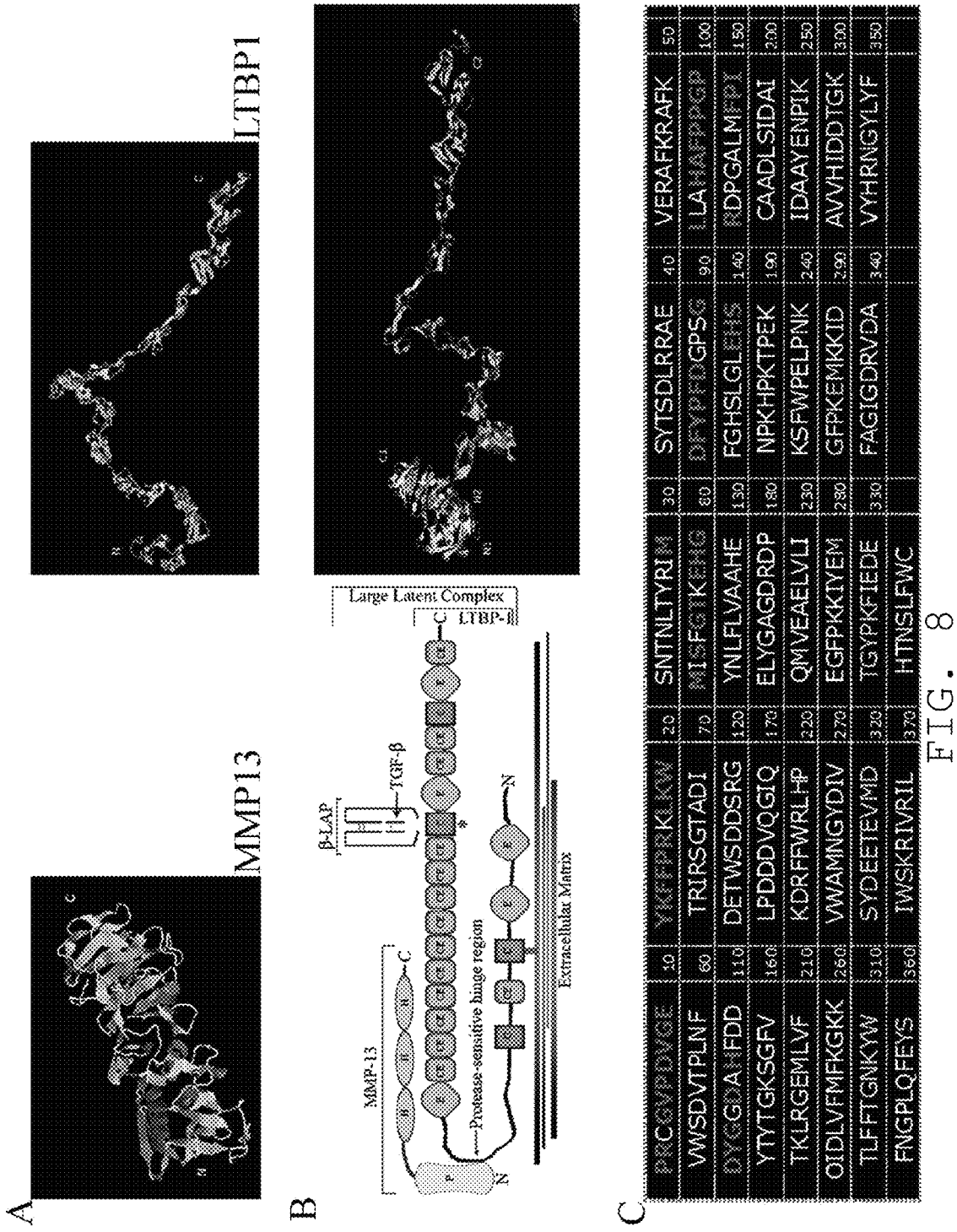
FIG. 8A-8C shows three-dimensional modeling of MMP13 and LTBP1 non-covalent interaction. (A) MMP13 and LTBP1 short (870 AA toward the C-terminal); Pink: Helices, Yellow: Beta sheets and White: coils. N: Amino terminal. C: Carboxyl terminal. (B) Three-dimensional model of MMP13-LTBP1 interaction; MMP13:green., LTBP1: blue. LLC=large latent complex; H=hemopexin domain; CE=EGF-Ca domain; C=cysteine; E=EGF-like domain; P=N-terminal catalytic domain of MMP13; Linker region=protease-sensitive hinge region of LTBP. (C) Protein-protein interface prediction of MMP13-LTBP1 complex shown in B. Red: Highest scoring patch (probable binding site). Yellow: Second highest scoring patch. Green: third highest scoring patch.

The present inventors have discovered a mechanism for the activation of TGFβ by MMP, preferably MMP14, MMP13, MMP9, MMP3, or MMP2. A schematic of the mechanism for MMP13 is shown in FIG. 8. The activation of TGFβ is triggered by the non-covalent interaction of the 1PEX domain of MMP13 with the LTBP-1 (particularly the calcium-EGF-like domains of LTBP-1) of the TGFβ large latent complex (TGFβ LLC). Once non-covalently associated with the TGFβ LLC, the catalytic domain of MMP13 comes into proximity of and cleaves the LTBP-1 protease-sensitive hinge region, thereby releasing a soluble form of TGFβ LLC. That soluble form of TGFβ LLC is more susceptible to proteolytic release of the TGFβ SLC and subsequent activation of the biologically active TGFβ homodimer. The compounds of the present invention are designed to compete with MMP13 for the association with the LTBP-1, and thereby preventing the activation of TGFβ.

It is well known in the art that some modifications and changes can be made in the structure of a peptide, such as those described herein, without substantially altering the characteristics of that peptide, and still obtain a biologically equivalent peptide. In one aspect of the invention, inventive compounds, peptides, and mimetics of the peptides described here may include peptides, compounds, and mimetics that differ from the peptide sequences disclosed herein (especially SEQ ID NOs: 35-123), by conservative amino acid substitutions. As used herein, the term "conserved amino acid substitutions" refers to the substitution of one amino acid for another at a given location in the protein, where the substitution can be made without substantial loss of the relevant function. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the protein by routine testing.

In some embodiments, conserved amino acid substitutions may be made where an amino acid residue is substituted for another having a similar hydrophilicity value (e.g., within a value of plus or minus 2.0), where the following may be an amino acid having a hydropathic index of about −1.6 such as Tyr (−1.3) or Pro (−1.6) are assigned to amino acid residues (as detailed in U.S. Pat. No. 4,554,101, incorporated herein by reference): Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4).

In alternative embodiments, conserved amino acid substitutions may be made where an amino acid residue is substituted for another having a similar hydropathic index (e.g., within a value of plus or minus 2.0). In such embodiments, each amino acid residue may be assigned a hydropathic index on the basis of its hydrophobicity and charge characteristics, as follows: Iie (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5).

In alternative embodiments, conserved amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr.

In alternative embodiments, conservative amino acid changes include changes based on considerations of hydrophilicity or hydrophobicity, size or volume, or charge. Amino acids can be generally characterized as hydrophobic or hydrophilic, depending primarily on the properties of the amino acid side chain. A hydrophobic amino acid exhibits a hydrophobicity of greater than zero, and a hydrophilic amino acid exhibits a hydrophilicity of less than zero, based on the normalized consensus hydrophobicity scale of Eisenberg et al. (J. Mol. Bio. 179:125-142, 184). Genetically encoded hydrophobic amino acids include Gly, Ala, Phe, Val, Leu, Iie, Pro, Met and Trp, and genetically encoded hydrophilic amino acids include Thr, H is, Glu, Gln, Asp, Arg, Ser, and Lys. Non-genetically encoded hydrophobic amino acids include t-butylalanine, while non-genetically encoded hydrophilic amino acids include citmlline and homocysteine.

Hydrophobic or hydrophilic amino acids can be further subdivided based on the characteristics of their side chains. For example, an aromatic amino acid is a hydrophobic amino acid with a side chain containing at least one aromatic or heteroaromatic ring, which may contain one or more substituents such as —OH, SH, —CN, —F, —Cl, —Br, —I, —NO2, —NO, —NH2, —NHR, —NRR, —C(O)R, —C(O)OH, —C(O)OR, —C(0)NH2, —C(O)NHR, —C(O)NRR, etc., where R is independently ($C_1$-$C_6$) alkyl, substituted ($C_1$-$C_6$) alkyl, ($C_0$-$C_6$) alkenyl, substituted ($C_1$-$C_6$) alkenyl, ($C_1$-$C_6$) alkynyl, substituted ($C_0$-$C_6$) alkynyl, ($C_5$-$C_{20}$) aryl, substituted ($C_5$-$C_{20}$) aryl, ($C_6$-$C_{26}$) alkaryl, substituted ($C_6$-$C_{26}$) alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe, Tyr, and Tryp.

An apolar amino acid is a hydrophobic amino acid with a side chain that is uncharged at physiological pH and which has bonds in which a pair of electrons shared in common by two atoms is generally held equally by each of the two atoms (i.e., the side chain is not polar). Genetically encoded apolar amino acids include Gly, Leu, Val, Ile, Ala, and Met. Apolar amino acids can be further subdivided to include aliphatic amino acids, which is a hydrophobic amino acid having an aliphatic hydrocarbon side chain. Genetically encoded aliphatic amino acids include Ala, Leu, Val, and Ile.

A polar amino acid is a hydrophilic amino acid with a side chain that is uncharged at physiological pH, but which has one bond in which the pair of electrons shared in common by two atoms is held more closely by one of the atoms. Genetically encoded polar amino acids include Ser, Thr, Asn, and Gin.

An acidic amino acid is a hydrophilic amino acid with a side chain pKa value of less than 7. Acidic amino acids typically have negatively charged side chains at physiological pH due to loss of a hydrogen ion. Genetically encoded acidic amino acids include Asp and Glu. A basic amino acid is a hydrophilic amino acid with a side chain pKa value of greater than 7. Basic amino acids typically have positively charged side chains at physiological pH due to association with hydronium ion. Genetically encoded basic amino acids include Arg, Lys, and His.

Conservative amino acid changes involve substitution of one type of amino acid for the same type of amino acid. For example, where charge is being conserved, changing Lysine to Arginine is a conservative change, whereas changing Lysine to Glutamic acid is non-conservative. Where size is being conserved, a change from Glutamic acid to Glutamine may be conservative, while a change from Glutamic acid to Glycine may be non-conservative It will be appreciated by one skilled in the art that the above classifications are not absolute and that an amino acid may be classified in more than one category. In addition, amino acids can be classified based on known behaviour and or characteristic chemical, physical, or biological properties based on specified assays or as compared with previously identified amino acids.

Thus an identical sequence will have the same order and type of amino acids, while a homologous or similar sequence may include conservative or non-conservative amino acid changes without departing from the inventive concept. Thus, for example, a peptide having a single conservative amino acid substitution may have higher similarity to the parent peptide than another peptide where that same single amino acid is substituted with a non-conservative amino acid.

In many embodiments, specific amino acid positions and identities in a sequence may be more important than other positions. In some embodiments, the importance of a position or amino acid may be analyzed by alanine-scanning or by multiple sequence alignment. For example, FIG. 41 shows a multiple sequence alignment of the 19 amino acid peptide sequence of MMP13 with other similar sequences in MMP proteins. This alignment shows that the glycine at position 3 and the proline at position 5 are both highly conserved within this family. Thus, maintenance of the position and identity of these two amino acids may be more important than at other positions. Moreover, the N-terminus of this embodiment of the inhibitory peptide may be more highly conserved than the C-terminus.

In many embodiments, the inventive compounds may be linear. In other embodiments, the inventive compounds may be circular or cyclized by natural or synthetic means. For example, disulfide bonds between cysteine residues may cyclize a peptide sequence. Bifunctional reagents can be used to provide a linkage between two or more amino acids of a peptide. Other methods for cyclization of peptides, such as those described by Anwer et. al. (Int. J Pep. Protein Res. 36:392-399, 1990) and Rivera-Baeza et al. (Neuropeptides 30:327-333, 1996) are also known in the art.

The compounds of the invention may be modified with non-peptide moieties that provide a stabilized structure or lessened biodegradation. Peptide mimetic analogs can be prepared based on the compound of the present invention by replacing one or more amino acid residues of the protein of interest by non-peptide moieties. Preferably, the non-peptide moieties permit the peptide to retain its natural conformation, or stabilize a preferred, e.g., bioactive conformation. One example of methods for preparation of non-peptide mimetic analogs from peptides is described in Nachman et al., Regul. Pept. 57:359-370 (1995). It is important that any modification does not significantly reduce binding affinity of the inventive compound with its target binding substrate. In some embodiments, it may be useful to modify an inventive compound to achieve greater thermodynamic or degradative stability even though the binding affinity may be slightly compromised. The term "peptide" as used herein can embrace non-peptide analogs, mimetics and modified peptides.

Peptidomimetics derivatives could be designed based on the two and three dimensions modeling of effective blocking peptides. A blocking peptide may be used to describe an inventive compound with competes for binding to MMP or a MMP substrate, resulting in disruption of the MMP-substrate interaction. For example, MMP13-19 (amino acids 93-111 of SEQ ID NO: 1) has an alpha helical structure. Peptidomimetic derivatives of indanes, terphenyl, oligophenyls, chalcones, trans-fused polycyclic ethers could be used to design peptidomimetics with alpha helix backbone similar to MMP13-19. For beta-sheet peptides the following methods could be used; use of ferrocene amino acid conjugates where either peptide monomers (Henrick et al., Tetrahedron Lett. 37:5289-5292, 1996, which is incorporated herein by reference) or dimers (Moriuchi et al., J. Am. Chem. Soc. 123:68-75, 2001, which is incorporated herein by reference), the attachment of the peptides to the cyclopentadienyl core to generate either 'parallel' or 'anti-parallel' strands (Barisic et al., Chem. Commun. 17:2004-2005, 2004, which is incorporated herein by reference) and using both covalent and non-covalent coordination methods to maintain the β-sheet conformation beyond two residues.

The compounds of the present invention may be modified in order to improve their efficacy. Such modification of the compounds may be used to decrease toxicity, increase bioavailability, increase binding affinity, or modify biodistribution. A strategy for improving drug viability is the utilization of water-soluble polymers. Various water-soluble polymers have been shown to modify biodistribution, improve the mode of cellular uptake, change the permeability through physiological barriers, and modify the rate of clearance from the body (Greenwald et al., Crit Rev Therap Drug Carrier Syst. 2000; 17:101-161; Kopecek et al., J Controlled Release, 74:147-158, 2001). To achieve either a targeting or sustained-release effect, water-soluble polymers have been synthesized that contain drug moieties as terminal groups, as part of the backbone, or as pendent groups on the polymer chain.

For example, polyethylene glycol (PEG), has been widely used as a drug carrier, given its high degree of biocompatibility and ease of modification (Harris et al., Clin Pharmacokinet. 2001; 40(7):539-51). Attachment to various drugs, proteins, and liposomes has been shown to improve residence time and decrease toxicity (Greenwald et al., Crit Rev Therap Drug Carrier Syst. 2000; 17:101-161; Zalipsky et al., Bioconjug Chem. 1997; 8:111-118). PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications (Nathan et al., Macromolecules. 1992; 25:4476-4484; Nathan et al., Bioconj. Chem. 1993; 4:54-62).

The compounds encompassed by the present invention may also be attached to magnetic beads or particles (preferably nano-particles) to control distribution of the compound. Such compounds can specifically be targeted using a magnetic field, which naturally increases the effectiveness of the compounds. Methods of attaching peptides to magnetic beads are known in the art and are disclosed, for example in U.S. Pat. No. 5,858,534.

The compounds encompassed by the present invention may be produced by conventional automated peptide synthesis methods or by recombinant expression. General principles for designing and making proteins are well known to those of skill in the art.

The peptides encompassed by the present invention can be made in solution or on a solid support in accordance with conventional FMOC-based techniques. The peptides can be prepared from a variety of synthetic or enzymatic schemes, which are well known in the art. Where short peptides are desired, such peptides are prepared using automated peptide synthesis in solution or on a solid support in accordance with conventional techniques. Various automatic synthesizers are commercially available and are used in accordance with known protocols. See, for example, Stewart and Young, Solid Phase Peptide Synthesis, 2d. ed., Pierce Chemical Co., (1984); Tam et al., J. Am. Chem. Soc., 105:6442, (1983); Merrifield, Science, 232:341-347, (1986); and Barany and Merrifield, The Peptides, Gross and Meienhofer, eds, Academic Press, New York, 1-284, (1979); Fields, (1997) Solid-Phase Peptide Synthesis. Academic Press, San Diego); Andersson et al., Large-scale synthesis of peptides. Biopolymers (Pept. Sci.), 55, 227-250 (2000); Burgess et al., J. Pept. Res., 57, 68-76, (2001); Peptides for the New Millennium, Fields, J. P. Tam & G. Barany (Eds.), Kluwer Academic Publisher, Dordrecht. Numerous other documents teaching solid phase synthesis of peptides are known to those of skill in the art and may be used to synthesis epitope arrays from any allergen.

For example, the peptides are synthesized by solid-phase technology employing a peptide synthesizer, such as a Model 433A from Applied Biosystems Inc. This instrument combines the FMOC chemistry with the HBTU activation to perform solid-phase peptide synthesis. Synthesis starts with the C-terminal amino acid. Amino acids are then added one at a time till the N-terminus is reached. In some embodiments, non-natural amino acids may be incorporated into a synthetically synthesized peptide. Three steps are repeated each time an amino acid is added. Initially, there is deprotection of the N-terminal amino acid of the peptide bound to the resin. The second step involves activation and addition of the next amino acid and the third step involves deprotection of the new N-terminal amino acid. In between each step there are washing steps. This type of synthesizer is capable of monitoring the deprotection and coupling steps.

At the end of the synthesis the protected peptide and the resin are collected, the peptide is then cleaved from the resin and the side-chain protection groups are removed from the peptide. Both the cleavage and deprotection reactions are typically carried out in the presence of 90% TPA, 5% thioanisole and 2.5% ethanedithiol. After the peptide is separated from the resin, e.g., by filtration through glass wool, the peptide is precipitated in the presence of MTBE (methyl t-butyl ether). Diethyl ether is used in the case of very hydrophobic peptides. The peptide is then washed a plurality of times with MTBE in order to remove the protection groups and to neutralize any leftover acidity. The purity of the peptide is further monitored by mass spectrometry and in some case by amino acid analysis and sequencing.

The peptides also may be modified, and such modifications may be carried out on the synthesizer with very minor interventions. An amide could be added at the C-terminus of the peptide. An acetyl group could be added to the N-terminus. Biotin, stearate and other modifications could also be added to the N-terminus.

The purity of any given peptide, generated through automated peptide synthesis or through recombinant methods, is typically determined using reverse phase HPLC analysis. Chemical authenticity of each peptide is established by any method well known to those of skill in the art. In certain embodiments, the authenticity is established by mass spectrometry. Additionally, the peptides also are quantified using amino acid analysis in which microwave hydrolyses are conducted. In one aspect, such analyses use a microwave oven such as the CEM Corporation's MDS 2000 microwave oven. The peptide (approximately 2 µg protein) is contacted with e.g., 6 N HCl (Pierce Constant Boiling e.g., about 4 ml) with approximately 0.5% (volume to volume) phenol (Mallinckrodt). Prior to the hydrolysis, the samples are alternately evacuated and flushed with $N^2$. The protein hydrolysis is conducted using a two-stage process. During the first stage, the peptides are subjected to a reaction temperature of about 100° C. and held that temperature for 1 minute. Immediately after this step, the temperature is increased to 150° C. and held at that temperature for about 25 minutes. After cooling, the samples are dried and amino acid from the hydrolysed peptides samples are derivatized using 6-aminoquinolyl-N-hydroxysuccinimidyl carbamate to yield stable areas that fluoresce at 395 nm (Waters AccQ Tag Chemistry Package). In certain aspects, the samples are analyzed by reverse phase HPLC and quantification is achieved using an enhanced integrator.

In certain embodiments, the peptides of the present invention are made using FMOC solid-phase synthetic methods such as those described above. However, it is also contemplated that those skilled in the art may employ recombinant techniques for the expression of the proteins wherein a nucleotide sequence which encodes a peptide of the invention is inserted into an expression vector, transformed or transfected into an appropriate host cell and cultivated under conditions suitable for expression as described herein below. Recombinant methods are especially preferred for producing longer polypeptides that comprise peptide sequences of the invention. Recombinant techniques are well known in the art. For example, U.S. Pat. No. 7,659,375 discloses several systems, including prokaryotic, yeast, mammalian and insect cell, for production of recombinant peptides. As such, in an embodiment, nucleic acid sequences encoding the peptides or polypeptides of the present invention, and vectors containing those nucleic acid sequences are also contemplated.

In another embodiment, the present invention provides methods for inhibiting the ability of MMP13 to activate TGFβ by contacting the LTBP1 with an inhibiting amount of a compound according to the present invention. Here, the compound of the present invention competes with MMP13 for interaction with LTBP1 thereby acting as a competitive inhibitor of MMP13. By preventing MMP13 from binding LTBP1, the compound of the present invention prevents cleavage of TGFβ LLC, and thereby, inhibits the activation of TGFβ. In that way, the methods of the present invention prevent activation of TGFβ without affecting the catalytic domain of MMP13, thereby, avoiding problems associated with the inhibition of MMP13 by directly affecting its catalytic domain.

In anther embodiment, the present invention provides methods for treating a mammal suffering from osteoarthritis or cartilage degeneration by administering to the mammal a compound of the invention in an amount sufficient to alleviate the effects of osteoarthritis or cartilage degeneration. Preferably, the compound is administered directly to the cartilage of the mammal, for example, by injection.

Specific amounts and route of administration may vary, and will be determined in the clinical trial of these agents. However, it is contemplated that those skilled in the art may administer the compounds of the present invention directly, such as by direct intra-joint injection, to effect contact of the TGFβ LLC with the compounds to prevent activation of TGFβ. In a preferred embodiment, the compound of the present invention are administered so to achieve a concentration of about 10-250 nM, preferably 150-250 nM, of that compound in the synovial fluid.

In some embodiments, the inventive compound may be administered by a transdermal patch or topical lotion, balm, cream, etc. In other embodiments, the inventive compound may be delivered systemically through oral, nasal, or intravenous delivery.

Pharmaceutical compositions for administration according to the present invention can comprise the compound of the present invention alone or in combination with other therapeutic agents or active ingredients. Regardless of whether the active component of the pharmaceutical composition is a compound alone or in combination with another active agent, each of these preparations is in some aspects provided in a pharmaceutically acceptable form optionally combined with a pharmaceutically acceptable carrier. Those compositions are administered by any methods that achieve their intended purposes. Individualized amounts and regimens for the administration of the compositions for the treatment of the given disorder are determined readily by those with ordinary skill in the art using assays that are used for the diagnosis of the disorder and determining the level of effect a given therapeutic intervention produces.

Pharmaceutical compositions are contemplated wherein a compound of the present invention and one or more therapeutically active agents are formulated. Formulations of compounds of the present invention are prepared for storage by mixing said compound having the desired degree of purity with optional pharmaceutically acceptable carriers, excipients or stabilizers (Remington's Pharmaceutical Sciences 16th edition, Osol, A. Ed., 1980, incorporated entirely by reference), in the form of lyophilized formulations or aqueous solutions. Acceptable carriers, excipients, or stabilizers are nontoxic to recipients at the dosages and concentrations employed, and include buffers such as phosphate, citrate, acetate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; sweeteners and other flavoring agents; fillers such as microcrystalline cellulose, lactose, corn and other starches; binding agents; additives; coloring agents; salt-forming counter-ions such as sodium; metal complexes (e.g. Zn-protein complexes); and/or non-ionic surfactants such as TWEEN™, PLURONICS™ or polyethylene glycol (PEG). In a preferred embodiment, the pharmaceutical composition that comprises the compound of the present invention may be in a water-soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. The formulations to be used for in vivo administration are preferably sterile. This is readily accomplished by filtration through sterile filtration membranes or other methods.

It is understood that the suitable dose of a composition according to the present invention will depend upon the age, health and weight of the recipient, kind of concurrent treatment, if any, frequency of treatment, and the nature of the effect desired. However, the dosage is tailored to the individual subject, as is understood and determinable by one of skill in the art, without undue experimentation. This typically involves adjustment of a standard dose, e.g., reduction of the dose if the patient has a low body weight.

The total dose of therapeutic agent may be administered in multiple doses or in a single dose. In certain embodiments, the compositions are administered alone, in other embodiments the compositions are administered in conjunction with other therapeutics directed to the disease or directed to other symptoms thereof.

In some aspects, the pharmaceutical compositions of the invention are formulated into suitable pharmaceutical compositions, i.e., in a form appropriate for applications in the therapeutic intervention of a given disease. Methods of formulating proteins and peptides for therapeutic administration also are known to those of skill in the art. Administration of those compositions according to the present invention will be via any common route so long as the target tissue is available via that route. Preferably, those compositions are formulated as an injectable. Appropriate routes of administration for the present invention may include oral, subcutaneous, intravenous, transdermal, intradermal, intramuscular, intramammary, intraperitoneal, intrathecal, intraocular, retrobulbar, intrapulmonary (e.g., term release), aerosol, sublingual, nasal, anal, vaginal, or transdermal delivery, or by surgical implantation at a particular site is also used, particularly when oral administration is problematic. The treatment may consist of a single dose or a plurality of doses over a period of time.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. In some aspects, the carrier is a solvent or dispersion medium containing, for example, water, ethanol, polyol (for example, glycerol, propylene glycol, and liquid polyethylene glycol, and the like), suitable mixtures thereof, and vegetable oils. The proper fluidity is maintained, for example, by the use of a coating, such as lecithin, by the maintenance of the required particle size in the case of dispersion and by the use of surfactants. The prevention of the action of microorganisms is brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions is brought about by the use in the compositions of agents delaying absorption, for example, aluminum monostearate and gelatin.

Sterile injectable solutions are prepared by incorporating the compounds of the present invention in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution is suitably buffered if necessary and the liquid diluent first rendered isotonic with sufficient saline or glucose. These particular aqueous solutions are especially suitable for intravenous, intramuscular, subcutaneous and intraperitoneal administration. Those of ordinary skill in the art will readily optimize effective dosages and administration regimens as determined by good medical practice and the clinical condition of the individual patient.

The frequency of dosing will depend on the pharmacokinetic parameters of the compounds and the routes of administration. The optimal pharmaceutical formulation will be determined by one of skill in the art depending on the route of administration and the desired dosage. Such formulations may influence the physical state, stability, rate of in vivo release and rate of in vivo clearance of the administered agents. Depending on the route of administration, a suitable dose is calculated according to body weight, body surface areas or organ size. The availability of animal models is particularly useful in facilitating a determination of appropriate dosages of a given therapeutic. Further refinement of the calculations necessary to determine the appropriate treatment dose is routinely made by those of ordinary skill in the art without undue experimentation, especially in light of the dosage information and assays disclosed herein as well as the pharmacokinetic data observed in animals or human clinical trials.

Typically, appropriate dosages are ascertained through the use of established assays for determining blood levels in conjunction with relevant dose response data. The final dosage regimen will be determined by the attending physician, considering factors which modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment for specific diseases and conditions. Those studies, however, are routine and within the level of skilled persons in the art.

It will be appreciated that the pharmaceutical compositions and treatment methods of the invention are useful in fields of human medicine and veterinary medicine. Thus, the subject to be treated is a mammal, such as a human or other mammalian animal. For veterinary purposes, subjects include for example, farm animals including cows, sheep, pigs, horses and goats, companion animals such as dogs and cats, exotic and/or zoo animals, and laboratory animals including mice, rats, rabbits, guinea pigs and hamsters.

In another embodiment, the present invention also provides antibodies for binding the compounds of the present invention which have MMP13 inhibitory activity. The antibodies can be generated using the compounds of the present invention as antigens in various methods known in the art. For example, the methods of U.S. Pat. No. 7,049,410, which is incorporated herein by reference, to make monoclonal and polyclonal antibodies can be used to make the antibodies against the compounds of the present invention. For example, a peptide having the amino acid sequence ELGLPKEVK-KISAAVHFED (amino acids 93-111 of SEQ ID NO: 1, variously referred to as MPP13-19, pxpt 001-1, the "inhibitory peptide," or the "peptide") can be used as an antigen to generate monoclonal or polyclonal antibodies to MMP13. The antibodies are useful as diagnostics, e.g. in detecting the specific peptides or polypeptides of the present invention or MMP13, or determining the presence or absence of the peptides or polypeptides in the body tissues. One skilled in the art would be able to utilize the antibodies in accordance with known diagnostic methods. In an embodiment, the antibodies may be labeled for easy detection. The labels can be, but are not limited to biotin, fluorescent molecules, radioactive molecules, chromogenic substrates, chemi-luminescence, and enzymes.

Without further description, it is believed that one of ordinary skill in the art can, using the preceding description and the following illustrative examples, make and utilize the compounds and methods of the present invention. The following examples are given to illustrate the present invention. It should be understood that the invention is not to be limited to the specific conditions or details described in those examples.

EXAMPLES

Example 1

Materials and Methods

Cartilage Extract Preparation, Immunoprecipitation and Immunoblot Analysis

Tibia from normal Sprague-Dawley 14 day old newborn rat pups or day 19 chick embryos were dissected free of tissue and the tibial growth plates isolated by microdissection. The cartilage was minced and extracted overnight in 0.5% 3-([3-chlomadipropyl]dimethylammonio)-1-propane-sulfonate (CHAPS) buffer [10 mM Tris, 100 mM NaCl, 2 mM EDTA, pH 7.6] (Sigma, St. Louis, Mo., USA). Avian tissue was immunoprecipitated with rabbit anti human LTBP-1 (a kind gift of Dr. Kohei Miyazono), rabbit anti avian MMP-13 (D'Angelo, et al., 2000) or rabbit pre-immune serum (Pierce Biochemicals, Rockford, Ill., USA). Rat tissue was immunoprecipitated with rabbit anti human LTBP-1 or rabbit anti human TGFβ2 polyclonal antibodies (Santa Cruz Biotechnology, Inc., Santa Cruz, Calif., USA). Concurrently, TGFβ antibody was biotinylated using the EZ-Link Sulfo-NHS-LC-Biotinylation Kit according to protocol (Pierce Biochemicals, Rockford, Ill., USA). Conditioned media from day 5 chondrocyte alginate cultures was incubated with biotin-labeled. TGFβ antibody for 30 minutes at room temperature and passed over a μMACS strep-avidin micro-bead column (Miltenyi Biotec, Inc, Auburn, Calif., USA). All immunoprecipitates were separated on 4-20% or 8-16% Tris-glycine, SDS-polyacrylamide gradient gels, (Invitrogen Life Technologies, Carlsbad, Calif., USA). Proteins were transferred to Protran nitrocellulose (Schleicher and Schull, Keene, N.H., USA) in a Bio-Rad Mini-blot transfer apparatus (Bio-Rad Laboratories, Inc., Hercules, Calif., USA), blocked for 2 hours at room temperature with 3% (wt/vol) nonfat milk in tris-buffered saline (TBS/Tween; 10 mM Trizma base (pH 8.0) and 150 mM sodium chloride and 0.05% Tween-20), and incubated in TBS/Tween containing 1% nonfat milk and primary antibody raised against TGFβ2 (Santa Cruz Biotechnology, Inc: Santa Cruz, Calif., USA) or primary antibody raised against avian MMP-13 (D'Angelo, et al., J. Cell. Biochem. 77:678-693, 2000, which is incorporated herein by reference). Immunoblots were then exposed to horseradish peroxidase-conjugated secondary antibody in TBS/Tween (Santa Cruz Biotechnology, Inc., Santa Cruz, Calif., USA) and bands of immunoreactivity were visualized with the Western Blotting Luminol Reagent (Santa Cruz Biotechnology, Inc., Santa Cruz, Calif., USA) and exposed to Kodak X-Omat Blue XB-1 film (Kodak, Rochester, N.Y., USA). CM and CAM samples were concentrated 5-10 fold by centrifugation in Centricon concentrators (molecular weight (MW) cut-off=10 kDa), (Pierce Biochemicals, Rockford, Ill., USA). Total protein was determined by the modified Lowry method (Pierce Biochemicals, Rockford, Ill., USA). 8-16% Tris-glycine, SDS-polyacrylamide gradient gels (Invitrogen Life Technologies, Carlsbad, Calif., USA) were loaded with 20 g total protein per lane in Laemelli's reducing sample buffer and 8M urea. Immunoblot analysis was conducted with primary antibody raised against avian collagen type X (Pacifici et al., Exp. Cell Res. 192:266-270, 1991, which is incorporated herein by reference). The main band of collagen type X protein was scanned and analyzed with the Phase III Image Pro analyzer software (Phase III, Malvern, Pa., USA).

Serum-Free Alginate Cultures

Chondrocytes were reared in serum-free alginate culture as previously described (D'Angelo et al., J. Bone Miner. Res. 16:2339-2347, 2001, which is incorporated herein by reference) Briefly, hypertrophic chondrocytes were isolated from day 17 avian embryonic cephalic sternal core (following 5 days in culture they are designated late hypertrophic (LH)) and cephalic sternal periphery (following 5 days in culture they are designated early hypertrophic (EH)) (D'Angelo et al., J. Bone Miner. Res. 12:1368-1377, 1997; and D'Angelo et al., 2001, which are incorporated herein by reference). The tissue was enzymatically digested in 0.25% trypsin and 0.1% crude collagenase and plated at final density of 5×106 cells/ml in 1.2% Keltone LVCR alginate (Kelco Clark, N.J., USA) or plated at 2×106 cells/35 mm well for high-density monolayer cultures. Complete Serum-free Media (DMEM-high glucose, 1 mM cysteine, 1 mM sodium pyruvate, 50 μg/ml penicillin/streptomycin, and 2 mM L-glutamine) (Invitrogen Corporation) was added to the alginate cultures. Media was changed and collected every 48 hrs with 30 μg/ml ascorbate added on day 2 of culture. Conditioned media was pooled from alginate cultures on day 5, the cells isolated by incubation with 55 mM sodium citrate and the supernatant designated as cell-associated matrix. Pelleted cells were extracted with 0.5% CHAPS detergent buffer [10 mM Tris, 100 mM NaCl, 2 mM EDTA, pH 7.6) and designated cell layer fraction (Sigma Biochemicals). Conditioned media and cell-associated matrix samples were concentrated four-fold in Centricon-10 filters (MW cut-off 10,000 Daltons) as per manufacturer's instructions (Fisher Scientific).

Reverse-Transcription Polymerase Chain Reaction

Cells were isolated from alginate culture following incubation in 0.5M EDTA, pH 8.0, then 5×106 cells resuspended per ml of Trizol reagent (Invitrogen Corporation) and total RNA isolated as per manufacturer's instructions. Reverse-transcribed cDNA was prepared with Superscript enzyme according to manufacturer's protocol (Invitrogen Corporation) and subjected to amplification using Ready-to-go PCR beads per manufacturer's instructions (GE Healthcare). The following primers were designed from the NCBI database: avian 18srRNA Forward 5'-TTA ACG AGG ATC CAT TGG AG-3' (SEQ ID NO: 21) Reverse 5'-AGC CTG CTT TGA ACA CTC TA-3' (SEQ ID NO: 22); avian collagen type X Forward 5'-AGA GGA GTA CTC CTG AAA GT-3' (SEQ ID NO: 23) Reverse 5'-ACT GCT GAA CAT AAG CTC CT-3' (SEQ ID NO: 24); human LTBP-1short Forward 5'-CCG CAT CAA GGT GGT CTT TA 3' (SEQ ID NO: 25) Reverse 5'-CAT ACA CTC ACC ATT AGG GC-3' (SEQ ID NO: 26); human LTBP-1 long Forward 5'-TGT GGA GGG CAG TGC TGC-3' (SEQ ID NO: 27) Reverse 5'-TAA AGA CCA CCT TGA TGC GG-3' (SEQ ID NO: 28); avian MMP-13 Forward 5'-TAC TGC TGA TAT CAT GAT CTC-3' (SEQ ID NO: 29) Reverse 5'-TCT AGA ATC ATC TGA CCA AGT-3' (SEQ ID NO: 30); avian TGFβ2 Forward 5'-AAT GAC AGC ATC AGG TAC GG-3' (SEQ ID NO: 31) Reverse 5'-ATG GTC AGG ACT GAG GCA C-3' (SEQ ID NO: 32); and avian caspase-3 Forward 5'-AGA TGT ATC AGA TGC AAG ATC T-3' (SEQ ID NO: 33) Reverse 5'-GAA GTC TGC TTC TAC AGG TAT-3' (SEQ ID NO: 34). PCR products were separated on 2% agarose gels, densitometrically scanned (Gel-Pro Analyzer, Media Cybernetics, Silver Springs, Md., USA), and normalized to 18srRNA as an internal standard. Densitometric values for a minimum of n=3 were plotted using Prism GraphPad software version 3.03 (GraphPad Software, San Diego, Calif., USA) with ANOVA and 95% C.I. Tukey's analysis.

Immunoblot Analysis

Immunoblot analysis was performed on the conditioned media (soluble fraction), cell-associated matrix fraction (territorial matrix) and the CHAPS buffer extract (cell layer). 20 μg total protein was loaded per well, electrophoretically separated on precast 8-16% gradient Tris-glycine SDS polyacrylamide gels (Invitrogen Corporation), transferred to nitrocellulose, and incubated with rabbit polyclonal anti-TGFβ2 (Santa Cruz Biotechnology, Inc.), rabbit polyclonal anti-MMP-13 (D'Angelo et al., 2000), and rabbit polyclonal anti-LTBP-1 (kind gift from K. Miyazono) followed by incubation with horse-radish peroxidase-conjugated secondary antibodies (Santa Cruz Biotechnology). Reactive bands were visualized through chemiluminescence and exposed film densitometrically scanned (Gel-Pro Analyzer, Media Cybernetics, Silver Springs, Md., USA).

Immunocytochemistry

Chondrocytes were isolated and plated 2×106 cells per 35 mm well onto 22×22 mm glass coverslips (VWR) and fed with Complete Media containing 10% NuSerum (Fisher Scientific). Cultures were incubated up to 48 hours until confluent, in the presence of 40 ng hyaluronidase per milliliter complete media. Cells were fixed in CytoFix/CytoPerm (BD Biosciences) per manufacturer's instructions and cell-free extracellular matrix samples were produced by lysing chondrocytes with cold phosphate buffered saline and 10% Triton X-100 as described (Dallas et al., J. Cell Biol. 131:539-549, 1995, which is incorporated herein by reference). Cells and extracellular matrix were incubated with primary antibodies (Santa Cruz Biotechnology): 100 mg/ml IgG TGFβ2 (V), 20 µg/ml IgG MMP-13 (E-20), and 20 µg/ml IgG LTBP-1 (N-20) followed by secondary antibodies: 1 ng/ml goat anti-rabbit Alexa Fluor 594 rhodamine in the case of TGFB and MMP-13 or 1 ng/ml donkey anti-goat Alexa Fluor 488 fluoroscene in the case of LTBP-1 (Santa Cruz Biotechnology). Nuclei were counterstained with 1 µg/ml Hoechst dye (Sigma-Aldrich), fluorescent images were captured with Nikon E600 fluorescent microscope (Nikon Inc., Melville, N.Y., USA) at 100× objective, and z-stacks acquired with ImagePro 4.5 (Media Cybernetics, Silver Springs, Md., USA) then deconvoluted with AutoDeblur AutoVisualize version 9.2.1 software (AutoQuant Imaging Inc., Watervliet, N.Y., USA).

Results

A Novel TGFβ Large Latent Complex Produced by Hypertrophic Chondrocytes Contains MMP-13

Figure 2:
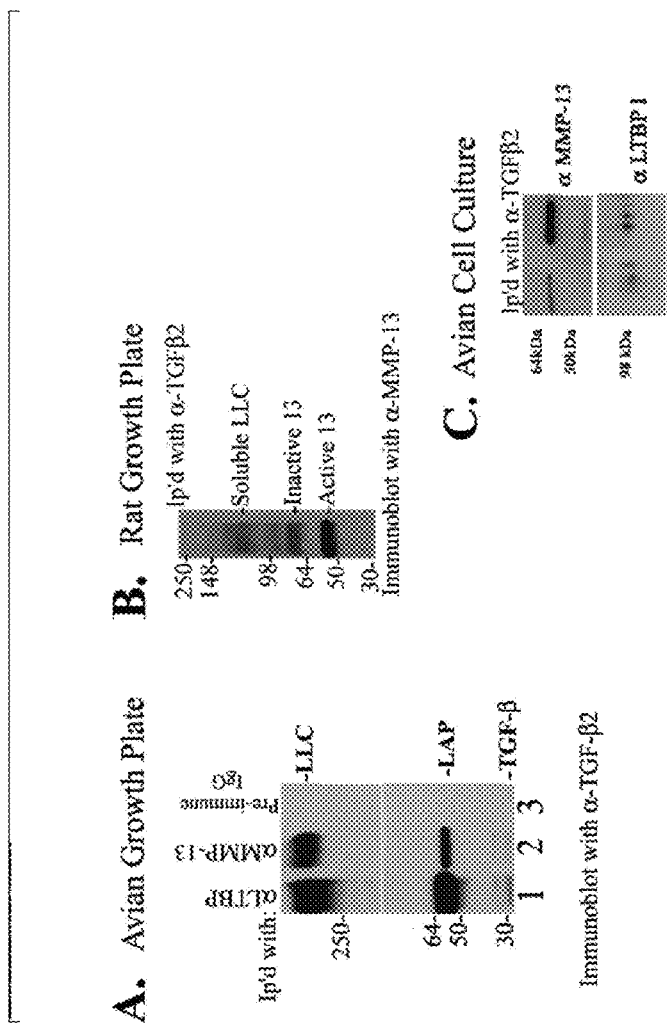
FIG. 2A-2C shows that hypertrophic chondrocytes produce a novel large latent TGFβ complex. (A) Day 19 embryonic chick tibial growth plates were extracted, immunoprecipitated with antiserum to LTBP-1 or MMP13 and immunoblotted with antiserum to TGFβ. Lane 1, immunoprecipitated with LTBP-1 antiserum; Lane 2 immunoprecipitated with MMP13 antiserum; Lane 3 immunoprecipitated with pre-immune serum IgG. LLC=TGFβ large latent complex; LAP=TGFβ latency associated peptide; TGFβ=active TGFβ homodimer (B) Day 14 rat newborn tibial growth plate cartilage was Immunoprecipitated with antiserum to TGFβ and immunoblotted with antiserum to MMP13. Soluble LLC=soluble form of the TGFβ large latent complex; Inactive 13=prozymogen form of MMP13; Active 13=activated form of MMP13. (C) Conditioned media from day 5, serum-free, late hypertrophic chondrocyte cultures was incubated with biotin-labeled, TGFβ polyclonal antibody, passed over a strep-avidin magnetic bead column and immunounoblotted with either NIMP13 or LTBP-1 antibodies as described in Materials and Methods. Lefthand lanes=flow through; Righthand lanes=eluted protein.

Early and late hypertrophic chondrocytes produce activated TGFβ and another hypertrophy-specific marker, the metalloprotease, MMP-13, has a role in the activation of TGFβ by hypertrophic chondrocytes (D'Angelo et al., 2001). Immunoblot analysis of conditioned media from early and late hypertrophic chondrocyte alginate cultures revealed that antibody to MMP-13 cross-reacted with a 280-300 kDa, putative TGF-β2 LLC complex (data not shown). To elaborate this observation, we prepared extracts from day 19 avian tibial hypertrophic chondrocytes, immunoprecipitated proteins with MMP-13 or LTBP-1 antibody and then subjected the immunoprecipitates to immunoblot analysis with TGFβ2 (FIG. 2A). TGFβ-immunoreactive bands were detected at approximately 290 kD, that is the putative large latent TGFβ complex produced by hypertrophic chondrocytes, 60 kD representing the N-terminal β-LAP fragment of TGFβ□ and 25 kD representing the homodimer of activated TGFβ□ whether immunoprecipitated with αLTBP-1 or αMMP-13 antibody (FIG. 2A). Rat tibial growth plate cartilage extracts immunoprecipitated with antibody to TGFβ2 contained MMP-13 immunoreactive bands at approximately 130 kDa representing the soluble form of the TGF-β large latent complex and 68 kDa and 52 kDa representing the proenzyme and activated enzyme forms of MMP-13 (FIG. 2B). Conditioned media from late hypertrophic chondrocyte alginate cultures were immunoprecipitated with biotin-labeled polyclonal antibody to TGFβ and immunoblotted with αMMP13 revealing an approximate 52 kDa immunoreactive band (FIG. 2C). These data indicate the production of a unique TGF-β LLC produced by mammalian and avian hypertrophic chondrocytes that includes MMP-13 in non-covalent association.

MMP-13 Associates with Hypertrophic Chondrocyte Produced TGF-β LLC

Total messenger RNA was examined in the alginate cultures to confirm that both populations of cells were hypertrophic (FIG. 3A). Indeed, expression of collagen type X mRNA and MMP-13 mRNA, markers of hypertrophy; was observed at high levels in both early and late hypertrophic chondrocytes (EH and LH, respectively) even though they had not progressed to terminal differentiation as evidenced by low levels of mRNA expression for caspase-3, an apoptotic marker (FIG. 3A). Both populations expressed message for LTBP-1 and TGFβ, components of the TGF-β LLC (FIG. 3B). It has been shown by other laboratories that LTBP-1 can be alternatively spliced to create a long form that maintains a complete N-terminus, or a short from that possesses a truncated N-terminus thought to be more easily removed from the extracellular matrix. We designed primers to differentiate between both forms of LTBP-1 and demonstrated that hypertrophic chondrocytes produce both the long and short forms of LTBP-1 (FIG. 3B) with late hypertrophic chondrocytes producing five-fold more of the short form of LTBP-1 than early hypertrophic chondrocytes.

Figure 4:
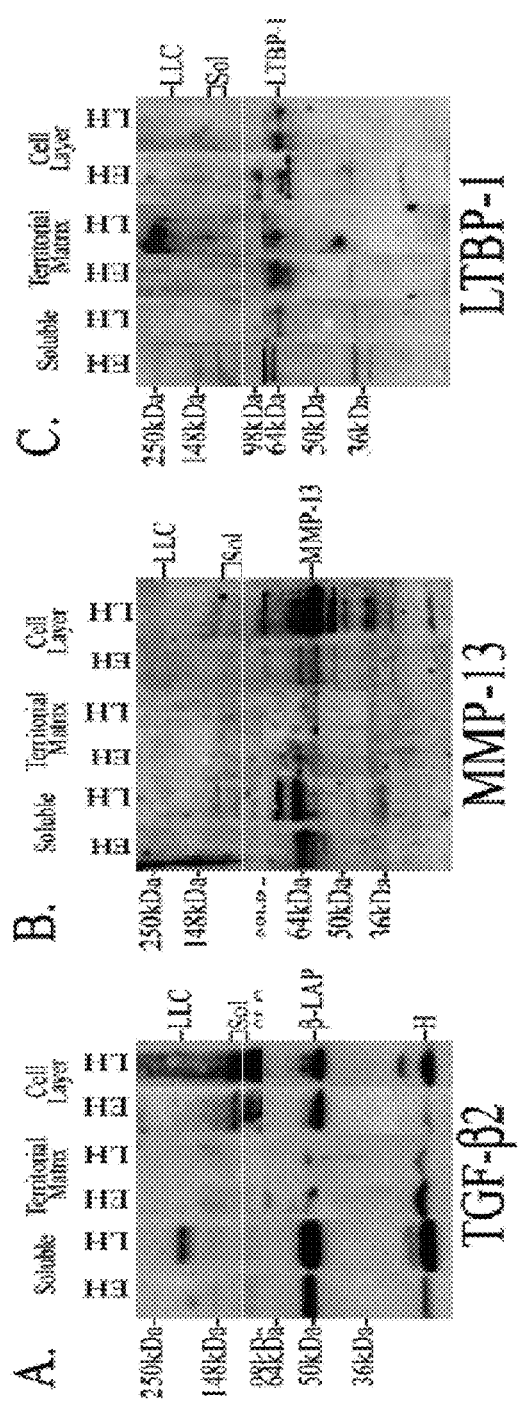
FIG. 4A-4C shows that hypertrophic chondrocytes produce the components of the TGFβ LLC. Early (EH) and late (LH) hypertrophic chondrocytes were reared in serum-free alginate culture. At day 5, 20 μg equal total protein of conditioned media (soluble), cell-associated matrix (territorial matrix) and CHAPS-extracted cell pellet (cell layer) were electrophoresed under reduced conditions as described in Materials and Methods. (A) TGFβ 2 polyclonal antibody; (B) MMP-13 polyclonal antibody; and (C) LTBP-1 polyclonal antibody. LLC=TGFβ large latent complex; Sol=soluble TGFβ LLC; SLC=TGFβ small latent complex; 6-LAP=TGFβ latency associated peptide and H=TGFβ homodimer.

We conducted immunoblot analysis on day 5 alginate chondrocyte cultures to ascertain what forms of the TGF-β LLC are produced and secreted. Protein components of the TGF-β LLC were identified either in the soluble conditioned media fraction (soluble) or the incorporated proteins of the extracellular matrix fraction (territorial matrix) or the proteins associated with the CHAPS-extracted cell pellet (cell layer) (FIG. 4). Reduced immunoblot analysis utilizing antibodies to TGFβ2 (FIG. 4A), MMP-13 (FIG. 4B), and LTBP-1 (FIG. 4C) revealed the presence of these proteins in all three fractions examined. Late hypertrophic chonchocytes, overall, produced more of the three proteins than did early hypertrophic chondrocytes. TGFβ antibody cross-reacted with bands at approximately 240 kDa, the TGF-β LLC, 130-190 kDa, the putative soluble species of the TGF-β LLC, 100 kDa, the TGF-β small latent complex, 60 kDa, the putative β-LAP, and 25 kDa, the TGFβ bioactive homodimer (FIG. 4A). The majority of detectable protein was present in the soluble and cell layer fractions indicating hypertrophic chondrocyte production and secretion of the TGF-β large and small latent complexes. In addition, late hypertrophic chondrocyte samples produced more TGFβ immunoreactive protein per total protein than did early hypertrophic chondrocytes (FIG. 4A, EH versus LH).

MMP-13 immunoblot analysis revealed an approximate 64 kDa band, the MMP-13 proenzyme and a 52 kDa band representing the active MMP-13 enzyme (FIG. 4B). In addition, a less intense immunoreactive band was visible at 130-190 kDa, representing the putative soluble species of TGF-β LLC and a detectable band at approximately 240 kDa representing the TGF-β LLC (FIG. 4B). LTBP-1 immunoblot revealed an 80 kDa band of LTBP-1 and a less intensely stained band of 240 kDa, the TGF-β LLC (FIG. 4C). The presence of a 130-190 kDa band in the soluble layer indicates production of the soluble species of the TGF-β LLC. In the LTBP-1 immunoblots, bands were detectable in the territorial matrix, as well as the secreted and cell layer fractions, indicating incorporation of LTBP-1 into the extracellular matrix produced by hypertrophic chondrocytes. Taken together, the immunoblot data suggest association of MMP-13 with the TGF-β LLC.

Figure 5:
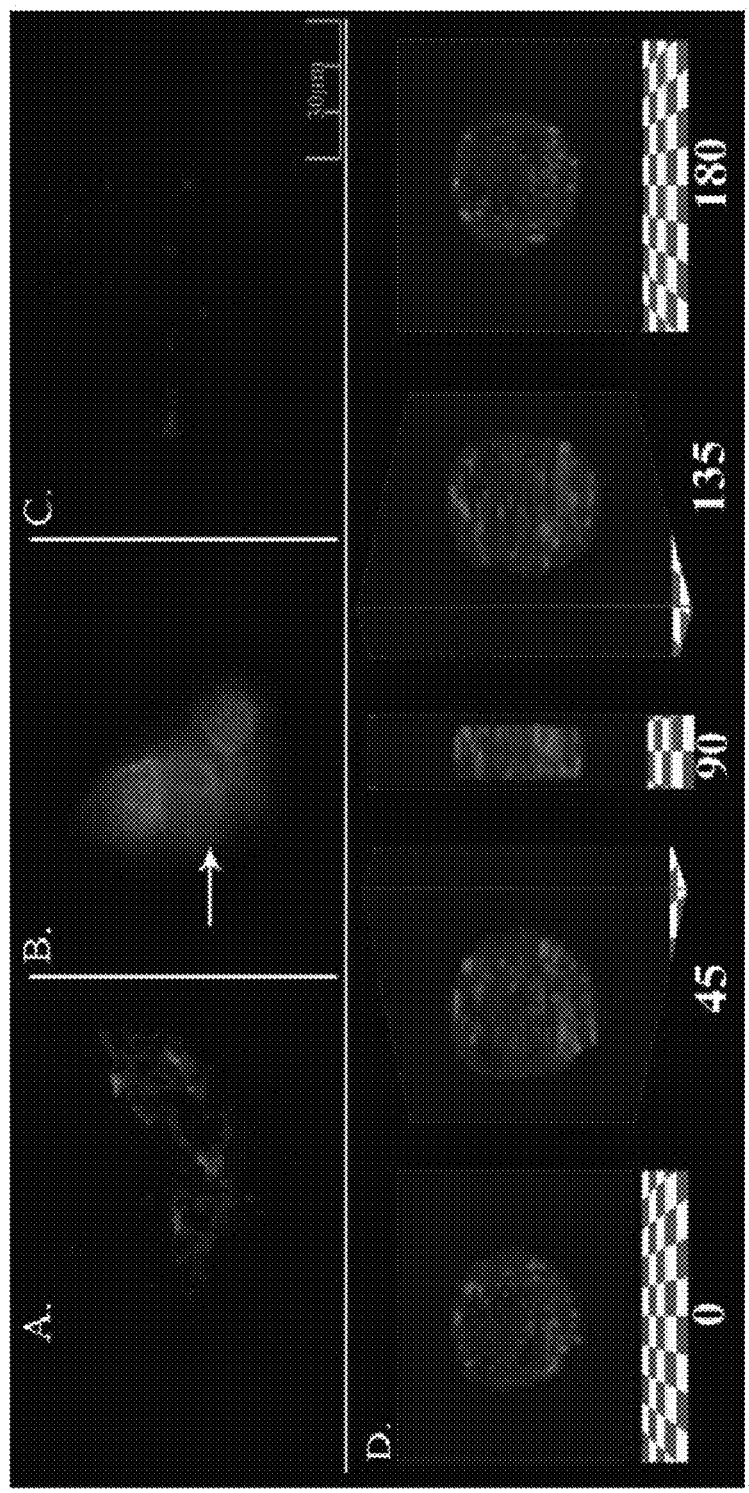
FIG. 5A-5D shows the detection of collagen type X in cell-free matrices. Late hypertrophic chondrocyte cell-free matrices were prepared, immunolabeled with collagen type X polyclonal antibody (red) and nuclei counterstained with Hoechst dye (blue) as described in Materials and Methods. Images were captured with a 100× objective and color compositions constructed using ImagePro software as described in Materials and Methods. (A) cell-free extracellular matrix; (B) cell cytoplasm; (C) secondary antibody control; (D) three-dimensional image capture at 45° of rotation.

Extracellular Immunolocalization of the Hypertrophic Chondrocyte-Produced TGF-β LLC Preparation of cell-free matrices from high-density plating of late hypertrophic chondrocytes was confirmed by collagen type X staining (FIG. 5). Cell-free extracellular matrices exhibited strong collagen type X labeling (FIG. 5A) compared to secondary antibody control (FIG. 5C) and cell cytoplasm stained intensely for collagen type X (FIG. 5B, arrow). Cytoplasmic and extracellular staining of collagen type X was confirmed by three-dimensional z-stack construction: two-dimensional slices were taken at stepped focal planes within the cell and then compiled to yield three-dimensional representations that can be rotated around an axis (FIG. 5D).

TGFβ2, MMP-13, and LTBP-1 were all present in high-density monolayers of late hypertrophic chondrocytes. All three proteins were observed within the extracellular matrix (FIG. 6A-C, arrows) and cytoplasm of the hypertrophic chondrocytes. Rotating three-dimensional z-stacks confirmed immunolocalization of all three proteins in the cytoplasm of the late hypertrophic chondrocytes, and extracellular matrix staining was detectable in the images after background subtraction. Marked extracellular matrix staining of LTBP-1 was evident, whereas, MMP-13 staining was more punctate and TGFβ staining more diffuse in the extracellular matrix (FIG. 6D-F).

Figure 1:
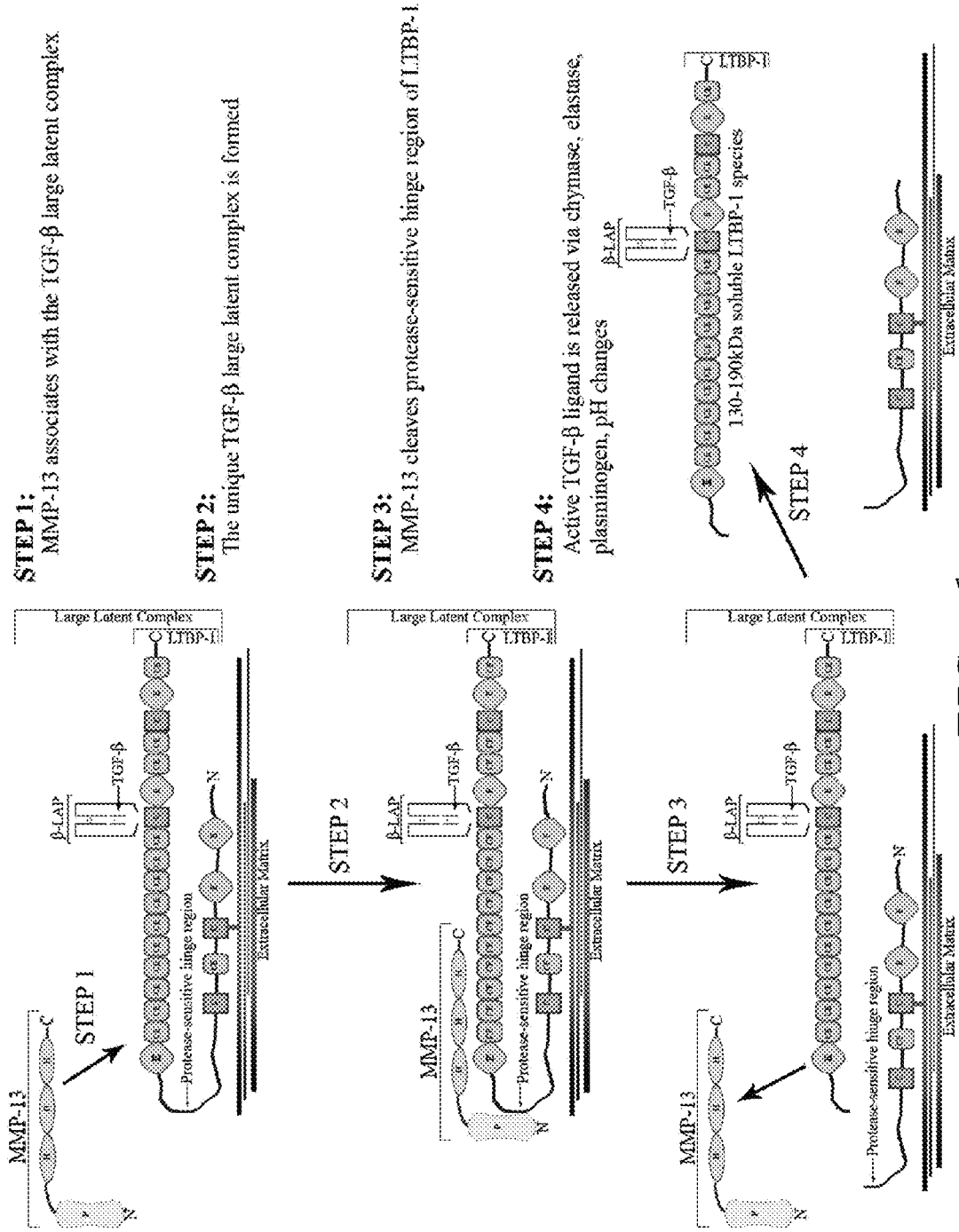
FIG. 1 is a schematic showing a model of MMP13 release of TGFβ from the large latent complex with LTBP1.
Figure 3:
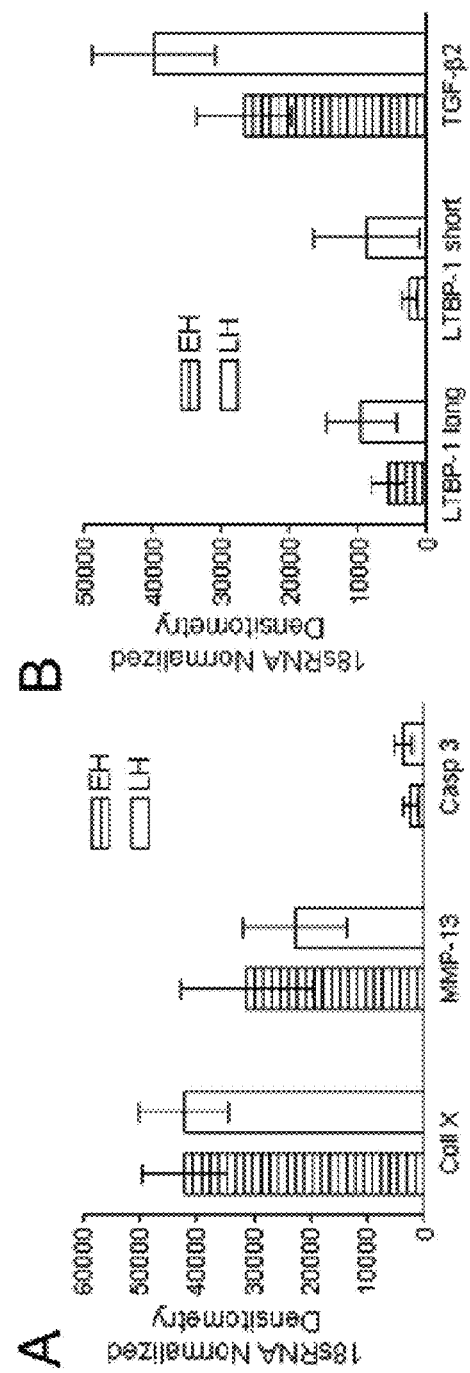
FIG. 3A-3B shows that hypertrophic chondrocytes produce the short form of LTBP-1. Total RNA was isolated from day 5 alginate early hypertrophic (EH) and late hypertrophic (LH) chondrocytes. Densitometric values are normalized to 18s rRNA from a sample n>5 separate cultured experiments. Graphs and statistics generated using Prism GraphPad version 3.03. (A) expression of markers of hypertrophy and (B) expression of the components of the TGFβ LLC.
Figure 7D:
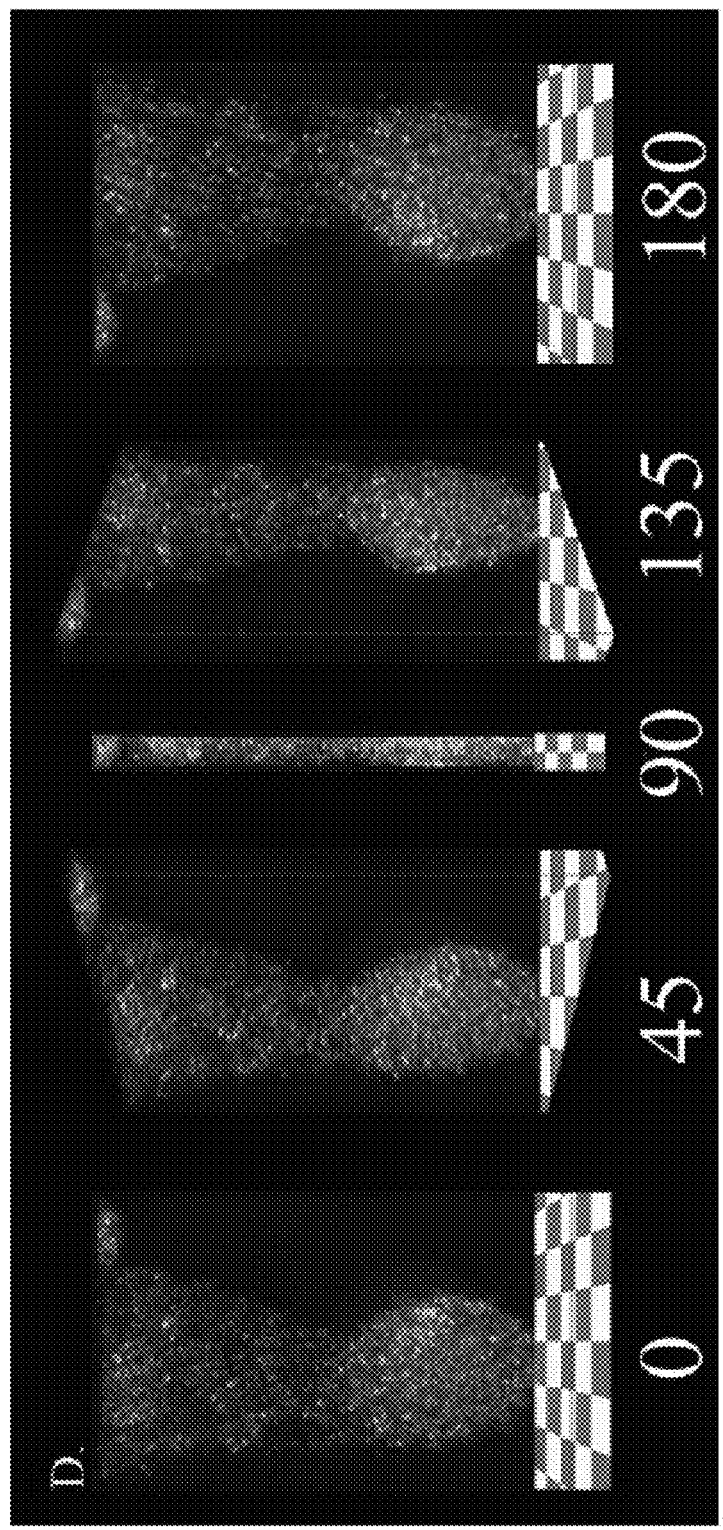

Co-Localization of MMP-13 and LTBP-1 in the Hypertrophic Chondrocyte-Produced TGF-β LLC Previous bioinformatics work from our laboratory indicated a plausible interaction of the hemopexin domains of MMP-13 with the calcium-EGF-like domains of LTBP-1 (Selim et al., J Bone Miner. Res. 20:S131, 2005; and Mattioli et al., J. Bone Miner. Res. 19:S216, 2004, which are incorporated herein by reference). To confirm this hypothesized interaction, we utilized immunocytochemical staining methods to co-localize MMP-13 and LTBP-1. Composite image overlay of MMP-13 and LTBP-1 staining confirmed co-localization of the two proteins observed as yellow-orange staining (FIG. 7C1-7C3). The overlay indicates that the proteins of interest are within close proximity and that staining is within the cytoplasm (FIG. 7C1, arrow) and within the extracellular matrix (FIG. 7C3, arrow). Rotated three-dimensional z-stacks confirmed co-localization of MMP-13 and LTBP-1 as evidence by most robust yellow to orange staining within the cytoplasm and extracellular matrix (FIG. 7D).

The data presented in this study support a mechanism for hypertrophic chondrocyte activation of the TGFβ LLC (FIG. 1). In this model, MMP-13 produced by hypertrophic chondrocytes interacts with the LTBP-1 portion of the TGF-β LLC. Once non-covalently associated with the TGF-β, LLC, MMP-13 cleaves the LTBP-1 protease-sensitive hinge region and release the soluble 130-190 kDa TGFβ LLC. This soluble form of TGFβ LLC would be more susceptible to proteolytic release of the TGFβ SLC and subsequent activation of the TGFβ homodimeric form. Even though the antibodies utilized in our immunocytochemical studies do not differentiate between the 130-190 kDa soluble species of the TGF-β LLC and the full length TGF-β LLC, we expect that MMP-13 cleavage of the protease-sensitive hinge region of LTBP-1 could occur both in the extracellular matrix (most likely site) and within the cell cytoplasm. Because our model includes a non-covalent interaction between LTBP-1 and MMP-13, the driving force for the formation of the unique TGFβ LLC would be concentrations of the molecules MMP13 and TGF-β LLC within close proximity to one another.

Example 2

Materials and Methods

Avian Chondrocyte Isolation and Serum-Free Cell Culture

Sterna were removed from day 17 chick embryos using microsurgical techniques as previously described (D'Angelo et al., J. Bone Miner. Res. 12:1368-1377, 1997). Cells were released by digestion of the extracellular matrix in 0.25% trypsin and 0.1% crude collagenase mixture (Sigma, St. Louis, Mo., USA) in Hanks' buffered saline solution for 3-4 hours at 37° C. Digestion was halted by suspension in high glucose Dulbecco's modified Eagle's medium (DMEM) containing 10% fetal bovine serum (FBS) (Invitrogen Life Technologies, Carlsbad, Calif., USA). The cell suspensions were then filtered through a 0.2 µm filter, counted, seeded onto Falcon 6-well, tissue culture treated plates and covered with 2 ml of high glucose DMEM containing 10% NuSerum and 50 µg/ml of penicillin/streptomycin, 2 mM of L-glutamine (Invitrogen Life Technologies, Carlsbad, Calif., USA). After 48 hours the cells were rinsed and processed for binding studies as described below.

Peptide Binding Assay

Twenty-five micrograms of total equal protein from cartilage CHAPS extracts or five nanograms recombinant protein of the calcium-like EGF binding domain of LTBP1 (a kind gift of Sarah Dallas) or hypertrophic cartilage from day 17 avian embryo sterna and tibial growth plate cartilage from day 14 newborn rat pups were extracted with 0.5% CHAPS buffer and eluates immunoprecipitated with polyclonal antibody to LTBP1 and then samples were plated onto poly-L-lysine coated 96 well plates. After overnight drying, the protein-coated wells were incubated with 100 nM fluorescent-labeled peptide in Tris buffered saline [150 mM NaCl, 10 mM Tris, pH 8.0] and 20% horse serum for 4 hours at 16° C. After incubation, the wells are washed twice with binding buffer, the protein layer solubilized with 5N NaOH and fluorescence bound measured at 495 nm excitation and 520 nm emission on the LabSystems Fluoroskan Ascent CF plate reader. Statistical analyses and graphing were performed with Prism GraphPad software (ANOVA with Turkey's Analysis). A scrambled peptide of the same amino acid composition was prepared as a negative control. Competition assays were conducted in the presence of 10-fold more (1 µM) naked peptide.

Bioinformatics Analysis

Amino acid sequences of proteins analyzed in the manuscript were obtained from Swiss-Prot data base (www.ebi.ac.uk/swissprot/). Pfam data base (www.sangerac.uk/Software/Pfam/) was used for protein domain analysis. Pfam-A is based on hidden Markox model (HMM) searches, as provided by the HMMER2 package (hmmer.janelia.org/). In HMMER2, like BLAST, E-values (expectation values) are calculated. The E-value is the number of hits that would be expected to have a score equal or better than this by chance alone. A good E-value is much smaller than 1 because 1 is what is expected that sequences are similar by chance. In principle, the significance of a match is predicated on a low E-value. 3D models were generated using I-TASSER database (zhang.bioinformatics.ku.edu/l-TASSER/). Protein docking models were generated using Vakser lab database (www.vakserbioinformatics.ku.edu/resources/gramm/grammx/). Protein-protein interface prediction data was generated using PIP-Pred database (bioinformatics.leeds.ac.uk/ppi_pred/index.html). Images were generated using Jmol software (jmol.sourceforge.net/).

Results

Model of the Novel TGFβ Large Latent Complex Produced by Hypertrophic Chondrocytes To examine the nature of interaction between MMP13 and LTBP1, we analyzed their structural domains. MMP13 has a peptidase-like domain (P) and three hemopexin-like domains (H) (Table 1 and FIG. 8A).

TABLE 1

| Domain MMP13 (avian) | Sequence | [a]E-Value |
|---|---|---|
| Peptidase (P) | 19-174 | 8.2e−104 |
| Hemopexin (H) | 197-239 | 6.9e−12 |
|  | 241-284 | 3.5e−10 |
|  | 289-336 | 2.5e−14 |
| LTBP1 short (human) |  |  |
| Cysteine-rich (C) | 687-728 | 4.4e−23 |
|  | 1358-1401 | 9.4e−20 |
|  | [b]1535-1577 | 2.1e−20 |

TABLE 1-continued

| Domain MMP13 (avian) | Sequence | ᵃE-Value |
|---|---|---|
| EGF-like (E) | 191-218 | 0.00024 |
|  | 403-430 | 3.7e−6 |
|  | 1626-1661 | 8.6e−5 |
| Calcium-binding EGF-like (CE) | 626-665 | 2.7e−9 |
|  | 916-956 | 2.7e−14 |
|  | 958-997 | 8.6e−14 |
|  | 999-1037 | 3.9e−10 |
|  | 1039-1078 | 2e−9 |
|  | 1080-1119 | 1e−10 |
|  | 1121-1160 | 3.9e−10 |
|  | 1162-1201 | 6.3e−14 |
|  | 1203-1243 | 1.2e−11 |
|  | 1245-1285 | 4.6e−11 |
|  | 1249-1285 | 1.6e−8 |
|  | 1287-1328 | 0.00033 |
|  | 1425-1466 | 0.0003 |
|  | 1468-1507 | 0.00012 |
|  | 1663-1706 | 3.2e−9 |

ᵃThe expectation values (E-value) of the homology of the regions of these molecules was determined as described in the Materials and Methods section. The lower the E-value the more likely the sequence is a specific match.
ᵇKnown sequence for the cysteine-rich area Where the TGFβ small latent complex covalently binds to LTBP1

The hemopexin-like domain is important for substrate specificity. It also facilitates binding to a variety of molecules and proteins, for example the hemopexin repeats of some matrixins bind tissue inhibitor of metalloproteases (TIMPs). LBTP1 is a larger molecule that consists of several domains: EGF-like domain (E), calcium-binding EGF-like domain (CE) and cysteine rich (the TGFβ small latent complex binding) domain (C) (Table 1 and FIG. 8A). The role of the calcium-binding EGF-like domain varies, depending on the function of the parent molecule, but it appears to be primarily involved in inter-domain interactions between some proteins. In addition, LBTP1 has a linker region that is sensitive to proteolytic cleavage.

The data suggests a model in which the hemopexin domain of MMP13 interacts with calcium-binding EGF-like domain of LBTP1 short in an orientation that places the peptidase domain of MMP13 at very close proximity to the linker region of LBTP1 short (FIG. 8B). This puts MMP13 in the correct conformation to line up the highly conserved sequence (HEXGHXXGXXHS (SEQ ID NO:152); HEXGHXXGXXHT (SEQ ID NO:153)) the catalytic domain of MMP13 (FIG. 8B, P) with the protease-sensitive hinge region of LTBP1 short (FIG. 8B, Linker region). This is the site thought to be the target for release of LTBP1 from the extracellular matrix. Furthermore, this orientation is supported by presence of candidate amino acids in this region of LTBP1 short, Gly-Ile bonds at positions 807/808 and 819/820, that are known to interact with the peptidase domain of MMP13.

As a result of these predictions, we embarked on a bioinformatics study to determine the potential interaction between MMP13 and LTBP1. The potential interaction of MMP13 hemopexin domains with the EGF-like calcium binding domains of LTBP1 was indicated by a protein database file generated by the protein docking program Vakser lab. Modeling with a protein-protein docking program resulted in a three-dimensional model that corroborates the MMP13 molecule interaction with LTBP1 (FIGS. 8A and B) and the site of interaction is toward the N-terminus, not the C terminal site of TGFβ linkage to LTBP1 (FIG. 8B). Binding motifs analysis within the MMP13-LTBP1 complex demonstrated a high affinity interfacing area within the catalytic domain and moderate affinity interfacing area within hemopexin like domains (FIG. 8C). In order to demonstrate these predicted interactions, we designed three candidate peptides from the hemopexin domain of MMP13 that could potentially interact non-covalently with the CE region of LTBP1.

Peptides Designed to MMP13 Hemopexin Domain Specifically Bind LTBP1 Proteins

We conducted binding studies with avian cartilage tissue extracts from the resting and hypertrophic zones of the cartilage growth plate. Both tissues produce TGFβ and store it in the extracellular matrix in the form of the LTBP1-containing TGFβ large latent complex. However, hypertrophic cartilage tissue produces more TGFβ, a larger percentage of which is activated, than that stored in the resting cartilage. In addition, only hypertrophic chondrocytes produce MMP13, thus offering us a model to compare different chondrocyte-produced cartilage tissue and its subsequent binding to MMP13-derived peptides.

Figure 9:
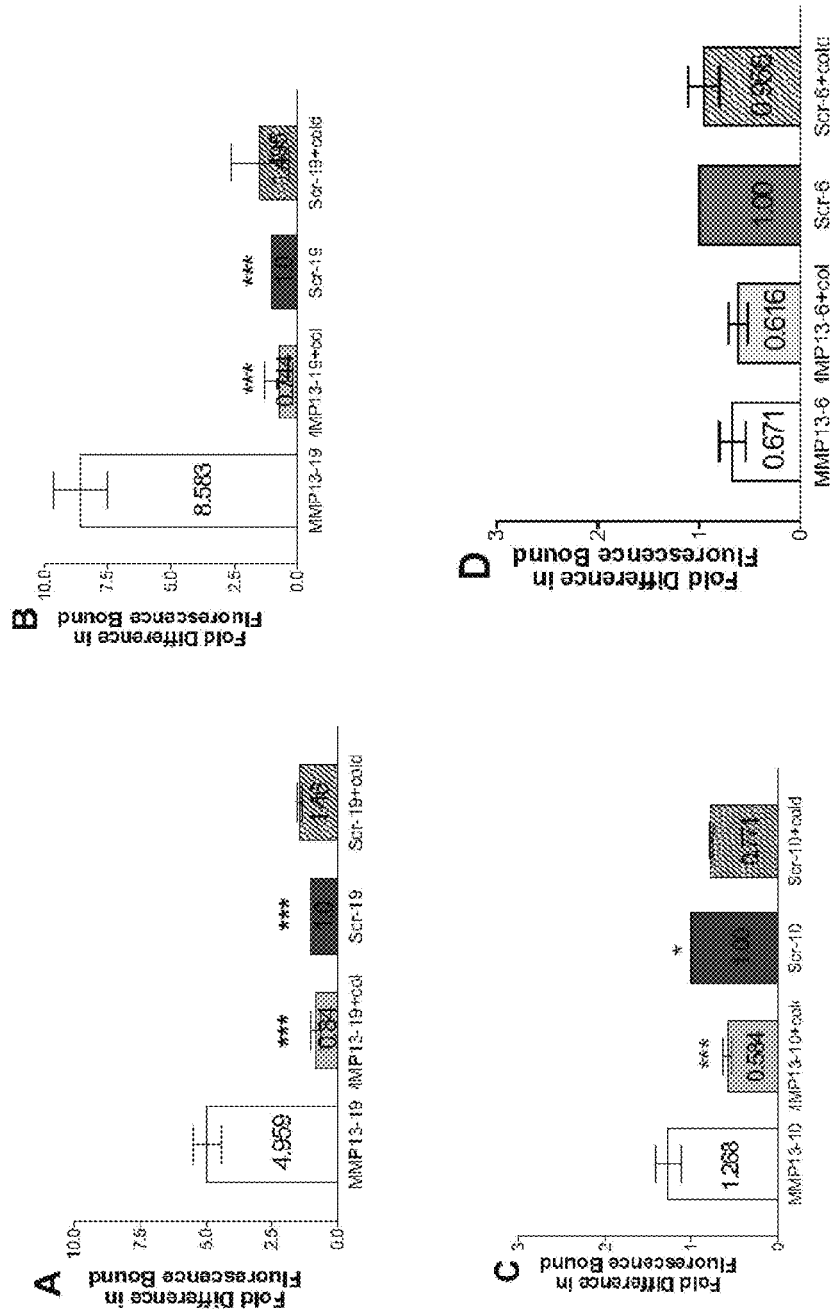
FIG. 9A-9C shows binding of MMP13-derived peptides with cartilage tissue extracts. Cartilage from day 17 avian embryo sterna was extracted with 0.5% CHAPS buffer and binding assays conducted. Scr=scrambled control; +cold=unlabeled competition. *=p<0.001 compared to scrambled. * * *=p<0.001 compared to MMP13-derived peptide by ANOVA with Tukey's Analysis. (A) Resting cartilage and MMP13-19 peptide. (B) Hypertrophic cartilage and MMP13-19 peptide. (C) Hypertrophic cartilage and MMP13-10 peptide D. hypertrophic cartilage and MMP13-6 peptide.

MMP13-19 peptide (amino acids 93-111 of SEQ ID NO: 1) bound to the hypertrophic cartilage tissue extract approximately nine-fold more than scrambled peptide control, as compared to a five-fold binding of resting cartilage tissue (FIGS. 9B and A, respectively). MMP13-10 peptide (amino acids 17-26 of SEQ ID NO: 1) bound less than two-fold the scrambled peptide whether it was the resting or hypertrophic cartilage tissue (FIG. 9C) and MMP13-6 peptide (amino acids 37-42 of SEQ ID NO: 1) did not specifically bind either cartilage tissue (FIG. 9D). All binding was competed with 10-fold excess non-fluorescent peptide.

Figure 10:
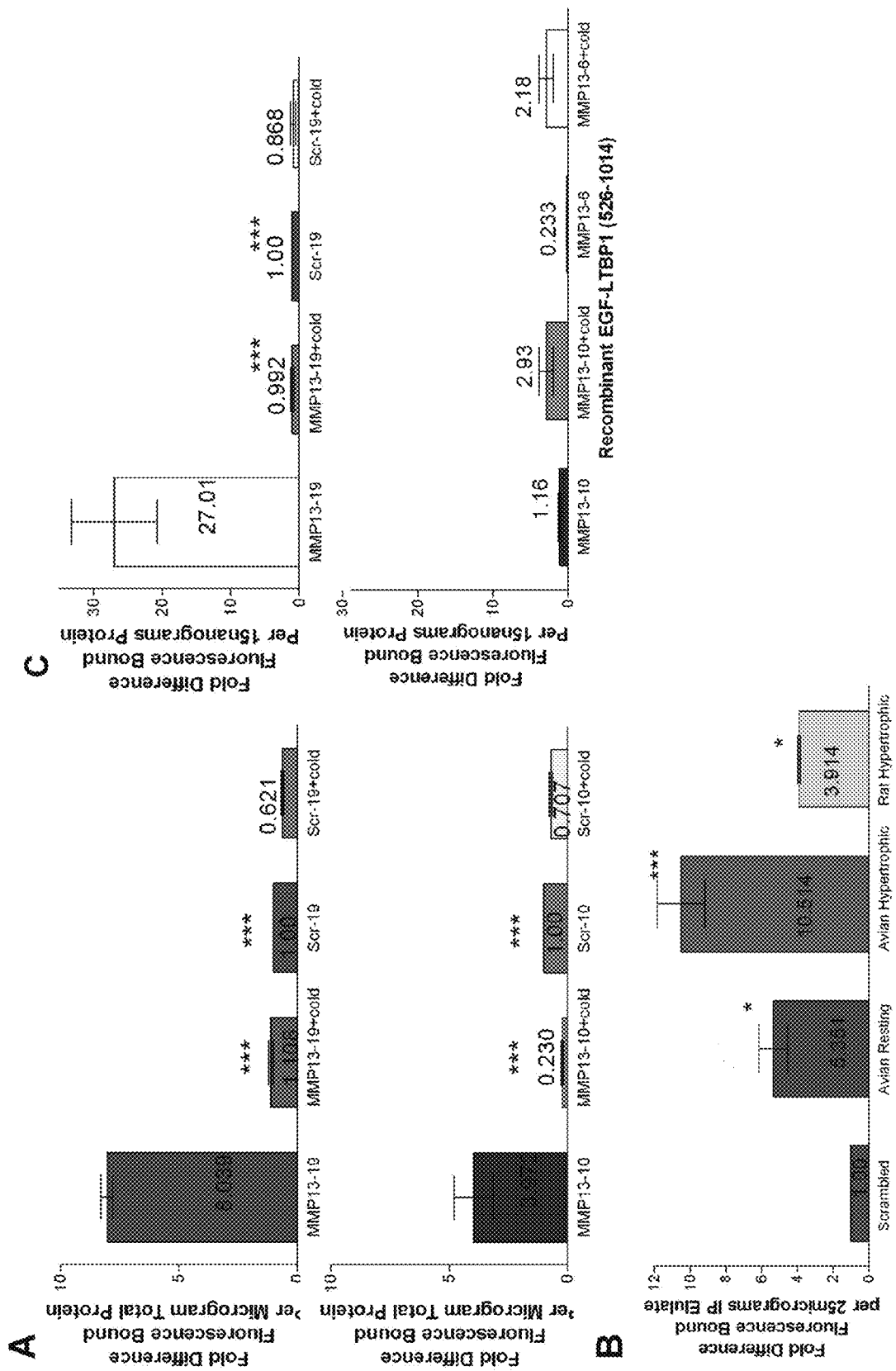
FIG. 10A-10C shows binding of MMP13-derived peptides with isolated extracellular matrix. Binding assays utilizing intact hypertrophic chondrocyte-produced extracellular matrix, LTBP1 immunoprecipitates of hypertrophic chondrocyte-produced extracellular matrix and recombinant protein of the calcium-binding, EGF-like domains of LTBP1 (30) were performed as described in Materials and Methods. *=p<0.001 compared to scrambled. * **=p<0.001 compared to MMP13-derived peptide by ANOVA with Tukey's analysis. (A) Intact hypertrophic chondrocyte-produced extracellular matrix and MMP13-19 or MMP13-10 peptide binding. (B) 25 μg eluates of hypertrophic cartilage immunoprecipitated with polyclonal antibody to LTBP1 and MMP13-19 peptide binding. (C) 15 ng of recombinant protein of the calcium-binding, EGF-like domains and MMP13-19 or MMP13-10 or MMP13-6 peptide binding.

To determine binding of the peptides to LTBP1 in its native conformation, hypertrophic chondrocytes were plated in monolayer to produce a native extracellular matrix. MMP13-19 and MMP13-10 peptides bound to the extracellular matrix of whole cell primary chondrocyte cultures eight-fold and four-fold, respectively, compared to scrambled peptide (FIG. 10A). Again, MMP13-6 did not bind specifically (data not shown).

Since total cell extracts and whole cell cultures contain more proteins than just LTBP1, we conducted binding studies on cartilage tissue samples immunoprecipitated with antibody to LTBP1. MMP13-19 peptide bound 10.5-fold more than scrambled control in the hypertrophic cartilage immunoprecipitates (FIG. 10B). Binding with rat tibial growth plate cartilage immunoprecipitated extracts was 3.9-fold higher than scrambled control (FIG. 10B) demonstrating a global interaction and not a species-specific binding between LTBP1 and the MMP-13 derived peptide.

To determine whether binding is occurring at the calcium-binding EGF-like domains of LTBP predicted by our bioinformatics model, we conducted binding studies with a recombinant protein designed from this region (CE-LTBP1). In these studies, MMP13-19 peptide bound 27-fold more recombinant protein than the scrambled peptide, whereas MMP13-10 and MMP13-6 did not bind specifically (FIG. 10C).

Example 3

Figure 11:
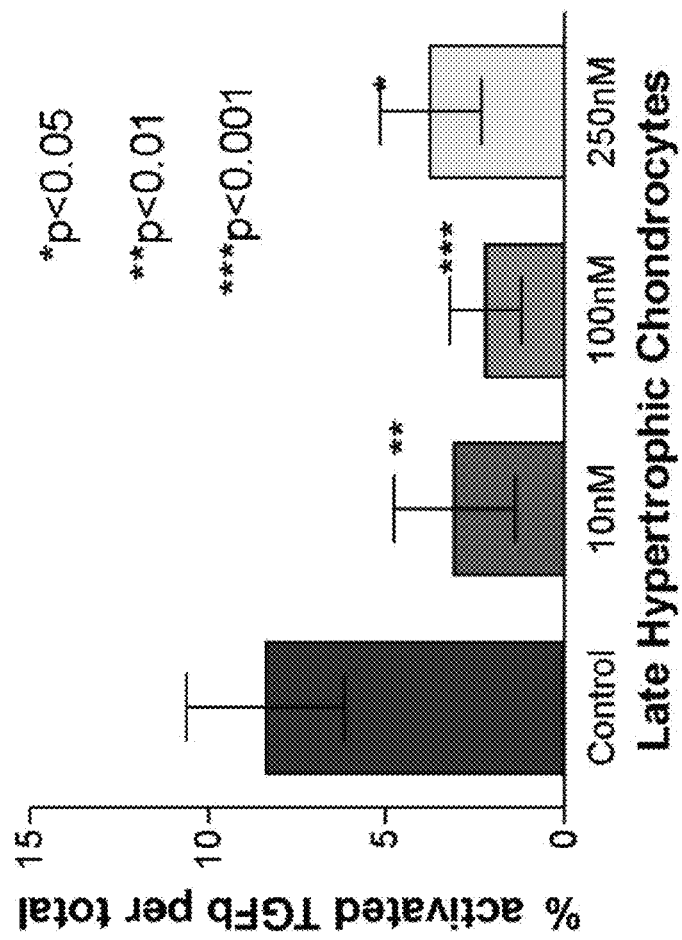
FIG. 11 shows MMP13-19 peptide effects on endogenous activation of TGFβ produced by hypertrophic chondrocytes. Primary sternal chondrocytes from day 17 avian embryos were isolated and plated in alginate culture (2). At day 5 in serum-free culture, 10 nM, 100 nM or 250 nM MMP13 peptide was added to the cultures for 24 hours. Conditioned media was collected and concentrated with Centricon-10 spin filters (Fisher Scientific) and an ELISA (R&D Systems) performed to measure total TGFβ produced versus endogenously activated TGFβ produced. The graph shows endogenously activated TGFβ as percentage of the total TGF β produced. Statistical analysis was calculated by ANOVA with Tukey's test utilizing Prism GraphPad software. n>5 separate culture experiments.
Figure 12:
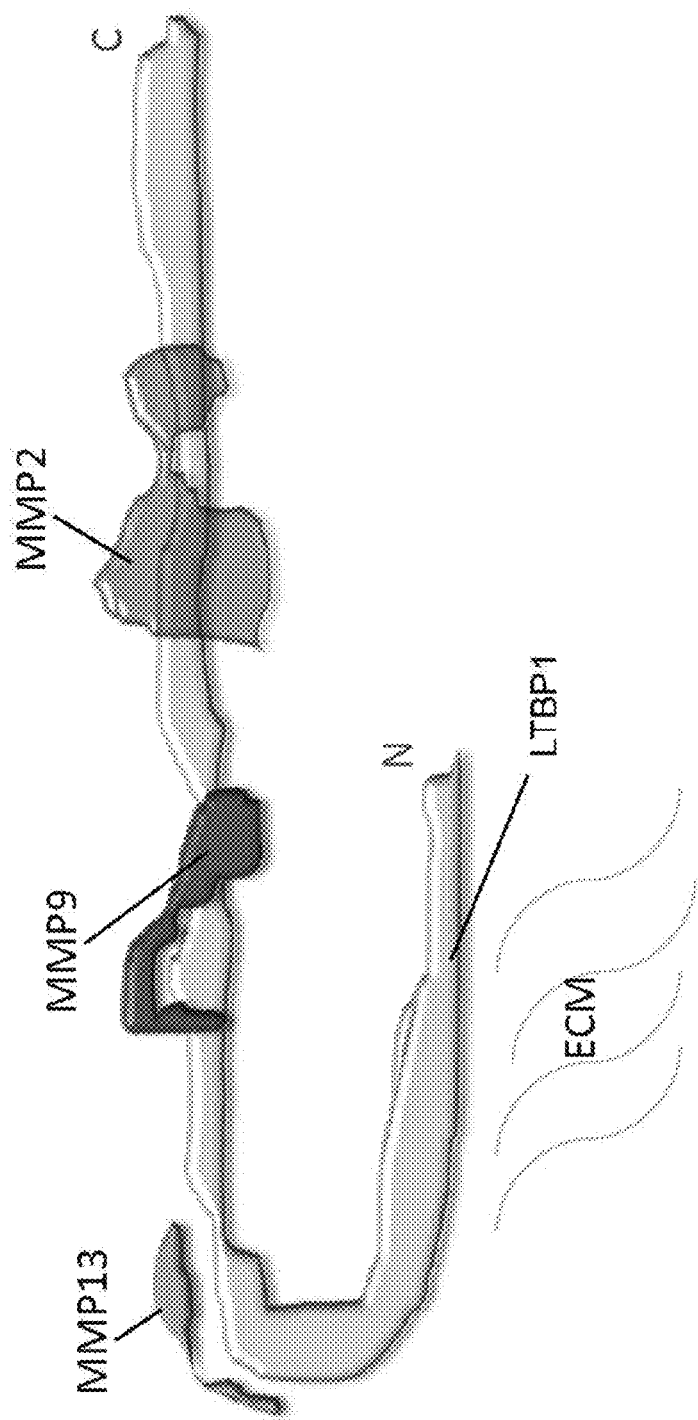
FIG. 12 is a drawing showing the 3-D docking interaction of MMP13, MMP2, and MMP9 with LTBP1. Amino acid sequences of proteins analyzed were obtained from Swiss-Prot data base (www.ebi.ac.uk/swissprot/). Pfam data base (www.sangerac.uk/Software/Pfam/) was used for protein domain analysis. Pfam-A is based on hidden Markox model (HMM) searches, as provided by the HMMER2 package (hmmer.janelia.org/). In HMMER2, like BLAST, E-values (expectation values) are calculated. The E-value is the number of hits that would be expected to have a score equal or better than this by chance alone. A good E-value is much smaller than 1 because 1 is what is expected that sequences are similar by chance. In principle, the significance of a match is predicated on a low E-value. 3D models were generated using I-TASSER database (zhang.bioinformatics.ku.edu/l-TASSER/). Protein docking models were generated using Vakser lab database (vakser.bioinformatics.ku.edu/resources/gramm/grammx/). Protein-protein interface prediction data was generated using PIP-Pred database (bioinformatics.leeds.ac.uk/ppi_pred/index.html). Images were generated using Jmol software (jmol.sourceforge.net./).

To measure the ability of MMP13-19 peptide to bind endogenous large latent complex of TGFβ and interfere with the activation of this growth factor, hypertrophic chondrocytes were cultured in alginate beads in serum-free medium for 24 hours with varying concentrations of MMP13-19 peptide. Conditioned media was then subjected to an ELISA to measure total TGFβ produced and the percentage of endogenously activated TGFβ (FIG. 11). All three doses (10, 100, and 750 nM) of MMP13-19 peptide resulted in a statistically significant decrease in endogenously activated TGFβ although the total amount of TGFβ produced was not affected. These data indicate that the MMP13-19 peptide can be used as an inhibitor of TGFβ activation.

Example 4

Animals were treated with MMP13-19 peptide or BMP-7 protein once a week for two (d14) or three (d21) weeks following an injection of mono-iodoacetate (MIA), a chemical agent that induces osteoarthritis pathology measurable at four weeks post injection. The samples that received saline are the positive disease control. 250 nM of MMP13-19 peptide and 50 uM BMP-7 were injected laterally below the patellar ligament. BMP-7 has been shown to be chondroprotective in a similar model of OA. But, it is also known that BMP-7 is bone-inducing. The data are shown in Tables 2-3 below.

TABLE 2

|  | Total Volume | Bone Volume | BV/TV |
| --- | --- | --- | --- |
| Patellar cartilage d14 | | | |
| OA saline | 8.0451 | 0.1486 | 0.0185 |
| OA MMP13-19 peptide | 9.1804 | 0.1247 | 0.0136 |
| OA BMP-7 | 6.6967 | 0.419 | 0.0626 |
| Patellar cartilage d21 | | | |
| OA saline | 6.0544 | 0.3204 | 0.0529 |
| OA MMP13-19 peptide | 7.7109 | 0.1912 | 0.0248 |
| OA BMP-7 | 10.7748 | 0.2037 | 0.0192 |

TABLE 3

|  | Total Volume | Bone Volume | BV/TV |
| --- | --- | --- | --- |
| Total Joint Cartilage d14 | | | |
| OA saline | 24.9735 | 0.5067 | 0.0243 |
| OA MMP13-19 peptide | 22.2703 | 0.6334 | 0.0284 |
| OA BMP-7 | 24.4891 | 1.0643 | 0.0435 |
| Total Joint Cartilage d21 | | | |
| OA saline | 24.5334 | 1.3883 | 0.0566 |
| OA MMP13-19 peptide | 24.367 | 0.6164 | 0.0253 |
| OA BMP-7 | 23.3101 | 0.9607 | 0.0412 |

NOTE:
A lower value for Bone Volume or Total Volume or a lower BV/TV ratio indicates cartilage that is NOT mineralized.

The amount of bone volume present in the samples indicates the areas of mineralization. Since cartilage is not normally mineralized, one would expect a low bone volume in these samples. In OA, cartilage will begin to mineralize. Of the conditions tested in this preliminary study, MMP13-19 peptide was the most effective at maintaining a normal range of cartilage with the lowest bone volume at each time point. This indicates a chondroprotective function for the MMP13-19 peptide that is even better than the known effects of BMP-7.

Example 5

Peptide Interaction with Collagen

Bioinformatics may be used to identify candidate fragments that can interact with substrates. For example, a three-dimensional model of dog MMP13 was generated. The dog MMP13 3D structure was docked with the 3D structure of substrate (such as type II collagen). The 3D structure of the complex was generated and then analyzed to identify interfacing residues in MMP13 and substrate (such as type II collagen). Peptides designed based on the interfacing residues (derived from MMP13 or the substrate) could be used to modify the interaction between MMP13 and its substrates. Preferably, the fragment contains at least 10 amino acids, more preferably 10 to 40 amino acids, Dog MMP13 amino acid sequence was obtained from Uni-Prot database (dog sequences may be found at SEQ ID NOs: 124-150). The chain was used to generate three dimensional (3D) model of dog MMP13 (FIG. 13). The 3D structure is showing the typical known structure of MMPs with collagenase domain toward the N-terminus. This is the first time to model dog MMP13. Collagen is a known substrate for different collagenases. The 3D structures of MMP13 and collagen triple helix complex (FIG. 14) was generated using protein docking servers. The complex demonstrated sandwich-like structure where collagen is lying within a groove within MMP13 (FIG. 15). The complex was visualized and interacting residues were identified. Peptide-based compound was designed and modeled (FIG. 16). To test the ability of the peptide to interfere with MMP13-collagen interaction, we docked MMP13, collagen and peptide together in one complex (FIG. 17). Complex modeling demonstrated that MMP13 derived peptide is interrupting the MMP13-collagenase interaction by interfering with the sandwich orientation (FIGS. 16 and 17). Sequences used for these figures, and other dog sequences are given in SEQ ID NOs: 124

These data suggested that such peptide has a potential competitive inhibitory effect on MMP13-collagen interaction. 124-151.

Example 6

Peptide Interaction with Aggrecan Molecule

Aggrecan is a known substrate for MMP13. Aggrecan is a major component of cartilage matrix. The peptide was docked with aggrecan (FIG. 18). Complex energy was −0.6 and two hydrogen bonds are predicted in the complex.

Example 7

Peptide Interaction with Fibronectin

Fibronectin is another known substrate for MMP13. The peptide was docked with fibronectin III (FIG. 19). Complex energy was −6.9 and three hydrogen bonds are predicted (FIG. 19).

Example 8

MMP13 Cleavage of LTBP1

Since TGFβ activation can be altered by competitive inhibition of the endogenous MMP13, then MMP13 should be able to utilize the protease-sensitive hinge region of LTBP1 as a substrate as indicated by our working model (FIG. 1). In order to test this, we utilized a fluorescence labeled peptide of the published protease-sensitive hinge region for LTBP1, REHGARS (Taipale, J; Miyazono, K; Heldin, C-H and J. Keski-Oja (1994) *JCB* 124, 171-181). Enzyme kinetic assays with a commercially available MMP13 catalytic domain (Enzo, Inc) were conducted with our hinge region peptide substrate. Michaelis-Menten non-linear fit for the MMP13 digest of the hinge substrate demonstrates a Km=1.628e-016

Figure 21:
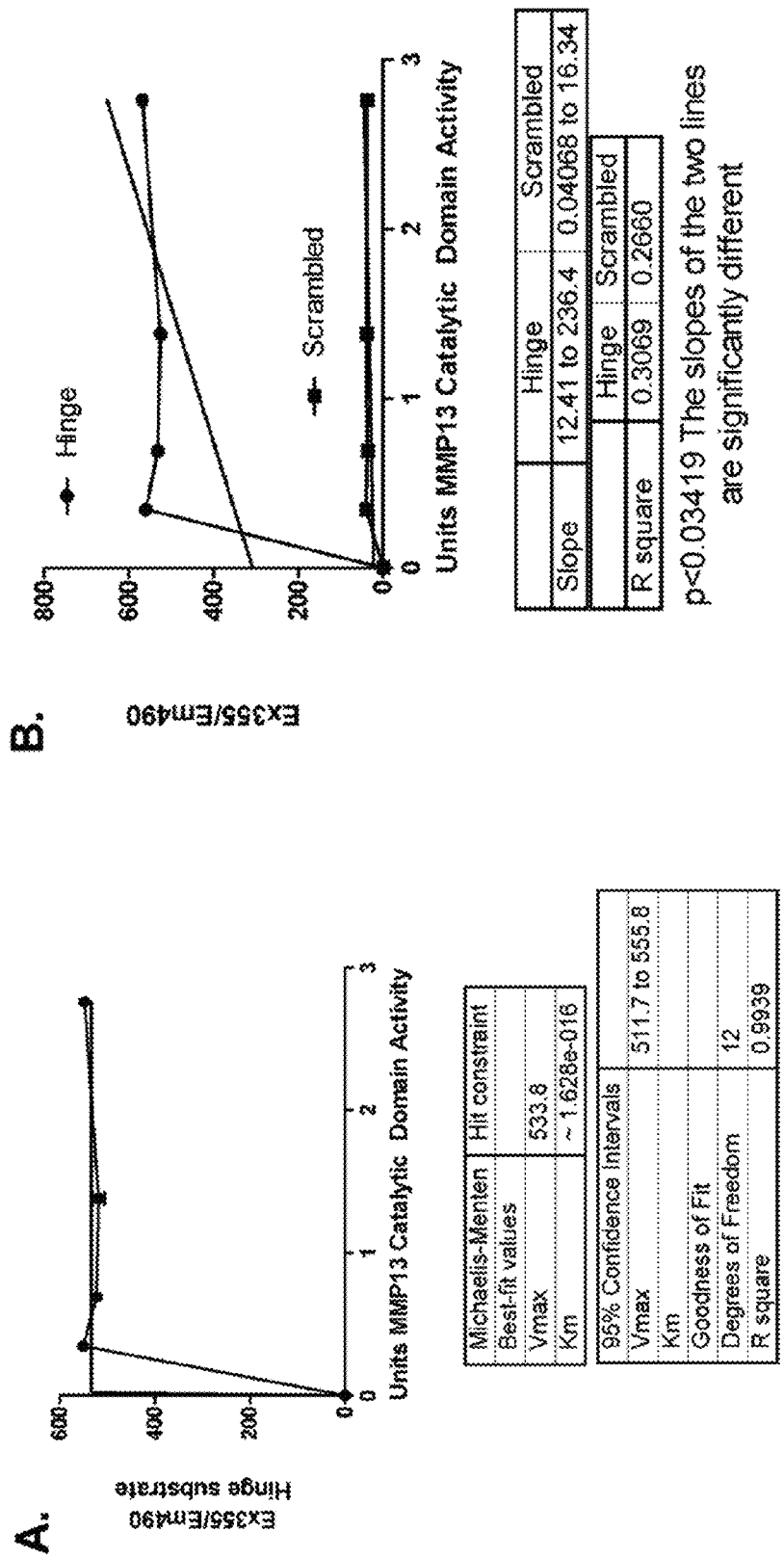
FIG. 21A-21B, shows digestion kinetics of MMP13 catalytic domain on hinge substrate 21A and scrambled substrate, 21B. EDAN-DABSYL fluorescence-labeled REHARGS peptide, representing the protease-sensitive hinge region of LTBP1, was assayed with MMP13 catalytic domain (Enzo Laboratories). Enzyme kinetics were calculated by Michaelis-Menten and non-linear regression software available with the Prism GraphPad program.

(FIG. 21A). When this activity is compared with a peptide substrate of scrambled sequence, the two lines have statistically significant differences in slopes (p<0.03419) (FIG. 21B). These data indicate that MMP13 can utilize the protease-sensitive hinge region of LTBP1 as a substrate. Thus, our modeled interaction of MMP13 with the TGFβ large latent complex could be a method of release of TGFβ from extracellular matrix stores.

Utilizing a standard curve with MMP13 and MMP9 catalytic domains (Enzo, Inc) we quantitated the amount of MMP13 and MMP9 activity in cartilage extracts (Table 4). Cartilage isolated from day 17 avian embryos contain 0.166 units and 0.152 units MMP13 per 40 µg total tissue in early hypertrophic and late hypertrophic tissue, respectively. As expected, resting cartilage does not contain measurable quantities of MMP13 activity. Inclusion of an inhibitor of MMP13 (Calbiochem) reduces the activity in both cartilage populations by 24% and 30% respectively.

All of the cartilage extracts contain enzymatic activity that can digest the hinge substrate (FIG. 22). MMP13 catalytic domain and resting, early and late hypertrophic cartilage all contain enzymatic activity that is statistically significant when compared to the scrambled substrate (FIG. 22A). The amount of activity in the cartilage extracts is significantly higher than the MMP13 catalytic domain alone (FIG. 22B) indicating that agents other than MMP13 are responsible for these data. This is further supported by the statistically significant activity present in resting cartilage, a tissue that does not contain MMP13 activity (see Table 4).

TABLE 4

MMP13 Enzymatic Activity in Cartilage Extracts.

| Sample ID | *Units MMP13 Activity | MMP13 Inhibitor | MMP13/9 Inhibitor |
|---|---|---|---|
| Resting chondrocytes | 0 | | |
| Early Hypertrophic | 0.166 | −23.68% | −20.39% |
| Late Hypertopic | 0.152 | −29.50% | −27.50% |

Table 4: CHAPS extracts of avian sterna cartilage were prepared from day 17 embryos. After dialysis with PBS, 20 ug total protein was assayed with MMP13 substrate (Enzo Laboratories). An MMP13 catalytic domain standard curve was prepared. Michaelis-Menten enzyme kinetics activity was calculated and units of enzyme activity interpolated from the MMP13 catalytic domain standard curve. Inhibitors of MMP13 and MMP13/9 activity were included in the assay (Calbiochem). n > 3 separate extractions was tested. All statistics were calculated with Prism GraphPad software.
*40 µg total protein Example 9

Chronic OA Pathology in the Articular Cartilage of the Tibial-Femoral Joint Space Rats were injected below the patella with mono-iodoacetate to induce OA pathology. One week following the initial insult, rats were injected with saline (Control OA) or 250 nM pxtx001-1 peptide (Peptide treated SEQ ID 36 (FIG. 22A) every other week out to 12 weeks. Rats were sacrificed and joints collected, dissected free of tissue, fixed in formalin, decalcified, paraffin-embedded, sectioned and stained with hematoxylin and eosin (H&E) or saffranin O (for total proteoglycan content). Grading was assessed by the OARSI (Pritzker, K. P., Gay, S., Jimenez, S. A., Ostergaard, K., Pelletier, J. P., Revell, P. A., Salter, D., and van den Berg, W. B. (2006) Osteoarthritis Cartilage 14, 13-29) scale for pathology. FIG. 23 shows histopathology results of the present experiment comparing normal (top), control (middle), and peptide inhibitor treated (bottom) stained with both safranin-O (right), and hematoxaylin+eosin (left). Histologically, the peptide treated joints have a lower grading on the OA scale than the untreated joints as evidenced by proteoglycan content and abnormal chondrocyte morphology.

Example 10

Acute Treatment of Osteoarthritis Model with High and Low Dose Peptide Inhibitor We have utilized an experimental rat model of OA by injection of mono-iodoacetate (MIA) through the infrapatellar ligament of 150 g, male, Wistar rats. This model is characterized by osteophyte formation at the joint edges, fibrillation and erosion of the cartilage and sclerosis of the subchondral bone within 30 days of the injection (Janusz, M. J., Hookfin, E. B., Heitmeyer, S. A. et al. (2001) Osteoarthritis Cartilage 9, 751-760, and Guingamp, C., Gegout-Pottie, P., Philippe, L., Terlain, B., Netter, P., and Gillet, P. (1997) Arthritis Rheum. 40, 1670-1679). We analyzed joint cartilage pathology in the MIA-induced OA model following injection of candidate peptides.

MIA (3 mg in 50 ul) was injected into the capsule of the stifle through the infrapatellar ligament of the right knee (Janusz, M. J., Hookfin, E. B., Heitmeyer, S. A. et al. (2001) Osteoarthritis Cartilage 9, 751-760, and Guingamp, C., Gegout-Pottie, P., Philippe, L., Terlain, B., Netter, P., and Gillet, P. (1997) Arthritis Rheum. 40, 1670-1679). Contralateral knees were injected with saline to serve as control for the experiment. Disease parameters were clearly measurable within three to four weeks following injection. Animals were injected weekly with various doses of peptide (SEQ ID 36 (FIG. 20A)), beginning with the concentration that was shown to be effective in in vitro assays, 250 nM. Saline and BMP-7 (500 ng=50 uM) were injected for negative and positive controls, respectively. Joints were X-rayed to measure joint space changes as an indicator of the progression of OA (Messent, E. A., Ward, R. J., Tonkin, C. J., and Buckland-Wright, C. (2005) Osteoarthritis Cartilage 13, 463-470).

All animals were sacrificed 1, 2 and 3 weeks post injection of MIA. Isolated joints were analyzed by Micro CT to measure cortical bone, trabecular bone and cartilage of the patella, femur and tibia, the production of chondrophytes and tissue mineralization in response to treatment. Total mineralization in the patella, femur and tibial cartilages, as well as subchondral bone, was calculated with Scanco µCT software. Micro-CT was conducted with a Scanco uCT 35 (Scanco Medical, Bassersdorf, Switzerland) system. Scans of 15 µm voxel size, 55 KVp, 0.36 degrees rotation step (180 degrees angular range) and a 600 ms exposure per view will be produced from joints immersed in phosphate buffered saline.

Whole patella for total, cortical and trabecular bone, 3 mm of both distal femur and proximal tibia for cancellous bone, the individually defined volume between patella and femur and fixed volume of joint between femur and tibia were evaluated. The Scanco µCT software (HP, DECwindows Motif 1.6) was used for 3D reconstruction and viewing of images. Volumes were segmented using a global threshold of 0.4 g/c for bone and 0.25 g/c for soft tissue. Cortical bone was evaluated for tissue mineral density (TMD) and thickness of the cortex. Bone volume fraction (BV/TV), surface to volume ratio (BS/BV), thickness (Tb.Th), number (Tb.N) and separation (Tb.Sp) was calculated for the trabecular bone. Cartilage was analyzed for total volume (TV), mineral to total volume ratio (BV/TV) and apparent mineral density.

TABLE 5

| Acute Treatment Week 4 Micro CT (n > 3) | | | | |
|---|---|---|---|---|
| | Normal | OA Control | pxtx001-1 | BMP7 |
| Patella | | | | |
| BV/TV | 0.7566 +/− 0.011 | 0.6952 +/− 0.054 | 0.7075 +/− 0.039 | 0.6846 +/− 0.084 |
| TbN | 7.3364 +/− 0.240 | 6.242 +/− 0.224 | 6.6528 +/− 0.564 | 6.2122 +/− 0.169 |
| Femur | | | | |
| BV/TV | 0.3603 +/− 0.086 | 0.2103 +/− 0.085 | 0.2201 +/− 0.086 | 0.2245 +/− 0.066 |
| TbN | 5.7179 +/− 0.951 | 3.540 +/− 0.675 | 4.075 +/− 0.877 | 4.200 +/− 0.830 |
| Tibia | | | | |
| BV/TV | 0.2773 +/− 0.047 | 0.157 +/− 0.063 | 0.1469 +/− 0.057 | 0.1757 +/− 0.087 |
| TbN | 6.0330 +/− 0.397 | 4.0766 +/− 1.045 | 4.2140 +/− 1.021 | 4.9095 +/− 0.719 |

BV/TV = The ratio of bone volume to total volume; TbN = trabecular number; Normal = age-matched untreated; OA Control = experimental OA and saline; pxtx001-1 = 250 nM peptide; BMP 7 = 500 ng. OA was induced with one injection of monoiodoacetate followed weekly through week 4 with infrapatellar injection.

Following microCT analysis, joints were, decalcified, paraffin-embedded, sectioned and stained with hematoxylin and eosin (H&E) or saffranin O (for total proteoglycan content). Grading was assessed by the OARSI scale (Pritzker, K. P., Gay, S., Jimenez, S. A., Ostergaard, K., Pelletier, J. P., Revell, P. A., Salter, D., and van den Berg, W. B. (2006) *Osteoarthritis Cartilage* 14, 13-29) for pathology. FIG. 23 shows histopathology results of the present experiment comparing normal (top), control (middle), and peptide inhibitor treated (bottom) stained with both safranin-O (right), and hematoxaylin+eosin (left). Histologically, the peptide treated joints have a lower grading on the OA scale than the untreated joints as evidenced by proteoglycan content and abnormal chondrocyte morphology. (FIGS. 24-35).

Example 11

Joint Space XRay Analysis of the OA Rat Model Treated with Inhibitory Peptide

For X ray analysis, the distance from the outside of the femoral head to the angle created by the calcaneus and the gastrocnemius tendon was measured and this distance was kept consistent for each joint. Both medial and lateral views were taken for each limb to gather more accurate measurements of the joint space and to duplicate data. We measured the shortest distance from the tibial cartilaginous surface to the femoral cartilaginous surface (joint space) with the aid of a high quality metal microcaliper and clear plastic ruler. The distance between the radiation source and the tissue was kept constant at 43.4 cm (distance to the film was kept at 85.9 cm). The kilovolt peak was kept at 50 kVp while the milliamp seconds were set at 1 mAs for all radiographs. We used a CMX 110 model x-ray machine by General Electric. Electron dense caliper set at 1 mm was included in each x-ray to allow for proper measurements. (FIGS. 36 and 37)

Stride tests were also administered weekly during the course of treatment to determine functional mobility in the animals. (FIG. 38). Briefly, rat's hind paws were inked, the animals were then timed while they walk a short path and the distance between hind leg strides was measured (Hruska, R. E., Kennedy, S., and Silbergeld, E. K. (1979) *Life Sci.* 25, 171-179).

Example 12

Chondrocyte Model

Primary chondrocytes from early and late hypertrophic stage were cultured from Day 17 avian upper sternum. Late hypertrophic chondrocytes were isolated from the core region of the avian sterna. Following 3-4 hours collagenase and trypsin digestion, cells were centrifuged and filtered through 0.45 um Nitex filter. Isolated cells were resuspended in 1.2% alginate and forced into beaded structures with 102 mM $CaCl_2$ and rinsed in 0.15M NaCl for a final density of $5\times10^6$ cells/ml. Alginate bead cultures were covered in 2 mls complete serum free DMEM high glucose media including 1 mM cysteine, 1 mM sodium pyruvate, 2 mM L-glutamine, 50 µg/ml penicillin/streptomycin. L-ascorbic acid was added to the culture at 30 ug/ml on day 2 and 50 ug/ml on day 5. Time course treatment was performed at 6, 12 or 24 hours with 10 nM, 100 nM, 250 nM PxTx001-1 or 6.5 uM commercially available MMP13 specific inhibitor (Calbiochem). Following a quick dissolution in 0.5M EDTA to release cells from alginate cultures, total RNA was isolated through Trizol method and reverse-transcribed via SuperScript First-Strand Synthesis System (Invitrogen). cDNA samples were subjected to QuantiTech SyBrGreen (Qiagen) real time PCR. Samples were loaded into a 96 well plate in triplicate as 1 ul or 2 ul cDNA for each condition and primers respectively. Expression of markers of chondrocyte maturation (collagen type X, MMP13 and alkaline phosphatase) was compared to an internal standard of 18srRNA using ABI Prism 7000 sequence detection system (Applied Biosystems). Fold difference compared to untreated cultures was graphed using Prism Graph Pad and statistical analysis of one-way ANOVA and standard error of the mean were calculated with associated software. (FIG. 40).

Cytotoxicity was assessed by Alomar Blue Assay (Invitrogen) on primary chondrocytes and a monocyte cell line incubated for 24 hours with PxTx001-1. Absorbance was recorded at 570 nm for every hour up to 24 hrs to monitor both proliferation and metabolic activity. (FIG. 39). Toxicity in vivo was determined by blood analysis from rats that had been injected with the peptide as described previously. Total cell count, blood components and serum proteins were measured (Table 5). All parameters measured were within normal ranges.

TABLE 5

| | 1 injection | 4 injections | Normal Range | |
|---|---|---|---|---|
| Renal Function | | | | |
| BUN | 15 | 18 | 9-21 | mg/dL |
| Creatinine | 0.4 | 0.3 | 0.05-0.65 | mg/dL |
| Liver Function | | | | |
| AST | 99 | 95 | 39-111 | U/L |
| Alk Phos | 272 | 194.5 | 16-302 | U/L |

TABLE 5-continued

| | 1 injection | 4 injections | Normal Range |
|---|---|---|---|
| ALT | 56 | 52 | 20-61 U/L |
| Total Bilirubin | 0.3 | 1.1 | 0.1-0.7 mg/dL |
| Cholesterol | 74 | 67.5 | 20-92 mg/dL |
| CBC | | | |
| WBC | 3.6 | 4.55 | $(5.5\text{-}11.0) \times 10^3/\mu l$ |
| RBC | 5.59 | 6.9 | $(5.5\text{-}10.5) \times 10^6/\mu l$ |

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A synthetic compound with binding affinity for a matrix metalloprotease (MMP) substrate protein, wherein the compound is able to competitively inhibit binding of MMP13 to the substrate protein,
   wherein the compound comprises a peptide or peptide mimetic of less than 50 amino acids, and
   wherein the compound comprises a sequence greater than about 50% identical to SEQ ID NO:36.

2. The compound of claim 1, wherein the compound inhibits the activation of transforming growth factor beta (TGFβ).

3. The compound of claim 1, further comprising a binding domain.

4. The compound of claim 3, wherein the binding domain binds hyaluronic acid.

5. A composition comprising the peptide or peptide mimetic of claim 1 and a pharmaceutically acceptable carrier.

6. The compound of claim 1, wherein the compound inhibits the cleavage of collagen.

7. The compound of claim 1 comprising a sequence greater than about 90% identical to SEQ ID NO:36.

8. The compound of claim 1 comprising a sequence greater than about 80% identical to SEQ ID NO:36.

9. The compound of claim 1 comprising SEQ ID NO:36.

10. A method for inhibiting the activation of TGFβ in a patient in need thereof, comprising the step of contacting a TGFβ large latent complex (LLC) with an effective amount of the peptide or peptide mimetic of claim 1.

11. A method for treating an indication selected from the group consisting of osteoarthritis and cartilage degeneration, in a patient in need thereof comprising the step of administering to the mammal an effective amount of the peptide or peptide mimetic of claim 1.

12. The method of claim 11, wherein the peptide or peptide mimetic is administered by a step selected from the group consisting of subcutaneous injection, application of a cream, balm, lotion, or transdermal patch, or oral or nasal medication.

13. The method of claim 12, wherein the method of application is injection into the joint space or cartilage of the patient.

\* \* \* \* \*

UNITED STATES PATENT AND TRADEMARK OFFICE
CERTIFICATE OF CORRECTION

PATENT NO. : 8,710,014 B2  
APPLICATION NO. : 13/269518  
DATED : April 29, 2014  
INVENTOR(S) : Marina D'Angelo et al.

Page 1 of 1

It is certified that error appears in the above-identified patent and that said Letters Patent is hereby corrected as shown below:

Specification

| Column | Line | PTO | Should Be |
|---|---|---|---|
| 4 | 53 | "cartilage was Immunoprecipitated" | -- cartilage was immunoprecipitated -- |
| 5 | 16 | "6-LAP=TGFβ latency" | -- β-LAP=TGFβ latency -- |
| 5 | 31 | "(A) TGF-132;" | -- (A) TGF-β2; -- |
| 6 | 31 | "of the total TGF β" | -- of the total TGFβ -- |
| 6 | 36 | "LTBP1.Amino acid" | -- LTBP1. Amino acid -- |
| 6 | 39 | "(www.sangerac.uk" | -- (www.sanger.ac.uk -- |
| 6 | 49-50 | "(zhang.bioinformatics.ku.edu/l-TASSER/)." | -- (zhang.bioinformatics.ku.edu/I-TASSER/). -- |
| 6 | 55 | "(jmol.sourceforge.net./)." | -- (jmol.sourceforge.net/). -- |
| 10 | 67 | "protein-protein interlace." | -- protein-protein interface. -- |
| 12 | 4 | "IL-1-β," | -- 1L-1-β, -- |
| 12 | 15 | "l-selecting," | -- I-selecting, -- |
| 14 | 35 | "Thr, H is, Glu," | -- Thr, His, Glu, -- |
| 28 | 30 | "(www.sangerac.uk/" | -- (www.sanger.ac.uk/ -- |
| 28 | 41 | "(zhang.bioinformatics.ku.edu/l-TASSER/)." | -- (zhang.bioinformatics.ku.edu/I-TASSER/). -- |
| 28 | 43 | "(www.vakserbioinformatics" | -- (www.vakser.bioinformatics -- |

Claims

| Column | Line | PTO | Should Be |
|---|---|---|---|
| 212 Claim 10 | 64 | "TGFβlarge latent complex" | -- TGFβ large latent complex -- |

Signed and Sealed this  
Eighth Day of July, 2014

Michelle K. Lee  
*Deputy Director of the United States Patent and Trademark Office*

SEQUENCE LISTING

```
<160> NUMBER OF SEQ ID NOS: 153

<210> SEQ ID NO 1
<211> LENGTH: 192
<212> TYPE: PRT
<213> ORGANISM: Homo sapiens

<400> SEQUENCE: 1

Thr Pro Asp Lys Cys Asp Pro Ser Leu Ser Leu Asp Ala Ile Thr Ser
1               5                   10                  15

Leu Arg Gly Glu Thr Met Ile Phe Lys Asp Arg Phe Phe Trp Arg Leu
                20                  25                  30

His Pro Gln Gln Val Asp Ala Glu Leu Phe Leu Thr Lys Ser Phe Trp
            35                  40                  45

Pro Glu Leu Pro Asn Arg Ile Asp Ala Ala Tyr Glu His Pro Ser His
        50                  55                  60

Asp Leu Ile Phe Ile Phe Arg Gly Arg Lys Phe Trp Ala Leu Asn Gly
65                  70                  75                  80

Tyr Asp Ile Leu Glu Gly Tyr Pro Lys Lys Ile Ser Glu Leu Gly Leu
                85                  90                  95

Pro Lys Glu Val Lys Lys Ile Ser Ala Ala Val His Phe Glu Asp Thr
            100                 105                 110

Gly Lys Thr Leu Leu Phe Ser Gly Asn Gln Val Trp Arg Tyr Asp Asp
        115                 120                 125

Thr Asn His Ile Met Asp Lys Asp Tyr Pro Arg Leu Ile Glu Glu Asp
    130                 135                 140

Phe Pro Gly Ile Gly Asp Lys Val Asp Ala Val Tyr Glu Lys Asn Gly
145                 150                 155                 160

Tyr Ile Tyr Phe Phe Asn Gly Pro Ile Gln Phe Glu Tyr Ser Ile Trp
                165                 170                 175

Ser Asn Arg Ile Val Arg Val Met Pro Ala Asn Ser Ile Leu Trp Cys
            180                 185                 190

<210> SEQ ID NO 2
<211> LENGTH: 582
<212> TYPE: PRT
<213> ORGANISM: Homo sapiens

<400> SEQUENCE: 2

Met Ser Pro Ala Pro Arg Pro Ser Arg Cys Leu Leu Leu Pro Leu Leu
1               5                   10                  15

Thr Leu Gly Thr Ala Leu Ala Ser Leu Gly Ser Ala Gln Ser Ser Ser
                20                  25                  30

Phe Ser Pro Glu Ala Trp Leu Gln Gln Tyr Gly Tyr Leu Pro Pro Gly
            35                  40                  45
```

-continued

Asp Leu Arg Thr His Thr Gln Arg Ser Pro Gln Ser Leu Ser Ala Ala
         50                  55                  60

Ile Ala Ala Met Gln Lys Phe Tyr Gly Leu Gln Val Thr Gly Lys Ala
 65                  70                  75                  80

Asp Ala Asp Thr Met Lys Ala Met Arg Arg Pro Arg Cys Gly Val Pro
                 85                  90                  95

Asp Lys Phe Gly Ala Glu Ile Lys Ala Asn Val Arg Arg Lys Arg Tyr
            100                 105                 110

Ala Ile Gln Gly Leu Lys Trp Gln His Asn Glu Ile Thr Phe Cys Ile
        115                 120                 125

Gln Asn Tyr Thr Pro Lys Val Gly Glu Tyr Ala Thr Tyr Glu Ala Ile
    130                 135                 140

Arg Lys Ala Phe Arg Val Trp Glu Ser Ala Thr Pro Leu Arg Phe Arg
145                 150                 155                 160

Glu Val Pro Tyr Ala Tyr Ile Arg Glu Gly His Glu Lys Gln Ala Asp
                165                 170                 175

Ile Met Ile Phe Phe Ala Glu Gly Phe His Gly Asp Ser Thr Pro Phe
            180                 185                 190

Asp Gly Glu Gly Gly Phe Leu Ala His Ala Tyr Phe Pro Gly Pro Asn
        195                 200                 205

Ile Gly Gly Asp Thr His Phe Asp Ser Ala Glu Pro Trp Thr Val Arg
    210                 215                 220

Asn Glu Asp Leu Asn Gly Asn Asp Ile Phe Leu Val Ala Val His Glu
225                 230                 235                 240

Leu Gly His Ala Leu Gly Leu Glu His Ser Ser Asp Pro Ser Ala Ile
                245                 250                 255

Met Ala Pro Phe Tyr Gln Trp Met Asp Thr Glu Asn Phe Val Leu Pro
            260                 265                 270

Asp Asp Asp Arg Arg Gly Ile Gln Gln Leu Tyr Gly Gly Glu Ser Gly
        275                 280                 285

Phe Pro Thr Lys Met Pro Pro Gln Pro Arg Thr Thr Ser Arg Pro Ser
    290                 295                 300

Val Pro Asp Lys Pro Lys Asn Pro Thr Tyr Gly Pro Asn Ile Cys Asp
305                 310                 315                 320

Gly Asn Phe Asp Thr Val Ala Met Leu Arg Gly Glu Met Phe Val Phe
                325                 330                 335

Lys Glu Arg Trp Phe Trp Arg Val Arg Asn Asn Gln Val Met Asp Gly
            340                 345                 350

Tyr Pro Met Pro Ile Gly Gln Phe Trp Arg Gly Leu Pro Ala Ser Ile
        355                 360                 365

Asn Thr Ala Tyr Glu Arg Lys Asp Gly Lys Phe Val Phe Phe Lys Gly
    370                 375                 380

Asp Lys His Trp Val Phe Asp Glu Ala Ser Leu Glu Pro Gly Tyr Pro
385                 390                 395                 400

Lys His Ile Lys Glu Leu Gly Arg Gly Leu Pro Thr Asp Lys Ile Asp
                405                 410                 415

Ala Ala Leu Phe Trp Met Pro Asn Gly Lys Thr Tyr Phe Phe Arg Gly
            420                 425                 430

Asn Lys Tyr Tyr Arg Phe Asn Glu Glu Leu Arg Ala Val Asp Ser Glu
        435                 440                 445

Tyr Pro Lys Asn Ile Lys Val Trp Glu Gly Ile Pro Glu Ser Pro Arg
    450                 455                 460

Gly Ser Phe Met Gly Ser Asp Glu Val Phe Thr Tyr Phe Tyr Lys Gly

```
                465                 470                 475                 480
Asn Lys Tyr Trp Lys Phe Asn Asn Gln Lys Leu Lys Val Glu Pro Gly
                    485                 490                 495

Tyr Pro Lys Ser Ala Leu Arg Asp Trp Met Gly Cys Pro Ser Gly Gly
                500                 505                 510

Arg Pro Asp Glu Gly Thr Glu Glu Thr Glu Val Ile Ile Ile Glu
            515                 520                 525

Val Asp Glu Glu Gly Gly Gly Ala Val Ser Ala Ala Val Val Leu
    530                 535                 540

Pro Val Leu Leu Leu Leu Val Leu Ala Val Gly Leu Ala Val Phe
545                 550                 555                 560

Phe Phe Arg Arg His Gly Thr Pro Arg Arg Leu Leu Tyr Cys Gln Arg
                565                 570                 575

Ser Leu Leu Asp Lys Val
                580

<210> SEQ ID NO 3
<211> LENGTH: 607
<212> TYPE: PRT
<213> ORGANISM: Homo sapiens

<400> SEQUENCE: 3

Met Ile Leu Leu Thr Phe Ser Thr Gly Arg Arg Leu Asp Phe Val His
1               5                   10                  15

His Ser Gly Val Phe Phe Leu Gln Thr Leu Leu Trp Ile Leu Cys Ala
            20                  25                  30

Thr Val Cys Gly Thr Glu Gln Tyr Phe Asn Val Glu Val Trp Leu Gln
        35                  40                  45

Lys Tyr Gly Tyr Leu Pro Pro Thr Asp Pro Arg Met Ser Val Leu Arg
    50                  55                  60

Ser Ala Glu Thr Met Gln Ser Ala Leu Ala Ala Met Gln Gln Phe Tyr
65                  70                  75                  80

Gly Ile Asn Met Thr Gly Lys Val Asp Arg Asn Thr Ile Asp Trp Met
                85                  90                  95

Lys Lys Pro Arg Cys Gly Val Pro Asp Gln Thr Arg Gly Ser Ser Lys
            100                 105                 110

Phe His Ile Arg Arg Lys Arg Tyr Ala Leu Thr Gly Gln Lys Trp Gln
        115                 120                 125

His Lys His Ile Thr Tyr Ser Ile Lys Asn Val Thr Pro Lys Val Gly
    130                 135                 140

Asp Pro Glu Thr Arg Lys Ala Ile Arg Arg Ala Phe Asp Val Trp Gln
145                 150                 155                 160

Asn Val Thr Pro Leu Thr Phe Glu Glu Val Pro Tyr Ser Glu Leu Glu
                165                 170                 175

Asn Gly Lys Arg Asp Val Asp Ile Thr Ile Ile Phe Ala Ser Gly Phe
            180                 185                 190

His Gly Asp Ser Ser Pro Phe Asp Gly Glu Gly Gly Phe Leu Ala His
        195                 200                 205

Ala Tyr Phe Pro Gly Pro Gly Ile Gly Gly Asp Thr His Phe Asp Ser
    210                 215                 220

Asp Glu Pro Trp Thr Leu Gly Asn Pro Asn His Asp Gly Asn Asp Leu
225                 230                 235                 240

Phe Leu Val Ala Val His Glu Leu Gly His Ala Leu Gly Leu Glu His
                245                 250                 255

Ser Asn Asp Pro Thr Ala Ile Met Ala Pro Phe Tyr Gln Tyr Met Glu
```

```
                    260             265                 270
Thr Asp Asn Phe Lys Leu Pro Asn Asp Leu Gln Gly Ile Gln Lys
            275                 280                 285

Ile Tyr Gly Pro Pro Asp Lys Ile Pro Pro Thr Arg Pro Leu Pro
            290                 295                 300

Thr Val Pro Pro His Arg Ser Ile Pro Ala Asp Pro Arg Lys Asn
305                 310                 315                 320

Asp Arg Pro Lys Pro Arg Pro Pro Thr Gly Arg Pro Ser Tyr Pro
            325                 330                 335

Gly Ala Lys Pro Asn Ile Cys Asp Gly Asn Phe Asn Thr Leu Ala Ile
            340                 345                 350

Leu Arg Arg Glu Met Phe Val Phe Lys Asp Gln Trp Phe Trp Arg Val
            355                 360                 365

Arg Asn Asn Arg Val Met Asp Gly Tyr Pro Met Gln Ile Thr Tyr Phe
            370                 375                 380

Trp Arg Gly Leu Pro Pro Ser Ile Asp Ala Val Tyr Glu Asn Ser Asp
385                 390                 395                 400

Gly Asn Phe Val Phe Lys Gly Asn Lys Tyr Trp Val Phe Lys Asp
                    405                 410                 415

Thr Thr Leu Gln Pro Gly Tyr Pro His Asp Leu Ile Thr Leu Gly Ser
                    420                 425                 430

Gly Ile Pro His Gly Ile Asp Ser Ala Ile Trp Trp Glu Asp Val
            435                 440                 445

Gly Lys Thr Tyr Phe Phe Lys Gly Asp Arg Tyr Trp Arg Tyr Ser Glu
            450                 455                 460

Glu Met Lys Thr Met Asp Pro Gly Tyr Pro Lys Pro Ile Thr Val Trp
465                 470                 475                 480

Lys Gly Ile Pro Glu Ser Pro Gln Gly Ala Phe Val His Lys Glu Asn
                    485                 490                 495

Gly Phe Thr Tyr Phe Tyr Lys Gly Lys Glu Tyr Trp Lys Phe Asn Asn
                    500                 505                 510

Gln Ile Leu Lys Val Glu Pro Gly Tyr Pro Arg Ser Ile Leu Lys Asp
            515                 520                 525

Phe Met Gly Cys Asp Gly Pro Thr Asp Arg Val Lys Glu Gly His Ser
530                 535                 540

Pro Pro Asp Asp Val Asp Ile Val Ile Lys Leu Asp Asn Thr Ala Ser
545                 550                 555                 560

Thr Val Lys Ala Ile Ala Ile Val Ile Pro Cys Ile Leu Ala Leu Cys
            565                 570                 575

Leu Leu Val Leu Val Tyr Thr Val Phe Gln Phe Lys Arg Lys Gly Thr
            580                 585                 590

Pro Arg His Ile Leu Tyr Cys Lys Arg Ser Met Gln Glu Trp Val
            595                 600                 605

<210> SEQ ID NO 4
<211> LENGTH: 660
<212> TYPE: PRT
<213> ORGANISM: Homo sapiens

<400> SEQUENCE: 4

Met Glu Ala Leu Met Ala Arg Gly Ala Leu Thr Gly Pro Leu Arg Ala
1               5                   10                  15

Leu Cys Leu Leu Gly Cys Leu Leu Ser His Ala Ala Ala Ala Pro Ser
            20                  25                  30

Pro Ile Ile Lys Phe Pro Gly Asp Val Ala Pro Lys Thr Asp Lys Glu
```

```
                    35                  40                  45
Leu Ala Val Gln Tyr Leu Asn Thr Phe Tyr Gly Cys Pro Lys Glu Ser
 50                  55                  60

Cys Asn Leu Phe Val Leu Lys Asp Thr Leu Lys Lys Met Gln Lys Phe
 65                  70                  75                  80

Phe Gly Leu Pro Gln Thr Gly Asp Leu Asp Gln Asn Thr Ile Glu Thr
                     85                  90                  95

Met Arg Lys Pro Arg Cys Gly Asn Pro Asp Val Ala Asn Tyr Asn Phe
                    100                 105                 110

Phe Pro Arg Lys Pro Lys Trp Asp Lys Asn Gln Ile Thr Tyr Arg Ile
                    115                 120                 125

Ile Gly Tyr Thr Pro Asp Leu Asp Pro Glu Thr Val Asp Asp Ala Phe
                    130                 135                 140

Ala Arg Ala Phe Gln Val Trp Ser Asp Val Thr Pro Leu Arg Phe Ser
145                 150                 155                 160

Arg Ile His Asp Gly Glu Ala Asp Ile Met Ile Asn Phe Gly Arg Trp
                    165                 170                 175

Glu His Gly Asp Gly Tyr Pro Phe Asp Gly Lys Asp Gly Leu Leu Ala
                    180                 185                 190

His Ala Phe Ala Pro Gly Thr Gly Val Gly Gly Asp Ser His Phe Asp
                    195                 200                 205

Asp Asp Glu Leu Trp Thr Leu Gly Glu Gly Gln Val Val Arg Val Lys
                    210                 215                 220

Tyr Gly Asn Ala Asp Gly Glu Tyr Cys Lys Phe Pro Phe Leu Phe Asn
225                 230                 235                 240

Gly Lys Glu Tyr Asn Ser Cys Thr Asp Thr Gly Arg Ser Asp Gly Phe
                    245                 250                 255

Leu Trp Cys Ser Thr Thr Tyr Asn Phe Glu Lys Asp Gly Lys Tyr Gly
                    260                 265                 270

Phe Cys Pro His Glu Ala Leu Phe Thr Met Gly Gly Asn Ala Glu Gly
                    275                 280                 285

Gln Pro Cys Lys Phe Pro Phe Arg Phe Gln Gly Thr Ser Tyr Asp Ser
                    290                 295                 300

Cys Thr Thr Glu Gly Arg Thr Asp Gly Tyr Arg Trp Cys Gly Thr Thr
305                 310                 315                 320

Glu Asp Tyr Asp Arg Asp Lys Lys Tyr Gly Phe Cys Pro Glu Thr Ala
                    325                 330                 335

Met Ser Thr Val Gly Gly Asn Ser Glu Gly Ala Pro Cys Val Phe Pro
                    340                 345                 350

Phe Thr Phe Leu Gly Asn Lys Tyr Glu Ser Cys Thr Ser Ala Gly Arg
                    355                 360                 365

Ser Asp Gly Lys Met Trp Cys Ala Thr Thr Ala Asn Tyr Asp Asp Asp
                    370                 375                 380

Arg Lys Trp Gly Phe Cys Pro Asp Gln Gly Tyr Ser Leu Phe Leu Val
385                 390                 395                 400

Ala Ala His Glu Phe Gly His Ala Met Gly Leu Glu His Ser Gln Asp
                    405                 410                 415

Pro Gly Ala Leu Met Ala Pro Ile Tyr Thr Tyr Thr Lys Asn Phe Arg
                    420                 425                 430

Leu Ser Gln Asp Asp Ile Lys Gly Ile Gln Glu Leu Tyr Gly Ala Ser
                    435                 440                 445

Pro Asp Ile Asp Leu Gly Thr Gly Pro Thr Pro Thr Leu Gly Pro Val
                    450                 455                 460
```

```
Thr Pro Glu Ile Cys Lys Gln Asp Ile Val Phe Asp Gly Ile Ala Gln
465                 470                 475                 480

Ile Arg Gly Glu Ile Phe Phe Lys Asp Arg Phe Ile Trp Arg Thr
                485                 490                 495

Val Thr Pro Arg Asp Lys Pro Met Gly Pro Leu Leu Val Ala Thr Phe
                500                 505                 510

Trp Pro Glu Leu Pro Glu Lys Ile Asp Ala Val Tyr Glu Ala Pro Gln
                515                 520                 525

Glu Glu Lys Ala Val Phe Phe Ala Gly Asn Glu Tyr Trp Ile Tyr Ser
                530                 535                 540

Ala Ser Thr Leu Glu Arg Gly Tyr Pro Lys Pro Leu Thr Ser Leu Gly
545                 550                 555                 560

Leu Pro Pro Asp Val Gln Arg Val Asp Ala Ala Phe Asn Trp Ser Lys
                565                 570                 575

Asn Lys Lys Thr Tyr Ile Phe Ala Gly Asp Lys Phe Trp Arg Tyr Asn
                580                 585                 590

Glu Val Lys Lys Lys Met Asp Pro Gly Phe Pro Lys Leu Ile Ala Asp
                595                 600                 605

Ala Trp Asn Ala Ile Pro Asp Asn Leu Asp Ala Val Val Asp Leu Gln
610                 615                 620

Gly Gly His Ser Tyr Phe Phe Lys Gly Ala Tyr Tyr Leu Lys Leu
625                 630                 635                 640

Glu Asn Gln Ser Leu Lys Ser Val Lys Phe Gly Ser Ile Lys Ser Asp
                645                 650                 655

Trp Leu Gly Cys
            660
```

<210> SEQ ID NO 5
<211> LENGTH: 711
<212> TYPE: PRT
<213> ORGANISM: Homo sapiens

<400> SEQUENCE: 5

```
Met Ser Leu Trp Gln Pro Leu Val Leu Val Leu Leu Val Leu Gly Cys
1               5                   10                  15

Cys Phe Ala Ala Pro Arg Gln Arg Gln Ser Thr Leu Val Leu Phe Pro
                20                  25                  30

Gly Asp Leu Arg Thr Asn Leu Thr Asp Arg Gln Leu Ala Glu Glu Tyr
                35                  40                  45

Leu Tyr Arg Tyr Gly Tyr Thr Arg Val Ala Glu Met Arg Gly Glu Ser
50                  55                  60

Lys Ser Leu Gly Pro Ala Leu Leu Leu Leu Gln Lys Gln Leu Ser Leu
65                  70                  75                  80

Pro Glu Thr Gly Glu Leu Asp Ser Ala Thr Leu Lys Ala Met Arg Thr
                85                  90                  95

Pro Arg Cys Gly Val Pro Asp Leu Gly Arg Phe Gln Thr Phe Glu Gly
                100                 105                 110

Asp Leu Lys Trp His His His Asn Ile Thr Tyr Trp Ile Gln Asn Tyr
                115                 120                 125

Ser Glu Asp Leu Pro Arg Ala Val Ile Asp Asp Ala Phe Ala Arg Ala
                130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
                165                 170                 175
```

```
Asp Gly Tyr Pro Phe Asp Gly Lys Asp Gly Leu Leu Ala His Ala Phe
            180                 185                 190

Pro Pro Gly Pro Gly Ile Gln Gly Asp Ala His Phe Asp Asp Asp Glu
        195                 200                 205

Leu Trp Ser Leu Gly Lys Gly Val Val Val Pro Thr Arg Phe Gly Asn
        210                 215                 220

Ala Asp Gly Ala Ala Cys His Phe Pro Phe Ile Phe Glu Gly Arg Ser
225                 230                 235                 240

Tyr Ser Ala Cys Thr Thr Asp Gly Arg Ser Asp Gly Leu Pro Trp Cys
                245                 250                 255

Ser Thr Thr Ala Asn Tyr Asp Thr Asp Arg Phe Gly Phe Cys Pro
            260                 265                 270

Ser Glu Arg Leu Tyr Thr Gln Asp Gly Asn Ala Asp Gly Lys Pro Cys
        275                 280                 285

Gln Phe Pro Phe Ile Phe Gln Gly Gln Ser Tyr Ser Ala Cys Thr Thr
        290                 295                 300

Asp Gly Arg Ser Asp Gly Tyr Arg Trp Cys Ala Thr Thr Ala Asn Tyr
305                 310                 315                 320

Asp Arg Asp Lys Leu Phe Gly Phe Cys Pro Thr Arg Ala Asp Ser Thr
                325                 330                 335

Val Met Gly Gly Asn Ser Ala Gly Glu Leu Cys Val Phe Pro Phe Thr
            340                 345                 350

Phe Leu Gly Lys Glu Tyr Ser Thr Cys Thr Ser Glu Gly Arg Gly Asp
        355                 360                 365

Gly Arg Leu Trp Cys Ala Thr Thr Ser Asn Phe Asp Ser Asp Lys Lys
        370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
                405                 410                 415

Ala Leu Met Tyr Pro Met Tyr Arg Phe Thr Glu Gly Pro Pro Leu His
            420                 425                 430

Lys Asp Asp Val Asn Gly Ile Arg His Leu Tyr Gly Pro Arg Pro Glu
        435                 440                 445

Pro Glu Pro Arg Pro Pro Thr Thr Thr Pro Gln Pro Thr Ala Pro
        450                 455                 460

Pro Thr Val Cys Pro Thr Gly Pro Pro Thr Val His Pro Ser Glu Arg
465                 470                 475                 480

Pro Thr Ala Gly Pro Thr Gly Pro Pro Ser Ala Gly Pro Thr Gly Pro
                485                 490                 495

Pro Thr Ala Gly Pro Ser Thr Ala Thr Thr Val Pro Leu Ser Pro Val
            500                 505                 510

Asp Asp Ala Cys Asn Val Asn Ile Phe Asp Ala Ile Ala Glu Ile Gly
        515                 520                 525

Pro Ala Gly Glu Asn Gln Leu Tyr Leu Phe Lys Asp Gly Lys Tyr Trp
        530                 535                 540

Arg Phe Ser Glu Gly Arg Gly Ser Arg Pro Gln Gly Pro Phe Leu Ile
545                 550                 555                 560

Ala Asp Lys Trp Pro Ala Leu Pro Arg Lys Leu Asp Ser Val Phe Glu
                565                 570                 575

Glu Arg Leu Ser Lys Lys Leu Phe Phe Phe Ser Gly Arg Gln Val Trp
            580                 585                 590

Val Tyr Thr Gly Ala Ser Val Leu Gly Pro Arg Arg Leu Asp Lys Leu
        595                 600                 605
```

Gly Leu Gly Ala Asp Val Ala Gln Val Thr Gly Ala Leu Arg Ser Gly
    610                 615                 620

Arg Gly Lys Met Leu Leu Phe Ser Gly Arg Arg Leu Trp Arg Phe Asp
625                 630                 635                 640

Val Lys Ala Gln Met Val Asp Pro Arg Ser Ala Ser Glu Val Asp Arg
                645                 650                 655

Met Phe Pro Gly Val Pro Leu Asp Thr His Asp Val Phe Gln Tyr Arg
                660                 665                 670

Glu Lys Ala Tyr Phe Cys Gln Asp Arg Phe Tyr Trp Arg Val Ser Ser
                675                 680                 685

Arg Ser Glu Leu Asn Gln Val Asp Gln Val Gly Tyr Val Thr Tyr Asp
                690                 695                 700

Ile Leu Gln Cys Pro Glu Asp
705                 710

<210> SEQ ID NO 6
<211> LENGTH: 508
<212> TYPE: PRT
<213> ORGANISM: Homo sapiens

<400> SEQUENCE: 6

Met Asn Cys Gln Gln Leu Trp Leu Gly Phe Leu Leu Pro Met Thr Val
1               5                   10                  15

Ser Gly Arg Val Leu Gly Leu Ala Glu Val Ala Pro Val Asp Tyr Leu
                20                  25                  30

Ser Gln Tyr Gly Tyr Leu Gln Lys Pro Leu Gly Ser Asn Asn Phe
            35                  40                  45

Lys Pro Glu Asp Ile Thr Glu Ala Leu Arg Ala Phe Gln Glu Ala Ser
    50                  55                  60

Glu Leu Pro Val Ser Gly Gln Leu Asp Asp Ala Thr Arg Ala Arg Met
65                  70                  75                  80

Arg Gln Pro Arg Cys Gly Leu Glu Asp Pro Phe Asn Gln Lys Thr Leu
                85                  90                  95

Lys Tyr Leu Leu Leu Gly Arg Trp Arg Lys Lys His Leu Thr Phe Arg
                100                 105                 110

Ile Leu Asn Leu Pro Ser Thr Leu Pro Pro His Thr Ala Arg Ala Ala
            115                 120                 125

Leu Arg Gln Ala Phe Gln Asp Trp Ser Asn Val Ala Pro Leu Thr Phe
130                 135                 140

Gln Glu Val Gln Ala Gly Ala Ala Asp Ile Arg Leu Ser Phe His Gly
145                 150                 155                 160

Arg Gln Ser Ser Tyr Cys Ser Asn Thr Phe Asp Gly Pro Gly Arg Val
                165                 170                 175

Leu Ala His Ala Asp Ile Pro Glu Leu Gly Ser Val His Phe Asp Glu
            180                 185                 190

Asp Glu Phe Trp Thr Glu Gly Thr Tyr Arg Gly Val Asn Leu Arg Ile
        195                 200                 205

Ile Ala Ala His Glu Val Gly His Ala Leu Gly Leu Gly His Ser Arg
    210                 215                 220

Tyr Ser Gln Ala Leu Met Ala Pro Val Tyr Glu Gly Tyr Arg Pro His
225                 230                 235                 240

Phe Lys Leu His Pro Asp Asp Val Ala Gly Ile Gln Ala Leu Tyr Gly
                245                 250                 255

Lys Lys Ser Pro Val Ile Arg Asp Glu Glu Glu Glu Thr Glu Leu
                260                 265                 270

```
Pro Thr Val Pro Pro Val Pro Thr Glu Pro Ser Pro Met Pro Asp Pro
        275                 280                 285

Cys Ser Ser Glu Leu Asp Ala Met Met Leu Gly Pro Arg Gly Lys Thr
        290                 295                 300

Tyr Ala Phe Lys Gly Asp Tyr Val Trp Thr Val Ser Asp Ser Gly Pro
305                 310                 315                 320

Gly Pro Leu Phe Arg Val Ser Ala Leu Trp Glu Gly Leu Pro Gly Asn
            325                 330                 335

Leu Asp Ala Ala Val Tyr Ser Pro Arg Thr Gln Trp Ile His Phe Phe
            340                 345                 350

Lys Gly Asp Lys Val Trp Arg Tyr Ile Asn Phe Lys Met Ser Pro Gly
        355                 360                 365

Phe Pro Lys Lys Leu Asn Arg Val Glu Pro Asn Leu Asp Ala Ala Leu
        370                 375                 380

Tyr Trp Pro Leu Asn Gln Lys Val Phe Leu Phe Lys Gly Ser Gly Tyr
385                 390                 395                 400

Trp Gln Trp Asp Glu Leu Ala Arg Thr Asp Phe Ser Ser Tyr Pro Lys
            405                 410                 415

Pro Ile Lys Gly Leu Phe Thr Gly Val Pro Asn Gln Pro Ser Ala Ala
            420                 425                 430

Met Ser Trp Gln Asp Gly Arg Val Tyr Phe Phe Lys Gly Lys Val Tyr
        435                 440                 445

Trp Arg Leu Asn Gln Gln Leu Arg Val Glu Lys Gly Tyr Pro Arg Asn
        450                 455                 460

Ile Ser His Asn Trp Met His Cys Arg Pro Arg Thr Ile Asp Thr Thr
465                 470                 475                 480

Pro Ser Gly Gly Asn Thr Thr Pro Ser Gly Thr Gly Ile Thr Leu Asp
            485                 490                 495

Thr Thr Leu Ser Ala Thr Glu Thr Thr Phe Glu Tyr
            500                 505

<210> SEQ ID NO 7
<211> LENGTH: 604
<212> TYPE: PRT
<213> ORGANISM: Homo sapiens

<400> SEQUENCE: 7

Met Arg Arg Arg Ala Ala Arg Gly Pro Gly Pro Pro Pro Pro Gly Pro
1               5                   10                  15

Gly Leu Ser Arg Leu Pro Leu Pro Leu Leu Leu Leu Ala Leu Gly
            20                  25                  30

Thr Arg Gly Gly Cys Ala Ala Pro Ala Pro Ala Pro Arg Ala Glu Asp
        35                  40                  45

Leu Ser Leu Gly Val Glu Trp Leu Ser Arg Phe Gly Tyr Leu Pro Pro
    50                  55                  60

Ala Asp Pro Thr Thr Gly Gln Leu Gln Thr Gln Glu Glu Leu Ser Lys
65              70                  75                  80

Ala Ile Thr Ala Met Gln Gln Phe Gly Gly Leu Glu Ala Thr Gly Ile
                85                  90                  95

Leu Asp Glu Ala Thr Leu Ala Leu Met Lys Thr Pro Arg Cys Ser Leu
            100                 105                 110

Pro Asp Leu Pro Val Leu Thr Gln Ala Arg Arg Arg Arg Gln Ala Pro
        115                 120                 125

Ala Pro Thr Lys Trp Asn Lys Arg Asn Leu Ser Trp Arg Val Arg Thr
    130                 135                 140
```

```
Phe Pro Arg Asp Ser Pro Leu Gly His Asp Thr Val Arg Ala Leu Met
145                 150                 155                 160

Tyr Tyr Ala Leu Lys Val Trp Ser Asp Ile Ala Pro Leu Asn Phe His
            165                 170                 175

Glu Val Ala Gly Ser Ala Ala Asp Ile Gln Ile Asp Phe Ser Lys Ala
        180                 185                 190

Asp His Asn Asp Gly Tyr Pro Phe Asp Gly Pro Gly Gly Thr Val Ala
    195                 200                 205

His Ala Phe Phe Pro Gly His His Thr Ala Gly Asp Thr His Phe
210                 215                 220

Asp Asp Asp Glu Ala Trp Thr Phe Arg Ser Ser Asp Ala His Gly Met
225                 230                 235                 240

Asp Leu Phe Ala Val Ala Val His Glu Phe Gly His Ala Ile Gly Leu
                245                 250                 255

Ser His Val Ala Ala Ala His Ser Ile Met Arg Pro Tyr Tyr Gln Gly
        260                 265                 270

Pro Val Gly Asp Pro Leu Arg Tyr Gly Leu Pro Tyr Glu Asp Lys Val
    275                 280                 285

Arg Val Trp Gln Leu Tyr Gly Val Arg Glu Ser Val Ser Pro Thr Ala
290                 295                 300

Gln Pro Glu Glu Pro Pro Leu Leu Pro Glu Pro Pro Asp Asn Arg Ser
305                 310                 315                 320

Ser Ala Pro Pro Arg Lys Asp Val Pro His Arg Cys Ser Thr His Phe
                325                 330                 335

Asp Ala Val Ala Gln Ile Arg Gly Glu Ala Phe Phe Phe Lys Gly Lys
            340                 345                 350

Tyr Phe Trp Arg Leu Thr Arg Asp Arg His Leu Val Ser Leu Gln Pro
        355                 360                 365

Ala Gln Met His Arg Phe Trp Arg Gly Leu Pro Leu His Leu Asp Ser
    370                 375                 380

Val Asp Ala Val Tyr Glu Arg Thr Ser Asp His Lys Ile Val Phe Phe
385                 390                 395                 400

Lys Gly Asp Arg Tyr Trp Val Phe Lys Asp Asn Asn Val Glu Glu Gly
                405                 410                 415

Tyr Pro Arg Pro Val Ser Asp Phe Ser Leu Pro Pro Gly Gly Ile Asp
            420                 425                 430

Ala Ala Phe Ser Trp Ala His Asn Asp Arg Thr Tyr Phe Phe Lys Asp
        435                 440                 445

Gln Leu Tyr Trp Arg Tyr Asp Asp His Thr Arg His Met Asp Pro Gly
    450                 455                 460

Tyr Pro Ala Gln Ser Pro Leu Trp Arg Gly Val Pro Ser Thr Leu Asp
465                 470                 475                 480

Asp Ala Met Arg Trp Ser Asp Gly Ala Ser Tyr Phe Phe Arg Gly Gln
                485                 490                 495

Glu Tyr Trp Lys Val Leu Asp Gly Glu Leu Glu Val Ala Pro Gly Tyr
            500                 505                 510

Pro Gln Ser Thr Ala Arg Asp Trp Leu Val Cys Gly Asp Ser Gln Ala
        515                 520                 525

Asp Gly Ser Val Ala Ala Gly Val Asp Ala Ala Glu Gly Pro Arg Ala
    530                 535                 540

Pro Pro Gly Gly Gln His Asp Gln Ser Arg Ser Glu Asp Gly Tyr Glu
545                 550                 555                 560

Val Cys Ser Cys Thr Ser Gly Ala Ser Ser Pro Pro Gly Ala Pro Gly
```

```
                    565                 570                 575
Pro Leu Val Ala Ala Thr Met Leu Leu Leu Pro Pro Leu Ser Pro
                580                 585                 590
Gly Ala Leu Trp Thr Ala Ala Gln Ala Leu Thr Leu
            595                 600

<210> SEQ ID NO 8
<211> LENGTH: 669
<212> TYPE: PRT
<213> ORGANISM: Homo sapiens

<400> SEQUENCE: 8

Met Gly Ser Asp Pro Ser Ala Pro Gly Arg Pro Gly Trp Thr Gly Ser
1               5                   10                  15
Leu Leu Gly Asp Arg Glu Glu Ala Ala Arg Pro Arg Leu Leu Pro Leu
            20                  25                  30
Leu Leu Val Leu Leu Gly Cys Leu Gly Leu Gly Val Ala Ala Glu Asp
        35                  40                  45
Ala Glu Val His Ala Glu Asn Trp Leu Arg Leu Tyr Gly Tyr Leu Pro
    50                  55                  60
Gln Pro Ser Arg His Met Ser Thr Met Arg Ser Ala Gln Ile Leu Ala
65                  70                  75                  80
Ser Ala Leu Ala Glu Met Gln Arg Phe Tyr Gly Ile Pro Val Thr Gly
                85                  90                  95
Val Leu Asp Glu Glu Thr Lys Glu Trp Met Lys Arg Pro Arg Cys Gly
            100                 105                 110
Val Pro Asp Gln Phe Gly Val Arg Val Lys Ala Asn Leu Arg Arg Arg
        115                 120                 125
Arg Lys Arg Tyr Ala Leu Thr Gly Arg Lys Trp Asn Asn His His Leu
    130                 135                 140
Thr Phe Ser Ile Gln Asn Tyr Thr Glu Lys Leu Gly Trp Tyr His Ser
145                 150                 155                 160
Met Glu Ala Val Arg Arg Ala Phe Arg Val Trp Glu Gln Ala Thr Pro
                165                 170                 175
Leu Val Phe Gln Glu Val Pro Tyr Glu Asp Ile Arg Leu Arg Arg Gln
            180                 185                 190
Lys Glu Ala Asp Ile Met Val Leu Phe Ala Ser Gly Phe His Gly Asp
        195                 200                 205
Ser Ser Pro Phe Asp Gly Thr Gly Gly Phe Leu Ala His Ala Tyr Phe
    210                 215                 220
Pro Gly Pro Gly Leu Gly Gly Asp Thr His Phe Asp Ala Asp Glu Pro
225                 230                 235                 240
Trp Thr Phe Ser Ser Thr Asp Leu His Gly Asn Asn Leu Phe Leu Val
                245                 250                 255
Ala Val His Glu Leu Gly His Ala Leu Gly Leu Glu His Ser Ser Asn
            260                 265                 270
Pro Asn Ala Ile Met Ala Pro Phe Tyr Gln Trp Lys Asp Val Asp Asn
        275                 280                 285
Phe Lys Leu Pro Glu Asp Asp Leu Arg Gly Ile Gln Gln Leu Tyr Gly
    290                 295                 300
Thr Pro Asp Gly Gln Pro Gln Pro Thr Gln Pro Leu Pro Thr Val Thr
305                 310                 315                 320
Pro Arg Arg Pro Gly Arg Pro Asp His Arg Pro Pro Arg Pro Pro Gln
                325                 330                 335
Pro Pro Pro Pro Gly Gly Lys Pro Glu Arg Pro Pro Lys Pro Gly Pro
```

```
            340                 345                 350
Pro Val Gln Pro Arg Ala Thr Glu Arg Pro Asp Gln Tyr Gly Pro Asn
            355                 360                 365
Ile Cys Asp Gly Asp Phe Asp Thr Val Ala Met Leu Arg Gly Glu Met
            370                 375                 380
Phe Val Phe Lys Gly Arg Trp Phe Trp Arg Val Arg His Asn Arg Val
385                 390                 395                 400
Leu Asp Asn Tyr Pro Met Pro Ile Gly His Phe Trp Arg Gly Leu Pro
                405                 410                 415
Gly Asp Ile Ser Ala Ala Tyr Glu Arg Gln Asp Gly Arg Phe Val Phe
            420                 425                 430
Phe Lys Gly Asp Arg Tyr Trp Leu Phe Arg Glu Ala Asn Leu Glu Pro
            435                 440                 445
Gly Tyr Pro Gln Pro Leu Thr Ser Tyr Gly Leu Gly Ile Pro Tyr Asp
            450                 455                 460
Arg Ile Asp Thr Ala Ile Trp Trp Glu Pro Thr Gly His Thr Phe Phe
465                 470                 475                 480
Phe Gln Glu Asp Arg Tyr Trp Arg Phe Asn Glu Glu Thr Gln Arg Gly
                485                 490                 495
Asp Pro Gly Tyr Pro Lys Pro Ile Ser Val Trp Gln Gly Ile Pro Ala
            500                 505                 510
Ser Pro Lys Gly Ala Phe Leu Ser Asn Asp Ala Ala Tyr Thr Tyr Phe
            515                 520                 525
Tyr Lys Gly Thr Lys Tyr Trp Lys Phe Asp Asn Glu Arg Leu Arg Met
            530                 535                 540
Glu Pro Gly Tyr Pro Lys Ser Ile Leu Arg Asp Phe Met Gly Cys Gln
545                 550                 555                 560
Glu His Val Glu Pro Gly Pro Arg Trp Pro Asp Val Ala Arg Pro Pro
                565                 570                 575
Phe Asn Pro His Gly Gly Ala Glu Pro Gly Ala Asp Ser Ala Glu Gly
            580                 585                 590
Asp Val Gly Asp Gly Asp Gly Asp Phe Gly Ala Gly Val Asn Lys Asp
            595                 600                 605
Gly Gly Ser Arg Val Val Gln Met Glu Glu Val Ala Arg Thr Val
            610                 615                 620
Asn Val Val Met Val Leu Val Pro Leu Leu Leu Leu Leu Cys Val Leu
625                 630                 635                 640
Gly Leu Thr Tyr Ala Leu Val Gln Met Gln Arg Lys Gly Ala Pro Arg
                645                 650                 655
Val Leu Leu Tyr Cys Lys Arg Ser Leu Gln Glu Trp Val
            660                 665

<210> SEQ ID NO 9
<211> LENGTH: 483
<212> TYPE: PRT
<213> ORGANISM: Homo sapiens

<400> SEQUENCE: 9

Met Lys Val Leu Pro Ala Ser Gly Leu Ala Val Phe Leu Ile Met Ala
1               5                   10                  15
Leu Thr Phe Ser Thr Ala Ala Pro Ser Leu Val Ala Ala Ser Pro Arg
            20                  25                  30
Thr Trp Arg Asn Asn Tyr Arg Leu Ala Gln Ala Tyr Leu Asp Lys Tyr
            35                  40                  45
Tyr Thr Asn Lys Glu Gly His Gln Ile Gly Glu Met Val Ala Arg Gly
```

-continued

```
              50                  55                  60
Ser Asn Ser Met Ile Arg Lys Ile Lys Glu Leu Gln Ala Phe Phe Gly
 65                  70                  75                  80

Leu Gln Val Thr Gly Lys Leu Asp Gln Thr Thr Met Asn Val Ile Lys
                 85                  90                  95

Lys Pro Arg Cys Gly Val Pro Asp Val Ala Asn Tyr Arg Leu Phe Pro
                100                 105                 110

Gly Glu Pro Lys Trp Lys Asn Thr Leu Thr Tyr Arg Ile Ser Lys
            115                 120                 125

Tyr Thr Pro Ser Met Ser Ser Val Glu Val Asp Lys Ala Val Glu Met
            130                 135                 140

Ala Leu Gln Ala Trp Ser Ser Ala Val Pro Leu Ser Phe Val Arg Ile
145                 150                 155                 160

Asn Ser Gly Glu Ala Asp Ile Met Ile Ser Phe Glu Asn Gly Asp His
                165                 170                 175

Gly Asp Ser Tyr Pro Phe Asp Gly Pro Arg Gly Thr Leu Ala His Ala
            180                 185                 190

Phe Ala Pro Gly Glu Gly Leu Gly Gly Asp Thr His Phe Asp Asn Ala
            195                 200                 205

Glu Lys Trp Thr Met Gly Thr Asn Gly Phe Asn Leu Phe Thr Val Ala
210                 215                 220

Ala His Glu Phe Gly His Ala Leu Gly Leu Ala His Ser Thr Asp Pro
225                 230                 235                 240

Ser Ala Leu Met Tyr Pro Thr Tyr Lys Tyr Lys Asn Pro Tyr Gly Phe
                245                 250                 255

His Leu Pro Lys Asp Asp Val Lys Gly Ile Gln Ala Leu Tyr Gly Pro
            260                 265                 270

Arg Lys Val Phe Leu Gly Lys Pro Thr Leu Pro His Ala Pro His His
            275                 280                 285

Lys Pro Ser Ile Pro Asp Leu Cys Asp Ser Ser Ser Phe Asp Ala
290                 295                 300

Val Thr Met Leu Gly Lys Glu Leu Leu Leu Phe Lys Asp Arg Ile Phe
305                 310                 315                 320

Trp Arg Arg Gln Val His Leu Arg Thr Gly Ile Arg Pro Ser Thr Ile
                325                 330                 335

Thr Ser Ser Phe Pro Gln Leu Met Ser Asn Val Asp Ala Ala Tyr Glu
            340                 345                 350

Val Ala Glu Arg Gly Thr Ala Tyr Phe Phe Lys Gly Pro His Tyr Trp
            355                 360                 365

Ile Thr Arg Gly Phe Gln Met Gln Gly Pro Pro Arg Thr Ile Tyr Asp
370                 375                 380

Phe Gly Phe Pro Arg His Val Gln Gln Ile Asp Ala Ala Val Tyr Leu
385                 390                 395                 400

Arg Glu Pro Gln Lys Thr Leu Phe Phe Val Gly Asp Glu Tyr Tyr Ser
                405                 410                 415

Tyr Asp Glu Arg Lys Arg Lys Met Glu Lys Asp Tyr Pro Lys Asn Thr
            420                 425                 430

Glu Glu Glu Phe Ser Gly Val Asn Gly Gln Ile Asp Ala Ala Val Glu
            435                 440                 445

Leu Asn Gly Tyr Ile Tyr Phe Phe Ser Gly Pro Lys Thr Tyr Lys Tyr
450                 455                 460

Asp Thr Glu Lys Glu Asp Val Val Ser Val Val Lys Ser Ser Ser Trp
465                 470                 475                 480
```

Ile Gly Cys

<210> SEQ ID NO 10
<211> LENGTH: 469
<212> TYPE: PRT
<213> ORGANISM: Homo sapiens

<400> SEQUENCE: 10

Met His Ser Phe Pro Pro Leu Leu Leu Leu Phe Trp Gly Val Val
1               5                   10                  15

Ser His Ser Phe Pro Ala Thr Leu Glu Thr Gln Glu Gln Asp Val Asp
                20                  25                  30

Leu Val Gln Lys Tyr Leu Glu Lys Tyr Tyr Asn Leu Lys Asn Asp Gly
                35                  40                  45

Arg Gln Val Glu Lys Arg Arg Asn Ser Gly Pro Val Val Glu Lys Leu
50                      55                  60

Lys Gln Met Gln Glu Phe Phe Gly Leu Lys Val Thr Gly Lys Pro Asp
65                  70                  75                  80

Ala Glu Thr Leu Lys Val Met Lys Gln Pro Arg Cys Gly Val Pro Asp
                85                  90                  95

Val Ala Gln Phe Val Leu Thr Glu Gly Asn Pro Arg Trp Glu Gln Thr
                100                 105                 110

His Leu Thr Tyr Arg Ile Glu Asn Tyr Thr Pro Asp Leu Pro Arg Ala
                115                 120                 125

Asp Val Asp His Ala Ile Glu Lys Ala Phe Gln Leu Trp Ser Asn Val
                130                 135                 140

Thr Pro Leu Thr Phe Thr Lys Val Ser Glu Gly Gln Ala Asp Ile Met
145                 150                 155                 160

Ile Ser Phe Val Arg Gly Asp His Arg Asp Asn Ser Pro Phe Asp Gly
                165                 170                 175

Pro Gly Gly Asn Leu Ala His Ala Phe Gln Pro Gly Pro Gly Ile Gly
                180                 185                 190

Gly Asp Ala His Phe Asp Glu Asp Glu Arg Trp Thr Asn Asn Phe Arg
                195                 200                 205

Glu Tyr Asn Leu His Arg Val Ala Ala His Glu Leu Gly His Ser Leu
210                 215                 220

Gly Leu Ser His Ser Thr Asp Ile Gly Ala Leu Met Tyr Pro Ser Tyr
225                 230                 235                 240

Thr Phe Ser Gly Asp Val Gln Leu Ala Gln Asp Asp Ile Asp Gly Ile
                245                 250                 255

Gln Ala Ile Tyr Gly Arg Ser Gln Asn Pro Val Gln Pro Ile Gly Pro
                260                 265                 270

Gln Thr Pro Lys Ala Cys Asp Ser Lys Leu Thr Phe Asp Ala Ile Thr
                275                 280                 285

Thr Ile Arg Gly Glu Val Met Phe Phe Lys Asp Arg Phe Tyr Met Arg
                290                 295                 300

Thr Asn Pro Phe Tyr Pro Glu Val Glu Leu Asn Phe Ile Ser Val Phe
305                 310                 315                 320

Trp Pro Gln Leu Pro Asn Gly Leu Glu Ala Ala Tyr Glu Phe Ala Asp
                325                 330                 335

Arg Asp Glu Val Arg Phe Phe Lys Gly Asn Lys Tyr Trp Ala Val Gln
                340                 345                 350

Gly Gln Asn Val Leu His Gly Tyr Pro Lys Asp Ile Tyr Ser Ser Phe
                355                 360                 365

Gly Phe Pro Arg Thr Val Lys His Ile Asp Ala Ala Leu Ser Glu Glu

```
              370                 375                 380
Asn Thr Gly Lys Thr Tyr Phe Val Ala Asn Lys Tyr Trp Arg Tyr
385                 390                 395                 400

Asp Glu Tyr Lys Arg Ser Met Asp Pro Gly Tyr Pro Lys Met Ile Ala
                    405                 410                 415

His Asp Phe Pro Gly Ile Gly His Lys Val Asp Ala Val Phe Met Lys
                    420                 425                 430

Asp Gly Phe Phe Tyr Phe Phe His Gly Thr Arg Gln Tyr Lys Phe Asp
                    435                 440                 445

Pro Lys Thr Lys Arg Ile Leu Thr Leu Gln Lys Ala Asn Ser Trp Phe
                    450                 455                 460

Asn Cys Arg Lys Asn
465

<210> SEQ ID NO 11
<211> LENGTH: 647
<212> TYPE: PRT
<213> ORGANISM: Homo sapiens

<400> SEQUENCE: 11

Met Pro Arg Ser Arg Gly Gly Arg Ala Ala Pro Gly Pro Pro Pro
1               5                   10                  15

Pro Pro Pro Pro Gly Gln Ala Pro Arg Trp Ser Arg Trp Arg Val Pro
                    20                  25                  30

Gly Arg Leu Leu Leu Leu Leu Leu Pro Ala Leu Cys Cys Leu Pro Gly
                35                  40                  45

Ala Ala Arg Ala Ala Ala Ala Ala Gly Ala Gly Asn Arg Ala Ala
50                  55                  60

Val Ala Val Ala Val Ala Arg Ala Asp Glu Ala Glu Ala Pro Phe Ala
65                  70                  75                  80

Gly Gln Asn Trp Leu Lys Ser Tyr Gly Tyr Leu Leu Pro Tyr Asp Ser
                85                  90                  95

Arg Ala Ser Ala Leu His Ser Ala Lys Ala Leu Gln Ser Ala Val Ser
                100                 105                 110

Thr Met Gln Gln Phe Tyr Gly Ile Pro Val Thr Gly Val Leu Asp Gln
                115                 120                 125

Thr Thr Ile Glu Trp Met Lys Lys Pro Arg Cys Gly Val Pro Asp His
130                 135                 140

Pro His Leu Ser Arg Arg Arg Asn Lys Arg Tyr Ala Leu Thr Gly
145                 150                 155                 160

Gln Lys Trp Arg Gln Lys His Ile Thr Tyr Ser Ile His Asn Tyr Thr
                165                 170                 175

Pro Lys Val Gly Glu Leu Asp Thr Arg Lys Ala Ile Arg Gln Ala Phe
                180                 185                 190

Asp Val Trp Gln Lys Val Thr Pro Leu Thr Phe Glu Glu Val Pro Tyr
                195                 200                 205

His Glu Ile Lys Ser Asp Arg Lys Glu Ala Asp Ile Met Ile Phe Phe
                210                 215                 220

Ala Ser Gly Phe His Gly Asp Ser Ser Pro Phe Asp Gly Glu Gly Gly
225                 230                 235                 240

Phe Leu Ala His Ala Tyr Phe Pro Gly Pro Gly Ile Gly Gly Asp Thr
                245                 250                 255

His Phe Asp Ser Asp Glu Pro Trp Thr Leu Gly Asn Ala Asn His Asp
                260                 265                 270

Gly Asn Asp Leu Phe Leu Val Ala Val His Glu Leu Gly His Ala Leu
```

275                 280                 285
Gly Leu Glu His Ser Ser Asp Pro Ser Ala Ile Met Ala Pro Phe Tyr
            290                 295                 300
Gln Tyr Met Glu Thr His Asn Phe Lys Leu Pro Gln Asp Asp Leu Gln
305                 310                 315                 320
Gly Ile Gln Lys Ile Tyr Gly Pro Pro Ala Glu Pro Leu Glu Pro Thr
                325                 330                 335
Arg Pro Leu Pro Thr Leu Pro Val Arg Arg Ile His Ser Pro Ser Glu
            340                 345                 350
Arg Lys His Glu Arg Gln Pro Arg Pro Arg Pro Pro Leu Gly Asp
        355                 360                 365
Arg Pro Ser Thr Pro Gly Thr Lys Pro Asn Ile Cys Asp Gly Asn Phe
        370                 375                 380
Asn Thr Val Ala Leu Phe Arg Gly Glu Met Phe Val Phe Lys Asp Arg
385                 390                 395                 400
Trp Phe Trp Arg Leu Arg Asn Asn Arg Val Gln Glu Gly Tyr Pro Met
                405                 410                 415
Gln Ile Glu Gln Phe Trp Lys Gly Leu Pro Ala Arg Ile Asp Ala Ala
            420                 425                 430
Tyr Glu Arg Ala Asp Gly Arg Phe Val Phe Lys Gly Asp Lys Tyr
        435                 440                 445
Trp Val Phe Lys Glu Val Thr Val Glu Pro Gly Tyr Pro His Ser Leu
        450                 455                 460
Gly Glu Leu Gly Ser Cys Leu Pro Arg Glu Gly Ile Asp Thr Ala Leu
465                 470                 475                 480
Arg Trp Glu Pro Val Gly Lys Thr Tyr Phe Phe Lys Gly Glu Arg Tyr
                485                 490                 495
Trp Arg Tyr Ser Glu Glu Arg Arg Ala Thr Asp Pro Gly Tyr Pro Lys
            500                 505                 510
Pro Ile Thr Val Trp Lys Gly Ile Pro Gln Ala Pro Gln Gly Ala Phe
        515                 520                 525
Ile Ser Lys Glu Gly Tyr Tyr Thr Tyr Phe Tyr Lys Gly Arg Asp Tyr
        530                 535                 540
Trp Lys Phe Asp Asn Gly Ile Asn Lys Leu Ser Val Glu Pro Gly Tyr
545                 550                 555                 560
Pro Arg Asn Ile Leu Arg Asp Trp Met Gly Cys Asn Gln Lys Glu Val
                565                 570                 575
Glu Arg Arg Lys Glu Arg Leu Pro Gln Asp Asp Val Asp Ile Met
            580                 585                 590
Val Thr Ile Asn Asp Val Pro Gly Ser Val Asn Ala Val Ala Val Val
        595                 600                 605
Ile Pro Cys Ile Leu Ser Leu Cys Ile Leu Val Leu Val Tyr Thr Ile
        610                 615                 620
Phe Gln Phe Lys Asn Lys Thr Gly Pro Gln Pro Val Thr Tyr Tyr Lys
625                 630                 635                 640
Arg Pro Val Gln Glu Trp Val
                645

<210> SEQ ID NO 12
<211> LENGTH: 562
<212> TYPE: PRT
<213> ORGANISM: Homo sapiens

<400> SEQUENCE: 12

Met Arg Leu Arg Leu Arg Leu Leu Ala Leu Leu Leu Leu Leu Leu Ala

-continued

```
1               5                   10                  15
Pro Pro Ala Arg Ala Pro Lys Pro Ser Ala Gln Asp Val Ser Leu Gly
            20                  25                  30

Val Asp Trp Leu Thr Arg Tyr Gly Tyr Leu Pro Pro His Pro Ala
            35                  40              45

Gln Ala Gln Leu Gln Ser Pro Glu Lys Leu Arg Asp Ala Ile Lys Val
50                      55                  60

Met Gln Arg Phe Ala Gly Leu Pro Glu Thr Gly Arg Met Asp Pro Gly
65                      70                  75                  80

Thr Val Ala Thr Met Arg Lys Pro Arg Cys Ser Leu Pro Asp Val Leu
                    85                  90                  95

Gly Val Ala Gly Leu Val Arg Arg Arg Arg Tyr Ala Leu Ser Gly
                100                 105                 110

Ser Val Trp Lys Lys Arg Thr Leu Thr Trp Arg Val Arg Ser Phe Pro
            115                 120                 125

Gln Ser Ser Gln Leu Ser Gln Glu Thr Val Arg Val Leu Met Ser Tyr
            130                 135                 140

Ala Leu Met Ala Trp Gly Met Glu Ser Gly Leu Thr Phe His Glu Val
145                     150                 155                 160

Asp Ser Pro Gln Gly Gln Glu Pro Asp Ile Leu Ile Asp Phe Ala Arg
                    165                 170                 175

Ala Phe His Gln Asp Ser Tyr Pro Phe Asp Gly Leu Gly Gly Thr Leu
                180                 185                 190

Ala His Ala Phe Phe Pro Gly Glu His Pro Ile Ser Gly Asp Thr His
                195                 200                 205

Phe Asp Asp Glu Glu Thr Trp Thr Phe Gly Ser Lys Asp Gly Glu Gly
    210                 215                 220

Thr Asp Leu Phe Ala Val Ala Val His Glu Phe Gly His Ala Leu Gly
225                     230                 235                 240

Leu Gly His Ser Ser Ala Pro Asn Ser Ile Met Arg Pro Phe Tyr Gln
                    245                 250                 255

Gly Pro Val Gly Asp Pro Asp Lys Tyr Arg Leu Ser Gln Asp Asp Arg
            260                 265                 270

Asp Gly Leu Gln Gln Leu Tyr Gly Lys Ala Pro Gln Thr Pro Tyr Asp
            275                 280                 285

Lys Pro Thr Arg Lys Pro Leu Ala Pro Pro Gln Pro Pro Ala Ser
            290                 295                 300

Pro Thr His Ser Pro Ser Phe Pro Ile Pro Asp Arg Cys Glu Gly Asn
305                     310                 315                 320

Phe Asp Ala Ile Ala Asn Ile Arg Gly Glu Thr Phe Phe Lys Gly
                    325                 330                 335

Pro Trp Phe Trp Arg Leu Gln Pro Ser Gly Gln Leu Val Ser Pro Arg
            340                 345                 350

Pro Ala Arg Leu His Arg Phe Trp Glu Gly Leu Pro Ala Gln Val Arg
            355                 360                 365

Val Val Gln Ala Ala Tyr Ala Arg His Arg Asp Gly Arg Ile Leu Leu
370                     375                 380

Phe Ser Gly Pro Gln Phe Trp Val Phe Gln Asp Arg Gln Leu Glu Gly
385                     390                 395                 400

Gly Ala Arg Pro Leu Thr Glu Leu Gly Leu Pro Pro Gly Glu Glu Val
                    405                 410                 415

Asp Ala Val Phe Ser Trp Pro Gln Asn Gly Lys Thr Tyr Leu Val Arg
                    420                 425                 430
```

```
Gly Arg Gln Tyr Trp Arg Tyr Asp Glu Ala Ala Arg Pro Asp Pro
            435                 440                 445

Gly Tyr Pro Arg Asp Leu Ser Leu Trp Glu Gly Ala Pro Ser Pro
        450                 455                 460

Asp Asp Val Thr Val Ser Asn Ala Gly Asp Thr Tyr Phe Phe Lys Gly
465                 470                 475                 480

Ala His Tyr Trp Arg Phe Pro Lys Asn Ser Ile Lys Thr Glu Pro Asp
                485                 490                 495

Ala Pro Gln Pro Met Gly Pro Asn Trp Leu Asp Cys Pro Ala Pro Ser
            500                 505                 510

Ser Gly Pro Arg Ala Pro Arg Pro Lys Ala Thr Pro Val Ser Glu
        515                 520                 525

Thr Cys Asp Cys Gln Cys Glu Leu Asn Gln Ala Ala Gly Arg Trp Pro
530                 535                 540

Ala Pro Ile Pro Leu Leu Leu Pro Leu Leu Val Gly Gly Val Ala
545                 550                 555                 560

Ser Arg

<210> SEQ ID NO 13
<211> LENGTH: 477
<212> TYPE: PRT
<213> ORGANISM: Homo sapiens

<400> SEQUENCE: 13

Met Lys Ser Leu Pro Ile Leu Leu Leu Cys Val Ala Val Cys Ser
1               5                   10                  15

Ala Tyr Pro Leu Asp Gly Ala Ala Arg Gly Glu Asp Thr Ser Met Asn
            20                  25                  30

Leu Val Gln Lys Tyr Leu Glu Asn Tyr Tyr Asp Leu Lys Lys Asp Val
        35                  40                  45

Lys Gln Phe Val Arg Arg Lys Asp Ser Gly Pro Val Val Lys Lys Ile
50                  55                  60

Arg Glu Met Gln Lys Phe Leu Gly Leu Glu Val Thr Gly Lys Leu Asp
65                  70                  75                  80

Ser Asp Thr Leu Glu Val Met Arg Lys Pro Arg Cys Gly Val Pro Asp
                85                  90                  95

Val Gly His Phe Arg Thr Phe Pro Gly Ile Pro Lys Trp Arg Lys Thr
            100                 105                 110

His Leu Thr Tyr Arg Ile Val Asn Tyr Thr Pro Asp Leu Pro Lys Asp
        115                 120                 125

Ala Val Asp Ser Ala Val Glu Lys Ala Leu Lys Val Trp Glu Glu Val
130                 135                 140

Thr Pro Leu Thr Phe Ser Arg Leu Tyr Glu Gly Glu Ala Asp Ile Met
145                 150                 155                 160

Ile Ser Phe Ala Val Arg Glu His Gly Asp Phe Tyr Pro Phe Asp Gly
                165                 170                 175

Pro Gly Asn Val Leu Ala His Ala Tyr Ala Pro Gly Pro Gly Ile Asn
            180                 185                 190

Gly Asp Ala His Phe Asp Asp Glu Gln Trp Thr Lys Asp Thr Thr
        195                 200                 205

Gly Thr Asn Leu Phe Leu Val Ala Ala His Glu Ile Gly His Ser Leu
210                 215                 220

Gly Leu Phe His Ser Ala Asn Thr Glu Ala Leu Met Tyr Pro Leu Tyr
225                 230                 235                 240

His Ser Leu Thr Asp Leu Thr Arg Phe Arg Leu Ser Gln Asp Asp Ile
```

```
                245                 250                 255
Asn Gly Ile Gln Ser Leu Tyr Gly Pro Pro Asp Ser Pro Glu Thr
            260                 265                 270

Pro Leu Val Pro Thr Glu Pro Val Pro Glu Pro Gly Thr Pro Ala
        275                 280                 285

Asn Cys Asp Pro Ala Leu Ser Phe Asp Ala Val Ser Thr Leu Arg Gly
        290                 295                 300

Glu Ile Leu Ile Phe Lys Asp Arg His Phe Trp Arg Lys Ser Leu Arg
305                 310                 315                 320

Lys Leu Glu Pro Glu Leu His Leu Ile Ser Ser Phe Trp Pro Ser Leu
                325                 330                 335

Pro Ser Gly Val Asp Ala Ala Tyr Glu Val Thr Ser Lys Asp Leu Val
            340                 345                 350

Phe Ile Phe Lys Gly Asn Gln Phe Trp Ala Ile Arg Gly Asn Glu Val
        355                 360                 365

Arg Ala Gly Tyr Pro Arg Gly Ile His Thr Leu Gly Phe Pro Pro Thr
        370                 375                 380

Val Arg Lys Ile Asp Ala Ala Ile Ser Asp Lys Glu Lys Asn Lys Thr
385                 390                 395                 400

Tyr Phe Phe Val Glu Asp Lys Tyr Trp Arg Phe Asp Glu Lys Arg Asn
                405                 410                 415

Ser Met Glu Pro Gly Phe Pro Lys Gln Ile Ala Glu Asp Phe Pro Gly
            420                 425                 430

Ile Asp Ser Lys Ile Asp Ala Val Phe Glu Glu Phe Gly Phe Phe Tyr
        435                 440                 445

Phe Phe Thr Gly Ser Ser Gln Leu Glu Phe Asp Pro Asn Ala Lys Lys
        450                 455                 460

Val Thr His Thr Leu Lys Ser Asn Ser Trp Leu Asn Cys
465                 470                 475

<210> SEQ ID NO 14
<211> LENGTH: 569
<212> TYPE: PRT
<213> ORGANISM: Homo sapiens

<400> SEQUENCE: 14

Met Leu Ala Ala Ser Ile Phe Arg Pro Thr Leu Leu Leu Cys Trp Leu
1               5                   10                  15

Ala Ala Pro Trp Pro Thr Gln Pro Glu Ser Leu Phe His Ser Arg Asp
                20                  25                  30

Arg Ser Asp Leu Glu Pro Ser Pro Leu Arg Gln Ala Lys Pro Ile Ala
            35                  40                  45

Asp Leu His Ala Ala Gln Arg Phe Leu Ser Arg Tyr Gly Trp Ser Gly
        50                  55                  60

Val Trp Ala Ala Trp Gly Pro Ser Pro Glu Gly Pro Glu Thr Pro
65                  70                  75                  80

Lys Gly Ala Ala Leu Ala Glu Ala Val Arg Arg Phe Gln Arg Ala Asn
                85                  90                  95

Ala Leu Pro Ala Ser Gly Glu Leu Asp Ala Ala Thr Leu Ala Ala Met
            100                 105                 110

Asn Arg Pro Arg Cys Gly Val Pro Asp Met Arg Pro Pro Pro Ser
        115                 120                 125

Ala Pro Pro Ser Pro Gly Pro Pro Arg Ala Arg Ser Arg Arg
        130                 135                 140

Ser Pro Arg Ala Pro Leu Ser Leu Ser Arg Arg Gly Trp Gln Pro Arg
```

```
                145                 150                 155                 160
Gly Tyr Pro Asp Gly Gly Ala Ala Gln Ala Phe Ser Lys Arg Thr Leu
                165                 170                 175

Ser Trp Arg Leu Leu Gly Glu Ala Leu Ser Ser Gln Leu Ser Ala Ala
                180                 185                 190

Asp Gln Arg Arg Ile Val Ala Leu Ala Phe Arg Met Trp Ser Glu Val
                195                 200                 205

Thr Pro Leu Asp Phe Arg Glu Asp Leu Ala Ala Pro Gly Ala Ala Val
    210                 215                 220

Asp Ile Lys Leu Gly Phe Gly Arg Gly Arg His Leu Gly Cys Pro Arg
225                 230                 235                 240

Ala Phe Asp Gly Ser Gly Gln Glu Phe Ala His Ala Trp Arg Leu Gly
                245                 250                 255

Asp Ile His Phe Asp Asp Asp Glu His Phe Thr Pro Pro Thr Ser Asp
                260                 265                 270

Thr Gly Ile Ser Leu Leu Lys Val Ala Val His Glu Ile Gly His Val
                275                 280                 285

Leu Gly Leu Pro His Thr Tyr Arg Thr Gly Ser Ile Met Gln Pro Asn
    290                 295                 300

Tyr Ile Pro Gln Glu Pro Ala Phe Glu Leu Asp Trp Ser Asp Arg Lys
305                 310                 315                 320

Ala Ile Gln Lys Leu Tyr Gly Ser Cys Glu Gly Ser Phe Asp Thr Ala
                325                 330                 335

Phe Asp Trp Ile Arg Lys Glu Arg Asn Gln Tyr Gly Glu Val Met Val
                340                 345                 350

Arg Phe Ser Thr Tyr Phe Phe Arg Asn Ser Trp Tyr Trp Leu Tyr Glu
                355                 360                 365

Asn Arg Asn Asn Arg Thr Arg Tyr Gly Asp Pro Ile Gln Ile Leu Thr
    370                 375                 380

Gly Trp Pro Gly Ile Pro Thr His Asn Ile Asp Ala Phe Val His Ile
385                 390                 395                 400

Trp Thr Trp Lys Arg Asp Glu Arg Tyr Phe Phe Gln Gly Asn Gln Tyr
                405                 410                 415

Trp Arg Tyr Asp Ser Asp Lys Asp Gln Ala Leu Thr Glu Asp Glu Gln
                420                 425                 430

Gly Lys Ser Tyr Pro Lys Leu Ile Ser Glu Gly Phe Pro Gly Ile Pro
                435                 440                 445

Ser Pro Leu Asp Thr Ala Phe Tyr Asp Arg Arg Gln Lys Leu Ile Tyr
    450                 455                 460

Phe Phe Lys Glu Ser Leu Val Phe Ala Phe Asp Val Asn Arg Asn Arg
465                 470                 475                 480

Val Leu Asn Ser Tyr Pro Lys Arg Ile Thr Glu Val Phe Pro Ala Val
                485                 490                 495

Ile Pro Gln Asn His Pro Phe Arg Asn Ile Asp Ser Ala Tyr Tyr Ser
                500                 505                 510

Tyr Ala Tyr Asn Ser Ile Phe Phe Lys Gly Asn Ala Tyr Trp Lys
                515                 520                 525

Val Val Asn Asp Lys Asp Lys Gln Gln Asn Ser Trp Leu Pro Ala Asn
    530                 535                 540

Gly Leu Phe Pro Lys Lys Phe Ile Ser Glu Lys Trp Phe Asp Val Cys
545                 550                 555                 560

Asp Val His Ile Ser Thr Leu Asn Met
                565
```

<210> SEQ ID NO 15
<211> LENGTH: 520
<212> TYPE: PRT
<213> ORGANISM: Homo sapiens

<400> SEQUENCE: 15

Met Val Ala Arg Val Gly Leu Leu Arg Ala Leu Gln Leu Leu Leu
1               5                   10                  15

Trp Gly His Leu Asp Ala Gln Pro Ala Glu Arg Gly Gln Glu Leu
                20                  25                  30

Arg Lys Glu Ala Glu Ala Phe Leu Glu Lys Tyr Gly Tyr Leu Asn Glu
            35                  40                  45

Gln Val Pro Lys Ala Pro Thr Ser Thr Arg Phe Ser Asp Ala Ile Arg
50                  55                  60

Ala Phe Gln Trp Val Ser Gln Leu Pro Val Ser Gly Val Leu Asp Arg
65                  70                  75                  80

Ala Thr Leu Arg Gln Met Thr Arg Pro Arg Cys Gly Val Thr Asp Thr
                85                  90                  95

Asn Ser Tyr Ala Ala Trp Ala Glu Arg Ile Ser Asp Leu Phe Ala Arg
            100                 105                 110

His Arg Thr Lys Met Arg Arg Lys Arg Phe Ala Lys Gln Gly Asn
        115                 120                 125

Lys Trp Tyr Lys Gln His Leu Ser Tyr Arg Leu Val Asn Trp Pro Glu
130                 135                 140

His Leu Pro Glu Pro Ala Val Arg Gly Ala Val Arg Ala Ala Phe Gln
145                 150                 155                 160

Leu Trp Ser Asn Val Ser Ala Leu Glu Phe Trp Glu Ala Pro Ala Thr
                165                 170                 175

Gly Pro Ala Asp Ile Arg Leu Thr Phe Phe Gln Gly Asp His Asn Asp
            180                 185                 190

Gly Leu Gly Asn Ala Phe Asp Gly Pro Gly Gly Ala Leu Ala His Ala
        195                 200                 205

Phe Leu Pro Arg Arg Gly Glu Ala His Phe Asp Gln Asp Glu Arg Trp
210                 215                 220

Ser Leu Ser Arg Arg Gly Arg Asn Leu Phe Val Val Leu Ala His
225                 230                 235                 240

Glu Ile Gly His Thr Leu Gly Leu Thr His Ser Pro Ala Pro Arg Ala
                245                 250                 255

Leu Met Ala Pro Tyr Tyr Lys Arg Leu Gly Arg Asp Ala Leu Leu Ser
            260                 265                 270

Trp Asp Asp Val Leu Ala Val Gln Ser Leu Tyr Gly Lys Pro Leu Gly
        275                 280                 285

Gly Ser Val Ala Val Gln Leu Pro Gly Lys Leu Phe Thr Asp Phe Glu
290                 295                 300

Thr Trp Asp Ser Tyr Ser Pro Gly Arg Pro Glu Thr Gln Gly
305                 310                 315                 320

Pro Lys Tyr Cys His Ser Ser Phe Asp Ala Ile Thr Val Asp Arg Gln
                325                 330                 335

Gln Gln Leu Tyr Ile Phe Lys Gly Ser His Phe Trp Glu Val Ala Ala
            340                 345                 350

Asp Gly Asn Val Ser Glu Pro Arg Pro Leu Gln Glu Arg Trp Val Gly
        355                 360                 365

Leu Pro Pro Asn Ile Glu Ala Ala Val Ser Leu Asn Asp Gly Asp
370                 375                 380

```
Phe Tyr Phe Phe Lys Gly Gly Arg Cys Trp Arg Phe Arg Gly Pro Lys
385                 390                 395                 400

Pro Val Trp Gly Leu Pro Gln Leu Cys Arg Ala Gly Gly Leu Pro Arg
            405                 410                 415

His Pro Asp Ala Ala Leu Phe Phe Pro Pro Leu Arg Arg Leu Ile Leu
            420                 425                 430

Phe Lys Gly Ala Arg Tyr Tyr Val Leu Ala Arg Gly Gly Leu Gln Val
            435                 440                 445

Glu Pro Tyr Tyr Pro Arg Ser Leu Gln Asp Trp Gly Gly Ile Pro Glu
450                 455                 460

Glu Val Ser Gly Ala Leu Pro Arg Pro Asp Gly Ser Ile Ile Phe Phe
465                 470                 475                 480

Arg Asp Asp Arg Tyr Trp Arg Leu Asp Gln Ala Lys Leu Gln Ala Thr
            485                 490                 495

Thr Ser Gly Arg Trp Ala Thr Glu Leu Pro Trp Met Gly Cys Trp His
            500                 505                 510

Ala Asn Ser Gly Ser Ala Leu Phe
            515                 520

<210> SEQ ID NO 16
<211> LENGTH: 475
<212> TYPE: PRT
<213> ORGANISM: Homo sapiens

<400> SEQUENCE: 16

Met Phe Ser Leu Lys Thr Leu Pro Phe Leu Leu Leu His Val Gln
1                 5                  10                  15

Ile Ser Lys Ala Phe Pro Val Ser Ser Lys Glu Lys Asn Thr Lys Thr
            20                  25                  30

Val Gln Asp Tyr Leu Glu Lys Phe Tyr Gln Leu Pro Ser Asn Gln Tyr
            35                  40                  45

Gln Ser Thr Arg Lys Asn Gly Thr Asn Val Ile Val Glu Lys Leu Lys
    50                  55                  60

Glu Met Gln Arg Phe Phe Gly Leu Asn Val Thr Gly Lys Pro Asn Glu
65                  70                  75                  80

Glu Thr Leu Asp Met Met Lys Lys Pro Arg Cys Gly Val Pro Asp Ser
            85                  90                  95

Gly Gly Phe Met Leu Thr Pro Gly Asn Pro Lys Trp Glu Arg Thr Asn
            100                 105                 110

Leu Thr Tyr Arg Ile Arg Asn Tyr Thr Pro Gln Leu Ser Glu Ala Glu
            115                 120                 125

Val Glu Arg Ala Ile Lys Asp Ala Phe Glu Leu Trp Ser Val Ala Ser
130                 135                 140

Pro Leu Ile Phe Thr Arg Ile Ser Gln Gly Glu Ala Asp Ile Asn Ile
145                 150                 155                 160

Ala Phe Tyr Gln Arg Asp His Gly Asp Asn Ser Pro Phe Asp Gly Pro
            165                 170                 175

Asn Gly Ile Leu Ala His Ala Phe Gln Pro Gly Gln Gly Ile Gly Gly
            180                 185                 190

Asp Ala His Phe Asp Ala Glu Glu Thr Trp Thr Asn Thr Ser Ala Asn
            195                 200                 205

Tyr Asn Leu Phe Leu Val Ala Ala His Glu Phe Gly His Ser Leu Gly
    210                 215                 220

Leu Ala His Ser Ser Asp Pro Gly Ala Leu Met Tyr Pro Asn Tyr Ala
225                 230                 235                 240
```

```
Phe Arg Glu Thr Ser Asn Tyr Ser Leu Pro Gln Asp Asp Ile Asp Gly
                245                 250                 255

Ile Gln Ala Ile Tyr Gly Leu Ser Ser Asn Pro Thr Ile Glu Gln Pro
            260                 265                 270

Thr Gly Pro Ser Thr Pro Lys Pro Cys Asp Pro Ser Leu Thr Phe Asp
        275                 280                 285

Ala Ile Thr Thr Leu Arg Gly Glu Thr Ile Glu Leu Phe Phe Lys Asp
    290                 295                 300

Arg Tyr Phe Trp Arg Arg His Pro Gln Leu Gln Arg Val Glu Met Asn
305                 310                 315                 320

Phe Ile Ser Leu Phe Trp Pro Ser Leu Pro Thr Gly Ile Gln Ala Ala
                325                 330                 335

Tyr Glu Asp Phe Asp Arg Asp Leu Ile Phe Leu Phe Lys Gly Asn Gln
            340                 345                 350

Tyr Trp Ala Leu Ser Gly Tyr Asp Ile Leu Gln Gly Tyr Pro Lys Asp
        355                 360                 365

Ile Ser Asn Tyr Gly Phe Pro Ser Ser Val Gln Ala Thr Ile Glu Asp
    370                 375                 380

Ala Ala Val Phe Tyr Arg Ser Lys Thr Tyr Phe Phe Val Asn Asp Gln
385                 390                 395                 400

Phe Trp Arg Tyr Asp Asn Gln Arg Gln Phe Met Glu Pro Gly Tyr Pro
                405                 410                 415

Lys Ser Ile Ser Gly Ala Phe Pro Gly Thr Ile Glu Glu Ser Lys Val
            420                 425                 430

Asp Ala Val Phe Gln Gln Glu His Phe Phe His Val Phe Ser Gly Pro
        435                 440                 445

Arg Tyr Tyr Ala Phe Asp Leu Ile Ala Gln Arg Val Thr Arg Val Ala
    450                 455                 460

Arg Gly Asn Lys Trp Leu Asn Cys Arg Tyr Gly
465                 470                 475

<210> SEQ ID NO 17
<211> LENGTH: 470
<212> TYPE: PRT
<213> ORGANISM: Homo sapiens

<400> SEQUENCE: 17

Met Lys Phe Leu Leu Ile Leu Leu Leu Gln Ala Thr Ala Ser Gly Ala
1               5                   10                  15

Leu Pro Leu Asn Ser Ser Thr Ser Leu Glu Lys Asn Asn Val Leu Phe
            20                  25                  30

Gly Glu Arg Tyr Leu Glu Lys Phe Tyr Gly Leu Glu Ile Asn Lys Leu
        35                  40                  45

Pro Val Thr Lys Met Lys Tyr Ser Gly Asn Leu Met Lys Glu Lys Ile
    50                  55                  60

Gln Glu Met Gln His Phe Leu Gly Leu Lys Val Thr Gly Gln Leu Asp
65                  70                  75                  80

Thr Ser Thr Leu Glu Met Met His Ala Pro Arg Cys Gly Val Pro Asp
                85                  90                  95

Val His His Phe Arg Glu Met Pro Gly Gly Pro Val Trp Arg Lys His
            100                 105                 110

Tyr Ile Thr Tyr Arg Ile Asn Asn Tyr Thr Pro Asp Met Asn Arg Glu
        115                 120                 125

Asp Val Asp Tyr Ala Ile Arg Lys Ala Phe Gln Val Trp Ser Asn Val
    130                 135                 140
```

```
Thr Pro Leu Lys Phe Ser Lys Ile Asn Thr Gly Met Ala Asp Ile Leu
145                 150                 155                 160

Val Val Phe Ala Arg Gly Ala His Gly Asp Phe His Ala Phe Asp Gly
                165                 170                 175

Lys Gly Gly Ile Leu Ala His Ala Phe Gly Pro Gly Ser Gly Ile Gly
            180                 185                 190

Gly Asp Ala His Phe Asp Glu Asp Glu Phe Trp Thr Thr His Ser Gly
        195                 200                 205

Gly Thr Asn Leu Phe Leu Thr Ala Val His Glu Ile Gly His Ser Leu
    210                 215                 220

Gly Leu Gly His Ser Ser Asp Pro Lys Ala Val Met Phe Pro Thr Tyr
225                 230                 235                 240

Lys Tyr Val Asp Ile Asn Thr Phe Arg Leu Ser Ala Asp Asp Ile Arg
                245                 250                 255

Gly Ile Gln Ser Leu Tyr Gly Asp Pro Lys Glu Asn Gln Arg Leu Pro
            260                 265                 270

Asn Pro Asp Asn Ser Glu Pro Ala Leu Cys Asp Pro Asn Leu Ser Phe
        275                 280                 285

Asp Ala Val Thr Thr Val Gly Asn Lys Ile Phe Phe Lys Asp Arg
    290                 295                 300

Phe Phe Trp Leu Lys Val Ser Glu Arg Pro Lys Thr Ser Val Asn Leu
305                 310                 315                 320

Ile Ser Ser Leu Trp Pro Thr Leu Pro Ser Gly Ile Glu Ala Ala Tyr
                325                 330                 335

Glu Ile Glu Ala Arg Asn Gln Val Phe Leu Phe Lys Asp Asp Lys Tyr
            340                 345                 350

Trp Leu Ile Ser Asn Leu Arg Pro Glu Pro Asn Tyr Pro Lys Ser Ile
        355                 360                 365

His Ser Phe Gly Phe Pro Asn Phe Val Lys Lys Ile Asp Ala Ala Val
    370                 375                 380

Phe Asn Pro Arg Phe Tyr Arg Thr Tyr Phe Phe Val Asp Asn Gln Tyr
385                 390                 395                 400

Trp Arg Tyr Asp Glu Arg Arg Gln Met Met Asp Pro Gly Tyr Pro Lys
                405                 410                 415

Leu Ile Thr Lys Asn Phe Gln Gly Ile Gly Pro Lys Ile Asp Ala Val
            420                 425                 430

Phe Tyr Ser Lys Asn Lys Tyr Tyr Phe Gln Gly Ser Asn Gln
        435                 440                 445

Phe Glu Tyr Asp Phe Leu Leu Gln Arg Ile Thr Lys Thr Leu Lys Ser
    450                 455                 460

Asn Ser Trp Phe Gly Cys
465                 470

<210> SEQ ID NO 18
<211> LENGTH: 513
<212> TYPE: PRT
<213> ORGANISM: Homo sapiens

<400> SEQUENCE: 18

Met Lys Arg Leu Leu Leu Leu Phe Leu Phe Phe Ile Thr Phe Ser Ser
1               5                   10                  15

Ala Phe Pro Leu Val Arg Met Thr Glu Asn Glu Glu Asn Met Gln Leu
                20                  25                  30

Ala Gln Ala Tyr Leu Asn Gln Phe Tyr Ser Leu Glu Ile Glu Gly Asn
            35                  40                  45
```

-continued

```
His Leu Val Gln Ser Lys Asn Arg Ser Leu Ile Asp Asp Lys Ile Arg
 50                  55                  60

Glu Met Gln Ala Phe Phe Gly Leu Thr Val Thr Gly Lys Leu Asp Ser
 65                  70                  75                  80

Asn Thr Leu Glu Ile Met Lys Thr Pro Arg Cys Gly Val Pro Asp Val
                 85                  90                  95

Gly Gln Tyr Gly Tyr Thr Leu Pro Gly Trp Arg Lys Tyr Asn Leu Thr
            100                 105                 110

Tyr Arg Ile Ile Asn Tyr Thr Pro Asp Met Ala Arg Ala Ala Val Asp
        115                 120                 125

Glu Ala Ile Gln Glu Gly Leu Glu Val Trp Ser Lys Val Thr Pro Leu
130                 135                 140

Lys Phe Thr Lys Ile Ser Lys Gly Ile Ala Asp Ile Met Ile Ala Phe
145                 150                 155                 160

Arg Thr Arg Val His Gly Arg Cys Pro Arg Tyr Phe Asp Gly Pro Leu
                165                 170                 175

Gly Val Leu Gly His Ala Phe Pro Pro Gly Pro Gly Leu Gly Gly Asp
            180                 185                 190

Thr His Phe Asp Glu Asp Glu Asn Trp Thr Lys Asp Gly Ala Gly Phe
        195                 200                 205

Asn Leu Phe Leu Val Ala Ala His Glu Phe Gly His Ala Leu Gly Leu
210                 215                 220

Ser His Ser Asn Asp Gln Thr Ala Leu Met Phe Pro Asn Tyr Val Ser
225                 230                 235                 240

Leu Asp Pro Arg Lys Tyr Pro Leu Ser Gln Asp Ile Asn Gly Ile
                245                 250                 255

Gln Ser Ile Tyr Gly Gly Leu Pro Lys Glu Pro Ala Lys Pro Lys Glu
            260                 265                 270

Pro Thr Ile Pro His Ala Cys Asp Pro Asp Leu Thr Phe Asp Ala Ile
        275                 280                 285

Thr Thr Phe Arg Arg Glu Val Met Phe Phe Lys Gly Arg His Leu Trp
290                 295                 300

Arg Ile Tyr Tyr Asp Ile Thr Asp Val Glu Phe Glu Leu Ile Ala Ser
305                 310                 315                 320

Phe Trp Pro Ser Leu Pro Ala Asp Leu Gln Ala Ala Tyr Glu Asn Pro
                325                 330                 335

Arg Asp Lys Ile Leu Val Phe Lys Asp Glu Asn Phe Trp Met Ile Arg
            340                 345                 350

Gly Tyr Ala Val Leu Pro Asp Tyr Pro Lys Ser Ile His Thr Leu Gly
        355                 360                 365

Phe Pro Gly Arg Val Lys Lys Ile Asp Ala Ala Val Cys Asp Lys Thr
370                 375                 380

Thr Arg Lys Thr Tyr Phe Phe Val Gly Ile Trp Cys Trp Arg Phe Asp
385                 390                 395                 400

Glu Met Thr Gln Thr Met Asp Lys Gly Phe Pro Gln Arg Val Val Lys
                405                 410                 415

His Phe Pro Gly Ile Ser Ile Arg Val Asp Ala Ala Phe Gln Tyr Lys
            420                 425                 430

Gly Phe Phe Phe Phe Ser Arg Gly Ser Lys Gln Phe Glu Tyr Asp Ile
        435                 440                 445

Lys Thr Lys Asn Ile Thr Arg Ile Met Arg Thr Asn Thr Trp Phe Gln
450                 455                 460

Cys Lys Glu Pro Lys Asn Ser Ser Phe Gly Phe Asp Ile Asn Lys Glu
465                 470                 475                 480
```

```
Lys Ala His Ser Gly Gly Ile Lys Ile Leu Tyr His Lys Ser Leu Ser
                485                 490                 495

Leu Phe Ile Phe Gly Ile Val His Leu Leu Lys Asn Thr Ser Ile Tyr
            500                 505                 510

Gln

<210> SEQ ID NO 19
<211> LENGTH: 488
<212> TYPE: PRT
<213> ORGANISM: Homo sapiens

<400> SEQUENCE: 19

Met Ala Pro Ala Ala Trp Leu Arg Ser Ala Ala Arg Ala Leu Leu
1               5                   10                  15

Pro Pro Met Leu Leu Leu Leu Gln Pro Pro Leu Leu Ala Arg
            20                  25                  30

Ala Leu Pro Pro Asp Val His His Leu His Ala Glu Arg Arg Gly Pro
            35                  40                  45

Gln Pro Trp His Ala Ala Leu Pro Ser Ser Pro Ala Pro Ala Pro Ala
50                  55                  60

Thr Gln Glu Ala Pro Arg Pro Ala Ser Ser Leu Arg Pro Pro Arg Cys
65                  70                  75                  80

Gly Val Pro Asp Pro Ser Asp Gly Leu Ser Ala Arg Asn Arg Gln Lys
                85                  90                  95

Arg Phe Val Leu Ser Gly Gly Arg Trp Glu Lys Thr Asp Leu Thr Tyr
            100                 105                 110

Arg Ile Leu Arg Phe Pro Trp Gln Leu Val Gln Glu Gln Val Arg Gln
            115                 120                 125

Thr Met Ala Glu Ala Leu Lys Val Trp Ser Asp Val Thr Pro Leu Thr
130                 135                 140

Phe Thr Glu Val His Glu Gly Arg Ala Asp Ile Met Ile Asp Phe Ala
145                 150                 155                 160

Arg Tyr Trp His Gly Asp Asp Leu Pro Phe Asp Gly Pro Gly Gly Ile
                165                 170                 175

Leu Ala His Ala Phe Phe Pro Lys Thr His Arg Glu Gly Asp Val His
            180                 185                 190

Phe Asp Tyr Asp Glu Thr Trp Thr Ile Gly Asp Asp Gln Gly Thr Asp
            195                 200                 205

Leu Leu Gln Val Ala Ala His Glu Phe Gly His Val Leu Gly Leu Gln
210                 215                 220

His Thr Thr Ala Ala Lys Ala Leu Met Ser Ala Phe Tyr Thr Phe Arg
225                 230                 235                 240

Tyr Pro Leu Ser Leu Ser Pro Asp Asp Cys Arg Gly Val Gln His Leu
                245                 250                 255

Tyr Gly Gln Pro Trp Pro Thr Val Thr Ser Arg Thr Pro Ala Leu Gly
            260                 265                 270

Pro Gln Ala Gly Ile Asp Thr Asn Glu Ile Ala Pro Leu Glu Pro Asp
            275                 280                 285

Ala Pro Pro Asp Ala Cys Glu Ala Ser Phe Asp Ala Val Ser Thr Ile
290                 295                 300

Arg Gly Glu Leu Phe Phe Phe Lys Ala Gly Phe Val Trp Arg Leu Arg
305                 310                 315                 320

Gly Gly Gln Leu Gln Pro Gly Tyr Pro Ala Leu Ala Ser Arg His Trp
                325                 330                 335
```

```
Gln Gly Leu Pro Ser Pro Val Asp Ala Ala Phe Glu Asp Ala Gln Gly
                340                 345                 350

His Ile Trp Phe Phe Gln Gly Ala Gln Tyr Trp Val Tyr Asp Gly Glu
            355                 360                 365

Lys Pro Val Leu Gly Pro Ala Pro Leu Thr Glu Leu Gly Leu Val Arg
370                 375                 380

Phe Pro Val His Ala Ala Leu Val Trp Gly Pro Glu Lys Asn Lys Ile
385                 390                 395                 400

Tyr Phe Phe Arg Gly Arg Asp Tyr Trp Arg Phe His Pro Ser Thr Arg
                405                 410                 415

Arg Val Asp Ser Pro Val Pro Arg Ala Thr Asp Trp Arg Gly Val
            420                 425                 430

Pro Ser Glu Ile Asp Ala Ala Phe Gln Asp Ala Asp Gly Tyr Ala Tyr
            435                 440                 445

Phe Leu Arg Gly Arg Leu Tyr Trp Lys Phe Asp Pro Val Lys Val Lys
450                 455                 460

Ala Leu Glu Gly Phe Pro Arg Leu Val Gly Pro Asp Phe Phe Gly Cys
465                 470                 475                 480

Ala Glu Pro Ala Asn Thr Phe Leu
                485

<210> SEQ ID NO 20
<211> LENGTH: 478
<212> TYPE: PRT
<213> ORGANISM: Homo sapiens

<400> SEQUENCE: 20

Met Met His Leu Ala Phe Leu Val Leu Leu Cys Leu Pro Val Cys Ser
1               5                   10                  15

Ala Tyr Pro Leu Ser Gly Ala Ala Lys Glu Glu Asp Ser Asn Lys Asp
                20                  25                  30

Leu Ala Gln Gln Tyr Leu Glu Lys Tyr Tyr Asn Leu Glu Lys Asp Val
            35                  40                  45

Lys Gln Phe Arg Arg Lys Asp Ser Asn Leu Ile Val Lys Lys Ile Gln
        50                  55                  60

Gly Met Gln Lys Phe Leu Gly Leu Glu Val Thr Gly Lys Leu Asp Thr
65                  70                  75                  80

Asp Thr Leu Glu Val Met Arg Lys Pro Arg Cys Gly Val Pro Asp Val
                85                  90                  95

Gly His Phe Ser Ser Phe Pro Gly Met Pro Lys Trp Arg Lys Thr His
                100                 105                 110

Leu Thr Tyr Arg Ile Val Asn Tyr Thr Pro Asp Leu Pro Arg Asp Ala
            115                 120                 125

Val Asp Ser Ala Ile Glu Lys Ala Leu Lys Val Trp Glu Glu Val Thr
        130                 135                 140

Pro Leu Thr Phe Ser Arg Leu Tyr Glu Gly Ala Asp Ile Met Ile
145                 150                 155                 160

Ser Phe Ala Val Lys Glu His Gly Asp Phe Tyr Ser Phe Asp Gly Pro
                165                 170                 175

Gly His Ser Leu Ala His Ala Tyr Pro Pro Gly Pro Gly Leu Tyr Gly
                180                 185                 190

Asp Ile His Phe Asp Asp Asp Glu Lys Trp Thr Glu Asp Ala Ser Gly
            195                 200                 205

Thr Asn Leu Phe Leu Val Ala Ala His Glu Leu Gly His Ser Leu Gly
        210                 215                 220
```

```
Leu Phe His Ser Ala Asn Thr Glu Ala Leu Met Tyr Pro Leu Tyr Asn
225                 230                 235                 240

Ser Phe Thr Glu Leu Ala Gln Phe Arg Leu Ser Gln Asp Asp Val Asn
            245                 250                 255

Gly Thr Ile Glu Gln Ser Leu Tyr Gly Pro Pro Ala Ser Thr Glu
        260                 265                 270

Glu Pro Leu Val Pro Thr Lys Ser Val Pro Ser Gly Ser Glu Met Pro
        275                 280                 285

Ala Lys Cys Asp Pro Ala Leu Ser Phe Asp Ala Ile Ser Thr Leu Arg
290                 295                 300

Gly Glu Tyr Leu Phe Phe Lys Asp Arg Tyr Phe Trp Arg Arg Ser His
305                 310                 315                 320

Trp Asn Pro Glu Pro Glu Phe His Leu Ile Ser Ala Phe Trp Pro Ser
            325                 330                 335

Leu Pro Ser Tyr Leu Asp Ala Ala Tyr Glu Val Asn Ser Arg Asp Thr
        340                 345                 350

Val Phe Ile Phe Lys Gly Asn Glu Phe Trp Ala Ile Arg Gly Asn Glu
        355                 360                 365

Val Gln Ala Gly Tyr Pro Arg Gly Ile His Thr Leu Gly Phe Pro Pro
370                 375                 380

Thr Ile Arg Lys Ile Asp Ala Ala Val Ser Asp Lys Glu Lys Lys Lys
385                 390                 395                 400

Thr Tyr Phe Phe Ala Ala Asp Lys Tyr Trp Arg Phe Asp Glu Asn Ser
            405                 410                 415

Gln Ser Met Glu Gln Gly Phe Pro Arg Leu Ile Ala Asp Asp Phe Pro
        420                 425                 430

Gly Val Glu Pro Lys Val Asp Ala Val Leu Gln Ala Phe Gly Phe Phe
        435                 440                 445

Tyr Phe Phe Ser Gly Ser Ser Gln Phe Glu Phe Asp Pro Asn Ala Arg
450                 455                 460

Met Val Thr His Ile Leu Lys Ser Asn Ser Trp Leu His Cys
465                 470                 475

<210> SEQ ID NO 21
<211> LENGTH: 20
<212> TYPE: DNA
<213> ORGANISM: Avian

<400> SEQUENCE: 21
ttaacgagga tccattggag                                                  20

<210> SEQ ID NO 22
<211> LENGTH: 20
<212> TYPE: DNA
<213> ORGANISM: Avian

<400> SEQUENCE: 22
agcctgcttt gaacactcta                                                  20

<210> SEQ ID NO 23
<211> LENGTH: 20
<212> TYPE: DNA
<213> ORGANISM: Avian

<400> SEQUENCE: 23
agaggagtac tcctgaaagt                                                  20

<210> SEQ ID NO 24
```

```
<211> LENGTH: 20
<212> TYPE: DNA
<213> ORGANISM: Avian

<400> SEQUENCE: 24
actgctgaac ataagctcct                                              20

<210> SEQ ID NO 25
<211> LENGTH: 20
<212> TYPE: DNA
<213> ORGANISM: Homo sapiens

<400> SEQUENCE: 25
ccgcatcaag gtggtcttta                                              20

<210> SEQ ID NO 26
<211> LENGTH: 20
<212> TYPE: DNA
<213> ORGANISM: Homo sapiens

<400> SEQUENCE: 26
catacactca ccattagggc                                              20

<210> SEQ ID NO 27
<211> LENGTH: 18
<212> TYPE: DNA
<213> ORGANISM: Homo sapiens

<400> SEQUENCE: 27
tgtggagggc agtgctgc                                                18

<210> SEQ ID NO 28
<211> LENGTH: 20
<212> TYPE: DNA
<213> ORGANISM: Homo sapiens

<400> SEQUENCE: 28
taaagaccac cttgatgcgg                                              20

<210> SEQ ID NO 29
<211> LENGTH: 21
<212> TYPE: DNA
<213> ORGANISM: Avian

<400> SEQUENCE: 29
tactgctgat atcatgatct c                                            21

<210> SEQ ID NO 30
<211> LENGTH: 21
<212> TYPE: DNA
<213> ORGANISM: Avian

<400> SEQUENCE: 30
tctagaatca tctgaccaag t                                            21

<210> SEQ ID NO 31
<211> LENGTH: 20
<212> TYPE: DNA
<213> ORGANISM: Avian

<400> SEQUENCE: 31
aatgacagca tcaggtacgg                                              20

<210> SEQ ID NO 32
```

```
<211> LENGTH: 19
<212> TYPE: DNA
<213> ORGANISM: Avian

<400> SEQUENCE: 32
atggtcagga ctgaggcac                                                19

<210> SEQ ID NO 33
<211> LENGTH: 22
<212> TYPE: DNA
<213> ORGANISM: Avian

<400> SEQUENCE: 33
agatgtatca gatgcaagat ct                                            22

<210> SEQ ID NO 34
<211> LENGTH: 21
<212> TYPE: DNA
<213> ORGANISM: Avian

<400> SEQUENCE: 34
gaagtctgct tctacaggta t                                             21

<210> SEQ ID NO 35
<211> LENGTH: 10
<212> TYPE: PRT
<213> ORGANISM: Homo sapiens

<400> SEQUENCE: 35

Leu Arg Gly Glu Thr Met Ile Phe Lys Asp
1               5                   10

<210> SEQ ID NO 36
<211> LENGTH: 19
<212> TYPE: PRT
<213> ORGANISM: Homo sapiens

<400> SEQUENCE: 36

Glu Leu Gly Leu Pro Lys Glu Val Lys Lys Ile Ser Ala Ala Val His
1               5                   10                  15

Phe Glu Asp

<210> SEQ ID NO 37
<211> LENGTH: 50
<212> TYPE: PRT
<213> ORGANISM: Homo sapiens

<400> SEQUENCE: 37

Lys Lys Ile Ser Ala Ala Val His Phe Glu Asp Thr Gly Lys Thr Leu
1               5                   10                  15

Leu Phe Ser Gly Asn Gln Val Trp Arg Tyr Asp Asp Thr Asn His Ile
            20                  25                  30

Met Asp Lys Asp Tyr Pro Arg Leu Ile Glu Glu Asp Phe Pro Gly Ile
        35                  40                  45

Gly Asp
    50

<210> SEQ ID NO 38
<211> LENGTH: 39
<212> TYPE: PRT
<213> ORGANISM: Homo sapiens

<400> SEQUENCE: 38
```

```
Phe Glu Asp Thr Gly Lys Thr Leu Leu Phe Ser Gly Asn Gln Val Trp
1               5                   10                  15

Arg Tyr Asp Asp Thr Asn His Ile Met Asp Lys Asp Tyr Pro Arg Leu
            20                  25                  30

Ile Glu Glu Asp Phe Pro Gly
            35
```

<210> SEQ ID NO 39
<211> LENGTH: 23
<212> TYPE: PRT
<213> ORGANISM: Homo sapiens

<400> SEQUENCE: 39

```
Arg Tyr Asp Asp Thr Asn His Ile Met Asp Lys Asp Tyr Pro Arg Leu
1               5                   10                  15

Ile Glu Glu Asp Phe Pro Gly
            20
```

<210> SEQ ID NO 40
<211> LENGTH: 42
<212> TYPE: PRT
<213> ORGANISM: Homo sapiens

<400> SEQUENCE: 40

```
Lys Val Asp Ala Val Tyr Glu Lys Asn Gly Tyr Ile Tyr Phe Phe Asn
1               5                   10                  15

Gly Pro Ile Gln Phe Glu Tyr Ser Ile Trp Ser Asn Arg Ile Val Arg
            20                  25                  30

Val Met Pro Ala Asn Ser Ile Leu Trp Cys
            35                  40
```

<210> SEQ ID NO 41
<211> LENGTH: 21
<212> TYPE: PRT
<213> ORGANISM: Homo sapiens

<400> SEQUENCE: 41

```
Gly Tyr Ile Tyr Phe Phe Asn Gly Pro Ile Gln Phe Glu Tyr Ser Ile
1               5                   10                  15

Trp Ser Asn Arg Ile
            20
```

<210> SEQ ID NO 42
<211> LENGTH: 48
<212> TYPE: PRT
<213> ORGANISM: Homo sapiens

<400> SEQUENCE: 42

```
Leu Pro Asn Arg Ile Asp Ala Ala Tyr Glu His Pro Ser His Asp Leu
1               5                   10                  15

Ile Phe Ile Phe Arg Gly Arg Lys Phe Trp Ala Leu Asn Gly Tyr Asp
            20                  25                  30

Ile Gly Tyr Pro Lys Lys Ile Ser Glu Leu Gly Leu Pro Lys Glu Val
            35                  40                  45
```

<210> SEQ ID NO 43
<211> LENGTH: 24
<212> TYPE: PRT
<213> ORGANISM: Homo sapiens

<400> SEQUENCE: 43

```
Glu His Pro Ser His Asp Leu Ile Phe Ile Phe Arg Gly Arg Lys Phe
```

```
                1               5                  10                  15
Trp Ala Leu Asn Gly Tyr Asp Ile
                20
```

<210> SEQ ID NO 44
<211> LENGTH: 50
<212> TYPE: PRT
<213> ORGANISM: Homo sapiens

<400> SEQUENCE: 44

```
Thr Pro Asp Lys Cys Asp Pro Ser Leu Ser Leu Asp Ala Ile Thr Ser
1               5                  10                  15
Leu Arg Gly Glu Thr Met Ile Phe Lys Asp Arg Phe Phe Trp Arg Leu
                20                  25                  30
His Pro Gln Gln Val Asp Ala Glu Leu Phe Leu Thr Lys Ser Phe Trp
            35                  40                  45
Pro Glu
    50
```

<210> SEQ ID NO 45
<211> LENGTH: 35
<212> TYPE: PRT
<213> ORGANISM: Homo sapiens

<400> SEQUENCE: 45

```
Ser Leu Arg Gly Glu Thr Met Ile Phe Lys Asp Arg Phe Phe Trp Arg
1               5                  10                  15
Leu His Pro Gln Gln Val Asp Ala Glu Leu Phe Leu Thr Lys Ser Phe
                20                  25                  30
Trp Pro Glu
        35
```

<210> SEQ ID NO 46
<211> LENGTH: 18
<212> TYPE: PRT
<213> ORGANISM: Homo sapiens

<400> SEQUENCE: 46

```
Pro Ile Gln Phe Glu Tyr Ser Ile Trp Ser Asn Arg Ile Val Arg Met
1               5                  10                  15
Pro Ala
```

<210> SEQ ID NO 47
<211> LENGTH: 21
<212> TYPE: PRT
<213> ORGANISM: Homo sapiens

<400> SEQUENCE: 47

```
Phe Glu Asp Thr Gly Lys Thr Leu Leu Phe Ser Gly Asn Gln Val Trp
1               5                  10                  15
Arg Tyr Asp Asp Thr
            20
```

<210> SEQ ID NO 48
<211> LENGTH: 44
<212> TYPE: PRT
<213> ORGANISM: Homo sapiens

<400> SEQUENCE: 48

```
Phe Asp Thr Val Ala Met Leu Arg Gly Glu Met Phe Val Phe Lys Glu
1               5                  10                  15
```

```
Arg Trp Phe Trp Arg Val Arg Asn Asn Gln Val Met Asp Gly Tyr Pro
            20                  25                  30

Met Pro Ile Gly Gln Phe Trp Arg Gly Leu Pro Ala
            35                  40
```

<210> SEQ ID NO 49
<211> LENGTH: 45
<212> TYPE: PRT
<213> ORGANISM: Homo sapiens

<400> SEQUENCE: 49

```
Ile Asn Thr Ala Tyr Glu Arg Lys Asp Gly Lys Phe Val Phe Lys
1               5                   10                  15

Gly Asp Lys His Trp Val Phe Asp Glu Ala Ser Leu Glu Pro Gly Tyr
            20                  25                  30

Pro Lys His Ile Lys Glu Leu Gly Arg Gly Leu Pro Thr
            35                  40                  45
```

<210> SEQ ID NO 50
<211> LENGTH: 47
<212> TYPE: PRT
<213> ORGANISM: Homo sapiens

<400> SEQUENCE: 50

```
Ile Asp Ala Ala Leu Phe Trp Met Pro Asn Gly Lys Thr Tyr Phe Phe
1               5                   10                  15

Arg Gly Asn Lys Tyr Tyr Arg Phe Asn Glu Glu Leu Arg Ala Val Asp
            20                  25                  30

Ser Glu Tyr Pro Lys Asn Ile Lys Val Trp Glu Gly Ile Pro Glu
            35                  40                  45
```

<210> SEQ ID NO 51
<211> LENGTH: 46
<212> TYPE: PRT
<213> ORGANISM: Homo sapiens

<400> SEQUENCE: 51

```
Pro Arg Gly Ser Phe Met Gly Ser Asp Glu Val Phe Thr Tyr Phe Tyr
1               5                   10                  15

Lys Gly Asn Lys Tyr Trp Lys Phe Asn Asn Gln Lys Leu Lys Val Glu
            20                  25                  30

Pro Gly Tyr Pro Lys Ser Ala Leu Arg Asp Trp Met Gly Cys
            35                  40                  45
```

<210> SEQ ID NO 52
<211> LENGTH: 44
<212> TYPE: PRT
<213> ORGANISM: Homo sapiens

<400> SEQUENCE: 52

```
Phe Asn Thr Leu Ala Ile Leu Arg Arg Glu Met Phe Val Phe Lys Asp
1               5                   10                  15

Gln Trp Phe Trp Arg Val Arg Asn Asn Arg Val Met Asp Gly Tyr Pro
            20                  25                  30

Met Gln Ile Thr Tyr Phe Trp Arg Gly Leu Pro Pro
            35                  40
```

<210> SEQ ID NO 53
<211> LENGTH: 45
<212> TYPE: PRT
<213> ORGANISM: Homo sapiens

<400> SEQUENCE: 53

Ile Asp Ala Val Tyr Glu Asn Ser Asp Gly Asn Phe Val Phe Lys
1               5                   10                  15

Gly Asn Lys Tyr Trp Val Phe Lys Asp Thr Thr Leu Gln Pro Gly Tyr
                20                  25                  30

Pro His Asp Leu Ile Thr Leu Gly Ser Gly Ile Pro Pro
            35                  40                  45

<210> SEQ ID NO 54
<211> LENGTH: 47
<212> TYPE: PRT
<213> ORGANISM: Homo sapiens

<400> SEQUENCE: 54

Ile Asp Ser Ala Ile Trp Trp Glu Asp Val Gly Lys Thr Tyr Phe Phe
1               5                   10                  15

Lys Gly Asp Arg Tyr Trp Arg Tyr Ser Glu Glu Met Lys Thr Met Asp
                20                  25                  30

Pro Gly Tyr Pro Lys Pro Ile Thr Val Trp Lys Gly Ile Pro Glu
            35                  40                  45

<210> SEQ ID NO 55
<211> LENGTH: 46
<212> TYPE: PRT
<213> ORGANISM: Homo sapiens

<400> SEQUENCE: 55

Pro Gln Gly Ala Phe Val His Lys Glu Asn Gly Phe Thr Tyr Phe Tyr
1               5                   10                  15

Lys Gly Lys Glu Tyr Trp Lys Phe Asn Asn Gln Ile Leu Lys Val Glu
                20                  25                  30

Pro Gly Tyr Pro Arg Ser Ile Leu Lys Asp Phe Met Gly Cys
            35                  40                  45

<210> SEQ ID NO 56
<211> LENGTH: 43
<212> TYPE: PRT
<213> ORGANISM: Homo sapiens

<400> SEQUENCE: 56

Phe Asp Gly Ile Ala Gln Ile Arg Gly Glu Ile Phe Phe Phe Lys Asp
1               5                   10                  15

Arg Phe Ile Trp Arg Thr Val Thr Pro Arg Asp Lys Pro Met Gly Pro
                20                  25                  30

Leu Leu Val Ala Thr Phe Trp Pro Glu Leu Pro
            35                  40

<210> SEQ ID NO 57
<211> LENGTH: 44
<212> TYPE: PRT
<213> ORGANISM: Homo sapiens

<400> SEQUENCE: 57

Ile Asp Ala Val Tyr Glu Ala Pro Gln Glu Glu Lys Ala Val Phe Phe
1               5                   10                  15

Ala Gly Asn Glu Tyr Trp Ile Tyr Ser Ala Ser Thr Leu Glu Arg Gly
                20                  25                  30

Tyr Pro Lys Pro Leu Thr Ser Leu Gly Leu Pro Pro
            35                  40

```
<210> SEQ ID NO 58
<211> LENGTH: 48
<212> TYPE: PRT
<213> ORGANISM: Homo sapiens

<400> SEQUENCE: 58

Val Asp Ala Ala Phe Asn Trp Ser Lys Asn Lys Thr Tyr Ile Phe
1               5                   10                  15

Ala Gly Asp Lys Phe Trp Arg Tyr Asn Glu Val Lys Lys Met Asp
            20                  25                  30

Pro Gly Phe Pro Lys Leu Ile Ala Asp Ala Trp Asn Ala Ile Pro Asp
        35                  40                  45

<210> SEQ ID NO 59
<211> LENGTH: 44
<212> TYPE: PRT
<213> ORGANISM: Homo sapiens

<400> SEQUENCE: 59

Leu Asp Ala Val Val Asp Leu Gln Gly Gly His Ser Tyr Phe Phe
1               5                   10                  15

Lys Gly Ala Tyr Tyr Leu Lys Leu Glu Asn Gln Ser Leu Lys Ser Val
            20                  25                  30

Lys Phe Gly Ser Ile Lys Ser Asp Trp Leu Gly Cys
        35                  40

<210> SEQ ID NO 60
<211> LENGTH: 45
<212> TYPE: PRT
<213> ORGANISM: Homo sapiens

<400> SEQUENCE: 60

Phe Asp Ala Ile Ala Glu Ile Gly Asn Gln Leu Tyr Leu Phe Lys Asp
1               5                   10                  15

Gly Lys Tyr Trp Arg Phe Ser Glu Gly Arg Gly Ser Arg Pro Gln Gly
            20                  25                  30

Pro Phe Leu Ile Ala Asp Lys Trp Pro Ala Leu Pro Arg
        35                  40                  45

<210> SEQ ID NO 61
<211> LENGTH: 42
<212> TYPE: PRT
<213> ORGANISM: Homo sapiens

<400> SEQUENCE: 61

Leu Asp Ser Val Phe Glu Glu Arg Leu Ser Lys Lys Leu Phe Phe Phe
1               5                   10                  15

Ser Gly Arg Gln Val Trp Val Tyr Thr Gly Ala Ser Val Leu Gly Pro
            20                  25                  30

Arg Arg Leu Asp Lys Leu Gly Leu Gly Ala
        35                  40

<210> SEQ ID NO 62
<211> LENGTH: 47
<212> TYPE: PRT
<213> ORGANISM: Homo sapiens

<400> SEQUENCE: 62

Val Thr Gly Ala Leu Arg Ser Gly Arg Gly Lys Met Leu Leu Phe Ser
1               5                   10                  15

Gly Arg Arg Leu Trp Arg Phe Asp Val Lys Ala Gln Met Val Asp Pro
            20                  25                  30
```

```
Arg Ser Ala Ser Glu Val Asp Arg Met Phe Pro Gly Val Pro Leu
        35                  40                  45
```

<210> SEQ ID NO 63
<211> LENGTH: 44
<212> TYPE: PRT
<213> ORGANISM: Homo sapiens

<400> SEQUENCE: 63

```
Thr His Asp Val Phe Gln Tyr Arg Glu Lys Ala Tyr Phe Cys Gln Asp
1               5                   10                  15

Arg Phe Tyr Trp Arg Val Ser Ser Arg Ser Glu Leu Asn Gln Val Asp
            20                  25                  30

Gln Val Gly Tyr Val Thr Tyr Asp Ile Leu Gln Cys
        35                  40
```

<210> SEQ ID NO 64
<211> LENGTH: 43
<212> TYPE: PRT
<213> ORGANISM: Homo sapiens

<400> SEQUENCE: 64

```
Leu Asp Ala Met Met Leu Gly Pro Arg Gly Lys Thr Tyr Ala Phe Lys
1               5                   10                  15

Gly Asp Tyr Val Trp Thr Val Ser Asp Ser Gly Pro Gly Pro Leu Phe
            20                  25                  30

Arg Val Ser Ala Leu Trp Glu Gly Leu Pro Gly
        35                  40
```

<210> SEQ ID NO 65
<211> LENGTH: 42
<212> TYPE: PRT
<213> ORGANISM: Homo sapiens

<400> SEQUENCE: 65

```
Leu Asp Ala Ala Val Tyr Ser Pro Arg Thr Gln Trp Ile His Phe Phe
1               5                   10                  15

Lys Gly Asp Lys Val Trp Arg Tyr Ile Asn Phe Lys Met Ser Pro Gly
            20                  25                  30

Phe Pro Lys Lys Leu Asn Arg Val Glu Pro
        35                  40
```

<210> SEQ ID NO 66
<211> LENGTH: 48
<212> TYPE: PRT
<213> ORGANISM: Homo sapiens

<400> SEQUENCE: 66

```
Leu Asp Ala Ala Leu Tyr Trp Pro Leu Asn Gln Lys Val Phe Leu Phe
1               5                   10                  15

Lys Gly Ser Gly Tyr Trp Gln Trp Asp Glu Leu Ala Arg Thr Asp Phe
            20                  25                  30

Ser Ser Tyr Pro Lys Pro Ile Lys Gly Leu Phe Thr Gly Val Pro Asn
        35                  40                  45
```

<210> SEQ ID NO 67
<211> LENGTH: 44
<212> TYPE: PRT
<213> ORGANISM: Homo sapiens

<400> SEQUENCE: 67

```
Pro Ser Ala Ala Met Ser Trp Gln Asp Gly Arg Val Tyr Phe Phe Lys
1               5                   10                  15

Gly Lys Val Tyr Trp Arg Leu Asn Gln Leu Arg Val Glu Lys Gly
            20                  25                  30

Tyr Pro Arg Asn Ile Ser His Asn Trp Met His Cys
            35                  40
```

<210> SEQ ID NO 68
<211> LENGTH: 45
<212> TYPE: PRT
<213> ORGANISM: Homo sapiens

<400> SEQUENCE: 68

```
Phe Asp Ala Val Ala Gln Ile Arg Gly Glu Ala Phe Phe Lys Gly
1               5                   10                  15

Lys Tyr Phe Trp Arg Leu Thr Arg Asp Arg His Leu Val Ser Leu Gln
            20                  25                  30

Pro Ala Gln Met His Arg Phe Trp Arg Gly Leu Pro Leu
            35                  40                  45
```

<210> SEQ ID NO 69
<211> LENGTH: 44
<212> TYPE: PRT
<213> ORGANISM: Homo sapiens

<400> SEQUENCE: 69

```
Val Asp Ala Val Tyr Glu Arg Thr Ser Asp His Lys Ile Val Phe Phe
1               5                   10                  15

Lys Gly Asp Arg Tyr Trp Val Phe Lys Asp Asn Asn Val Glu Glu Gly
            20                  25                  30

Tyr Pro Arg Pro Val Ser Asp Phe Ser Leu Pro Pro
            35                  40
```

<210> SEQ ID NO 70
<211> LENGTH: 44
<212> TYPE: PRT
<213> ORGANISM: Homo sapiens

<400> SEQUENCE: 70

```
Val Asp Ala Val Tyr Glu Arg Thr Ser Asp His Lys Ile Val Phe Phe
1               5                   10                  15

Lys Gly Asp Arg Tyr Trp Val Phe Lys Asp Asn Asn Val Glu Glu Gly
            20                  25                  30

Tyr Pro Arg Pro Val Ser Asp Phe Ser Leu Pro Pro
            35                  40
```

<210> SEQ ID NO 71
<211> LENGTH: 47
<212> TYPE: PRT
<213> ORGANISM: Homo sapiens

<400> SEQUENCE: 71

```
Ile Asp Ala Ala Phe Ser Trp Ala His Asn Asp Arg Thr Tyr Phe Phe
1               5                   10                  15

Lys Asp Gln Leu Tyr Trp Arg Tyr Asp Asp His Thr Arg His Met Asp
            20                  25                  30

Pro Gly Tyr Pro Ala Gln Ser Pro Leu Trp Arg Gly Val Pro Ser
            35                  40                  45
```

<210> SEQ ID NO 72
<211> LENGTH: 44

<212> TYPE: PRT
<213> ORGANISM: Homo sapiens

<400> SEQUENCE: 72

```
Phe Asp Thr Val Ala Met Leu Arg Gly Glu Met Phe Val Phe Lys Gly
1               5                   10                  15

Arg Trp Phe Trp Arg Val Arg His Asn Arg Val Leu Asp Asn Tyr Pro
                20                  25                  30

Met Pro Ile Gly His Phe Trp Arg Gly Leu Pro Gly
            35                  40
```

<210> SEQ ID NO 73
<211> LENGTH: 45
<212> TYPE: PRT
<213> ORGANISM: Homo sapiens

<400> SEQUENCE: 73

```
Ile Ser Ala Ala Tyr Glu Arg Gln Asp Gly Arg Phe Val Phe Phe Lys
1               5                   10                  15

Gly Asp Arg Tyr Trp Leu Phe Arg Glu Ala Asn Leu Glu Pro Gly Tyr
                20                  25                  30

Pro Gln Pro Leu Thr Ser Tyr Gly Leu Gly Ile Pro Tyr
            35                  40                  45
```

<210> SEQ ID NO 74
<211> LENGTH: 47
<212> TYPE: PRT
<213> ORGANISM: Homo sapiens

<400> SEQUENCE: 74

```
Ile Asp Thr Ala Ile Trp Trp Glu Pro Thr Gly His Thr Phe Phe Phe
1               5                   10                  15

Gln Glu Asp Arg Tyr Trp Arg Phe Asn Glu Glu Thr Gln Arg Gly Asp
                20                  25                  30

Pro Gly Tyr Pro Lys Pro Ile Ser Val Trp Gln Gly Ile Pro Ala
            35                  40                  45
```

<210> SEQ ID NO 75
<211> LENGTH: 46
<212> TYPE: PRT
<213> ORGANISM: Homo sapiens

<400> SEQUENCE: 75

```
Pro Lys Gly Ala Phe Leu Ser Asn Asp Ala Ala Tyr Thr Tyr Phe Tyr
1               5                   10                  15

Lys Gly Thr Lys Tyr Trp Lys Phe Asp Asn Glu Arg Leu Arg Met Glu
                20                  25                  30

Pro Gly Tyr Pro Lys Ser Ile Leu Arg Asp Phe Met Gly Cys
            35                  40                  45
```

<210> SEQ ID NO 76
<211> LENGTH: 44
<212> TYPE: PRT
<213> ORGANISM: Homo sapiens

<400> SEQUENCE: 76

```
Phe Asp Ala Val Thr Met Leu Gly Lys Glu Leu Leu Phe Lys Asp
1               5                   10                  15

Arg Ile Phe Trp Arg Arg Gln Val His Leu Arg Thr Gly Ile Arg Pro
                20                  25                  30

Ser Thr Ile Thr Ser Ser Phe Pro Gln Leu Met Ser
```

<210> SEQ ID NO 77
<211> LENGTH: 43
<212> TYPE: PRT
<213> ORGANISM: Homo sapiens

<400> SEQUENCE: 77

Val Asp Ala Ala Tyr Glu Val Ala Glu Arg Gly Thr Ala Tyr Phe Phe
1               5                   10                  15

Lys Gly Pro His Tyr Trp Ile Thr Arg Gly Phe Gln Met Gln Gly Pro
            20                  25                  30

Pro Arg Thr Ile Tyr Asp Phe Gly Phe Pro Arg
        35                  40

<210> SEQ ID NO 78
<211> LENGTH: 48
<212> TYPE: PRT
<213> ORGANISM: Homo sapiens

<400> SEQUENCE: 78

Ile Asp Ala Ala Val Tyr Leu Arg Glu Pro Gln Lys Thr Leu Phe Phe
1               5                   10                  15

Val Gly Asp Glu Tyr Tyr Ser Tyr Asp Glu Arg Lys Arg Lys Met Glu
            20                  25                  30

Lys Asp Tyr Pro Lys Asn Thr Glu Glu Glu Phe Ser Gly Val Asn Gly
        35                  40                  45

<210> SEQ ID NO 79
<211> LENGTH: 41
<212> TYPE: PRT
<213> ORGANISM: Homo sapiens

<400> SEQUENCE: 79

Ile Asp Ala Ala Val Glu Leu Asn Gly Tyr Ile Tyr Phe Phe Ser Gly
1               5                   10                  15

Pro Lys Thr Tyr Lys Tyr Asp Thr Glu Lys Glu Asp Val Val Ser Val
            20                  25                  30

Val Lys Ser Ser Ser Trp Ile Gly Cys
        35                  40

<210> SEQ ID NO 80
<211> LENGTH: 43
<212> TYPE: PRT
<213> ORGANISM: Homo sapiens

<400> SEQUENCE: 80

Phe Asp Ala Ile Thr Thr Ile Arg Gly Glu Val Met Phe Phe Lys Asp
1               5                   10                  15

Arg Phe Tyr Met Arg Thr Asn Pro Phe Tyr Pro Glu Val Glu Leu Asn
            20                  25                  30

Phe Ile Ser Val Phe Trp Pro Gln Leu Pro Asn
        35                  40

<210> SEQ ID NO 81
<211> LENGTH: 35
<212> TYPE: PRT
<213> ORGANISM: Homo sapiens

<400> SEQUENCE: 81

Leu Glu Ala Ala Tyr Glu Phe Ala Asp Arg Asp Glu Val Arg Phe Phe
1               5                   10                  15

```
Lys Gly Asn Lys Tyr Trp Ala Val Gln Gly Gln Asn Val Leu His Gly
            20                  25                  30

Tyr Pro Lys
        35

<210> SEQ ID NO 82
<211> LENGTH: 48
<212> TYPE: PRT
<213> ORGANISM: Homo sapiens

<400> SEQUENCE: 82

Ile Asp Ala Ala Leu Ser Glu Glu Asn Thr Gly Lys Thr Tyr Phe Phe
1               5                   10                  15

Val Ala Asn Lys Tyr Trp Arg Tyr Asp Glu Tyr Lys Arg Ser Met Asp
            20                  25                  30

Pro Gly Tyr Pro Lys Met Ile Ala His Asp Phe Pro Gly Ile Gly His
        35                  40                  45

<210> SEQ ID NO 83
<211> LENGTH: 41
<212> TYPE: PRT
<213> ORGANISM: Homo sapiens

<400> SEQUENCE: 83

Val Asp Ala Val Phe Met Lys Asp Gly Phe Phe Tyr Phe Phe His Gly
1               5                   10                  15

Thr Arg Gln Tyr Lys Phe Asp Pro Lys Thr Lys Arg Ile Leu Thr Leu
            20                  25                  30

Gln Lys Ala Asn Ser Trp Phe Asn Cys
        35                  40

<210> SEQ ID NO 84
<211> LENGTH: 42
<212> TYPE: PRT
<213> ORGANISM: Homo sapiens

<400> SEQUENCE: 84

Arg Gln Pro Arg Pro Pro Arg Pro Leu Gly Asp Arg Pro Ser Thr
1               5                   10                  15

Pro Gly Thr Lys Pro Asn Ile Cys Asp Gly Asn Phe Asn Thr Val Phe
            20                  25                  30

Arg Gly Glu Met Phe Val Phe Lys Asp Arg
        35                  40

<210> SEQ ID NO 85
<211> LENGTH: 45
<212> TYPE: PRT
<213> ORGANISM: Homo sapiens

<400> SEQUENCE: 85

Phe Trp Arg Leu Arg Asn Asn Arg Val Gln Glu Gly Tyr Pro Met Gln
1               5                   10                  15

Ile Glu Gln Phe Trp Lys Gly Leu Pro Ala Arg Ile Asp Ala Ala Tyr
            20                  25                  30

Glu Arg Ala Asp Gly Arg Phe Val Phe Phe Lys Gly Asp
        35                  40                  45

<210> SEQ ID NO 86
<211> LENGTH: 47
<212> TYPE: PRT
<213> ORGANISM: Homo sapiens
```

```
<400> SEQUENCE: 86

Trp Val Phe Lys Glu Val Thr Val Glu Pro Gly Tyr Pro His Ser Leu
1               5                   10                  15

Gly Glu Leu Gly Ser Cys Leu Pro Arg Glu Gly Ile Asp Thr Ala Leu
            20                  25                  30

Arg Trp Glu Pro Val Gly Lys Thr Tyr Phe Phe Lys Gly Glu Arg
        35                  40                  45

<210> SEQ ID NO 87
<211> LENGTH: 46
<212> TYPE: PRT
<213> ORGANISM: Homo sapiens

<400> SEQUENCE: 87

Trp Arg Tyr Ser Glu Glu Arg Arg Ala Thr Asp Pro Gly Tyr Pro Lys
1               5                   10                  15

Pro Ile Thr Val Trp Lys Gly Ile Pro Gln Ala Pro Gln Gly Ala Phe
            20                  25                  30

Ile Ser Lys Glu Gly Tyr Tyr Thr Tyr Phe Tyr Lys Gly Arg
        35                  40                  45

<210> SEQ ID NO 88
<211> LENGTH: 44
<212> TYPE: PRT
<213> ORGANISM: Homo sapiens

<400> SEQUENCE: 88

Phe Asp Ala Ile Ala Asn Ile Arg Gly Glu Thr Phe Phe Phe Lys Gly
1               5                   10                  15

Pro Trp Phe Trp Arg Leu Gln Pro Ser Gly Gln Leu Val Ser Pro Arg
            20                  25                  30

Pro Ala Arg Leu His Arg Phe Trp Glu Gly Leu Pro
        35                  40

<210> SEQ ID NO 89
<211> LENGTH: 43
<212> TYPE: PRT
<213> ORGANISM: Homo sapiens

<400> SEQUENCE: 89

Val Gln Ala Ala Tyr Ala Arg His Arg Asp Gly Arg Ile Leu Leu Phe
1               5                   10                  15

Ser Gly Pro Gln Phe Trp Val Phe Gln Asp Arg Gln Leu Glu Gly Gly
            20                  25                  30

Ala Arg Pro Leu Thr Glu Leu Gly Leu Pro Pro
        35                  40

<210> SEQ ID NO 90
<211> LENGTH: 47
<212> TYPE: PRT
<213> ORGANISM: Homo sapiens

<400> SEQUENCE: 90

Val Asp Ala Val Phe Ser Trp Pro Gln Asn Gly Lys Thr Tyr Leu Val
1               5                   10                  15

Arg Gly Arg Gln Tyr Trp Arg Tyr Asp Glu Ala Ala Arg Pro Asp
            20                  25                  30

Pro Gly Tyr Pro Arg Asp Leu Ser Leu Trp Glu Gly Ala Pro Pro
        35                  40                  45
```

<210> SEQ ID NO 91
<211> LENGTH: 45
<212> TYPE: PRT
<213> ORGANISM: Homo sapiens

<400> SEQUENCE: 91

Pro Asp Asp Val Thr Val Ser Asn Ala Gly Asp Thr Tyr Phe Phe Lys
1               5                   10                  15

Gly Ala His Tyr Trp Arg Phe Pro Lys Asn Ser Ile Lys Thr Glu Pro
            20                  25                  30

Asp Ala Pro Gln Pro Met Gly Pro Asn Trp Leu Asp Cys
        35                  40                  45

<210> SEQ ID NO 92
<211> LENGTH: 42
<212> TYPE: PRT
<213> ORGANISM: Homo sapiens

<400> SEQUENCE: 92

Phe Asp Ala Val Ser Thr Leu Arg Gly Glu Ile Leu Ile Phe Lys Asp
1               5                   10                  15

Arg His Phe Trp Arg Lys Ser Leu Arg Lys Leu Glu Pro Glu Leu His
            20                  25                  30

Leu Ile Ser Ser Phe Trp Pro Ser Leu Pro
        35                  40

<210> SEQ ID NO 93
<211> LENGTH: 43
<212> TYPE: PRT
<213> ORGANISM: Homo sapiens

<400> SEQUENCE: 93

Val Asp Ala Ala Tyr Glu Val Thr Ser Lys Asp Leu Val Phe Ile Phe
1               5                   10                  15

Lys Gly Asn Gln Phe Trp Ala Ile Arg Gly Asn Glu Val Arg Ala Gly
            20                  25                  30

Tyr Pro Arg Gly Ile His Thr Leu Gly Phe Pro
        35                  40

<210> SEQ ID NO 94
<211> LENGTH: 48
<212> TYPE: PRT
<213> ORGANISM: Homo sapiens

<400> SEQUENCE: 94

Ile Asp Ala Ala Ile Ser Asp Lys Glu Lys Asn Lys Thr Tyr Phe Phe
1               5                   10                  15

Val Glu Asp Lys Tyr Trp Arg Phe Asp Glu Lys Arg Asn Ser Met Glu
            20                  25                  30

Pro Gly Phe Pro Lys Gln Ile Ala Glu Asp Phe Pro Gly Ile Asp Ser
        35                  40                  45

<210> SEQ ID NO 95
<211> LENGTH: 41
<212> TYPE: PRT
<213> ORGANISM: Homo sapiens

<400> SEQUENCE: 95

Pro Ser Gly Val Asp Ala Ala Tyr Glu Val Thr Ser Lys Asp Leu Val
1               5                   10                  15

Phe Ile Phe Lys Gly Asn Gln Phe Trp Ala Ile Arg Gly Asn Glu Val

```
                    20                  25                  30

Arg Ala Gly Tyr Pro Arg Gly Ile His
            35                  40

<210> SEQ ID NO 96
<211> LENGTH: 59
<212> TYPE: PRT
<213> ORGANISM: Homo sapiens

<400> SEQUENCE: 96

Phe Asp Thr Ala Phe Asp Trp Ile Arg Lys Glu Arg Asn Gln Tyr Gly
1               5                   10                  15

Glu Val Met Val Arg Phe Ser Thr Tyr Phe Phe Arg Asn Ser Trp Tyr
                20                  25                  30

Trp Leu Tyr Glu Asn Arg Asn Asn Arg Thr Arg Tyr Gly Asp Pro Ile
            35                  40                  45

Gln Ile Leu Thr Gly Trp Pro Gly Ile Pro Thr
        50                  55

<210> SEQ ID NO 97
<211> LENGTH: 56
<212> TYPE: PRT
<213> ORGANISM: Homo sapiens

<400> SEQUENCE: 97

Ile Asp Ala Phe Val His Ile Trp Thr Trp Lys Arg Asp Glu Arg Tyr
1               5                   10                  15

Phe Phe Gln Gly Asn Gln Tyr Trp Arg Tyr Asp Ser Asp Lys Asp Gln
                20                  25                  30

Ala Leu Thr Glu Asp Glu Gln Gly Lys Ser Tyr Pro Lys Leu Ile Ser
            35                  40                  45

Glu Gly Phe Pro Gly Ile Pro Ser
        50                  55

<210> SEQ ID NO 98
<211> LENGTH: 49
<212> TYPE: PRT
<213> ORGANISM: Homo sapiens

<400> SEQUENCE: 98

Leu Asp Thr Ala Phe Tyr Asp Arg Arg Gln Lys Leu Ile Tyr Phe Phe
1               5                   10                  15

Lys Glu Ser Leu Val Phe Ala Phe Asp Val Asn Arg Asn Arg Val Leu
                20                  25                  30

Asn Ser Tyr Pro Lys Arg Ile Thr Glu Val Thr Pro Ala Val Ile Pro
            35                  40                  45

Gln

<210> SEQ ID NO 99
<211> LENGTH: 44
<212> TYPE: PRT
<213> ORGANISM: Homo sapiens

<400> SEQUENCE: 99

Ile Asp Ser Ala Tyr Tyr Ser Tyr Ala Tyr Asn Ser Ile Phe Phe Phe
1               5                   10                  15

Lys Gly Asn Ala Tyr Trp Lys Val Val Asn Asp Lys Asp Lys Gln Gln
                20                  25                  30

Asn Ser Trp Leu Pro Ala Asn Gly Leu Phe Pro Lys
            35                  40
```

<210> SEQ ID NO 100
<211> LENGTH: 44
<212> TYPE: PRT
<213> ORGANISM: Homo sapiens

<400> SEQUENCE: 100

Phe Asp Ala Ile Thr Val Asp Arg Gln Gln Leu Tyr Ile Phe Lys
1               5                   10                  15

Gly Ser His Phe Trp Glu Val Ala Ala Asp Gly Asn Val Ser Glu Pro
            20                  25                  30

Arg Pro Leu Gln Glu Arg Trp Val Gly Leu Pro Pro
        35                  40

<210> SEQ ID NO 101
<211> LENGTH: 44
<212> TYPE: PRT
<213> ORGANISM: Homo sapiens

<400> SEQUENCE: 101

Ile Glu Ala Ala Ala Val Ser Leu Asn Asp Gly Asp Phe Tyr Phe Phe
1               5                   10                  15

Lys Gly Gly Arg Cys Trp Arg Phe Arg Gly Pro Lys Pro Val Trp Gly
            20                  25                  30

Leu Pro Gln Leu Cys Arg Ala Gly Gly Leu Pro Arg
        35                  40

<210> SEQ ID NO 102
<211> LENGTH: 45
<212> TYPE: PRT
<213> ORGANISM: Homo sapiens

<400> SEQUENCE: 102

Pro Asp Ala Ala Leu Phe Phe Pro Pro Leu Arg Arg Leu Ile Leu Phe
1               5                   10                  15

Lys Gly Ala Arg Tyr Tyr Val Leu Arg Gly Leu Gln Val Glu Pro Tyr
            20                  25                  30

Tyr Pro Arg Ser Leu Gln Asp Trp Gly Gly Ile Pro Glu
        35                  40                  45

<210> SEQ ID NO 103
<211> LENGTH: 45
<212> TYPE: PRT
<213> ORGANISM: Homo sapiens

<400> SEQUENCE: 103

Val Ser Gly Ala Leu Pro Arg Pro Asp Gly Ser Ile Ile Phe Phe Arg
1               5                   10                  15

Asp Asp Arg Tyr Trp Arg Leu Asp Gln Ala Lys Leu Gln Ala Thr Thr
            20                  25                  30

Ser Gly Arg Trp Ala Thr Glu Leu Pro Trp Met Gly Cys
        35                  40                  45

<210> SEQ ID NO 104
<211> LENGTH: 42
<212> TYPE: PRT
<213> ORGANISM: Homo sapiens

<400> SEQUENCE: 104

Phe Asp Ala Ile Thr Thr Leu Arg Gly Glu Ile Leu Phe Phe Lys Asp
1               5                   10                  15

Arg Tyr Trp Arg Arg His Pro Gln Leu Gln Arg Val Glu Met Asn Phe
            20                  25                  30

Ile Ser Leu Phe Trp Pro Ser Leu Pro Thr
            35                  40

<210> SEQ ID NO 105
<211> LENGTH: 44
<212> TYPE: PRT
<213> ORGANISM: Homo sapiens

<400> SEQUENCE: 105

Ile Gln Ala Ala Tyr Glu Asp Phe Asp Arg Asp Leu Ile Phe Leu Phe
1               5                   10                  15

Lys Gly Asn Gln Tyr Trp Ala Leu Ser Gly Tyr Asp Ile Leu Gln Gly
            20                  25                  30

Tyr Pro Lys Asp Ile Ser Asn Tyr Gly Phe Pro Ser
            35                  40

<210> SEQ ID NO 106
<211> LENGTH: 46
<212> TYPE: PRT
<213> ORGANISM: Homo sapiens

<400> SEQUENCE: 106

Ile Asp Ala Ala Val Phe Tyr Arg Ser Lys Thr Tyr Phe Phe Val Asn
1               5                   10                  15

Asp Gln Phe Trp Arg Tyr Asp Asn Gln Arg Gln Phe Met Glu Pro Gly
            20                  25                  30

Tyr Pro Lys Ser Ile Ser Gly Ala Phe Pro Gly Ile Glu Ser
            35                  40                  45

<210> SEQ ID NO 107
<211> LENGTH: 39
<212> TYPE: PRT
<213> ORGANISM: Homo sapiens

<400> SEQUENCE: 107

Val Asp Ala Val Phe Gln Gln Glu His Phe Phe His Val Phe Ser Gly
1               5                   10                  15

Pro Arg Tyr Tyr Ala Phe Asp Leu Ile Ala Gln Arg Val Thr Arg Val
            20                  25                  30

Arg Asn Lys Trp Leu Asn Cys
            35

<210> SEQ ID NO 108
<211> LENGTH: 41
<212> TYPE: PRT
<213> ORGANISM: Homo sapiens

<400> SEQUENCE: 108

Phe Asp Ala Val Thr Thr Val Gly Asn Lys Ile Phe Phe Lys Asp
1               5                   10                  15

Arg Phe Phe Trp Leu Lys Val Ser Pro Lys Thr Ser Val Asn Leu Ile
            20                  25                  30

Ser Ser Leu Trp Pro Thr Leu Pro Ser
            35                  40

<210> SEQ ID NO 109
<211> LENGTH: 44
<212> TYPE: PRT
<213> ORGANISM: Homo sapiens

```
<400> SEQUENCE: 109

Ile Glu Ala Ala Tyr Glu Ile Glu Ala Arg Asn Gln Val Phe Leu Phe
1               5                   10                  15

Lys Asp Asp Lys Tyr Trp Leu Ile Ser Asn Leu Arg Pro Glu Pro Asn
            20                  25                  30

Tyr Pro Lys Ser Ile His Ser Phe Gly Phe Pro Asn
        35                  40

<210> SEQ ID NO 110
<211> LENGTH: 47
<212> TYPE: PRT
<213> ORGANISM: Homo sapiens

<400> SEQUENCE: 110

Ile Asp Ala Ala Val Phe Asn Pro Arg Phe Tyr Arg Thr Tyr Phe Phe
1               5                   10                  15

Val Asp Asn Gln Tyr Trp Arg Tyr Asp Glu Arg Arg Gln Met Met Asp
            20                  25                  30

Pro Gly Tyr Pro Lys Leu Ile Thr Lys Asn Phe Gln Gly Ile Gly
        35                  40                  45

<210> SEQ ID NO 111
<211> LENGTH: 42
<212> TYPE: PRT
<213> ORGANISM: Homo sapiens

<400> SEQUENCE: 111

Ile Asp Ala Val Phe Tyr Ser Lys Asn Lys Tyr Tyr Tyr Phe Phe Gln
1               5                   10                  15

Gly Ser Asn Gln Phe Glu Tyr Asp Phe Leu Leu Gln Arg Ile Thr Lys
            20                  25                  30

Thr Leu Lys Ser Asn Ser Trp Phe Gly Cys
        35                  40

<210> SEQ ID NO 112
<211> LENGTH: 43
<212> TYPE: PRT
<213> ORGANISM: Homo sapiens

<400> SEQUENCE: 112

Phe Asp Ala Ile Thr Thr Phe Arg Arg Glu Val Met Phe Phe Lys Gly
1               5                   10                  15

Arg His Leu Trp Arg Ile Tyr Tyr Asp Ile Thr Asp Val Glu Phe Glu
            20                  25                  30

Leu Ile Ala Ser Phe Trp Pro Ser Leu Pro Ala
        35                  40

<210> SEQ ID NO 113
<211> LENGTH: 43
<212> TYPE: PRT
<213> ORGANISM: Homo sapiens

<400> SEQUENCE: 113

Leu Gln Ala Ala Tyr Glu Asn Pro Arg Asp Lys Ile Leu Val Phe Lys
1               5                   10                  15

Asp Glu Asn Phe Trp Met Ile Arg Gly Tyr Ala Val Leu Pro Asp Tyr
            20                  25                  30

Pro Lys Ser Ile His Thr Leu Gly Phe Pro Gly
        35                  40
```

```
<210> SEQ ID NO 114
<211> LENGTH: 48
<212> TYPE: PRT
<213> ORGANISM: Homo sapiens

<400> SEQUENCE: 114

Ile Asp Ala Ala Val Cys Asp Lys Thr Thr Arg Lys Thr Tyr Phe Phe
1               5                   10                  15

Val Gly Ile Trp Cys Trp Arg Phe Asp Glu Met Thr Gln Thr Met Asp
            20                  25                  30

Lys Gly Phe Pro Gln Arg Val Val Lys His Phe Pro Gly Ile Ser Ile
        35                  40                  45

<210> SEQ ID NO 115
<211> LENGTH: 41
<212> TYPE: PRT
<213> ORGANISM: Homo sapiens

<400> SEQUENCE: 115

Val Asp Ala Ala Phe Gln Tyr Lys Gly Phe Phe Phe Ser Arg Gly
1               5                   10                  15

Ser Lys Gln Phe Glu Tyr Asp Ile Lys Thr Lys Asn Ile Thr Arg Ile
            20                  25                  30

Met Arg Thr Asn Thr Trp Phe Gln Cys
        35                  40

<210> SEQ ID NO 116
<211> LENGTH: 42
<212> TYPE: PRT
<213> ORGANISM: Homo sapiens

<400> SEQUENCE: 116

Phe Asp Ala Val Ser Thr Ile Arg Gly Glu Leu Phe Phe Phe Lys Ala
1               5                   10                  15

Gly Phe Val Trp Arg Leu Arg Gly Gly Gln Leu Gln Pro Gly Tyr Pro
            20                  25                  30

Ala Ser Arg His Trp Gln Gly Leu Pro Ser
        35                  40

<210> SEQ ID NO 117
<211> LENGTH: 42
<212> TYPE: PRT
<213> ORGANISM: Homo sapiens

<400> SEQUENCE: 117

Val Asp Ala Ala Phe Glu Asp Ala Gln Gly His Ile Trp Phe Phe Gln
1               5                   10                  15

Gly Ala Gln Tyr Trp Val Tyr Asp Gly Glu Lys Pro Val Leu Gly Pro
            20                  25                  30

Ala Pro Leu Thr Glu Leu Gly Leu Val Arg
        35                  40

<210> SEQ ID NO 118
<211> LENGTH: 48
<212> TYPE: PRT
<213> ORGANISM: Homo sapiens

<400> SEQUENCE: 118

Val His Ala Ala Leu Val Trp Gly Pro Glu Lys Asn Lys Ile Tyr Phe
1               5                   10                  15

Phe Arg Gly Arg Asp Tyr Trp Arg Phe His Pro Ser Thr Arg Arg Val
            20                  25                  30
```

```
Asp Ser Pro Val Pro Arg Arg Ala Thr Asp Trp Arg Gly Val Pro Ser
        35                  40                  45
```

<210> SEQ ID NO 119
<211> LENGTH: 45
<212> TYPE: PRT
<213> ORGANISM: Homo sapiens

<400> SEQUENCE: 119

```
Ile Asp Ala Ala Phe Gln Asp Ala Asp Gly Tyr Ala Tyr Phe Leu Arg
1               5                   10                  15

Gly Arg Leu Tyr Trp Lys Phe Asp Pro Val Lys Val Lys Ala Leu Glu
            20                  25                  30

Gly Phe Pro Arg Leu Val Gly Pro Asp Phe Phe Gly Cys
        35                  40                  45
```

<210> SEQ ID NO 120
<211> LENGTH: 43
<212> TYPE: PRT
<213> ORGANISM: Homo sapiens

<400> SEQUENCE: 120

```
Phe Asp Ala Ile Ser Thr Leu Arg Gly Glu Tyr Leu Phe Phe Lys Asp
1               5                   10                  15

Arg Tyr Phe Trp Arg Arg Ser His Trp Asn Pro Glu Pro Glu Phe His
            20                  25                  30

Leu Ile Ser Ala Phe Trp Pro Ser Leu Pro Ser
        35                  40
```

<210> SEQ ID NO 121
<211> LENGTH: 44
<212> TYPE: PRT
<213> ORGANISM: Homo sapiens

<400> SEQUENCE: 121

```
Leu Asp Ala Ala Tyr Glu Val Asn Ser Arg Asp Thr Val Phe Ile Phe
1               5                   10                  15

Lys Gly Asn Glu Phe Trp Ala Ile Arg Gly Asn Glu Val Gln Ala Gly
            20                  25                  30

Tyr Pro Arg Gly Ile His Thr Leu Gly Phe Pro Pro
        35                  40
```

<210> SEQ ID NO 122
<211> LENGTH: 48
<212> TYPE: PRT
<213> ORGANISM: Homo sapiens

<400> SEQUENCE: 122

```
Ile Asp Ala Ala Val Ser Asp Lys Glu Lys Lys Lys Thr Tyr Phe Phe
1               5                   10                  15

Ala Ala Asp Lys Tyr Trp Arg Phe Asp Glu Asn Ser Gln Ser Met Glu
            20                  25                  30

Gln Gly Phe Pro Arg Leu Ile Ala Asp Phe Pro Gly Val Glu Pro
        35                  40                  45
```

<210> SEQ ID NO 123
<211> LENGTH: 41
<212> TYPE: PRT
<213> ORGANISM: Homo sapiens

<400> SEQUENCE: 123

```
Val Asp Ala Val Leu Gln Ala Phe Gly Phe Tyr Phe Phe Ser Gly
1               5                   10                  15

Ser Ser Gln Phe Glu Phe Asp Pro Asn Ala Arg Met Val Thr His Ile
                20                  25                  30

Leu Lys Ser Asn Ser Trp Leu His Cys
            35                  40

<210> SEQ ID NO 124
<211> LENGTH: 448
<212> TYPE: PRT
<213> ORGANISM: Dog

<400> SEQUENCE: 124

Ala Phe Leu Phe Leu Ser Trp Thr Gln Cys Trp Ser Leu Pro Leu Pro
1               5                   10                  15

Ser Asp Gly Asp Asp Leu Ser Glu Glu Asp Phe Gln Leu Ala Glu
                20                  25                  30

Arg Tyr Leu Lys Ser Tyr Tyr Pro Leu Asn Pro Ala Gly Ile Leu
            35                  40                  45

Lys Lys Ser Ala Ala Gly Ser Val Ala Asp Arg Leu Arg Glu Met Gln
50                  55                  60

Ser Phe Phe Gly Leu Glu Val Thr Gly Lys Leu Asp Asp Asn Thr Leu
65                  70                  75                  80

Asp Ile Met Lys Lys Pro Arg Cys Gly Val Pro Asp Val Gly Glu Tyr
                85                  90                  95

Asn Val Phe Pro Arg Thr Leu Trp Ser Lys Thr Asn Leu Tyr Ile
            100                 105                 110

Val Asn Tyr Thr Pro Asp Leu Thr His Ser Glu Val Glu Lys Ala Phe
            115                 120                 125

Lys Lys Ala Phe Lys Val Trp Ser Asp Val Thr Pro Leu Asn Phe Thr
130                 135                 140

Arg Leu His Asp Gly Thr Ala Asp Ile Met Ile Ser Phe Gly Thr Lys
145                 150                 155                 160

Glu His Gly Asp Phe Tyr Pro Phe Asp Gly Pro Ser Gly Leu Leu Ala
                165                 170                 175

His Ala Phe Pro Pro Gly Pro Asn Tyr Gly Gly Asp Ala His Phe Asp
                180                 185                 190

Asp Asp Glu Thr Trp Thr Ser Ser Lys Gly Tyr Asn Leu Phe Leu
            195                 200                 205

Val Ala Ala His Glu Phe Gly His Ser Leu Gly Leu Asp His Ser Lys
210                 215                 220

Asp Pro Gly Ala Leu Met Phe Pro Ile Tyr Thr Tyr Thr Gly Lys Ser
225                 230                 235                 240

His Phe Met Leu Pro Asp Asp Val Gln Gly Ile Gln Ser Leu Tyr
                245                 250                 255

Gly Pro Gly Asp Glu Asp Pro Asn Pro Arg His Pro Lys Thr Pro Asp
                260                 265                 270

Lys Cys Asp Pro Ser Leu Ser Leu Asp Ala Ile Thr Ser Leu Arg Gly
            275                 280                 285

Glu Thr Met Ile Phe Lys Asp Arg Phe Phe Trp Arg Leu His Pro Gln
290                 295                 300

Gln Val Asp Ala Glu Leu Phe Leu Thr Lys Ser Phe Trp Pro Glu Leu
305                 310                 315                 320

Pro Asn Arg Ile Asp Ala Ala Tyr Glu His Pro Ser Arg Asp Leu Ile
                325                 330                 335
```

Phe Ile Phe Arg Gly Arg Lys Tyr Trp Ala Leu Asn Gly Tyr Asp Ile
                340                 345                 350

Gly Tyr Pro Gln Lys Ile Ser Glu Leu Gly Phe Pro Lys Glu Val Lys
                355                 360                 365

Lys Ile Ser Ala Ala Val His Phe Glu Asp Thr Gly Lys Thr Leu Phe
            370                 375                 380

Phe Ser Gly Asn Gln Val Trp Ser Tyr Asp Asp Thr Asn Gln Ile Met
385                 390                 395                 400

Asp Lys Asp Tyr Pro Arg Leu Ile Glu Glu Asp Phe Pro Gly Ile Gly
                405                 410                 415

Asp Lys Val Asp Ala Val Tyr Glu Lys Asn Gly Tyr Ile Tyr Phe Phe
            420                 425                 430

Asn Gly Pro Ile Gln Phe Glu Tyr Asn Ile Trp Ser Asn Pro Tyr Cys
            435                 440                 445

<210> SEQ ID NO 125
<211> LENGTH: 1348
<212> TYPE: PRT
<213> ORGANISM: Dog

<400> SEQUENCE: 125

Met Leu Ser Phe Val Asp Thr Arg Thr Leu Leu Leu Ala Val Thr
1               5                   10                  15

Ser Cys Leu Ala Thr Cys Gln Ser Leu Gln Glu Ala Thr Ala Arg Lys
                20                  25                  30

Gly Pro Thr Gly Asp Arg Gly Pro Arg Gly Glu Arg Gly Pro Pro Gly
            35                  40                  45

Pro Pro Gly Arg Asp Gly Asp Asp Gly Ile Pro Gly Pro Pro Gly Pro
50                  55                  60

Pro Gly Pro Pro Gly Pro Gly Leu Gly Gly Asn Phe Ala Ala Gln
65                  70                  75                  80

Tyr Asp Gly Lys Gly Val Gly Leu Gly Pro Gly Pro Met Gly Leu Met
                85                  90                  95

Gly Pro Arg Gly Pro Pro Gly Ala Ser Gly Ala Pro Gly Pro Gln Gly
                100                 105                 110

Phe Gln Gly Pro Ala Gly Glu Pro Gly Glu Pro Gly Gln Thr Gly Pro
            115                 120                 125

Ala Gly Arg Pro Gly Pro Pro Gly Lys Ala Gly Glu Asp Gly His
            130                 135                 140

Pro Gly Lys Pro Gly Arg Pro Gly Glu Arg Gly Val Val Gly Pro Gln
145                 150                 155                 160

Gly Arg Phe Pro Gly Thr Pro Gly Leu Pro Gly Phe Lys Gly Ile Arg
                165                 170                 175

Gly His Asn Gly Leu Asp Gly Leu Lys Gly Gln Pro Gly Ala Pro Gly
                180                 185                 190

Val Lys Gly Glu Pro Gly Ala Pro Gly Glu Asn Gly Thr Pro Gly Gln
            195                 200                 205

Thr Gly Arg Leu Pro Gly Glu Arg Gly Arg Val Gly Ala Pro Gly Pro
210                 215                 220

Ala Gly Arg Ser Asp Gly Ser Val Gly Pro Val Gly Pro Ala Gly Pro
225                 230                 235                 240

Ile Gly Ser Ala Gly Pro Pro Gly Phe Pro Gly Ala Pro Gly Pro Lys
                245                 250                 255

Gly Glu Ile Gly Pro Val Gly Asn Pro Gly Pro Ala Gly Pro Ala Gly
                260                 265                 270

-continued

```
Pro Arg Gly Glu Val Gly Leu Pro Gly Val Ser Gly Pro Val Gly Pro
        275                 280                 285
Pro Gly Asn Pro Gly Ala Asn Gly Leu Thr Gly Ala Lys Gly Ala Ala
    290                 295                 300
Gly Leu Pro Gly Val Ala Gly Ala Pro Gly Leu Pro Gly Pro Arg Gly
305                 310                 315                 320
Ile Pro Gly Pro Val Gly Ala Ala Gly Ala Thr Gly Arg Ile Val Gly
                325                 330                 335
Glu Pro Gly Pro Ala Gly Ser Lys Gly Glu Ser Gly Asn Lys Gly Glu
                340                 345                 350
Pro Gly Ser Ala Gly Ala Gln Gly Pro Gly Pro Ser Gly Glu Glu
            355                 360                 365
Gly Lys Arg Gly Pro Asn Gly Glu Ala Gly Ser Ala Gly Pro Ser Gly
    370                 375                 380
Pro Pro Gly Leu Arg Gly Ser Pro Gly Ser Arg Gly Leu Pro Gly Ala
385                 390                 395                 400
Asp Gly Pro Ala Gly Val Met Gly Pro Pro Gly Arg Gly Ala Thr
                405                 410                 415
Gly Pro Ala Gly Val Arg Gly Pro Asn Gly Asp Ser Gly Arg Pro Gly
            420                 425                 430
Glu Pro Gly Leu Met Gly Pro Arg Gly Phe Pro Gly Ala Pro Gly Asn
            435                 440                 445
Val Gly Pro Ala Gly Lys Glu Gly Pro Met Gly Leu Pro Gly Ile Asp
        450                 455                 460
Gly Arg Pro Gly Pro Ile Gly Pro Ala Gly Arg Glu Pro Gly Asn Ile
465                 470                 475                 480
Gly Phe Pro Gly Pro Lys Gly Pro Thr Gly Asp Pro Gly Lys Asn Gly
                485                 490                 495
Asp Lys Gly His Ala Gly Leu Ala Gly Arg Ala Pro Gly Pro Asp Gly
            500                 505                 510
Asn Asn Gly Ala Gln Gly Pro Pro Gly Pro Gln Gly Val Gln Gly Gly
        515                 520                 525
Lys Gly Glu Gln Gly Pro Ala Gly Pro Pro Gly Phe Gln Gly Leu Pro
    530                 535                 540
Gly Pro Ala Gly Thr Ala Gly Glu Val Gly Lys Pro Gly Glu Arg Gly
545                 550                 555                 560
Leu Pro Gly Glu Phe Gly Leu Pro Gly Pro Ala Gly Pro Arg Gly Glu
                565                 570                 575
Arg Gly Pro Pro Gly Glu Ser Gly Ala Ala Gly Pro Ser Gly Pro Ile
            580                 585                 590
Gly Ser Arg Gly Pro Ser Gly Pro Pro Gly Pro Asp Gly Asn Lys Gly
        595                 600                 605
Glu Pro Gly Val Leu Gly Ala Pro Gly Thr Ala Gly Ala Ser Gly Pro
    610                 615                 620
Gly Gly Leu Pro Gly Glu Arg Gly Ala Ala Gly Ile Pro Gly Gly Lys
625                 630                 635                 640
Gly Glu Lys Gly Glu Thr Gly Leu Arg Gly Glu Ile Gly Asn Pro Gly
                645                 650                 655
Arg Asp Gly Arg Ala Pro Gly Ala Met Gly Ala Pro Gly Pro Ala Gly
            660                 665                 670
Ala Thr Gly Asp Arg Gly Glu Ala Gly Pro Ala Gly Pro Ala Gly Pro
        675                 680                 685
Ala Gly Pro Arg Gly Thr Pro Gly Glu Arg Gly Glu Val Gly Pro Ala
    690                 695                 700
```

```
Gly Pro Asn Gly Phe Ala Gly Pro Ala Gly Ala Ala Gly Gln Pro Gly
705                 710                 715                 720

Ala Lys Gly Glu Arg Gly Thr Lys Gly Pro Lys Gly Glu Asn Gly Pro
            725                 730                 735

Val Gly Pro Thr Gly Pro Ile Gly Ser Ala Gly Pro Ser Gly Pro Asn
                740                 745                 750

Gly Pro Pro Gly Pro Ala Gly Ser Arg Gly Asp Gly Gly Pro Pro Gly
            755                 760                 765

Ala Thr Gly Phe Pro Gly Ala Ala Gly Arg Thr Gly Pro Pro Gly Pro
    770                 775                 780

Ser Gly Ile Thr Gly Pro Pro Gly Pro Pro Gly Ala Ala Gly Lys Glu
785                 790                 795                 800

Gly Leu Arg Gly Pro Arg Gly Asp Gln Gly Pro Val Gly Arg Thr Gly
            805                 810                 815

Glu Thr Gly Ala Ser Gly Pro Pro Gly Phe Thr Gly Glu Lys Gly Pro
        820                 825                 830

Ser Gly Glu Pro Gly Thr Ala Gly Pro Pro Gly Thr Pro Gly Pro Gln
            835                 840                 845

Gly Leu Leu Gly Ala Pro Gly Ile Leu Gly Leu Pro Gly Ser Arg Gly
    850                 855                 860

Glu Arg Gly Leu Pro Gly Val Ala Gly Ser Val Gly Glu Pro Gly Pro
865                 870                 875                 880

Leu Gly Ile Ala Gly Pro Pro Gly Arg Pro Gly Ala Val Gly Ala
            885                 890                 895

Pro Gly Val Asn Gly Ala Pro Gly Glu Ala Gly Arg Asp Gly Asn Pro
                900                 905                 910

Gly Asn Asp Gly Pro Pro Gly Arg Asp Gly Gln Ala Gly His Lys Gly
            915                 920                 925

Glu Arg Gly Tyr Pro Gly Asn Ile Gly Pro Val Gly Ala Val Gly Ala
        930                 935                 940

Pro Gly Pro His Gly Pro Val Gly Pro Thr Gly Lys His Gly Asn Arg
945                 950                 955                 960

Gly Glu Pro Gly Pro Ala Gly Ser Val Gly Pro Val Gly Ala Val Gly
            965                 970                 975

Pro Arg Gly Pro Ser Gly Pro Gln Gly Ile Arg Gly Asp Lys Gly Glu
            980                 985                 990

Pro Gly Glu Lys Gly Pro Arg Gly  Leu Pro Gly Leu Lys  Gly His Asn
            995                 1000                1005

Gly Leu  Gln Gly Leu Pro Gly  Leu Ala Gly Gln His  Gly Asp Gln
    1010                1015                1020

Gly Ala  Pro Gly Ser Val Gly  Pro Ala Gly Pro Arg  Gly Pro Ala
1025                1030                1035

Gly Pro  Ser Gly Pro Ala Gly  Lys Asp Gly Arg Thr  Gly Gln Pro
1040                1045                1050

Gly Thr  Val Gly Pro Ala Gly  Ile Arg Gly Ser Gln  Gly Ser Gln
1055                1060                1065

Gly Pro  Ala Gly Pro Pro Gly  Pro Pro Gly Pro Pro  Gly Pro Pro
1070                1075                1080

Gly Pro  Ser Gly Gly Gly Tyr  Asp Phe Gly Tyr Glu  Gly Asp Phe
1085                1090                1095

Tyr Arg  Ala Asp Gln Pro Arg  Ser Pro Pro Ser Leu  Arg Pro Lys
1100                1105                1110

Asp Tyr  Glu Val Asp Ala Thr  Leu Lys Ser Leu Asn  Asn Gln Ile
```

-continued

```
                1115                1120                1125

Glu Thr Leu Leu Thr Pro Glu Gly Ser Arg Lys Asn Pro Ala Arg
1130                1135                1140

Thr Cys Arg Asp Leu Arg Leu Ser His Pro Glu Trp Ser Ser Gly
1145                1150                1155

Tyr Tyr Trp Ile Asp Pro Asn Gln Gly Cys Thr Met Asp Ala Ile
1160                1165                1170

Lys Val Tyr Cys Asp Phe Ser Thr Gly Glu Thr Cys Ile Arg Ala
1175                1180                1185

Gln Pro Glu Asn Ile Pro Ala Lys Asn Trp Tyr Arg Asn Ser Lys
1190                1195                1200

Val Lys Lys His Ile Trp Leu Gly Glu Thr Ile Asn Gly Gly Thr
1205                1210                1215

Gln Phe Glu Tyr Asn Val Glu Gly Val Thr Thr Lys Glu Met Ala
1220                1225                1230

Thr Gln Leu Ala Phe Met Arg Leu Leu Ala Asn His Ala Ser Gln
1235                1240                1245

Asn Ile Thr Tyr His Cys Lys Asn Ser Ile Ala Tyr Met Asp Glu
1250                1255                1260

Glu Thr Gly Asn Leu Lys Lys Ala Val Ile Leu Gln Gly Ser Asn
1265                1270                1275

Asp Val Glu Leu Val Ala Glu Gly Asn Ser Arg Phe Thr Tyr Thr
1280                1285                1290

Val Leu Val Asp Gly Cys Ser Lys Lys Thr Asn Glu Trp Arg Lys
1295                1300                1305

Thr Ile Ile Glu Tyr Lys Thr Asn Lys Pro Ser Arg Leu Pro Ile
1310                1315                1320

Leu Asp Ile Ala Pro Leu Asp Ile Gly Asp Ala Asp Gln Glu Phe
1325                1330                1335

Arg Val Asp Val Gly Pro Val Cys Phe Lys
1340                1345

<210> SEQ ID NO 126
<211> LENGTH: 2321
<212> TYPE: PRT
<213> ORGANISM: Dog

<400> SEQUENCE: 126

Met Thr Thr Leu Leu Trp Val Phe Val Thr Leu Arg Val Ile Thr Ala
1               5                   10                  15

Ala Ser Ser Glu Glu Thr Ser Asp His Asp Asn Ser Leu Ser Val Ser
                20                  25                  30

Ile Pro Glu Pro Ser Pro Met Arg Val Leu Leu Gly Ser Ser Leu Thr
            35                  40                  45

Ile Pro Cys Tyr Phe Ile Asp Pro Met His Pro Val Thr Thr Ala Pro
        50                  55                  60

Ser Thr Ala Pro Leu Ala Pro Arg Ile Lys Trp Ser Arg Ile Thr Lys
65                  70                  75                  80

Glu Lys Glu Val Val Leu Leu Val Ala Thr Glu Gly Gln Val Arg Ile
                85                  90                  95

Asn Ser Ala Tyr Gln Asp Lys Val Ser Leu Pro Asn Tyr Pro Ala Ile
            100                 105                 110

Pro Ser Asp Ala Thr Leu Glu Ile Gln Asn Leu Arg Ser Asn Asp Ser
        115                 120                 125

Gly Ile Tyr Arg Cys Glu Val Met His Gly Ile Glu Asp Ser Glu Ala
```

```
                130                 135                 140
Thr Leu Glu Val Val Lys Gly Ile Val Phe His Tyr Arg Ala Ile
145                 150                 155                 160

Ser Thr Arg Tyr Thr Leu Asp Phe Asp Arg Ala Gln Arg Ala Cys Leu
                165                 170                 175

Gln Asn Ser Ala Ile Ile Ala Thr Pro Glu Gln Leu Gln Ala Ala Tyr
                180                 185                 190

Glu Asp Gly Phe His Gln Cys Asp Ala Gly Trp Leu Ala Asp Gln Thr
                195                 200                 205

Val Arg Tyr Pro Ile His Thr Pro Arg Glu Gly Cys Tyr Gly Asp Lys
    210                 215                 220

Asp Glu Phe Pro Gly Val Arg Thr Tyr Gly Ile Arg Asp Thr Asn Glu
225                 230                 235                 240

Thr Tyr Asp Val Tyr Cys Phe Ala Glu Glu Met Glu Gly Glu Val Leu
                245                 250                 255

Tyr Ala Thr Ser Pro Glu Lys Phe Thr Phe Gln Glu Ala Ala Asn Glu
                260                 265                 270

Cys Arg Arg Leu Gly Ala Arg Leu Ala Thr Thr Gly Gln Leu Tyr Leu
                275                 280                 285

Ala Trp Gln Gly Gly Met Asp Met Cys Ser Ala Gly Trp Leu Ala Asp
                290                 295                 300

Arg Ser Val Arg Tyr Pro Ile Ser Lys Ala Arg Pro Asn Cys Gly Gly
305                 310                 315                 320

Asn Leu Leu Gly Val Arg Thr Val Tyr Leu His Ala Asn Gln Thr Gly
                325                 330                 335

Tyr Pro Asp Pro Ser Ser Arg Tyr Asp Ala Ile Cys Tyr Thr Gly Glu
                340                 345                 350

Asp Phe Val Asp Ile Pro Glu Asn Phe Phe Gly Val Gly Gly Glu Glu
                355                 360                 365

Asp Ile Thr Ile Gln Thr Val Thr Trp Pro Asp Val Glu Leu Pro Leu
                370                 375                 380

Pro Arg Asn Ile Thr Glu Gly Glu Arg Asn Val Ile Leu Thr Val Lys
385                 390                 395                 400

Pro Ile Phe Asp Leu Ser Pro Thr Ala Pro Glu Pro Glu Glu Pro Phe
                405                 410                 415

Thr Phe Val Pro Glu Pro Glu Lys Pro Phe Thr Phe Ala Thr Asp Val
                420                 425                 430

Gly Val Thr Ala Phe Pro Glu Ala Glu Asn Arg Thr Gly Glu Ala Thr
                435                 440                 445

Arg Pro Trp Gly Val Pro Glu Glu Ser Thr Pro Gly Pro Ala Phe Thr
450                 455                 460

Ala Phe Thr Ser Glu Asp His Val Val Gln Val Thr Ala Val Pro Gly
465                 470                 475                 480

Ala Ala Glu Val Pro Gly Gln Pro Arg Leu Pro Gly Gly Val Val Phe
                485                 490                 495

His Tyr Arg Pro Gly Ser Ala Arg Tyr Ser Leu Thr Phe Glu Glu Ala
                500                 505                 510

Gln Gln Ala Cys Leu Arg Thr Gly Ala Val Ile Asp Glu Gln Leu Gln
                515                 520                 525

Ala Ala Tyr Glu Ala Gly Tyr Glu Gln Cys Asp Ala Gly Trp Leu Gln
                530                 535                 540

Asp Gln Thr Val Arg Tyr Pro Ile Val Ser Pro Arg Thr Pro Cys Val
545                 550                 555                 560
```

-continued

```
Gly Asp Lys Asp Ser Ser Pro Gly Val Arg Thr Tyr Gly Val Arg Pro
            565                 570                 575

Pro Ser Glu Thr Tyr Asp Val Tyr Cys Tyr Val Asp Lys Leu Glu Gly
                580                 585                 590

Glu Val Phe Phe Ile Thr Arg Leu Glu Gln Phe Thr Phe Gln Glu Ala
            595                 600                 605

Phe Cys Glu Ser His Asn Ala Thr Leu Ala Ser Thr Gly Gln Leu Tyr
        610                 615                 620

Ala Ala Trp Arg Gln Gly Leu Asp Lys Cys Tyr Ala Gly Trp Leu Ser
625                 630                 635                 640

Asp Gly Ser Leu Arg Tyr Pro Ile Val Thr Pro Arg Pro Ser Cys Gly
                645                 650                 655

Gly Asp Lys Pro Gly Val Arg Thr Val Tyr Leu Tyr Pro Asn Gln Thr
            660                 665                 670

Gly Leu Pro Asp Pro Leu Ser Arg His His Val Phe Cys Phe Arg Gly
        675                 680                 685

Val Ser Gly Val Pro Ser Pro Gly Glu Glu Glu Gly Thr Pro Thr
690                 695                 700

Pro Ser Val Val Glu Asp Trp Ile Pro Thr Gln Val Gly Pro Val Val
705                 710                 715                 720

Pro Ser Val Pro Met Gly Glu Glu Thr Thr Ala Ile Leu Asp Phe Thr
                725                 730                 735

Ile Glu Pro Glu Asn Gln Thr Glu Trp Glu Pro Ala Tyr Ser Pro Ala
            740                 745                 750

Gly Thr Ser Pro Leu Pro Gly Ile Pro Pro Thr Trp Pro Pro Thr Ser
        755                 760                 765

Thr Ala Thr Glu Glu Ser Thr Glu Gly Pro Ser Gly Thr Glu Val Pro
770                 775                 780

Ser Val Ser Glu Glu Pro Ser Pro Ser Glu Glu Pro Phe Pro Trp Glu
785                 790                 795                 800

Glu Leu Ser Thr Leu Ser Pro Pro Gly Pro Ser Gly Thr Glu Leu Pro
                805                 810                 815

Gly Ser Gly Glu Ala Ser Gly Val Pro Glu Val Ser Gly Asp Phe Thr
            820                 825                 830

Gly Ser Gly Glu Val Ser Gly His Pro Asp Ser Ser Gly Gln Leu Ser
        835                 840                 845

Gly Glu Ser Ala Ser Gly Leu Pro Ser Glu Asp Leu Asp Ser Ser Gly
850                 855                 860

Leu Thr Ser Ala Val Gly Ser Gly Leu Ala Gly Asp Glu Asp Arg
865                 870                 875                 880

Ile Thr Leu Ser Ser Ile Pro Lys Val Glu Gly Glu Gly Leu Glu Thr
                885                 890                 895

Ser Ala Ser Gly Val Glu Asp Leu Ser Gly Leu Pro Ser Gly Arg Glu
            900                 905                 910

Gly Leu Glu Thr Ser Thr Ser Gly Val Gly Asp Leu Ser Gly Leu Pro
        915                 920                 925

Ser Gly Glu Gly Leu Glu Val Ser Ala Ser Gly Val Glu Asp Leu Ser
930                 935                 940

Gly Leu Pro Ser Gly Glu Gly Pro Glu Thr Ser Thr Ser Gly Val Gly
945                 950                 955                 960

Asp Leu Ser Arg Leu Pro Ser Gly Glu Gly Pro Glu Val Ser Ala Ser
                965                 970                 975

Gly Val Gly Asp Leu Ser Gly Leu Pro Ser Gly Arg Glu Gly Leu Glu
            980                 985                 990
```

```
Thr Ser Thr Ser Gly Val Glu Asp Leu Ser Gly Leu Pro Ser Gly Glu
        995                 1000                1005

Gly Pro Glu Ala Ser Thr Ser Gly Val Gly Asp Leu Ser Arg Leu
    1010            1015                1020

Pro Ser Gly Glu Gly Pro Glu Val Ser Ala Ser Gly Val Glu Asp
1025            1030                1035

Leu Ser Gly Leu Pro Ser Gly Glu Gly Leu Glu Ala Ser Ala Ser
1040            1045                1050

Gly Val Gly Asp Leu Ser Gly Leu Pro Ser Gly Glu Gly Pro Glu
1055            1060                1065

Ala Ser Ala Ser Gly Val Gly Asp Leu Ser Arg Leu Pro Ser Gly
1070            1075                1080

Glu Gly Pro Glu Val Ser Ala Ser Gly Val Glu Asp Leu Ser Gly
1085            1090                1095

Leu Ser Ser Gly Glu Ser Pro Glu Ala Ser Ala Ser Gly Val Gly
1100            1105                1110

Asp Leu Ser Gly Leu Pro Ser Gly Arg Glu Gly Leu Glu Thr Ser
1115            1120                1125

Ala Ser Gly Val Gly Asp Leu Ser Gly Leu Pro Ser Gly Glu Gly
1130            1135                1140

Gln Glu Ala Ser Ala Ser Gly Val Glu Asp Leu Ser Arg Leu Pro
1145            1150                1155

Ser Gly Glu Gly Pro Glu Ala Ser Ala Ser Gly Val Gly Glu Leu
1160            1165                1170

Ser Gly Leu Pro Ser Gly Arg Glu Gly Leu Glu Thr Ser Ala Ser
1175            1180                1185

Gly Val Gly Asp Leu Ser Gly Leu Pro Ser Gly Glu Gly Pro Glu
1190            1195                1200

Ala Phe Ala Ser Gly Val Glu Asp Leu Ser Ile Leu Pro Ser Gly
1205            1210                1215

Glu Gly Pro Glu Ala Ser Ala Ser Gly Val Gly Asp Leu Ser Gly
1220            1225                1230

Leu Pro Ser Gly Arg Glu Gly Leu Glu Thr Ser Thr Ser Gly Val
1235            1240                1245

Gly Asp Leu Ser Gly Leu Pro Ser Gly Arg Glu Gly Leu Glu Thr
1250            1255                1260

Ser Thr Ser Gly Val Gly Asp Leu Ser Gly Leu Pro Ser Gly Glu
1265            1270                1275

Gly Pro Glu Ala Ser Ala Ser Gly Ile Gly Asp Ile Ser Gly Leu
1280            1285                1290

Pro Ser Gly Arg Glu Gly Leu Glu Thr Ser Ser Ser Gly Val Glu
1295            1300                1305

Asp His Pro Glu Thr Ser Ala Ser Gly Val Glu Asp Leu Ser Gly
1310            1315                1320

Leu Pro Ser Gly Val Glu Gly His Pro Glu Thr Ser Ala Ser Gly
1325            1330                1335

Val Glu Asp Leu Ser Asp Leu Ser Ser Gly Gly Glu Gly Leu Glu
1340            1345                1350

Thr Ser Ala Ser Gly Ala Glu Asp Leu Ser Gly Phe Pro Ser Gly
1355            1360                1365

Lys Glu Asp Leu Ile Gly Ser Ala Ser Gly Ala Leu Asp Phe Gly
1370            1375                1380

Arg Ile Pro Ser Gly Thr Leu Gly Ser Gly Gln Ala Pro Glu Ala
```

|  |  |  |  |  |  |  |  |  |  |
|---|---|---|---|---|---|---|---|---|---|
| | | | 1385 | | | 1390 | | | 1395 |
| Ser | Ser | Leu | Pro | Ser | Gly | Phe | Ser | Gly | Glu | Tyr | Ser | Gly | Val | Asp |
| 1400 | | | | 1405 | | | | 1410 | |
| Phe | Gly | Ser | Gly | Pro | Ile | Ser | Gly | Leu | Pro | Asp | Phe | Ser | Gly | Leu |
| 1415 | | | | 1420 | | | | 1425 | |
| Pro | Ser | Gly | Phe | Pro | Thr | Ile | Ser | Leu | Val | Asp | Thr | Thr | Leu | Val |
| 1430 | | | | 1435 | | | | 1440 | |
| Glu | Val | Ile | Thr | Thr | Thr | Ser | Ala | Ser | Glu | Leu | Glu | Gly | Arg | Gly |
| 1445 | | | | 1450 | | | | 1455 | |
| Thr | Ile | Gly | Ile | Ser | Gly | Ala | Gly | Glu | Thr | Ser | Gly | Leu | Pro | Val |
| 1460 | | | | 1465 | | | | 1470 | |
| Ser | Glu | Leu | Asp | Ile | Ser | Gly | Ala | Val | Ser | Gly | Leu | Pro | Ser | Gly |
| 1475 | | | | 1480 | | | | 1485 | |
| Ala | Glu | Leu | Ser | Gly | Gln | Ala | Ser | Gly | Ser | Pro | Asp | Met | Ser | Gly |
| 1490 | | | | 1495 | | | | 1500 | |
| Glu | Thr | Ser | Gly | Phe | Phe | Gly | Val | Ser | Gly | Gln | Pro | Ser | Gly | Phe |
| 1505 | | | | 1510 | | | | 1515 | |
| Pro | Asp | Ile | Ser | Gly | Gly | Thr | Ser | Gly | Leu | Phe | Glu | Val | Ser | Gly |
| 1520 | | | | 1525 | | | | 1530 | |
| Gln | Pro | Ser | Gly | Phe | Ser | Gly | Glu | Thr | Ser | Gly | Val | Thr | Glu | Leu |
| 1535 | | | | 1540 | | | | 1545 | |
| Ser | Gly | Ser | Gly | Gln | Pro | Asp | Val | Ser | Gly | Glu | Ala | Ser | Gly | Val |
| 1550 | | | | 1555 | | | | 1560 | |
| Pro | Ser | Gly | Ser | Gly | Gln | Pro | Phe | Gly | Met | Thr | Asp | Leu | Ser | Gly |
| 1565 | | | | 1570 | | | | 1575 | |
| Glu | Thr | Ser | Gly | Val | Pro | Asp | Ile | Ser | Gly | Gln | Pro | Ser | Gly | Leu |
| 1580 | | | | 1585 | | | | 1590 | |
| Pro | Glu | Phe | Ser | Gly | Thr | Thr | Ser | Gly | Ile | Pro | Asp | Leu | Val | Ser |
| 1595 | | | | 1600 | | | | 1605 | |
| Ser | Thr | Met | Ser | Gly | Ser | Gly | Glu | Ser | Ser | Gly | Ile | Thr | Phe | Val |
| 1610 | | | | 1615 | | | | 1620 | |
| Asp | Thr | Ser | Leu | Val | Glu | Val | Thr | Pro | Thr | Thr | Phe | Lys | Glu | Lys |
| 1625 | | | | 1630 | | | | 1635 | |
| Lys | Arg | Leu | Gly | Ser | Val | Glu | Leu | Ser | Gly | Leu | Pro | Ser | Gly | Glu |
| 1640 | | | | 1645 | | | | 1650 | |
| Val | Asp | Leu | Ser | Gly | Ala | Ser | Gly | Thr | Met | Asp | Ile | Ser | Gly | Gln |
| 1655 | | | | 1660 | | | | 1665 | |
| Ser | Ser | Gly | Ala | Thr | Asp | Ser | Ser | Gly | Leu | Thr | Ser | His | Leu | Pro |
| 1670 | | | | 1675 | | | | 1680 | |
| Lys | Phe | Ser | Gly | Leu | Pro | Ser | Gly | Ala | Ala | Glu | Val | Ser | Gly | Glu |
| 1685 | | | | 1690 | | | | 1695 | |
| Ser | Ser | Gly | Ala | Glu | Val | Gly | Ser | Ser | Leu | Pro | Ser | Gly | Thr | Tyr |
| 1700 | | | | 1705 | | | | 1710 | |
| Glu | Gly | Ser | Gly | Asn | Phe | His | Pro | Ala | Phe | Pro | Thr | Val | Phe | Leu |
| 1715 | | | | 1720 | | | | 1725 | |
| Val | Asp | Arg | Thr | Leu | Val | Glu | Ser | Val | Thr | Gln | Ala | Pro | Thr | Ala |
| 1730 | | | | 1735 | | | | 1740 | |
| Gln | Glu | Ala | Gly | Glu | Gly | Pro | Ser | Gly | Ile | Leu | Ser | Gly | Ala | His |
| 1745 | | | | 1750 | | | | 1755 | |
| Ser | Gly | Ala | Pro | Asp | Val | Ser | Gly | Asp | His | Ser | Gly | Ser | Leu | Asp |
| 1760 | | | | 1765 | | | | 1770 | |
| Leu | Ser | Gly | Met | Gln | Ser | Gly | Leu | Val | Glu | Pro | Ser | Gly | Glu | Pro |
| 1775 | | | | 1780 | | | | 1785 | |

```
Ser Ser Thr Pro Tyr Phe Ser Gly Asp Phe Ser Gly Thr Met Asp
1790            1795                1800

Val Thr Gly Glu Pro Ser Thr Ala Met Ser Ala Ser Gly Glu Ala
1805            1810                1815

Ser Gly Leu Leu Glu Val Thr Leu Ile Thr Ser Glu Phe Val Glu
1820            1825                1830

Gly Val Thr Glu Pro Thr Val Ser Gln Glu Leu Ala Gln Arg Pro
1835            1840                1845

Pro Val Thr His Thr Pro Gln Leu Phe Glu Ser Ser Gly Glu Ala
1850            1855                1860

Ser Ala Ser Gly Glu Ile Ser Gly Ala Thr Pro Ala Phe Pro Gly
1865            1870                1875

Ser Gly Leu Glu Ala Ser Ser Val Pro Glu Ser Ser Ser Glu Thr
1880            1885                1890

Ser Asp Phe Pro Glu Arg Ala Val Gly Val Ser Ala Ala Pro Glu
1895            1900                1905

Ala Ser Gly Gly Ala Ser Gly Ala Pro Asp Val Ser Glu Ala Thr
1910            1915                1920

Ser Thr Phe Pro Glu Ala Asp Val Glu Gly Ala Ser Gly Leu Gly
1925            1930                1935

Val Ser Gly Gly Thr Ser Ala Phe Pro Glu Ala Pro Arg Glu Gly
1940            1945                1950

Ser Ala Thr Pro Glu Val Gln Glu Glu Pro Thr Thr Ser Tyr Asp
1955            1960                1965

Val Gly Arg Glu Ala Leu Gly Trp Pro Ser Ala Thr Pro Thr Ala
1970            1975                1980

Ser Gly Asp Arg Ile Glu Val Ser Gly Asp Leu Ser Gly His Thr
1985            1990                1995

Ser Gly Leu Asp Val Val Ile Ser Thr Ser Val Pro Glu Ser Glu
2000            2005                2010

Trp Ile Gln Gln Thr Gln Arg Pro Ala Glu Ala His Leu Glu Ile
2015            2020                2025

Glu Ala Ser Ser Pro Leu His Ser Gly Glu Thr Gln Thr Ala
2030            2035                2040

Glu Thr Ala Thr Ser Pro Thr Asp Asp Ala Ser Ile Pro Thr Ser
2045            2050                2055

Pro Ser Gly Thr Asp Glu Ser Ala Pro Ala Ile Pro Asp Ile Asp
2060            2065                2070

Glu Cys Leu Ser Ser Pro Cys Leu Asn Gly Ala Thr Cys Val Asp
2075            2080                2085

Ala Ile Asp Ser Phe Thr Cys Leu Cys Leu Pro Ser Tyr Arg Gly
2090            2095                2100

Asp Leu Cys Glu Ile Asp Gln Glu Leu Cys Glu Glu Gly Trp Thr
2105            2110                2115

Lys Phe Gln Gly His Cys Tyr Arg Tyr Phe Pro Asp Arg Glu Ser
2120            2125                2130

Trp Val Asp Ala Glu Ser Arg Cys Arg Ala Gln Gln Ser His Leu
2135            2140                2145

Ser Ser Ile Val Thr Pro Glu Glu Gln Glu Phe Val Asn Asn Asn
2150            2155                2160

Ala Gln Asp Tyr Gln Trp Ile Gln Asp Arg Thr Ile Glu Gly Asp
2165            2170                2175

Phe Arg Trp Ser Asp Gly His Ser Leu Gln Phe Glu Asn Trp Arg
2180            2185                2190
```

-continued

```
Pro Asn Gln Pro Asp Asn Phe Phe Val Ser Gly Glu Asp Cys Val
2195                2200                2205

Val Met Ile Trp His Glu Lys Gly Glu Trp Asn Asp Val Pro Cys
2210                2215                2220

Asn Tyr Tyr Leu Pro Phe Thr Cys Lys Lys Gly Thr Val Ala Cys
2225                2230                2235

Gly Asp Pro Pro Val Val Glu His Ala Arg Thr Phe Gly Gln Lys
2240                2245                2250

Lys Asp Arg Tyr Glu Ile Asn Ser Leu Val Arg Tyr Gln Cys Thr
2255                2260                2265

Glu Gly Phe Val Gln Arg His Val Pro Thr Ile Arg Cys Gln Pro
2270                2275                2280

Ser Gly His Trp Glu Lys Pro Arg Ile Thr Cys Thr Asp Pro Ser
2285                2290                2295

Thr Tyr Lys Arg Arg Leu Gln Lys Arg Ser Ser Arg Ala Pro Arg
2300                2305                2310

Arg Ser Arg Pro Ser Thr Ala His
2315                2320

<210> SEQ ID NO 127
<211> LENGTH: 518
<212> TYPE: PRT
<213> ORGANISM: Dog

<400> SEQUENCE: 127

Tyr Glu Val Ser Val Tyr Ala Leu Lys Asp Thr Leu Thr Ser Arg Pro
1               5                   10                  15

Ala Gln Gly Val Val Thr Thr Leu Glu Asn Val Ser Pro Pro Arg Arg
                20                  25                  30

Ala Arg Val Thr Asp Ala Thr Glu Thr Thr Ile Thr Ile Ser Trp Arg
            35                  40                  45

Thr Lys Thr Glu Thr Ile Thr Gly Phe Gln Val Asp Ala Ile Pro Ala
        50                  55                  60

Asn Gly Gln Asn Pro Ile Gln Arg Thr Ile Arg Pro Asp Val Arg Ser
65                  70                  75                  80

Tyr Thr Ile Thr Gly Leu Gln Pro Gly Thr Asp Tyr Lys Ile Tyr Leu
                85                  90                  95

Tyr Thr Leu Asn Asp Asn Ala Arg Ser Ser Pro Val Val Ile Asp Ala
            100                 105                 110

Ser Thr Ala Ile Asp Ala Pro Ser Asn Leu Arg Phe Leu Ala Thr Thr
        115                 120                 125

Pro Asn Ser Leu Leu Val Ser Trp Gln Pro Pro Arg Ala Arg Ile Thr
    130                 135                 140

Gly Tyr Ile Ile Lys Tyr Glu Lys Pro Gly Ser Pro Pro Arg Glu Val
145                 150                 155                 160

Val Pro Arg Pro Arg Pro Gly Val Thr Glu Ala Thr Ile Thr Gly Leu
                165                 170                 175

Glu Pro Gly Thr Glu Tyr Thr Ile Gln Val Ile Ala Leu Lys Asn Asn
            180                 185                 190

Gln Lys Ser Glu Pro Leu Ile Gly Arg Lys Lys Thr Asp Glu Leu Pro
        195                 200                 205

Gln Leu Val Thr Leu Pro His Pro Asn Leu His Gly Pro Glu Ile Leu
    210                 215                 220

Asp Val Pro Ser Thr Val Gln Lys Thr Pro Phe Ile Thr Asn Pro Gly
225                 230                 235                 240
```

Tyr Asp Thr Gly Asn Gly Ile Gln Leu Pro Gly Thr Ser Gln Gln
            245                 250                 255

Pro Ser Val Gly Gln Gln Met Ile Phe Glu Glu His Gly Phe Arg Arg
            260                 265                 270

Thr Thr Pro Pro Thr Thr Ala Thr Pro Val Arg His Arg Pro Arg Pro
            275                 280                 285

Tyr Pro Pro Asn Val Asn Glu Glu Ile Gln Val Gly His Val Pro Arg
            290                 295                 300

Gly Asp Val Asp His His Leu Tyr Pro His Val Met Gln Pro Asn Ala
305                 310                 315                 320

Ser Thr Gly Gln Glu Ala Leu Ser Gln Thr Thr Ile Ser Trp Thr Pro
            325                 330                 335

Phe Gln Glu Ser Ser Glu Tyr Ile Ile Ser Cys His Pro Val Gly Ile
            340                 345                 350

Asp Glu Glu Pro Leu Gln Phe Arg Val Pro Gly Thr Ser Ala Ser Ala
            355                 360                 365

Thr Leu Thr Gly Leu Thr Arg Gly Ala Thr Tyr Asn Ile Ile Val Glu
            370                 375                 380

Ala Leu Lys Asp Gln Lys Arg His Lys Val Arg Glu Glu Val Val Thr
385                 390                 395                 400

Val Gly Asn Ser Val Asp Gln Gly Leu Asn Gln Pro Thr Asp Asp Ser
            405                 410                 415

Cys Phe Asp Pro Tyr Thr Val Ser His Tyr Ala Ile Gly Glu Glu Trp
            420                 425                 430

Glu Arg Leu Ser Glu Ser Gly Phe Lys Leu Ser Cys Gln Cys Leu Gly
            435                 440                 445

Phe Gly Ser Gly His Phe Arg Cys Asp Ser Ser Lys Trp Cys His Asp
            450                 455                 460

Asn Gly Val Asn Tyr Lys Ile Gly Glu Lys Trp Asp Arg Gln Gly Glu
465                 470                 475                 480

Asn Gly Gln Met Met Ser Cys Thr Cys Leu Gly Asn Gly Lys Gly Glu
            485                 490                 495

Phe Lys Cys Asp Phe Ala Thr Cys Tyr Asp Asp Gly Lys Thr Tyr His
            500                 505                 510

Val Gly Glu His Trp Gln
        515

<210> SEQ ID NO 128
<211> LENGTH: 700
<212> TYPE: PRT
<213> ORGANISM: Dog

<400> SEQUENCE: 128

Met Ser Pro Arg Gln Pro Leu Val Leu Val Phe Leu Val Leu Gly Cys
1               5                   10                  15

Cys Ser Ala Ala Pro Arg Pro His Lys Pro Thr Val Val Val Phe Pro
            20                  25                  30

Gly Asp Leu Arg Thr Asn Leu Thr Asp Lys Gln Leu Ala Glu Glu Tyr
            35                  40                  45

Leu Phe Arg Tyr Gly Tyr Thr Gln Val Ala Glu Leu Ser Asn Asp Lys
            50                  55                  60

Gln Ser Leu Ser Arg Gly Leu Arg Leu Gln Arg Arg Leu Ala Leu
65                  70                  75                  80

Pro Glu Thr Gly Glu Leu Asp Lys Thr Thr Leu Glu Ala Met Arg Ala
            85                  90                  95

-continued

```
Pro Arg Cys Gly Val Pro Asp Leu Gly Lys Phe Gln Thr Phe Glu Gly
            100                 105                 110
Asp Leu Lys Trp His His Asn Asp Ile Thr Tyr Trp Ile Gln Asn Tyr
        115                 120                 125
Ser Glu Asp Leu Pro Arg Asp Val Ile Asp Ala Phe Ala Arg Ala
    130                 135                 140
Phe Ala Val Trp Ser Ala Val Thr Pro Leu Thr Phe Thr Arg Val Tyr
145                 150                 155                 160
Gly Pro Glu Ala Asp Ile Ile Ile Gln Phe Gly Val Arg Glu His Gly
                165                 170                 175
Asp Gly Tyr Pro Phe Asp Gly Lys Asn Gly Leu Leu Ala His Ala Phe
            180                 185                 190
Pro Pro Gly Pro Gly Ile Gln Gly Asp Ala His Phe Asp Asp Glu Glu
        195                 200                 205
Leu Trp Thr Leu Gly Lys Gly Val Val Val Pro Thr His Phe Gly Asn
    210                 215                 220
Ala Asp Gly Ala Pro Cys His Phe Pro Phe Thr Phe Glu Gly Arg Ser
225                 230                 235                 240
Tyr Ser Ala Cys Thr Thr Asp Gly Arg Ser Asp Thr Pro Trp Cys
                245                 250                 255
Ser Thr Thr Ala Asp Tyr Asp Thr Asp Arg Arg Phe Gly Phe Cys Pro
            260                 265                 270
Ser Glu Lys Leu Tyr Ala Gln Asp Gly Asn Gly Asp Gly Lys Pro Cys
        275                 280                 285
Val Phe Pro Phe Thr Phe Glu Gly Arg Ser Tyr Ser Thr Cys Thr Thr
    290                 295                 300
Asp Gly Arg Ser Asp Gly Tyr Arg Trp Cys Ser Thr Thr Ala Asp Tyr
305                 310                 315                 320
Asp Gln Asp Lys Leu Tyr Gly Phe Cys Pro Thr Arg Val Asp Ser Ala
                325                 330                 335
Val Thr Gly Gly Asn Ser Ala Gly Glu Pro Cys Val Phe Pro Phe Ile
            340                 345                 350
Phe Leu Gly Lys Gln Tyr Ser Thr Cys Thr Arg Glu Gly Arg Gly Asp
        355                 360                 365
Gly His Leu Trp Cys Ala Thr Thr Ser Asn Phe Asp Arg Asp Lys Lys
    370                 375                 380
Trp Gly Phe Cys Pro Asp Gln Gly Tyr Ser Leu Phe Leu Val Ala Ala
385                 390                 395                 400
His Glu Phe Gly His Ala Leu Gly Leu Asp His Ser Ser Val Pro Glu
                405                 410                 415
Ala Leu Met Tyr Pro Met Tyr Ser Phe Thr Glu Gly Pro Pro Leu His
            420                 425                 430
Glu Asp Asp Val Arg Gly Ile Gln His Leu Tyr Gly Pro Arg Pro Glu
        435                 440                 445
Pro Glu Pro Gln Pro Pro Thr Ala Pro Thr Ala Pro Pro Thr Val
    450                 455                 460
Cys Ala Thr Gly Pro Pro Thr Trp Ser Pro Thr Ala Gly Pro Thr Gly
465                 470                 475                 480
Pro Pro Ala Ala Gly Pro Thr Gly Pro Pro Thr Ala Gly Pro Ser Glu
                485                 490                 495
Ala Pro Thr Val Pro Val Asp Pro Ala Glu Asp Ile Cys Lys Val Asn
            500                 505                 510
Ile Phe Asp Ala Ile Ala Glu Ile Arg Asn Tyr Leu His Phe Phe Lys
```

```
                515                 520                 525
Glu Gly Lys Tyr Trp Arg Phe Ser Lys Gly Lys Gly Arg Arg Val Gln
            530                 535                 540

Gly Pro Phe Leu Ser Pro Ser Thr Trp Pro Ala Leu Pro Arg Lys Leu
545                 550                 555                 560

Asp Ser Ala Phe Glu Asp Gly Leu Thr Lys Lys Thr Phe Phe Phe Ser
                565                 570                 575

Gly Arg Gln Val Trp Val Tyr Thr Gly Thr Ser Val Val Gly Pro Arg
            580                 585                 590

Arg Leu Asp Lys Leu Gly Leu Gly Pro Glu Val Thr Gln Val Thr Gly
        595                 600                 605

Ala Leu Pro Gln Gly Gly Lys Val Leu Leu Phe Ser Arg Gln Arg
    610                 615                 620

Phe Trp Ser Phe Asp Val Lys Thr Gln Thr Val Asp Pro Arg Ser Ala
625                 630                 635                 640

Gly Ser Val Glu Gln Met Tyr Pro Gly Val Pro Leu Asn Thr His Asp
                645                 650                 655

Ile Phe Gln Tyr Gln Glu Lys Ala Tyr Phe Cys Gln Asp Arg Phe Tyr
            660                 665                 670

Trp Arg Val Asn Ser Arg Asn Glu Val Asn Gln Val Asp Glu Val Gly
        675                 680                 685

Tyr Val Thr Phe Asp Ile Leu Gln Cys Pro Glu Asp
    690                 695                 700

<210> SEQ ID NO 129
<211> LENGTH: 478
<212> TYPE: PRT
<213> ORGANISM: Dog

<400> SEQUENCE: 129

Met Gln Asn Leu Pro Ala Leu Leu Phe Cys Gly Val Val Cys Ser
1               5                   10                  15

Ala Tyr Pro Val Asp Arg Ala Ala Glu Asp Glu Asn Asn Met Glu
            20                  25                  30

Leu Thr Gln Gln Tyr Leu Glu Asn Tyr Tyr Asn Leu Gly Lys Asp Val
        35                  40                  45

Lys Pro Phe Val Arg Arg Arg Asn Ser Gly Pro Val Val Glu Lys Ile
50                  55                  60

Arg Glu Met Gln Lys Phe Leu Gly Leu Glu Val Thr Gly Lys Val Asp
65                  70                  75                  80

Ser Asp Thr Leu Ala Met Met Arg Arg Pro Arg Cys Gly Val Pro Asp
                85                  90                  95

Val Gly Asp Phe Thr Thr Phe Pro Gly Met Pro Lys Trp Arg Lys Thr
            100                 105                 110

His Leu Thr Tyr Arg Ile Met Asn Tyr Thr Pro Asp Leu Pro Arg Asp
        115                 120                 125

Ala Val Asp Ser Ala Ile Glu Lys Ala Leu Asn Val Trp Lys Glu Val
    130                 135                 140

Thr Pro Leu Thr Phe Ser Arg Thr Asp Glu Gly Glu Ala Asp Ile Lys
145                 150                 155                 160

Ile Ser Phe Ala Val Arg Asp His Gly Asp Phe Asn Pro Phe Asp Gly
                165                 170                 175

Pro Gly Asn Val Leu Gly His Ala Tyr Pro Pro Gly Pro Gly Ile Tyr
            180                 185                 190

Gly Asp Ala His Phe Asp Asp Asp Glu Gln Trp Thr Ser Asp Thr Ser
```

```
                    195                 200                 205
Gly Thr Asn Leu Phe Leu Val Ala Ala His Glu Leu Gly His Ser Leu
210                 215                 220

Gly Leu Phe His Ser Ala Asp Pro Ser Ala Leu Met Tyr Pro Val Tyr
225                 230                 235                 240

Asn Val Leu Ala Asp Leu Ala Arg Phe His Leu Ser Gln Asp Asp Val
                    245                 250                 255

Asn Gly Ile Gln Ser Leu Tyr Gly Gly Pro Ser Asp Ser Ser Asn
                260                 265                 270

Asp Pro Val Val Pro Thr Glu Ser Val Pro Gly Pro Gly Thr Pro
                275                 280                 285

Ala Ala Cys Asp Pro Thr Leu Ser Phe Asp Ala Ile Ser Thr Leu Arg
290                 295                 300

Gly Glu Phe Leu Phe Phe Lys Asp Arg His Phe Trp Arg Lys Ser Leu
305                 310                 315                 320

Arg Thr Leu Glu Pro Gly Phe Tyr Leu Ile Ser Ser Phe Trp Pro Ser
                325                 330                 335

Leu Pro Ser Gly Leu Asp Ala Ala Tyr Glu Glu Thr Ser Lys Asp Ile
                340                 345                 350

Val Phe Ile Phe Lys Gly Asn Gln Phe Trp Ala Met Arg Gly Thr Glu
                355                 360                 365

Val Gln Ala Gly Tyr Pro Lys Gly Ile His Thr Leu Gly Phe Pro Pro
370                 375                 380

Thr Val Lys Lys Ile Asp Ala Ala Val Phe Asp Lys Glu Lys Lys Lys
385                 390                 395                 400

Thr Tyr Phe Phe Val Gly Asp Lys Tyr Trp Arg Phe Asp Glu Lys Arg
                405                 410                 415

Gln Ser Met Glu Pro Gly Phe Pro Lys Gln Ile Ala Glu Asp Phe Pro
                420                 425                 430

Gly Val Asp Ser Lys Val Asp Ala Ala Phe Glu Ala Phe Gly Phe Tyr
                435                 440                 445

Tyr Phe Phe Asn Gly Ser Ser Gln Leu Glu Phe Asp Pro Asn Ala Lys
450                 455                 460

Lys Val Thr His Val Leu Lys Ser Asn Ser Trp Leu Asn Cys
465                 470                 475

<210> SEQ ID NO 130
<211> LENGTH: 445
<212> TYPE: PRT
<213> ORGANISM: Dog

<400> SEQUENCE: 130

Val Arg Arg Gly Pro Gln Pro Trp His Glu Ala Gly Pro Ser Ser Leu
1               5                   10                  15

Val Pro Ala Pro Thr Ala Gln Asp Thr Pro Gln Pro Ala Ser Ser Pro
                20                  25                  30

Arg Pro Pro Arg Cys Gly Val Pro Asp Pro Asp Gly Leu Ser Ala
                35                  40                  45

Arg Asn Arg Gln Lys Arg Phe Val Leu Ser Gly Gly Arg Trp Asp Lys
                50                  55                  60

Thr Asp Leu Thr Tyr Arg Ile Leu Arg Phe Pro Trp Gln Leu Val Arg
65                  70                  75                  80

Glu Gln Val Arg Gln Thr Val Ala Glu Ala Leu Gln Val Trp Ser Glu
                85                  90                  95

Val Thr Pro Leu Thr Phe Thr Glu Val His Glu Gly Arg Ala Asp Ile
```

```
            100                 105                 110
Met Ile Asp Phe Thr Arg Tyr Trp His Gly Asp Asn Leu Pro Phe Asp
            115                 120                 125

Gly Pro Gly Gly Ile Leu Ala His Ala Phe Pro Lys Thr His Arg
        130                 135                 140

Glu Gly Asp Val His Phe Asp Tyr Asp Glu Thr Trp Thr Ile Gly Asn
145                 150                 155                 160

Asn Gln Gly Thr Asp Leu Leu Gln Val Ala Ala His Glu Phe Gly His
                165                 170                 175

Thr Leu Gly Leu Gln His Thr Thr Ala Ala Lys Ala Leu Met Ser Pro
            180                 185                 190

Phe Tyr Thr Phe Arg Tyr Pro Leu Ser Leu Ser Pro Asp Asp Arg Arg
        195                 200                 205

Gly Ile Gln His Leu Tyr Gly Gln Pro Arg Thr Ala Pro Thr Ser Arg
210                 215                 220

Pro Pro Ala Val Gly Pro Gln Ala Gly Val Asp Thr Asn Glu Ile Ala
225                 230                 235                 240

Pro Leu Glu Pro Glu Ala Pro Pro Asp Ala Cys Glu Ile Thr Phe Asp
                245                 250                 255

Ala Val Ser Thr Ile Arg Gly Glu Leu Phe Phe Phe Lys Ala Gly Phe
            260                 265                 270

Val Trp Arg Leu Arg Gly Gly Arg Leu Gln Pro Gly Tyr Pro Ala Leu
        275                 280                 285

Ala Ser Arg His Trp Gln Gly Leu Pro Ser Pro Val Asp Ala Ala Phe
        290                 295                 300

Glu Asp Ala Gln Gly His Ile Trp Phe Phe Gln Gly Ala Gln Tyr Trp
305                 310                 315                 320

Val Tyr Asn Gly Glu Lys Pro Val Leu Gly Pro Ala Pro Leu Ser Glu
                325                 330                 335

Leu Gly Leu Leu Gly Ser Pro Ile Gln Ala Ala Leu Ala Trp Gly Pro
            340                 345                 350

Glu Lys Asn Lys Ile Tyr Phe Phe Gly Gly Arg Asp Tyr Trp Arg Phe
        355                 360                 365

His Leu Ser Thr Arg Arg Val Asp Ser Pro Val Pro Arg Arg Ala Thr
370                 375                 380

Asp Trp Arg Gly Val Pro Ser Glu Ile Asp Ala Ala Phe Arg Asp Ala
385                 390                 395                 400

Asp Gly Tyr Ala Tyr Phe Leu Arg Gly Arg Leu Tyr Trp Lys Phe Asp
                405                 410                 415

Pro Val Lys Val Lys Ala Leu Glu Gly Phe Pro Arg Leu Val Gly Pro
            420                 425                 430

Asp Phe Phe Gly Cys Thr Glu Pro Ala Asn Thr Phe Arg
        435                 440                 445

<210> SEQ ID NO 131
<211> LENGTH: 582
<212> TYPE: PRT
<213> ORGANISM: Dog

<400> SEQUENCE: 131

Met Ser Pro Ala Pro Arg Pro Ala Gly Gly Arg Leu Leu Pro Leu Leu
1               5                   10                  15

Thr Leu Ala Thr Ala Leu Ala Ser Leu Ser Ser Ala Gln Ser Ser Phe
            20                  25                  30

Ser Pro Glu Ala Trp Leu Gln Gln Tyr Gly Tyr Leu Pro Pro Gly Asp
```

```
                35                  40                  45
Leu Arg Thr His Thr Gln Arg Ser Pro Gln Ser Phe Ser Ala Ala Ile
 50                      55                  60

Ala Ala Met Gln Lys Phe Tyr Gly Leu Arg Val Thr Gly Lys Ala Asp
 65                  70                  75                  80

Ala Asp Thr Met Lys Ala Met Arg Arg Pro Arg Cys Gly Val Pro Asp
                 85                  90                  95

Lys Phe Gly Ala Glu Ile Lys Ala Asn Val Arg Arg Lys Arg Tyr Ala
            100                 105                 110

Ile Gln Gly Leu Lys Trp Gln His Asn Glu Ile Thr Phe Cys Ile Gln
        115                 120                 125

Asn Tyr Thr Pro Lys Val Gly Glu Tyr Ala Thr Phe Glu Ala Ile Arg
    130                 135                 140

Lys Ala Phe Arg Val Trp Glu Ser Ala Thr Pro Leu Arg Phe Arg Glu
145                 150                 155                 160

Val Pro Tyr Ala Tyr Ile Arg Glu Gly His Glu Lys Gln Ala Asp Ile
                165                 170                 175

Met Ile Phe Phe Ala Glu Gly Phe His Gly Asp Ser Thr Pro Phe Asp
            180                 185                 190

Gly Glu Gly Gly Phe Leu Ala His Ala Tyr Phe Pro Gly Pro Asn Ile
        195                 200                 205

Gly Gly Asp Thr His Phe Asp Ser Ala Glu Pro Trp Thr Val Arg Asn
    210                 215                 220

Glu Asp Leu Asn Gly Asn Asp Ile Phe Leu Val Ala Val His Glu Leu
225                 230                 235                 240

Gly His Ala Leu Gly Leu Glu His Ser Asn Asp Pro Ser Ala Ile Met
                245                 250                 255

Ala Pro Phe Tyr Gln Trp Met Asp Thr Glu Asn Phe Val Leu Pro Asp
            260                 265                 270

Asp Asp Arg Arg Gly Ile Gln Gln Leu Tyr Gly Ser Glu Ser Gly Ser
        275                 280                 285

Pro Thr Lys Met Pro Pro Gln Pro Arg Thr Thr Ser Arg Pro Ser Val
    290                 295                 300

Pro Asp Lys Pro Lys Asn Pro Thr Tyr Gly Pro Asn Ile Cys Asp Gly
305                 310                 315                 320

Asn Phe Asp Thr Val Ala Val Leu Arg Gly Glu Met Phe Val Phe Lys
                325                 330                 335

Glu Arg Trp Phe Trp Arg Val Arg Asn Asn Gln Val Met Asp Gly Tyr
            340                 345                 350

Pro Met Pro Ile Gly Gln Phe Trp Arg Gly Leu Pro Ala Ser Ile Asn
        355                 360                 365

Thr Ala Tyr Glu Arg Lys Asp Gly Lys Phe Val Phe Phe Lys Gly Asp
    370                 375                 380

Lys His Trp Val Phe Asp Glu Ala Ser Leu Glu Pro Gly Tyr Pro Lys
385                 390                 395                 400

His Ile Lys Glu Leu Gly Arg Gly Leu Pro Thr Asp Lys Ile Asp Ala
                405                 410                 415

Ala Leu Phe Trp Met Pro Asn Gly Lys Thr Tyr Phe Phe Arg Gly Asn
            420                 425                 430

Lys Tyr Tyr Arg Phe Asn Glu Glu Leu Arg Ala Val Asp Ser Glu Tyr
        435                 440                 445

Pro Lys Asn Ile Lys Val Trp Glu Gly Ile Pro Glu Ser Pro Arg Gly
    450                 455                 460
```

```
Ser Phe Met Gly Ser Asp Glu Val Phe Thr Tyr Phe Tyr Lys Gly Asn
465                 470                 475                 480

Lys Tyr Trp Lys Phe Asn Asn Gln Lys Leu Lys Val Glu Pro Gly Tyr
                485                 490                 495

Pro Lys Ser Ala Leu Arg Asp Trp Met Gly Cys Pro Ser Ser Gly Ser
            500                 505                 510

Arg Pro Asp Glu Gly Thr Glu Glu Thr Glu Val Ile Ile Ile Glu
        515                 520                 525

Val Asp Glu Glu Gly Ser Gly Ala Val Ser Ala Ala Ala Val Val Leu
    530                 535                 540

Pro Val Leu Leu Leu Leu Val Leu Ala Val Gly Leu Ala Val Phe
545                 550                 555                 560

Phe Phe Arg Arg His Gly Thr Pro Lys Arg Leu Leu Tyr Cys Gln Arg
                565                 570                 575

Ser Leu Leu Asp Lys Val
            580

<210> SEQ ID NO 132
<211> LENGTH: 261
<212> TYPE: PRT
<213> ORGANISM: Dog

<400> SEQUENCE: 132

Met Gln Ala Ala Ile Leu Lys Val Thr Val Phe Leu Pro Trp Cys Leu
1               5                   10                  15

Ala Phe Pro Val Pro Pro Ala Thr Asp Leu Lys Gly Leu Asp Phe Val
                20                  25                  30

Lys Asn Tyr Phe His Gln Leu Phe Leu Thr Lys Arg Glu Leu Pro Leu
            35                  40                  45

Phe Thr Gln Glu Asp Lys Ile Gln Arg Leu Lys Gln Phe His Leu Asn
    50                  55                  60

Glu Thr Val Leu Gln Asp Glu Gln Met Leu Val Val Ser Arg Gln Pro
65                  70                  75                  80

His Cys Gly Gly Asn Asp Gly Ala Lys Asp Ser Thr Phe Pro Gly Ser
                85                  90                  95

Ser Met Trp Asp Lys His Thr Leu Thr Tyr Arg Ile Ile Asn Tyr Pro
            100                 105                 110

Arg Asp Ile Asn Pro Ser Thr Val Lys Asn Ile Met Gln Asn Ala Val
        115                 120                 125

Ser Ile Trp Ser Asn Val Thr Pro Leu Ile Phe Gln Gln Val Lys Ser
    130                 135                 140

Gln Asp Ala Asp Ile Lys Ile Ser Phe Trp Asp Leu Ala His Gly Asp
145                 150                 155                 160

Cys Trp Pro Phe Asp Gly Pro Gly Gly Val Leu Gly His Ala Phe Leu
                165                 170                 175

Pro Asn Ser Arg Ala Pro Gly Val Ile His Phe Asp Arg Gly Glu His
            180                 185                 190

Trp Ser Thr Ser Tyr Arg Gly Phe Asn Leu Phe Leu Val Ala Ile His
        195                 200                 205

Glu Leu Gly His Ser Leu Gly Leu Leu His Ser Lys Ser Leu Asn Ser
    210                 215                 220

Ile Met Tyr Pro Arg Tyr Val Asn Arg Asp Pro Arg Thr Phe His Leu
225                 230                 235                 240

Asp Gly Asp Asp Ile Lys Arg Ile Gln Gln Leu Tyr Gly Glu Arg Cys
                245                 250                 255
```

```
Ser Ser Glu Met Pro
            260

<210> SEQ ID NO 133
<211> LENGTH: 267
<212> TYPE: PRT
<213> ORGANISM: Dog

<400> SEQUENCE: 133

Met Trp Pro Ala Val Leu Cys Ala Leu Cys Leu Pro Ser Cys Leu
1               5                   10                  15

Ala Leu Pro Leu Pro Arg Glu Ala Gly Gly Met Ser Glu Pro Gln Trp
            20                  25                  30

Lys Gln Ala Gln Asp Tyr Leu Lys Arg Phe Tyr Pro Ser Asp Ser Lys
            35                  40                  45

Thr Arg Asp Ala Asp Ser Phe Lys Thr Lys Leu Lys Glu Met Gln Lys
        50                  55                  60

Phe Phe Arg Leu Pro Val Thr Gly Ile Leu Asn Ser Arg Thr Ile Glu
65                  70                  75                  80

Ile Met Gln Lys Pro Arg Cys Gly Val Pro Asp Val Ala His Phe Ser
                85                  90                  95

Leu Phe Pro Asn Arg Pro Lys Trp Thr Ser Glu Val Ile Thr Tyr Arg
            100                 105                 110

Ile Ala Ser Tyr Thr Pro Asp Leu Pro Arg Phe Arg Val Asn Gln Leu
            115                 120                 125

Val Ala Lys Ala Leu Ala Met Trp Ser Lys Glu Ile Pro Leu Ser Phe
        130                 135                 140

Arg Arg Val Pro Arg Gly Thr Ala Asp Ile Met Ile Gly Phe Ala Arg
145                 150                 155                 160

Gly Ala His Gly Asp Tyr Tyr Pro Phe Asp Gly Pro Gly Asn Ile Leu
                165                 170                 175

Ala His Ala Phe Ala Pro Gly Pro Asp Leu Gly Gly Asp Ala His Phe
            180                 185                 190

Asp Glu Asp Glu Arg Trp Thr Asp Gly Ser Arg Ile Gly Ile Asn Phe
            195                 200                 205

Leu Ile Ala Ala Thr His Glu Leu Gly His Ser Leu Gly Leu Gly His
        210                 215                 220

Ser Ser Asp Pro Asp Ala Val Met Tyr Pro Thr Tyr Ser Ile Arg Asp
225                 230                 235                 240

Ser Lys Ser Phe Lys Leu Ser Gln Asp Ile Glu Gly Ile Gln Lys
                245                 250                 255

Leu Tyr Val Leu Gln Asp Asn Pro Gln Gln Arg
            260                 265

<210> SEQ ID NO 134
<211> LENGTH: 423
<212> TYPE: PRT
<213> ORGANISM: Dog

<400> SEQUENCE: 134

Met Gln Arg Phe Gly Gly Leu Glu Ala Thr Gly Ile Leu Asp Val Ala
1               5                   10                  15

Thr Leu Ala Leu Met Lys Thr Pro Arg Cys Ser Leu Pro Asp Leu Pro
            20                  25                  30

Ala Ala Ala Pro Ala Arg Arg Arg Gln Ala Pro Ala Pro Thr Thr
            35                  40                  45

Trp His Lys Arg Ser Leu Ser Trp Arg Val Arg Thr Phe Pro Arg Asp
```

|   |   |   |   |   | 50 |   |   |   | 55 |   |   |   | 60 |   |   |
|---|---|---|---|---|---|---|---|---|---|---|---|---|---|---|---|

Ser Pro Leu Gly Pro Asp Thr Val Arg Ala Leu Met His Tyr Ala Leu
65                  70                  75                  80

Lys Val Trp Ser Asp Ile Thr Pro Leu Asn Phe His Glu Val Ala Gly
                85                  90                  95

Ser Ala Ala Asp Ile Gln Ile Asp Phe Ser Lys Ala Asp His Asn Asp
            100                 105                 110

Ala Tyr Pro Phe Asp Gly Pro Gly Gly Thr Val Ala His Ala Phe Phe
        115                 120                 125

Pro Gly Asp His His Thr Ala Gly Asp Ala His Phe Asp Asp Asp Glu
    130                 135                 140

Ser Trp Ala Phe Arg Ser Ser Asp Ala His Asp Met Asp Leu Phe Ala
145                 150                 155                 160

Val Ala Val His Glu Phe Gly His Ala Ile Gly Leu Ser His Val Ala
                165                 170                 175

Ala Thr Ser Ser Ile Met Gln Pro Tyr Tyr Gln Gly Pro Val Gly Asp
            180                 185                 190

Pro Leu His Tyr Arg Leu Pro Tyr Glu Asp Arg Val Arg Ile Trp Gln
        195                 200                 205

Leu Tyr Gly Glu Ser Phe Pro Ser Asn Leu Pro Leu Ser Pro Gln Asp
210                 215                 220

Val Pro His Arg Cys Ser Thr Asp Phe Asp Ala Val Ala Gln Ile Arg
225                 230                 235                 240

Gly Glu Ala Phe Phe Phe Lys Gly Lys Tyr Phe Trp Arg Leu Thr Arg
                245                 250                 255

Asp Gly His Leu Val Ser Leu Gln Pro Ala Gln Met His Arg Phe Trp
            260                 265                 270

Arg Gly Leu Pro Leu Gln Leu Asp Ser Val Asp Ala Val Tyr Glu Arg
        275                 280                 285

Thr Ser Asp His Lys Ile Val Phe Phe Lys Gly Asp Arg Tyr Trp Val
290                 295                 300

Phe Lys Asp Asn Asn Val Glu Glu Gly Tyr Pro Arg Pro Val Ser Asp
305                 310                 315                 320

Phe Gly Leu Pro Pro Gly Gly Val Asp Ala Ala Phe Ser Trp Ser His
                325                 330                 335

Asn Asp Lys Thr Tyr Phe Phe Lys Asp Gln Leu Tyr Trp Arg Phe Asp
            340                 345                 350

Glu His Thr Arg Arg Met Asp Pro Gly His Pro Ala Arg Ser Pro Pro
        355                 360                 365

Trp Arg Gly Ile Pro Ser Thr Leu Asp Asp Ala Met Cys Trp Ser Asp
370                 375                 380

Gly Ala Ala Tyr Phe Phe Arg Gly Lys Glu Tyr Trp Lys Val Leu Asp
385                 390                 395                 400

Ser Glu Leu Glu Val Ala Pro Gly Tyr Pro Gln Ser Thr Ala Arg Asp
                405                 410                 415

Trp Leu Val Cys Arg Asp Leu
            420

<210> SEQ ID NO 135
<211> LENGTH: 560
<212> TYPE: PRT
<213> ORGANISM: Dog

<400> SEQUENCE: 135

Met Leu Arg Leu Leu Val Leu Leu Leu Ser Val Leu Pro Pro Pro Ala

```
1               5                   10                  15
Arg Ala Arg Glu Pro Ser Ala Gln Asp Val Ser Leu Gly Val Asp Trp
                20                  25                  30

Leu Thr Arg Tyr Gly Tyr Leu Pro Ser Pro His Pro Ala Gln Ala Gln
            35                  40                  45

Leu Gln Ser Pro Thr Lys Leu Arg Asp Ala Ile Lys Val Met Gln Arg
        50                  55                  60

Phe Ala Gly Leu Pro Glu Thr Gly Val Leu Asp Ser Ala Thr Met Ala
 65                  70                  75                  80

Thr Met Gln Lys Pro Arg Cys Ser Leu Pro Asp Val Leu Gly Val Ala
                85                  90                  95

Glu Leu Val Arg Arg Arg Arg Arg Tyr Ala Leu Ser Gly Ser
            100                 105                 110

Met Trp Arg Lys Arg Thr Leu Thr Trp Arg Val Arg Ser Phe Pro Gln
            115                 120                 125

Ser Ser Ala Leu Thr Gln Glu Thr Val Arg Thr Leu Met His His Ala
            130                 135                 140

Leu Thr Thr Trp Gly Val Glu Ser Gly Leu Ile Gln Glu Leu Val Ser
145                 150                 155                 160

Gln Ala Pro Thr Glu Pro Asp Ile Leu Ile Asp Phe Ala Arg Ala Tyr
                165                 170                 175

His Gln Asp Ser Tyr Pro Phe Asp Gly Gln Gly Gly Thr Leu Ala His
            180                 185                 190

Ala Phe Phe Pro Gly Glu His Pro Ile Ser Gly Asp Thr His Phe Asp
            195                 200                 205

Asp Glu Glu Thr Trp Thr Tyr Gly Ser Lys Asp Gly Glu Gly Thr Asp
        210                 215                 220

Leu Phe Ala Val Ala Val His Glu Phe Gly His Ala Leu Gly Leu Gly
225                 230                 235                 240

His Ser Ser Ala Pro Asn Ser Ile Met Arg Pro Phe Tyr Gln Gly Pro
                245                 250                 255

Val Gly Asp Pro His Glu Tyr Arg Leu Ser Asp Asp Arg Glu Gly
            260                 265                 270

Leu Gln Gln Leu Tyr Gly Lys Val Pro Gln Thr Pro Tyr Asp Lys Pro
        275                 280                 285

Thr Arg Lys Pro Leu Ala Pro Pro Pro Pro Ala Leu Pro Pro
    290                 295                 300

Asp Ser Pro Ser Leu Pro Ile Pro Asp Arg Cys Asp Gly Asn Phe Asp
305                 310                 315                 320

Ala Ile Ala Asn Ile Arg Gly Glu Ile Phe Phe Phe Lys Gly Pro Trp
                325                 330                 335

Phe Trp Arg Leu Gln Pro Ser Gly Gln Leu Val Ser Pro Arg Pro Ala
            340                 345                 350

Arg Leu His Arg Phe Trp Glu Gly Leu Pro Ala Ala Val Asp Val Val
            355                 360                 365

Gln Ala Ala Tyr Ala Arg His Pro Asp Gly Arg Ile Leu Leu Phe Ser
        370                 375                 380

Gly Pro Arg Phe Trp Val Phe Arg Asp Arg Gln Leu Glu Gly Ala Pro
385                 390                 395                 400

Arg Pro Leu Lys Gly Leu Gly Leu Pro Ala Gly Glu Gln Gly Asp Pro
                405                 410                 415

Gln Phe Ser Trp Pro Leu Asn Gly Lys Thr His Leu Ile Arg Gly Arg
            420                 425                 430
```

```
Gly Tyr Trp Gly Tyr His Lys Ala Ala Arg Ala Asp Pro Gly Tyr
        435                 440                 445

Pro Arg Asp Leu Ser Leu Trp Glu Gly Ala Pro His Ala Pro Asp Asp
450                 455                 460

Val Thr Val Ser Asn Thr Gly Asp Thr Tyr Phe Phe Lys Gly Ala His
465                 470                 475                 480

Tyr Trp Arg Phe Pro Lys Gly Ser Val Lys Ala Glu Pro Asp Ser Pro
                485                 490                 495

Gln Pro Met Gly Pro Lys Trp Leu Asp Cys Pro Ala Ala Ser Ala Asp
            500                 505                 510

Pro Arg Ala Pro Arg Pro Arg Gly Thr Leu Ala Pro Gly Thr Cys
        515                 520                 525

Asp Cys His Cys Glu Ile Asn Gln Ala Ser Gly Arg Pro Ser Leu Ser
530                 535                 540

Leu Glu Val Ser Leu Leu Ala Leu Leu Leu Gly Gly Val Ala Ser Val
545                 550                 555                 560

<210> SEQ ID NO 136
<211> LENGTH: 531
<212> TYPE: PRT
<213> ORGANISM: Dog

<400> SEQUENCE: 136

Met Asn Trp Gln Trp Leu Cys Leu Gly Phe Leu Leu Pro Ala Thr Val
1               5                   10                  15

Ser Gly Arg Ala Leu Gly Thr Ala Arg Lys Glu Thr Ala Val Asp Tyr
            20                  25                  30

Leu Leu Gln Tyr Gly Tyr Leu Gln Lys Pro Leu Glu Gly Pro Asp Asn
        35                  40                  45

Phe Arg Pro Glu Asp Ile Met Glu Ala Leu Arg Thr Phe Gln Glu Ala
50                  55                  60

Ser Glu Leu Pro Val Ser Gly Gln Leu Asp Asp Ala Thr Arg Ala Arg
65                  70                  75                  80

Met Arg Gln Pro Arg Cys Gly Leu Glu Asp Pro Phe Asn Gln Lys Thr
                85                  90                  95

Leu Lys Tyr Leu Leu Leu Gly Arg Trp Arg Lys Lys His Leu Thr Phe
            100                 105                 110

Arg Ile Phe Asn Leu Pro Ser Thr Leu Pro Pro Asp Thr Ala Arg Ala
        115                 120                 125

Ala Leu Leu Gln Ala Phe Gln Tyr Trp Ser Ser Ala Ala Pro Leu Thr
130                 135                 140

Phe Arg Glu Val Gln Ala Gly Trp Ala Asp Ile Arg Leu Ser Phe His
145                 150                 155                 160

Gly Arg Gln Ser Pro Tyr Cys Ser Asn Ser Phe Asp Gly Pro Gly Arg
                165                 170                 175

Val Leu Ala His Ala Asp Ile Pro Glu Leu Gly Ser Val His Phe Asp
            180                 185                 190

Glu Asp Glu Leu Trp Thr Glu Arg Thr Tyr Arg Gly Val Asn Leu Arg
        195                 200                 205

Ile Ile Ala Ala His Glu Leu Gly His Ala Leu Gly Leu Gly His Ser
210                 215                 220

Arg Tyr Thr Gln Ala Leu Met Ala Pro Val Tyr Ala Gly Tyr Arg Pro
225                 230                 235                 240

His Phe Lys Leu His Pro Asp Asp Val Ala Gly Ile Gln Ala Leu Tyr
                245                 250                 255
```

```
Gly Lys Lys Ser Pro Glu Thr Glu Glu Glu Glu Met Glu Leu
            260             265             270

Pro Ala Ile Pro His Met Pro Thr Glu Pro Gly Met Pro Asp Pro
            275             280             285

Cys Ser Gly Glu Leu Asp Ala Ile Met Leu Gly Pro Arg Gly Lys Thr
            290             295             300

Tyr Ala Phe Lys Gly Asn Tyr Val Trp Thr Val Thr Asp Ser Gly Leu
305             310             315             320

Gly Pro Leu Phe Gln Val Ser Ala Leu Trp Glu Gly Leu Pro Gly Asn
            325             330             335

Leu Asp Ala Ala Val Tyr Ser Pro Arg Thr Gln Trp Ile His Phe Phe
            340             345             350

Lys Gly Asp Lys Val Trp Arg Tyr Ile Asn Phe Lys Arg Ser Pro Gly
            355             360             365

Phe Pro Lys Lys Leu Asn Arg Ile Glu Pro Asn Leu Asp Ala Ala Leu
            370             375             380

Tyr Trp Pro Phe Asn Gln Lys Val Phe Leu Phe Lys Gly Ser Gly Tyr
385             390             395             400

Trp Gln Trp Asp Glu Leu Ala Arg Thr Asp Phe Ser His Tyr Pro Lys
            405             410             415

Pro Ile Lys Arg Leu Phe Thr Gly Val Pro Asp Gln Pro Ser Ala Ala
            420             425             430

Val Ser Trp Arg Asp Gly Arg Val Tyr Phe Phe Lys Asp Lys Gln Tyr
            435             440             445

Trp Arg Leu Asn Arg Gln Leu Arg Val Glu Lys Gly Tyr Pro Arg Asp
450             455             460

Thr Ala Pro Asn Trp Met His Cys His Pro Gln Thr Ser Asp Pro Pro
465             470             475             480

Pro Ser Gly Gly Asp Ile Arg Pro Ser Ala Thr Ala Ile Asp Thr Thr
            485             490             495

Leu Asn Asn Asp Pro Ser Pro Gly Asp Pro Ile Leu Asp Ile Thr Pro
            500             505             510

Ser Ala Thr Ala Ser Pro Thr Leu Ser Phe Pro Gly Thr Val Thr Leu
            515             520             525

Pro Glu Ala
    530

<210> SEQ ID NO 137
<211> LENGTH: 632
<212> TYPE: PRT
<213> ORGANISM: Dog

<400> SEQUENCE: 137

Ala Ala Pro Ser Pro Ile Ile Lys Phe Pro Gly Asp Val Ala Pro Lys
1               5               10              15

Thr Asp Lys Glu Leu Ala Val Gln Tyr Leu Asn Thr Tyr Tyr Gly Cys
            20              25              30

Pro Lys Glu Arg Cys Asn Leu Phe Val Leu Lys Asp Thr Leu Lys Lys
            35              40              45

Met Gln Lys Phe Phe Gly Leu Pro Gln Thr Gly Glu Leu Asp Gln Ser
    50              55              60

Thr Ile Glu Thr Met Arg Lys Pro Arg Cys Gly Asn Pro Asp Val Ala
65              70              75              80

Asn Tyr Asn Phe Phe Pro Arg Lys Pro Lys Trp Asp Lys Asn Gln Ile
            85              90              95
```

```
            Thr Tyr Arg Ile Ile Gly Tyr Thr Pro Asp Leu Asp Pro Glu Thr Val
                        100                 105                 110

Asp Asp Ala Phe Ala Arg Ala Phe Gln Val Trp Ser Asp Val Thr Pro
                        115                 120                 125

Leu Arg Phe Ser Arg Ile His Asp Gly Glu Ala Asp Ile Met Ile Asn
                        130                 135                 140

Phe Gly Arg Trp Glu His Gly Asp Gly Tyr Pro Phe Asp Gly Lys Asp
            145                 150                 155                 160

Gly Leu Leu Ala His Ala Phe Ala Pro Gly Pro Gly Val Gly Gly Asp
                            165                 170                 175

Ser His Phe Asp Asp Glu Leu Trp Thr Leu Gly Glu Gly Gln Val
                        180                 185                 190

Val Arg Val Lys Tyr Gly Asn Ala Asp Gly Glu Tyr Cys Lys Phe Pro
                        195                 200                 205

Phe Leu Phe Asn Gly Arg Glu Tyr Thr Ser Cys Thr Asp Thr Gly Arg
                        210                 215                 220

Ser Asp Gly Phe Leu Trp Cys Ser Thr Thr Tyr Asn Phe Glu Lys Asp
            225                 230                 235                 240

Gly Lys Tyr Gly Phe Cys Pro His Glu Ala Leu Phe Thr Met Gly Gly
                            245                 250                 255

Asn Ala Asp Gly Gln Pro Cys Lys Phe Pro Phe Arg Phe Gln Gly Thr
                        260                 265                 270

Ser Tyr Asp Ser Cys Thr Thr Glu Gly Arg Thr Asp Gly Tyr Arg Trp
                        275                 280                 285

Cys Gly Thr Thr Glu Asp Tyr Asp Arg Asp Lys Lys Tyr Gly Phe Cys
            290                 295                 300

Pro Glu Thr Ala Met Ser Thr Ile Gly Gly Asn Ser Glu Gly Ala Pro
            305                 310                 315                 320

Cys Val Phe Pro Phe Thr Phe Leu Gly Asn Lys His Glu Ser Cys Thr
                        325                 330                 335

Ser Ala Gly Arg Ser Asp Gly Lys Val Trp Cys Ala Thr Thr Ala Asn
                        340                 345                 350

Tyr Asp Asp Asp Arg Lys Trp Gly Phe Cys Pro Asp Gln Gly Tyr Ser
                        355                 360                 365

Leu Phe Leu Val Ala Ala His Glu Phe Gly His Ala Met Gly Leu Glu
                        370                 375                 380

His Ser Glu Asp Pro Gly Ala Leu Met Ala Pro Ile Tyr Thr Tyr Thr
            385                 390                 395                 400

Lys Asn Phe Arg Leu Ser Gln Asp Asp Ile Lys Gly Ile Gln Glu Leu
                        405                 410                 415

Tyr Gly Ala Ser Pro Asp Ala Gly Thr Gly Thr Gly Pro Thr Pro Thr
                        420                 425                 430

Leu Gly Pro Val Thr Pro Glu Ile Cys Lys Gln Asp Ile Val Phe Asp
                        435                 440                 445

Gly Ile Ser Gln Ile Arg Gly Glu Ile Phe Phe Phe Lys Asp Arg Phe
                        450                 455                 460

Ile Trp Arg Thr Val Thr Pro Arg Asn Lys Pro Met Gly Pro Leu Leu
            465                 470                 475                 480

Val Ala Thr Phe Trp Pro Glu Leu Pro Glu Lys Ile Asp Ala Val Tyr
                        485                 490                 495

Glu Ala Pro Gln Glu Glu Lys Ala Val Phe Phe Ala Gly Asn Glu Tyr
                        500                 505                 510

Trp Val Tyr Ser Ala Ser Thr Leu Glu Arg Gly Tyr Pro Lys Pro Leu
                        515                 520                 525
```

```
Thr Ser Leu Gly Leu Pro Pro Asp Val Gln Arg Val Asp Ala Ala Phe
        530                 535                 540

Asn Trp Ser Lys Asn Lys Thr Tyr Ile Phe Ala Gly Asp Lys Phe
545                 550                 555                 560

Trp Arg Tyr Asn Glu Val Lys Lys Lys Met Asp Pro Gly Phe Pro Lys
                565                 570                 575

Leu Ile Ala Asp Ala Trp Asn Ala Ile Pro Asp Asn Leu Asp Ala Val
                580                 585                 590

Val Asp Leu Gln Gly Ser Gly His Ser Tyr Phe Phe Lys Gly Ala Tyr
                595                 600                 605

Tyr Leu Lys Leu Glu Asn Gln Ser Leu Lys Ser Val Lys Phe Gly Ser
        610                 615                 620

Ile Lys Ser Asp Trp Leu Gly Cys
625                 630

<210> SEQ ID NO 138
<211> LENGTH: 512
<212> TYPE: PRT
<213> ORGANISM: Dog

<400> SEQUENCE: 138

Met Lys Ser Leu Leu Gln Phe Phe Leu Phe Ile Thr Phe Ser Ser
1               5                   10                  15

Ala Phe Pro Thr Glu Gln Lys Met Asp Thr Glu Asn Met Gln Leu
                20                  25                  30

Ala Gln Val Tyr Leu Asn Gln Phe Tyr Ser Leu Glu Ile Glu Gly Ser
        35                  40                  45

His Leu Ala Gln Ser Lys Asn Lys Ser Leu Leu Val Gly Lys Ile Arg
    50                  55                  60

Glu Met Gln Ala Phe Phe Gly Leu Thr Val Thr Gly Gln Leu Asp Ser
65                  70                  75                  80

Asn Thr Leu Glu Ile Met Lys Thr Pro Arg Cys Gly Val Pro Asp Val
                85                  90                  95

Gly Gln Tyr Gly Tyr Thr Leu Pro Gly Trp Arg Lys Tyr Asn Leu Thr
            100                 105                 110

Tyr Arg Ile Val Asn Tyr Thr Pro Asp Met Ala Arg Val Asp Val Asp
        115                 120                 125

Lys Ala Ile Gln Asn Gly Leu Glu Val Trp Ser Gly Val Thr Pro Leu
    130                 135                 140

Thr Phe Thr Lys Ile Ser Lys Gly Ile Ala Asp Ile Met Ile Ala Phe
145                 150                 155                 160

Arg Thr Arg Val His Gly Trp Cys Pro Arg Tyr Phe Asp Gly Pro Leu
                165                 170                 175

Gly Val Leu Gly His Ala Phe Pro Pro Gly Leu Gly Leu Gly Gly Asp
            180                 185                 190

Thr His Phe Asp Glu Asp Glu Asp Trp Thr Lys Asp Gly Ala Gly Phe
        195                 200                 205

Asn Leu Phe Leu Val Ala Ala His Glu Phe Gly His Ala Leu Gly Leu
    210                 215                 220

Ser His Ser Asn Asp Gln Thr Ala Leu Met Phe Pro Asn Tyr Val Ser
225                 230                 235                 240

Leu Asp Pro Asn Lys Tyr Pro Leu Ser Gln Asp Asp Ile Asn Gly Ile
                245                 250                 255

Gln Ser Ile Tyr Gly Ser Leu Pro Thr Ala Ser Ala Lys Pro Lys Glu
            260                 265                 270
```

Ser Thr Ile Leu His Ala Cys Asp Pro Asp Leu Thr Phe Asp Ala Ile
            275                 280                 285

Thr Thr Phe Arg Arg Glu Val Met Phe Phe Lys Gly Arg His Val Trp
        290                 295                 300

Arg Ile Tyr Tyr Asp Ile Thr Asp Val Glu Phe Glu Leu Ile Ser Ser
305                 310                 315                 320

Phe Trp Pro Ser Leu Pro Ala Asp Ile Gln Ala Ala Tyr Glu Asn Pro
                325                 330                 335

Lys Asp Lys Met Leu Val Phe Lys Asp Asp Asn Phe Trp Met Ile Arg
            340                 345                 350

Gly Tyr Ala Val Leu Pro Asp Phe Pro Lys Pro Ile Arg Thr Leu Gly
        355                 360                 365

Phe Pro Arg Ser Val Lys Lys Ile Asp Ala Ala Val Cys Asp His Ser
    370                 375                 380

Thr Arg Lys Thr Tyr Phe Phe Val Gly Ile Trp Cys Trp Arg Tyr Asp
385                 390                 395                 400

Glu Val Thr Gln Thr Met Asp Lys Gly Tyr Pro Arg Arg Val Val Lys
                405                 410                 415

Tyr Phe Pro Gly Val Gly Leu Arg Val Asp Ala Ala Phe Gln His Lys
            420                 425                 430

Gly Phe Phe Tyr Phe Phe Arg Gly Ser Lys Gln Phe Glu Tyr Asp Leu
        435                 440                 445

Lys Ala Lys Asn Ile Thr Arg Ile Met Lys Ile Asn Thr Trp Phe Arg
    450                 455                 460

Cys Lys Glu Pro Leu Asn Val Ser Ser Asp Phe Ser Ile Ser Glu Glu
465                 470                 475                 480

Val His Ser Gly Gly Val Glu Thr Phe Tyr His Lys Asn Leu Asn Leu
                485                 490                 495

Leu Ile Phe Asn Ile Val His Val Leu Lys Lys Ile Tyr Ser Tyr Gln
            500                 505                 510

<210> SEQ ID NO 139
<211> LENGTH: 520
<212> TYPE: PRT
<213> ORGANISM: Dog

<400> SEQUENCE: 139

Met Ala Ala Arg Val Gly Leu Leu Leu Arg Ala Leu Trp Leu Leu Leu
1               5                   10                  15

Trp Gly Gly Leu Asp Ala Gln Leu Ala Glu Arg Gly Gly Gln Glu Leu
            20                  25                  30

Arg Arg Glu Ala Glu Ala Phe Leu Glu Lys Tyr Gly Tyr Leu Asn Glu
        35                  40                  45

Gln Val Pro Lys Asp Leu Thr Ser Ala Arg Phe Ser Asn Ala Ile Arg
    50                  55                  60

Glu Phe Gln Trp Val Ser Gln Leu Pro Ile Ser Gly Val Leu Asp Pro
65                  70                  75                  80

Val Thr Leu Arg Gln Met Thr Arg Pro Arg Cys Gly Val Ala Asp Thr
                85                  90                  95

Asp Ser Gln Ala Ala Trp Asn Glu Arg Val Ser Ala Leu Phe Ala Gly
            100                 105                 110

Gly Arg Ala Lys Met Arg Arg Lys Lys Arg Phe Ala Lys Gln Gly Ser
        115                 120                 125

Lys Trp Tyr Lys Gln His Leu Ser Tyr Arg Leu Val Asn Trp Pro Gln
    130                 135                 140

His Leu Pro Glu Pro Ala Val Arg Gly Ala Val Arg Ala Ala Phe Gln
145                 150                 155                 160

Leu Trp Ser Asn Val Ser Ala Leu Glu Phe Trp Glu Ala Pro Ala Thr
                165                 170                 175

Val Pro Ala Asp Ile Arg Leu Thr Phe Phe Gln Gly Asp His Asn Asp
            180                 185                 190

Gly Leu Gly Asn Ala Phe Asp Gly Pro Gly Gly Ala Leu Gly His Ala
        195                 200                 205

Phe Leu Pro Arg Arg Gly Glu Ala His Phe Asp Gly Asp Glu Arg Trp
    210                 215                 220

Ser Leu Ser Arg Arg Arg Gly Arg Asn Leu Phe Val Gly Leu Ala His
225                 230                 235                 240

Glu Ile Gly His Thr Leu Gly Leu Ala His Ser Pro Ala Pro Arg Ala
                245                 250                 255

Leu Met Ala Pro Tyr Tyr Lys Arg Leu Gly Arg Asp Ala Leu Leu Ser
            260                 265                 270

Trp Asp Val Leu Ala Val Gln Gly Leu Tyr Gly Lys Pro Gln Gly
        275                 280                 285

Gly Ser Val Ala Ile Gln Leu Pro Gly Lys Leu Phe Thr Asp Phe Glu
    290                 295                 300

Ala Trp Asp Pro His Arg Pro Gln Gly Arg Arg Pro Glu Ile Gln Gly
305                 310                 315                 320

Pro Lys Tyr Cys His Ser Ser Phe Asp Ala Ile Thr Val Asp Gly Gln
                325                 330                 335

Gln Arg Leu Tyr Ile Phe Gln Gly Ser His Phe Trp Glu Val Ala Pro
            340                 345                 350

Asp Gly Asn Val Ser Glu Pro Leu Pro Leu Gln Glu Arg Trp Ala Gly
        355                 360                 365

Leu Pro Pro His Ile Glu Ala Ala Ala Val Ser Leu Asp Ser Gly Asp
    370                 375                 380

Phe His Phe Phe Lys Gly Ser Arg Cys Trp Arg Phe Arg Gly Pro Lys
385                 390                 395                 400

Pro Val Trp Gly Ser Pro Gln Leu Cys Arg Ala Gly Gly Leu Pro Arg
                405                 410                 415

His Pro Asp Ala Ala Leu Phe Phe Pro Pro Leu Gly Arg Leu Val Leu
            420                 425                 430

Phe Lys Gly Ala Arg Tyr Tyr Val Leu Ala Arg Asp Gly Leu Gln Val
        435                 440                 445

Glu Pro Tyr Tyr Pro Arg Gly Leu Gln Asp Trp Gly Gly Val Pro Lys
    450                 455                 460

Glu Val Asn Gly Ala Leu Pro Arg Pro Asp Gly Ser Ile Ile Phe Phe
465                 470                 475                 480

Arg Asp Asp Arg Tyr Trp Arg Leu Asp Gln Ala Lys Leu Gln Ala Thr
                485                 490                 495

Ala Trp Gly Arg Trp Ala Ala Glu Leu Pro Trp Met Gly Cys Trp His
            500                 505                 510

Ala Asn Ser Glu Gly Ala Leu Phe
        515                 520

<210> SEQ ID NO 140
<211> LENGTH: 483
<212> TYPE: PRT
<213> ORGANISM: Dog

<400> SEQUENCE: 140

```
Met Thr Val Leu Pro Met Cys Gly Leu Ala Leu Leu Gly Ala Ala
1               5                   10                  15

Leu Glu Phe Cys Thr Ala Ala Pro Ser Val Ser Ala Ala Pro Arg
            20                  25                  30

Thr Thr Gln Asn Lys Tyr His Leu Ala Gln Ala Tyr Leu Asp Lys Tyr
            35                  40                  45

Tyr Thr Ser Lys Ala Gly Pro Gln Val Gly Glu Met Gly Ala Pro Gly
50                  55                  60

Gly Arg Ala Leu Ile Lys Lys Ile Lys Glu Leu Gln Ala Phe Phe Gly
65                  70                  75                  80

Leu Arg Ile Thr Gly Lys Leu Asp Arg Pro Thr Met Asp Met Ile Lys
                85                  90                  95

Arg Pro Arg Cys Gly Val Pro Asp Val Ala Asn Tyr Arg Leu Phe Pro
                100                 105                 110

Gly Glu Pro Lys Trp Lys Lys Asn Thr Leu Thr Tyr Arg Ile Ser Lys
                115                 120                 125

Tyr Thr Ser Ser Met Ser Pro Ala Glu Val Asp Lys Ala Val Glu Met
        130                 135                 140

Ala Leu Gln Ala Trp Gly Ser Ala Val Pro Leu Ser Phe Ile Arg Val
145                 150                 155                 160

Asn Ser Gly Glu Ala Asp Ile Met Ile Ser Phe Glu Thr Gly Asp His
                165                 170                 175

Gly Asp Ser Tyr Pro Phe Asp Gly Pro Arg Gly Thr Leu Ala His Ala
                180                 185                 190

Phe Ala Pro Gly Glu Gly Leu Gly Gly Asp Thr His Phe Asp Asn Ala
            195                 200                 205

Glu Lys Trp Thr Met Gly Met Asn Gly Phe Asn Leu Phe Thr Val Ala
    210                 215                 220

Ala His Glu Phe Gly His Ala Leu Gly Leu Ala His Ser Thr Asp Pro
225                 230                 235                 240

Ser Ala Leu Met Tyr Pro Thr Tyr Lys Tyr Gln His Pro Tyr Gly Phe
                245                 250                 255

His Leu Pro Lys Asp Asp Val Lys Gly Ile Gln Ala Leu Tyr Gly Pro
                260                 265                 270

Arg Lys Thr Leu Leu Gly Lys Pro Thr Val Pro His Ala Pro Pro Gln
            275                 280                 285

Ser Pro Ser Ile Pro Asp Leu Cys Asp Ser Ser Ser Phe Asp Ala
            290                 295                 300

Val Thr Met Leu Gly Lys Glu Leu Leu Leu Phe Arg Asp Arg Ile Phe
305                 310                 315                 320

Trp Arg Arg Gln Val His Leu Met Ala Gly Ile Arg Pro Ser Thr Ile
                325                 330                 335

Thr Ser Ser Phe Pro Gln Leu Met Ser Asn Val Asp Ala Ala Tyr Glu
            340                 345                 350

Val Ala Glu Arg Gly Thr Ala Tyr Phe Phe Lys Gly Pro His Tyr Trp
            355                 360                 365

Ile Thr Arg Gly Phe Gln Met Gln Gly Pro Pro Arg Thr Ile Tyr Asp
        370                 375                 380

Phe Gly Phe Pro Arg Tyr Val Gln Arg Ile Asp Ala Ala Val Tyr Leu
385                 390                 395                 400

Lys Asp Val Gln Lys Thr Leu Phe Phe Val Gly Asp Glu Tyr Tyr Ser
                405                 410                 415

Tyr Asp Glu Arg Lys Arg Lys Met Glu Lys Asp Tyr Pro Lys Asn Thr
```

-continued

```
                420                 425                 430
Glu Glu Glu Phe Ser Gly Val Asn Gly Gln Ile Asp Ala Ala Val Glu
            435                 440                 445

Leu Asn Gly Tyr Ile Tyr Phe Phe Ser Gly Pro Lys Ala Tyr Lys Tyr
        450                 455                 460

Asp Thr Glu Lys Glu Asp Val Val Ser Val Leu Lys Ser Ser Ser Trp
465                 470                 475                 480

Ile Gly Cys

<210> SEQ ID NO 141
<211> LENGTH: 394
<212> TYPE: PRT
<213> ORGANISM: Dog

<400> SEQUENCE: 141

Met Gly Leu Gly Ala Cys Val Ser Ser Ala Ser Gly Ala Gln Ala
1               5                   10                  15

Gln Ala Arg Trp Leu Gly Ala Val Leu Gly Ala Leu Cys Leu Leu Pro
            20                  25                  30

Val Leu Leu Leu Leu Ala Arg Pro Gly Ala Pro Ala Arg Leu Gly
        35                  40                  45

Ala Ser Ala Ala Gln Gly Asp Leu Ala Ala Pro Tyr Pro Val Gly Val
    50                  55                  60

Phe Ala Thr Pro Gly Pro Ser Pro Leu Pro Leu Gln Ala Pro Arg Arg
65                  70                  75                  80

Arg Arg Tyr Thr Leu Thr Pro Ala Arg Leu Arg Trp Asp His Phe Asn
                85                  90                  95

Leu Thr Tyr Arg Ile Leu Ser Phe Pro Arg Asn Leu Leu Ser Pro Ser
            100                 105                 110

Glu Thr Arg Arg Gly Leu Ala Thr Ala Phe Arg Met Trp Ser Asp Val
        115                 120                 125

Ser Pro Phe Ser Phe Arg Glu Val Ala Pro Glu Gln Pro Ser Asp Leu
    130                 135                 140

Arg Ile Gly Phe Tyr Pro Val Asn His Thr Asp Cys Leu Val Ser Ala
145                 150                 155                 160

Leu His His Cys Phe Asp Gly Pro Thr Gly Glu Leu Ala His Ala Phe
                165                 170                 175

Phe Pro Pro His Gly Ile His Phe Asp Asp Ser Glu Tyr Trp Val
            180                 185                 190

Leu Gly Pro Thr Arg Tyr Ser Trp Lys Lys Gly Val Trp Leu Thr Asp
        195                 200                 205

Leu Val His Val Ala Ala His Glu Ile Gly His Ala Leu Gly Leu Met
    210                 215                 220

His Ser Gln His Gly Arg Ala Leu Met His Leu Asn Ala Thr Leu Arg
225                 230                 235                 240

Gly Trp Lys Thr Leu Ser Gln Asp Glu Leu Trp Gly Leu His Arg Leu
                245                 250                 255

Tyr Gly Cys Leu Asp Arg Leu Phe Val Cys Thr Ser Trp Ala Arg Arg
            260                 265                 270

Gly Phe Cys Asp Thr Arg Arg Leu Met Lys Arg Leu Cys Pro Ser
        275                 280                 285

Ser Cys Asp Phe Cys Tyr Glu Phe Pro Phe Pro Thr Val Ala Ala Thr
    290                 295                 300

Ala Pro Pro Pro Arg Thr Lys Thr Arg Leu Val Pro Glu Gly Arg Asn
305                 310                 315                 320
```

```
Val Thr Phe Arg Cys Gly Gln Lys Ile Leu His Lys Gly Lys Val
            325                 330                 335

Tyr Trp Tyr Lys Asp Gln Glu Pro Leu Glu Phe Ser Tyr Pro Gly Tyr
            340                 345                 350

Leu Ala Leu Gly Glu Ala His Leu Ser Ile Ile Ala Asn Ala Ile Asn
            355                 360                 365

Glu Gly Thr Tyr Thr Cys Val Val Arg Arg Gln Arg Val Leu Ser
370                 375                 380

Thr Tyr Ser Trp Arg Val Arg Val Arg Gly
385                 390

<210> SEQ ID NO 142
<211> LENGTH: 240
<212> TYPE: PRT
<213> ORGANISM: Dog

<400> SEQUENCE: 142

Ser Ser Gly Thr Leu Glu Ala Ser Val Leu Val Thr Ile Glu Pro Ser
1               5                   10                  15

Ser Pro Gly Pro Ile Pro Ala Pro Gly Leu Ala Gln Pro Ile Tyr Ile
            20                  25                  30

Glu Ala Ser Ser His Val Ala Glu Gly Gln Ser Leu Asp Leu Asn
            35                  40                  45

Cys Val Val Pro Gly Gln Ala His Ala Gln Val Thr Trp Tyr Lys Arg
50                  55                  60

Gly Gly Ser Leu Pro Ala Arg His Gln Thr His Gly Ser Arg Leu Arg
65                  70                  75                  80

Leu His His Val Ser Pro Ala Asp Ser Gly Glu Tyr Val Cys Arg Val
                85                  90                  95

Val Gly Gly Ser Gly Pro Glu Gln Glu Ala Ser Phe Thr Val Thr Val
            100                 105                 110

Leu Pro Ser Ala Gly Ser Ser Tyr Arg Leu Arg Ser Pro Val Ile Ser
            115                 120                 125

Ile Asp Pro Pro Ser Ser Thr Val Gln Gln Gly Gln Asp Ala Ser Phe
130                 135                 140

Lys Cys Leu Ile His Asp Gly Ala Ala Pro Ile Ser Leu Glu Trp Lys
145                 150                 155                 160

Thr Arg Asn Gln Glu Leu Glu Asp Asn Val His Ile Ser Pro Asn Gly
                165                 170                 175

Ser Ile Ile Thr Ile Val Gly Thr Arg Pro Ser Asn His Gly Thr Tyr
            180                 185                 190

Arg Cys Val Ala Ser Asn Ala Tyr Gly Val Ala Gln Ser Val Val Asn
            195                 200                 205

Leu Ser Val His Gly Pro Pro Thr Val Ser Val Leu Pro Glu Gly Pro
            210                 215                 220

Val Arg Val Lys Val Gly Lys Ser Val Thr Leu Glu Cys Val Ser Ala
225                 230                 235                 240

<210> SEQ ID NO 143
<211> LENGTH: 171
<212> TYPE: PRT
<213> ORGANISM: Dog

<400> SEQUENCE: 143

Phe Phe Gln Ile Arg Tyr Met Arg Val Asn Pro Phe Tyr Pro Glu
1               5                   10                  15
```

```
Val Glu Leu Asn Phe Ile Ser Val Phe Trp Pro Asn Leu Pro Asn Gly
             20                  25                  30

Leu Gln Ala Ala Tyr Glu Val Ser Glu Arg Asp Glu Val Arg Phe Phe
         35                  40                  45

Lys Gly Asp Lys Tyr Trp Val Val Gln Gly Gln Asp Val Leu Tyr Gly
 50                  55                  60

Tyr Pro Lys Asp Ile His Arg Ser Phe Gly Phe Pro Arg Thr Val Lys
 65                  70                  75                  80

Ser Ile Asp Ala Ala Val Ser Asp Glu Asn Thr Gly Lys Thr Tyr Phe
                 85                  90                  95

Phe Val Ala Asn Lys Tyr Trp Arg Tyr Asp Glu Tyr Lys Gln Ser Met
            100                 105                 110

Asp Ala Gly Tyr Pro Gln Met Ile Ala Ala Gly Phe Pro Gly Ile Gly
        115                 120                 125

His Lys Val Asp Ala Val Phe Gln Lys Asp Gly Phe Phe Tyr Phe Phe
130                 135                 140

His Gly Lys Arg Gln Tyr Lys Phe Asp Leu Arg Thr Lys Arg Val Leu
145                 150                 155                 160

Ser Leu Asp Lys Ala Asn Ser Trp Phe Asn Cys
                165                 170

<210> SEQ ID NO 144
<211> LENGTH: 564
<212> TYPE: PRT
<213> ORGANISM: Dog

<400> SEQUENCE: 144

Gln Asn Trp Leu Lys Ser Tyr Gly Tyr Leu Leu Pro Tyr Asp Ser Arg
1               5                   10                  15

Ala Ser Ala Leu His Ser Gly Lys Ala Leu Gln Ser Ala Val Ser Thr
            20                  25                  30

Met Gln Gln Phe Tyr Gly Ile Pro Val Thr Gly Val Leu Asp Gln Thr
        35                  40                  45

Thr Ile Glu Trp Met Lys Lys Pro Arg Cys Gly Val Pro Asp His Pro
 50                  55                  60

His Leu Ser Arg Arg Arg Asn Lys Arg Tyr Ala Leu Thr Gly Gln
65                  70                  75                  80

Lys Trp Arg Gln Lys His Ile Thr Tyr Ser Ile His Asn Tyr Thr Pro
                85                  90                  95

Lys Val Gly Glu Leu Asp Thr Arg Lys Ala Ile Arg Gln Ala Phe Asp
            100                 105                 110

Val Trp Gln Lys Val Thr Pro Leu Thr Phe Glu Glu Val Pro Tyr His
        115                 120                 125

Glu Ile Lys Ser Asp Arg Lys Glu Ala Asp Ile Met Ile Phe Phe Ala
130                 135                 140

Ser Gly Phe His Gly Asp Ser Ser Pro Phe Asp Gly Glu Gly Gly Phe
145                 150                 155                 160

Leu Ala His Ala Tyr Phe Pro Gly Pro Gly Ile Gly Gly Asp Thr His
                165                 170                 175

Phe Asp Ser Asp Glu Pro Trp Thr Leu Gly Asn Ala Asn His Asp Gly
            180                 185                 190

Asn Asp Leu Phe Leu Val Ala Val His Glu Leu Gly His Ala Leu Gly
        195                 200                 205

Leu Glu His Ser Asn Asp Pro Ser Ala Ile Met Ala Pro Phe Tyr Gln
210                 215                 220
```

```
Tyr Met Glu Thr His Asn Phe Lys Leu Pro Gln Asp Asp Leu Gln Gly
225                 230                 235                 240

Ile Gln Lys Ile Tyr Gly Pro Pro Ala Glu Pro Leu Glu Pro Thr Arg
            245                 250                 255

Pro Leu Pro Thr Leu Pro Val Arg Arg Ile His Ser Pro Ser Glu Arg
        260                 265                 270

Lys His Glu Arg Gln Pro Arg Pro Arg Pro Pro Leu Gly Asp Arg
    275                 280                 285

Pro Ser Thr Pro Gly Ala Lys Pro Asn Ile Cys Asp Gly Asn Phe Asn
        290                 295                 300

Thr Val Ala Leu Phe Arg Gly Glu Met Phe Val Phe Lys Asp Arg Trp
305                 310                 315                 320

Phe Trp Arg Leu Arg Asn Asn Arg Val Gln Glu Gly Tyr Pro Met Gln
                325                 330                 335

Ile Glu Gln Phe Trp Lys Gly Leu Pro Ala Arg Ile Asp Ala Ala Tyr
            340                 345                 350

Glu Arg Ala Asp Gly Arg Phe Val Phe Lys Gly Asp Lys Tyr Trp
    355                 360                 365

Val Phe Lys Glu Val Thr Val Glu Pro Gly Tyr Pro His Ser Leu Gly
370                 375                 380

Glu Leu Gly Ser Cys Leu Pro Arg Glu Gly Ile Asp Thr Ala Leu Arg
385                 390                 395                 400

Trp Glu Pro Val Gly Lys Thr Tyr Phe Phe Lys Gly Glu Arg Tyr Trp
                405                 410                 415

Arg Tyr Ser Glu Glu Arg Arg Ala Thr Asp Pro Gly Tyr Pro Lys Pro
                420                 425                 430

Ile Thr Val Trp Lys Gly Ile Pro Gln Ala Pro Gln Gly Ala Phe Ile
            435                 440                 445

Ser Lys Glu Gly Tyr Tyr Thr Tyr Phe Tyr Lys Gly Arg Asp Tyr Trp
    450                 455                 460

Lys Phe Asp Asn Gln Lys Leu Ser Val Glu Pro Gly Tyr Pro Arg Asn
465                 470                 475                 480

Ile Leu Arg Asp Trp Met Gly Cys Asn Gln Lys Glu Val Glu Arg Arg
                485                 490                 495

Lys Glu Arg Arg Leu Pro Gln Asp Asp Val Asp Ile Met Val Thr Ile
                500                 505                 510

Asn Asp Val Pro Gly Ser Val Asn Ala Val Ala Val Ile Pro Cys
            515                 520                 525

Ile Leu Ser Leu Cys Ile Leu Val Leu Val Tyr Thr Ile Phe Gln Phe
    530                 535                 540

Lys Asn Lys Ala Gly Pro Gln Pro Val Thr Tyr Tyr Lys Arg Pro Val
545                 550                 555                 560

Gln Glu Trp Val

<210> SEQ ID NO 145
<211> LENGTH: 571
<212> TYPE: PRT
<213> ORGANISM: Dog

<400> SEQUENCE: 145

Lys Glu Leu Tyr Leu Leu Gln Val Trp Leu Gln Lys Tyr Gly Tyr Leu
1               5                   10                  15

Pro Pro Thr Asp Pro Arg Met Ser Val Leu Arg Ser Ala Glu Thr Met
            20                  25                  30

Gln Ala Ala Leu Ala Ala Met Gln Gln Phe Tyr Gly Ile Asn Met Thr
```

```
                35                  40                  45
Gly Lys Val Asp Arg Asn Thr Ile Asp Trp Met Lys Lys Pro Arg Cys
 50                  55                  60
Gly Val Pro Asp Gln Thr Arg Gly Ser Ser Lys Phe Asn Ile Arg Arg
 65                  70                  75                  80
Lys Arg Tyr Ala Leu Thr Gly Gln Lys Trp Gln His Lys His Ile Thr
                 85                  90                  95
Tyr Ser Ile Lys Asn Val Thr Pro Lys Val Gly Asp Pro Glu Thr Arg
            100                 105                 110
Lys Ala Ile Arg Arg Ala Phe Asp Val Trp Gln Asn Val Thr Pro Leu
        115                 120                 125
Thr Phe Glu Glu Val Pro Tyr Ser Glu Leu Glu Asn Gly Lys Arg Asp
    130                 135                 140
Val Asp Ile Thr Ile Ile Phe Ala Ser Gly Phe His Gly Asp Ser Ser
145                 150                 155                 160
Pro Phe Asp Gly Glu Gly Gly Phe Leu Ala His Ala Tyr Phe Pro Gly
                165                 170                 175
Pro Gly Ile Gly Gly Asp Thr His Phe Asp Ser Asp Glu Pro Trp Thr
            180                 185                 190
Leu Gly Asn Pro Asn His Asp Gly Asn Asp Leu Phe Leu Val Ala Val
        195                 200                 205
His Glu Leu Gly His Ala Leu Gly Leu Glu His Ser Asn Asp Pro Thr
    210                 215                 220
Ala Ile Met Ala Pro Phe Tyr Gln Tyr Met Glu Thr Asp Asn Phe Lys
225                 230                 235                 240
Leu Pro Asn Asp Asp Leu Gln Gly Ile Gln Lys Ile Tyr Gly Pro Pro
                245                 250                 255
Asp Lys Ile Pro Pro Thr Arg Pro Leu Pro Thr Val Pro Pro His
            260                 265                 270
Arg Ser Ile Pro Pro Ala Asp Pro Arg Lys Asn Asp Arg Pro Lys Pro
        275                 280                 285
Pro Arg Pro Pro Thr Gly Arg Pro Ser Tyr Pro Gly Ala Lys Pro Asn
    290                 295                 300
Ile Cys Asp Gly Asn Phe Asn Thr Leu Ala Ile Leu Arg Arg Glu Met
305                 310                 315                 320
Phe Val Phe Lys Asp Gln Trp Phe Trp Arg Val Arg Asn Asn Arg Val
                325                 330                 335
Met Asp Gly Tyr Pro Met Gln Ile Thr Tyr Phe Trp Arg Gly Leu Pro
            340                 345                 350
Pro Ser Ile Asp Ala Val Tyr Glu Asn Ser Asp Gly Asn Phe Val Phe
        355                 360                 365
Phe Lys Gly Asn Lys Tyr Trp Val Phe Lys Asp Thr Thr Leu Gln Pro
    370                 375                 380
Gly Tyr Pro His Asp Leu Ile Thr Leu Gly Ser Gly Ile Pro Pro His
385                 390                 395                 400
Gly Ile Asp Ser Ala Ile Trp Trp Glu Asp Val Gly Lys Thr Tyr Phe
                405                 410                 415
Phe Lys Gly Asp Arg Tyr Trp Arg Tyr Ser Glu Glu Met Lys Thr Met
            420                 425                 430
Asp Pro Gly Tyr Pro Lys Pro Ile Thr Val Trp Lys Gly Ile Pro Glu
        435                 440                 445
Ser Pro Gln Gly Ala Phe Val Glu Lys Lys Asn Lys Gly Phe Thr Tyr
    450                 455                 460
```

```
Phe Tyr Lys Gly Lys Glu Tyr Trp Lys Phe Asn Asn Gln Ile Leu Lys
465                 470                 475                 480

Val Glu Pro Gly Tyr Pro Arg Ser Ile Leu Lys Asp Phe Met Gly Cys
            485                 490                 495

Asp Gly Pro Thr Asp Arg Asp Lys Glu Gly His Ser Pro Pro Asp Asp
        500                 505                 510

Val Asp Ile Val Ile Lys Leu Asp Asn Thr Ala Ser Thr Val Lys Ala
        515                 520                 525

Ile Ala Ile Val Ile Pro Cys Ile Leu Ala Leu Cys Leu Leu Val Leu
        530                 535                 540

Val Tyr Thr Val Phe Gln Phe Lys Arg Lys Gly Thr Pro Arg His Ile
545                 550                 555                 560

Leu Tyr Cys Lys Arg Ser Met Gln Glu Trp Val
                565                 570

<210> SEQ ID NO 146
<211> LENGTH: 523
<212> TYPE: PRT
<213> ORGANISM: Dog

<400> SEQUENCE: 146

Cys Arg Arg Leu Ser Leu Ala Pro Pro Ser Leu Leu Pro Cys Pro Pro
1               5                   10                  15

Pro Pro Ser Phe Pro Arg Asn Ser Phe Arg Ala Gly Gly His Ser Pro
            20                  25                  30

Ala Arg Leu Pro Ala Ala Ala His Lys Ala Gln Pro Ile Ala Asp Leu
        35                  40                  45

Pro Ala Ala Gln Arg Gly Ala Leu Thr Pro Gly Arg Ala His Ala Gly
50                  55                  60

His Arg Trp Gly Leu Pro Gln Pro Ala Gly Thr Pro His Trp Lys Gly
65                  70                  75                  80

Arg Ser Leu Ala Gln Ala Val Arg Phe Gln Lys Val Asn Ala Leu
                85                  90                  95

Pro Ala Ser Gly Arg Leu Asp Ala Ala Thr Leu Ala Ala Met Asn Arg
            100                 105                 110

Pro Arg Cys Gly Val Pro Asp Thr Arg Ala Glu Val Phe Ala Lys Arg
        115                 120                 125

Thr Leu Ser Trp Arg Leu Leu Arg Glu Gly Ala Ser Gly Gln Leu Ala
130                 135                 140

Glu Ala Glu Gln Arg Arg Ile Leu Arg Leu Ala Phe Arg Met Trp Ser
145                 150                 155                 160

Glu Val Met Pro Leu His Phe Arg Glu Asp Leu Ala Ala Pro Gly Ala
            165                 170                 175

Ala Val Asp Ile Lys Leu Ala Phe Gly Arg Gly Arg His Leu Gly Cys
        180                 185                 190

Pro Arg Val Phe Asp Gly Ser Gly Gln Glu Phe Ala His Ala Trp Arg
    195                 200                 205

Leu Gly Asp Ile His Phe Asp Asp Glu His Phe Thr Pro Thr
210                 215                 220

Ser Asp Ser Gly Ile Ser Leu Leu Lys Val Ala Val His Glu Ile Gly
225                 230                 235                 240

His Val Leu Gly Leu Pro His Thr Tyr Arg Ala Gly Ser Ile Met Gln
                245                 250                 255

Pro Asn Tyr Val Pro Gln Glu Pro Val Phe Glu Leu Asp Trp Ser Asp
            260                 265                 270
```

-continued

```
Arg Lys Ala Ile Gln Lys Leu Tyr Gly Ser Cys Glu Gly Ser Phe Asp
        275                 280                 285
Thr Ala Phe Asp Trp Ile Arg Lys Glu Arg Asn Gln His Gly Ala Val
        290                 295                 300
Arg Met Arg Phe Ser Thr Tyr Phe Arg Asn Ser Trp Tyr Trp Leu
305                 310                 315                 320
Tyr Glu Asn Arg Asn Asn Arg Thr Arg Tyr Gly Asp Pro Ile Gln Ile
                325                 330                 335
Leu Ser Gly Trp His Gly Ile Pro Thr Gln His Ile Asp Ala Phe Val
                340                 345                 350
His Leu Trp Thr Trp Arg Arg Asp Glu Arg Tyr Phe Phe Lys Gly Asn
        355                 360                 365
Gln Tyr Trp Arg Tyr Asp Ser Asp Lys Asp Gln Ala Tyr Thr Glu Asp
        370                 375                 380
Glu Gln Gly Asn Ile Tyr Pro Lys Leu Ile Ser Gly Phe Pro Gly
385                 390                 395                 400
Ile Pro Ser Pro Leu Asp Thr Ala Phe Tyr Asp Arg Arg Lys Gln Leu
                405                 410                 415
Ile Tyr Phe Phe Lys Glu Ser Leu Val Phe Ala Phe Asp Val Asn Arg
                420                 425                 430
Asn Gln Val Leu Asp Ser Tyr Pro Met Lys Ile Thr Glu Val Phe Pro
        435                 440                 445
Gly Ile Glu Pro Gln Asn His Pro Phe Arg Asn Ile Asp Ser Ala Tyr
        450                 455                 460
Tyr Ser Tyr Ala His Asn Ser Leu Phe Phe Lys Gly Ser Ala Tyr
465                 470                 475                 480
Trp Lys Val Val Asn Asp Lys Asp Lys Gln Gln His Ser Trp Leu Pro
                485                 490                 495
Ser Asn Gly Leu Phe Pro Lys Gln Ser Ile Ser Glu Arg Trp Phe Asp
                500                 505                 510
Ile Cys Asp Val His Ala Ser Thr Leu Thr Val
                515                 520

<210> SEQ ID NO 147
<211> LENGTH: 523
<212> TYPE: PRT
<213> ORGANISM: Dog

<400> SEQUENCE: 147

Cys Arg Arg Leu Ser Leu Ala Pro Pro Ser Leu Leu Pro Cys Pro Pro
1               5                   10                  15
Pro Pro Ser Phe Pro Arg Asn Ser Phe Arg Ala Gly Gly His Ser Pro
                20                  25                  30
Ala Arg Leu Pro Ala Ala Ala His Lys Ala Gln Pro Ile Ala Asp Leu
        35                  40                  45
Pro Ala Ala Gln Arg Gly Ala Leu Thr Pro Gly Arg Ala His Ala Gly
        50                  55                  60
His Arg Trp Gly Leu Pro Gln Pro Ala Gly Thr Pro His Trp Lys Gly
65                  70                  75                  80
Arg Ser Leu Ala Gln Ala Val Arg Arg Phe Gln Lys Val Asn Ala Leu
                85                  90                  95
Pro Ala Ser Gly Arg Leu Asp Ala Ala Thr Leu Ala Ala Met Asn Arg
                100                 105                 110
Pro Arg Cys Gly Val Pro Asp Thr Arg Ala Glu Val Phe Ala Lys Arg
        115                 120                 125
```

Thr Leu Ser Trp Arg Leu Leu Arg Glu Gly Ala Ser Gly Gln Leu Ala
130                 135                 140

Glu Ala Glu Gln Arg Arg Ile Leu Arg Leu Ala Phe Arg Met Trp Ser
145                 150                 155                 160

Glu Val Met Pro Leu His Phe Arg Glu Asp Leu Ala Ala Pro Gly Ala
                165                 170                 175

Ala Val Asp Ile Lys Leu Ala Phe Gly Arg Gly Arg His Leu Gly Cys
            180                 185                 190

Pro Arg Val Phe Asp Gly Ser Gln Glu Phe Ala His Ala Trp Arg
        195                 200                 205

Leu Gly Asp Ile His Phe Asp Asp Glu His Phe Thr Pro Pro Thr
210                 215                 220

Ser Asp Ser Gly Ile Ser Leu Leu Lys Val Ala Val His Glu Ile Gly
225                 230                 235                 240

His Val Leu Gly Leu Pro His Thr Tyr Arg Ala Gly Ser Ile Met Gln
                245                 250                 255

Pro Asn Tyr Val Pro Gln Glu Pro Val Phe Glu Leu Asp Trp Ser Asp
            260                 265                 270

Arg Lys Ala Ile Gln Lys Leu Tyr Gly Ser Cys Glu Gly Ser Phe Asp
275                 280                 285

Thr Ala Phe Asp Trp Ile Arg Lys Glu Arg Asn Gln His Gly Ala Val
        290                 295                 300

Arg Met Arg Phe Ser Thr Tyr Phe Arg Asn Ser Trp Tyr Trp Leu
305                 310                 315                 320

Tyr Glu Asn Arg Asn Asn Arg Thr Arg Tyr Gly Asp Pro Ile Gln Ile
                325                 330                 335

Leu Ser Gly Trp His Gly Ile Pro Thr Gln His Ile Asp Ala Phe Val
            340                 345                 350

His Leu Trp Thr Trp Arg Arg Asp Glu Arg Tyr Phe Phe Lys Gly Asn
        355                 360                 365

Gln Tyr Trp Arg Tyr Asp Ser Asp Lys Asp Gln Ala Tyr Thr Glu Asp
370                 375                 380

Glu Gln Gly Asn Ile Tyr Pro Lys Leu Ile Ser Glu Gly Phe Pro Gly
385                 390                 395                 400

Ile Pro Ser Pro Leu Asp Thr Ala Phe Tyr Asp Arg Arg Lys Gln Leu
                405                 410                 415

Ile Tyr Phe Phe Lys Glu Ser Leu Val Phe Ala Phe Asp Val Asn Arg
            420                 425                 430

Asn Gln Val Leu Asp Ser Tyr Pro Met Lys Ile Thr Glu Val Phe Pro
        435                 440                 445

Gly Ile Glu Pro Gln Asn His Pro Phe Arg Asn Ile Asp Ser Ala Tyr
450                 455                 460

Tyr Ser Tyr Ala His Asn Ser Leu Phe Phe Lys Gly Ser Ala Tyr
465                 470                 475                 480

Trp Lys Val Val Asn Asp Lys Asp Lys Gln Gln His Ser Trp Leu Pro
                485                 490                 495

Ser Asn Gly Leu Phe Pro Lys Gln Ser Ile Ser Glu Arg Trp Phe Asp
            500                 505                 510

Ile Cys Asp Val His Ala Ser Thr Leu Thr Val
        515                 520

<210> SEQ ID NO 148
<211> LENGTH: 635
<212> TYPE: PRT
<213> ORGANISM: Dog

<400> SEQUENCE: 148

```
Arg Met Pro Arg Glu Leu Gln Glu Ser Pro Ser Gln Ser Pro Pro Ile
1               5                   10                  15

Phe Val Phe Ala Gln Asp Tyr Leu Glu Lys Tyr Gln Leu Pro Arg
            20                  25                  30

Asn Arg Phe Gln Ser Glu Arg Lys Asn Ser Thr Ser Val Ile Met Glu
            35                  40                  45

Lys Leu Arg Glu Met Gln Arg Phe Phe Gly Leu Asn Glu Thr Gly Lys
50                  55                  60

Pro Asn Gln Glu Thr Leu Glu Met Met Gln Lys Pro Arg Cys Gly Val
65                  70                  75                  80

Pro Asp Ser Gly Asp Phe Met Leu Thr Pro Gly Asn Pro Lys Trp Lys
                85                  90                  95

Gln Thr Asn Leu Thr Tyr Arg Ile Ile Lys Tyr Thr Pro Gln Leu Ser
            100                 105                 110

Glu Ala Asn Val Glu Thr Ala Ile Gln Lys Ala Phe Gln Val Trp Ser
            115                 120                 125

Asn Val Ser Pro Leu Thr Phe Thr Lys Val Ser Gln Gly Glu Val Asp
130                 135                 140

Ile Arg Ile Ser Phe Val Gln Gly Asp His Gly Asp Asn Ser Pro Phe
145                 150                 155                 160

Asp Gly Pro Asn Gly Ile Leu Ala His Ala Phe Gln Pro Gly Gln Gly
                165                 170                 175

Ile Gly Gly Asp Val His Phe Asp Ala Glu Glu Thr Trp Thr Glu Asn
                180                 185                 190

Ser Ser Ser Gln Val Glu Leu His Lys Ala Thr Gly Gln Gln Tyr Thr
            195                 200                 205

Thr Glu His Cys Arg Lys Gln Glu Arg Lys Leu Leu Ser Leu Leu Gly
210                 215                 220

Ile Cys Ser Ser His His Phe Leu Asn Ile Tyr Ile Val Phe Ile Ser
225                 230                 235                 240

Pro Lys Ser Leu Tyr Trp Glu Leu Cys Glu Pro Lys Glu Leu Asn Asp
                245                 250                 255

Pro Asn Ser His Leu Asp Cys Gln Pro Pro Ile Ser Pro Thr Leu Lys
                260                 265                 270

Phe Ser Gln His Ala Ser Lys Ile Cys Ile Trp Lys Val His Leu Arg
            275                 280                 285

Leu Cys His Met Leu Pro His Leu Asp Phe Gln Gln Lys Trp Gly Leu
290                 295                 300

Ser Pro Gln Asn Ala Asn Ser Leu Cys Phe Ser Phe Ser Asn Cys Ser
305                 310                 315                 320

Pro His Cys Ala Val Pro Phe Thr Leu Leu Ala Tyr Ile Ser Leu Ser
                325                 330                 335

Gln Leu Cys Phe Met Thr Glu Pro Pro Glu Pro Leu Thr Thr Tyr Ser
            340                 345                 350

Arg Pro Ser Lys Met Ser Ser Glu Met Tyr Ser Gly Met Gln Lys Met
            355                 360                 365

Gln Gly Tyr Tyr Asn Leu Phe Leu Val Ala Ala His Glu Val Gly His
            370                 375                 380

Ser Leu Gly Leu Ser His Ser Thr Asp Pro Gly Ala Leu Met Tyr Pro
385                 390                 395                 400

Asn Tyr Val Phe His Asp Pro Ser Thr Tyr Thr Leu Pro Gln Asp Asp
                405                 410                 415
```

-continued

```
Ile Asn Gly Ile Gln Thr Ile Tyr Gly Lys Ser Val Gly Arg Thr Leu
            420                 425                 430
Ser Thr Cys Asn Pro Val Gln Pro Thr Gly Pro Ser Thr Pro Thr Thr
        435                 440                 445
Cys Asp Pro Arg Leu Thr Phe Asp Ala Ile Ala Thr Leu Arg Gly Glu
450                 455                 460
Ile Leu Phe Phe Lys Asp Lys Tyr Phe Trp Arg Arg His Pro Gln Leu
465                 470                 475                 480
Pro Arg Val Glu Leu Asn Phe Ile Ser Leu Phe Trp Pro Ser Leu Pro
                485                 490                 495
Asp Gly Ile Gln Ala Ala Tyr Glu Asp Val Asp Lys Asp Leu Val Phe
            500                 505                 510
Leu Phe Lys Gly Ser Gln Tyr Trp Ala Leu Ser Gly Tyr Asp Ile Lys
        515                 520                 525
Gln Gly Tyr Pro Lys Asp Ile Ser Asp Tyr Ser Phe Pro Ser Ser Val
530                 535                 540
Gln Ala Ile Asp Ala Ala Val Tyr Tyr Arg Arg Lys Thr Tyr Phe Phe
545                 550                 555                 560
Val Asn Asp Gln Val Trp Ser Arg Tyr Asp Asn Gln Arg Gln Ser Met
                565                 570                 575
Glu Pro Gly Tyr Pro Lys Ser Ile Ala Ser Ile Phe Pro Gly Ile Glu
            580                 585                 590
Ser Thr Val Asp Ala Val Phe Gln Gln Asn His Val Phe Leu Phe Phe
        595                 600                 605
Ser Gly Pro Arg Tyr Tyr Ala Phe Asp Leu Gly Ala His Glu Val Ile
610                 615                 620
Arg Val Gly Arg Ser Asn Arg Trp Leu Asn Cys
625                 630                 635

<210> SEQ ID NO 149
<211> LENGTH: 470
<212> TYPE: PRT
<213> ORGANISM: Dog

<400> SEQUENCE: 149

Met Lys Phe Leu Leu Leu Val Leu Ile Leu Gln Val Thr Ala Ser Gly
1               5                   10                  15
Thr Ile Pro Leu Thr Asn Ser Ala Ser Ser Lys Glu Asn Asp Val Ala
            20                  25                  30
Ser Ser Gln Arg Tyr Leu Glu Asn Phe Tyr Gly Phe Val Met Asp Gly
        35                  40                  45
Ile Pro Lys Thr Lys Met Gly Val Gly Gly Asn Leu Met Glu Asn Lys
50                  55                  60
Ile Gln Glu Met Gln Gln Phe Leu Gly Leu Lys Val Thr Gly Lys Leu
65                  70                  75                  80
Asp Ala Ser Thr Leu Asp Met Met His Met Pro Arg Cys Gly Leu Pro
                85                  90                  95
Asp Val Gln His Phe Ser Thr Met Gln Gly Arg Pro Val Trp Lys Lys
            100                 105                 110
His Leu Ile Thr Tyr Arg Ile Asn Asn Tyr Thr Pro Asp Met Gln Pro
        115                 120                 125
Ala Asp Val Asp Tyr Ala Ile His Lys Ala Phe Glu Val Trp Ser Asn
130                 135                 140
Val Thr Pro Leu Lys Phe Arg Lys Val Asn Ser Gly Glu Ala Asp Ile
145                 150                 155                 160
```

```
Met Ile Leu Phe Ala Ser Arg Ala His Gly Asp Phe Ser Pro Phe Asp
            165                 170                 175
Gly Arg Gly Gly Val Ile Ala His Ala Phe Gly Pro Gly Pro Gln Ile
            180                 185                 190
Gly Gly Asp Met His Phe Asp Glu Ala Glu Ile Trp Thr Lys Thr Tyr
            195                 200                 205
Lys Gly Thr Asn Leu Phe Leu Val Ala Val His Glu Leu Gly His Ser
        210                 215                 220
Leu Gly Leu Gly His Ser Ser Asp Pro Lys Ala Ile Met Phe Pro Thr
225                 230                 235                 240
Tyr Ser Tyr Val Asn Pro Asn Thr Phe His Leu Ser Ala Asp Asp Ile
                245                 250                 255
His Gly Ile Gln Ser Leu Tyr Gly Gly Pro Glu Lys Gln Phe Ser
            260                 265                 270
Ser Asn Thr Asp Gly Thr Glu Ser Ala Asn Cys Asp Ser Asn Leu Ser
        275                 280                 285
Phe Asp Ala Val Thr Thr Val Gly Asn Lys Ile Phe Phe Lys Asp
290                 295                 300
Arg Phe Leu Trp Trp Arg His Pro Glu Ser Pro Lys Asn Ser Val Thr
305                 310                 315                 320
Leu Ile Ser Ser Leu Trp Pro Thr Leu Pro Ser Gly Ile Gln Ala Ala
                325                 330                 335
Tyr Glu Ile Gly Ala Arg Asn Gln Val Phe Leu Phe Lys Asp Asp Lys
                340                 345                 350
Tyr Trp Leu Ile Ser Asn Leu Arg Pro Gln Pro His Tyr Pro Lys Asn
            355                 360                 365
Ile His Ser Leu Gly Phe Pro Asp Ser Val Lys Lys Ile Asp Ala Ala
        370                 375                 380
Val Phe Asn Pro Leu Leu Tyr Lys Thr Tyr Phe Phe Val Asp Asp Gln
385                 390                 395                 400
Phe Trp Arg Tyr Asp Glu Lys Thr Gln Phe Met Asp Pro Gly Tyr Pro
                405                 410                 415
Lys Leu Ile Thr Lys Tyr Phe Pro Gly Ile Lys Pro Thr Val Asp Ala
            420                 425                 430
Val Tyr Tyr Tyr Asn Arg His Tyr Tyr Phe Phe Gln Gly Pro Asp Val
            435                 440                 445
Phe Glu Tyr Asp Val Ile Ser His Arg Ile Thr Lys Lys Pro Lys Gln
450                 455                 460
Ser Ile Met Ser Gly Cys
465                 470

<210> SEQ ID NO 150
<211> LENGTH: 13
<212> TYPE: PRT
<213> ORGANISM: Dog
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 150
```

```
His Glu Xaa Gly His Xaa Xaa Gly Xaa Xaa His Ser Thr
1               5                   10

<210> SEQ ID NO 151
<211> LENGTH: 7
<212> TYPE: PRT
<213> ORGANISM: Dog

<400> SEQUENCE: 151

Arg Glu His Gly Ala Arg Ser
1               5

<210> SEQ ID NO 152
<211> LENGTH: 12
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 152

His Glu Xaa Gly His Xaa Xaa Gly Xaa Xaa His Ser
1               5                   10

<210> SEQ ID NO 153
<211> LENGTH: 12
<212> TYPE: PRT
<213> ORGANISM: Homo Sapiens
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 153

His Glu Xaa Gly His Xaa Xaa Gly Xaa Xaa His Thr
1               5                   10
```